United States Patent
Terasaka et al.

(10) Patent No.: US 8,273,745 B2
(45) Date of Patent: Sep. 25, 2012

(54) POLYCYCLIC ACID COMPOUNDS USEFUL AS CRTH2 ANTAGONISTS AND ANTIALLERGIC AGENTS

(75) Inventors: Tadashi Terasaka, Chuo-ku (JP); Tatsuya Zenkoh, Chuo-ku (JP); Hisashi Hayashida, Chuo-ku (JP); Hiroshi Matsuda, Chuo-ku (JP); Junji Sato, Chuo-ku (JP); Yoshimasa Imamura, Chuo-ku (JP); Hiroshi Nagata, Chuo-ku (JP); Norio Seki, Chuo-ku (JP); Yoshiyuki Tenda, Chuo-ku (JP); Mamoru Tasaki, Chuo-ku (JP); Masahiro Takeda, Chuo-ku (JP); Seiichiro Tabuchi, Chuo-ku (JP); Minoru Yasuda, Tsukuba (JP); Kazunori Tsubaki, Kyoto (JP)

(73) Assignee: Astellas Pharma Inc, Tokyo (JP)

( * ) Notice: Subject to any disclaimer, the term of this patent is extended or adjusted under 35 U.S.C. 154(b) by 360 days.

(21) Appl. No.: 12/518,280

(22) PCT Filed: Dec. 13, 2007

(86) PCT No.: PCT/JP2007/074475
§ 371 (c)(1),
(2), (4) Date: Jun. 9, 2009

(87) PCT Pub. No.: WO2008/072784
PCT Pub. Date: Jun. 19, 2008

(65) Prior Publication Data
US 2010/0009991 A1    Jan. 14, 2010

Related U.S. Application Data

(60) Provisional application No. 60/870,014, filed on Dec. 14, 2006.

(51) Int. Cl.
*A61K 31/50* (2006.01)
*C07D 413/00* (2006.01)

(52) U.S. Cl. .................... 514/252.01; 544/140

(58) Field of Classification Search .......... 544/140; 514/252.01
See application file for complete search history.

(56) References Cited

U.S. PATENT DOCUMENTS
6,399,611 B1  6/2002  Jonas et al.

FOREIGN PATENT DOCUMENTS

| | | |
|---|---|---|
| EP | 0 711 759 A1 | 5/1996 |
| EP | 1 550 461 A1 | 7/2005 |
| EP | 1 553 075 A1 | 7/2005 |
| WO | WO 95/24393 | 9/1995 |
| WO | WO 96/07633 | 3/1996 |
| WO | WO 00/69810 | 11/2000 |
| WO | WO 02/072103 A1 | 9/2002 |
| WO | WO 2005/115382 A1 | 12/2005 |
| WO | WO 2007/065518 A1 | 6/2007 |
| WO | WO 2008/017361 A2 | 2/2008 |

OTHER PUBLICATIONS

Vippagunta et al.*
Office Action issued May 6, 2011, in European Patent Application No. 07 859 872.9.
Aaron N. Hata, et al., "Structural Determinants of Arylacetic Acid Nonsteroidal Anti-Inflammatory Drugs Necessary for Binding and Activation of the Prostaglandin $D_2$ Receptor CRTH2", Molecular Pharmacology, The American Society for Pharmacology and Experimental Therapeutics, vol. 67, No. 3, XP009051298, 2005, pp. 640-647.
Kazunori Tsubaki, et al., "A Novel Pyridazinone Derivative as a Nonprostanoid $PGI_2$ Agonist", Bioorganic & Medicinal Chemistry Letters, vol. 10, 2000, pp. 2787-2790.

* cited by examiner

*Primary Examiner* — Paul V. Ward
(74) *Attorney, Agent, or Firm* — Oblon, Spivak, McClelland, Maier & Neustadt, L.L.P.

(57) ABSTRACT

The present invention relates to a novel compound or a salt thereof, which is useful as a CRTH2 antagonist, especially as a medicament for disorder that participates eosinophil, for example, allergic disorder such as asthma, allergic rhinitis, allergic dermatitis, conjunctival inflammation, hives, eosinophilic bronchitis, food allergy, inflammation of the nasal sinuses, multiple sclerosis, angiitis, or chronic obstructive pulmonary disease (COPD) and the like.

8 Claims, No Drawings

POLYCYCLIC ACID COMPOUNDS USEFUL AS CRTH2 ANTAGONISTS AND ANTIALLERGIC AGENTS

TECHNICAL FIELD

This invention relates to a novel compound and to a medicament containing the compound as an active ingredient, and more particularly, to an inflammatory disease treating agent.

BACKGROUND ART

Mast cells, known as conductor cells in allergic inflammation, are activated by numerous stimuli including antigens and produce various inflammatory mediators.

Prostaglandin $D_2$ ($PGD_2$) is a major prostanoid produced by activated mast cells. Some reports showed that antigen challenge induces remarkable $PGD_2$ production in the airway of asthmatic patient (New England Journal of Medicine, 1986, 315 (13), pp. 800-804), in the nasal mucosa of the allergic rhinitis patient or in the skin of the atopic dermatitis patient (Journal of Immunology, 1991, 146(2), pp. 671-676.).

Fujitani et al. reported that overexpression of PGD synthase in transgenic mice which $PGD_2$ production is increased leads to enhanced airway eosinophil infiltration and Th2 cytokine production in an antigen induced asthma model (Journal of Immunology, 2002, 168(1), pp. 443-449.). In this way, it is thought that $PGD_2$ is closely related to the pathogenesis of the allergic diseases and their exacerbation.

At first, it was thought that most of the biological actions of $PGD_2$ are mediated through the classical $PGD_2$ receptor DP. However, several actions of $PGD_2$ such as eosinophil activation could not be mimicked by BW245C, a selective DP agonist (Investigate Opthlmology & Visual Science, 1990, 1, pp. 138-146.), and proposed that eosinophils are activated by $PGD_2$ through a novel $PGD_2$ receptor (Blood, 2001, 98(6), pp. 1942-1948). Around the same time, Hirai et al. reported that $PGD_2$ induces chemotaxis of Th2 cells, eosinophils and basophils through Chemoattractant receptor homologous molecule expressed on Th2 cells (CRTH2) (The Journal of Experimental Medicine, 2001, 193(2), pp. 255-261). Originally, CRTH2 was cloned as an orphan chemoattractant-like receptor and the ligand activity was found in conditioned medium of activated mast cells. Nagata et al. showed that CRTH2 is selectively expressed by Th2 cells, eosinophils and basophils which are inflammatory cells related to allergic reactions (Journal of Immunology, 1999, 162(3), pp. 1278-1286, FEBS Letter, 1999, 459 (2), pp. 195-199).

The functions of CRTH2 are reported that induction of cell migration (on Th2 cells, eosinophils or basophils), up-regulation of adhesion molecules (on Th2 cells or eosinophils), promotion of Th2 cytokine production (on Th2 cells), from previous researches using CRTH2/DP agonist and/or antagonist. On the other hand, the functions of DP are reported that inhibition of platelet aggregation, vasodilatation, relaxation of smooth muscle, inhibition of cell migration (on eosinophils or dendritic cells), induction of apoptosis (on eosinophils), induction of sleep. Therefore, it is thought that $PGD_2$ induces local vasodilation through DP which enhances vascular permeability, and induces inflammatory cells infiltration and activation through CRTH2. Thus, the $PGD_2$-CRTH2 system plays a significant role in allergic inflammation (Prostaglandins Leukotrienes & Essential Fatty Acids, 2003, 69 (2-3), pp. 169-177, Natural Review Drug Discovery, 2007, 6(4), pp. 313-325).

In conclusion, $PGD_2$, the major prostanoid produced by mast cells, activates inflammatory cells including Th2 cells, eosinophils and basophils and play an important roll for the allergic inflammation through CRTH2. Therefore, CRTH2 antagonist is expected to be developed as an anti-inflammatory medicine for treatment of patients with allergic diseases.

Benzhydryl-pyridazinone and benzhydryl-pyridone compounds are disclosed in International publication No. WO 95/24393 and Bioorganic & Medicinal Chemistry Letters, 2000, 10(24), pp. 2787-2790.

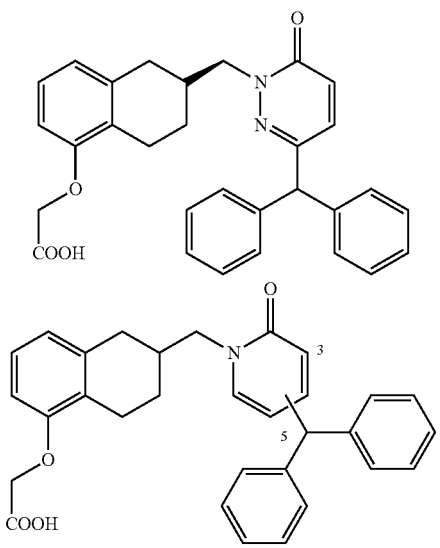

The publications disclosed that the compounds of each publications are identified as non prostanoid PGI2 agonist, and that these compounds show inhibitory activity on platelet aggregation, a vasodilating activity, an antihypertensive, activity and the like, and that the compounds are useful as medicaments for the therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension and the like. However each of the publications does not mention or give suggestions on allergic reaction.

DISCLOSURE OF THE INVENTION

This invention provides a compound of the following formula (I) or a pharmaceutically acceptable salt thereof that is useful as an antiallergic agent. This invention is directed to derivatives that are CRTH2 receptor antagonists and that are useful in the treatment and/or prevention of diseases mediated with CRTH2 receptor.

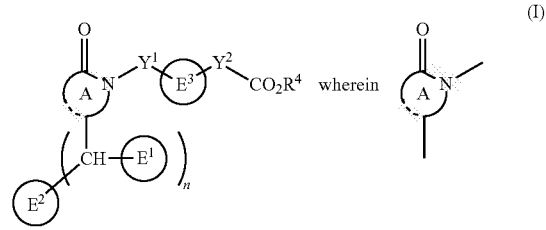

is a group selected from the group consisting of (i), (ii) and (iii).

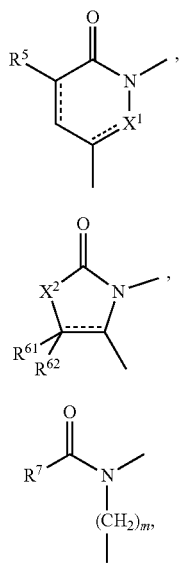

$X^1$ is —CH=, —CH$_2$— or —N=;
$X^2$ is —NH—, —N(C$_1$-C$_6$ alkyl)-, —O— or —S—;
---- is single bond or double bond;
$Y^1$ and $Y^2$ are each C$_1$-C$_6$ alkylene or C$_2$-C$_6$ alkenylene,
  wherein each methylene unit may be replaced with —O—, —NH—, —N(C$_1$-C$_6$ alkyl)-, —NHC(=O)—, —N{C(=O) (C$_1$-C$_6$ alkyl)}-, —S—, —S(=O)— —S(=O)$_2$—, arylene, 5- or 6-membered heteroarylene or C$_3$-C$_{10}$ cycloalkylene;
$E^1$ is —H or phenyl which may be substituted with one or more substituent (s) selected from the group consisting of —R$^1$;
$E^2$ is phenyl or xanthenyl,
  each of which may be substituted with one or more substituents selected from the group consisting of —R$^2$;
$E^3$ is benzene ring which may be fused with 5-membered ring,
  wherein benzene ring which may be fused with 5-membered ring may be substituted with one or more substituent(s) selected from the group consisting of —R$^3$;
$R^1$ is halogen, C$_1$-C$_6$ alkyl or —O— (C$_1$-C$_6$ alkyl)
$R^2$ is R$^1$, aryl, —O-aryl or heteroaryl,
  wherein aryl, —O-aryl or heteroaryl may be substituted with one or more substituent(s) selected from the group consisting of —R$^1$;
$R^3$ is halogen or C$_1$-C$_6$ alkyl;
$R^4$ is —H, C$_1$-C$_6$ alkyl or alkali metal;
$R^5$ is —H or halogen;
$R^{61}$ is —H, C$_1$-C$_6$ alkyl or aryl;
$R^{62}$ is —H, C$_1$-C$_6$ alkyl, aryl or absent;
$R^7$ is phenyl, —O-phenyl, 5- or 6-membered heteroaryl, C$_3$-C$_8$ cycloalkyl, C$_1$-C$_6$ alkyl or C$_2$-C$_6$ alkenyl,
  wherein each of which may be substituted with one or more substituent(s) selected from the group consisting of —R$_{71}$;
$R^{71}$ is halogen, —OH, C$_1$-C$_6$ alkyl, —NHS(=O)$_2$(C$_1$-C$_6$ alkyl), —S(=O)$_2$(C$_1$-C$_6$ alkyl), —NHC(=O) (C$_1$-C$_6$ alkyl), —C(=O)OH, —O—(C$_1$-C$_6$ alkyl), —O—(C$_1$-C$_6$ alkyl)-aryl, —S(=O)$_2$—NH$_2$ or —C(=O)NH$_2$;
n is 0 or 1;
m is 1 or 2;
or a pharmaceutically acceptable salt thereof, or prodrug thereof.

The present invention will be explained in more detail herein below.

In the definition of the general formula (I) for the compound in the present invention, Suitable "one or more" includes the number of 1 to 5, preferably 1 to 3.

The term "alkyl" as used herein includes a monovalent group of a straight or branched alkyl having 1 to 12 carbon atom(s).

The term "C$_1$-C$_6$ alkyl" as used herein includes "alkyl" having 1 to 6 carbon atom(s) such as methyl, ethyl, propyl, isopropyl, butyl, isobutyl, sec-butyl, tert-butyl, pentyl, tert-pentyl, neopentyl, hexyl, isohexyl and the like. Suitable "C$_1$-C$_6$ alkyl" includes methyl, ethyl, propyl, isopropyl, butyl, isobutyl, sec-butyl, tert-butyl, pentyl, tert-pentyl, neopentyl and the like.

The term "alkylene" as used herein includes a divalent group having a straight or branched carbon chain.

The term "C$_2$-C$_6$ alkylene" as used herein includes a "alkylene" having 2 to 6 carbon atom(s) such as methylenyl, ethylene, trimethylene, tetramethylene, dimethylmethylene, dimethylethylene and the like. Suitable "C$_2$-C$_6$ alkylene" as used herein includes methylenyl, ethylene, trimethylene, tetramethylene and the like.

The term "alkenyl" as used herein includes a monovalent group of alkene.

The term "C$_2$-C$_6$ alkenyl" as used herein includes "alkenyl" having 2 to 6 carbon atom(s) such as ethenyl, propenyl, buthenyl, pentenyl, hexenyl, isopropenyl, neopenteyl and the like. Suitable "C$_2$-C$_6$ alkenyl" as used herein includes such as ethenyl, allyl, propenyl and the like.

The term "C$_2$-C$_6$ alkenylene" as used herein includes straight or branched alkenylene having 2 to 6 carbon atom(s) such as ethen-1,1-diylene, ethen-1,2-diylene, propendiylene, butendiylene vinylene, 1-methylvinylene, 2-methylvinylene, 1-propenylene, 2-propenylene, 2-methyl-1-propenylene, 2-methyl-2-propenylene, 1-butenylene, 2-butenylene, 3-butenylene and the like. Suitable "C$_2$-C$_6$ alkenylene" as used herein includes such as then-1,1-diylene, ethen-1,2-diylene, propendiylene, butendiylene vinylene, 1-methylvinylene, 2-methylvinylene, 1-propenylene, 2-propenylene, 2-methyl-1-propenylene, 2-methyl-2-propenylene and the like.

The term "cycloalkyl" as used herein includes
1) cycloalkyl having 3 to 10 carbon atoms such as cyclopropyl, cyclobutyl, cyclopentyl, cyclohexyl, cycloheptyl, cyclooctyl, cyclononyl;
2) a non-aromatic carbon ring which may have partial unsaturation having 3 to 10 carbon atom(s) such as cyclopropyl, cyclobutyl, cyclopentyl, cyclohexyl, cycloheptyl, cyclooctyl, cyclohexenyl, cyclooctadienyl; and
3) may fused with benzene and/or bridged, such as indanyl and the like.

Suitable "cycloalkyl" as used herein includes "C$_3$-C$_{10}$ cycloalkyl" having 3 to 10 carbon atom(s) such as cyclopropyl, cyclobutyl, cyclopentyl, cyclohexyl, cycloheptyl, cyclooctyl, cyclohexenyl, cyclooctadienyl, indanyl, adamantyl and the like. Suitable "C$_3$-C$_{10}$ cycloalkyl" as used herein includes cyclobutyl, cyclopentyl, cyclohexyl and the like.

The term "C$_3$-C$_{10}$ cycloalkylene" as used herein includes divalent "C$_3$-C$_{10}$ cycloalkyl" such as cyclopropylene, cyclobutylene, cyclopentylene, cyclohexylene and the like.

The term "aryl" as used herein includes a mono- to tricyclic aromatic carbon ring such as phenyl, naphthyl, anthryl, pyrenyl, phenanthryl, azulenyl and the like, of which phenyl and naphthyl are preferred, and phenyl is more preferred.

The term "arylene" as used herein includes divalent aromatic ring such as phenylene and the like.

The term "heteroatom" as used herein includes nitrogen atom, oxygen atom and sulfur atom.

The term "heteroaryl" as used herein includes a monovalent group of a 5 to 10 membered aromatic heterocycle having one or more hetero atoms selected from the group consisting of a nitrogen, an oxygen and a sulfur atom, which may be fused with benzene. Suitable "heteroaryl" as used herein includes such as thienyl, benzothienyl, furyl, benzofuryl, dibenzofuryl, pyrrolyl, imidazolyl, pyrazolyl, pyridyl, pyrazinyl, pyrimidinyl, pyridazinyl, tetrazolyl, oxazolyl, thiazolyl, isoxazolyl indolyl, benzothiazolyl, quinolyl, isoquinolyl and the like.

The term "5- or 6-membered heteroaryl" as used herein includes "heteroaryl" having 5 or 6 ring atom such as thienyl, thiazolyl, oxazolyl, imidazolyl, isothiazolyl, isoxazolyl, pyrazolyl, pyridyl and the like. The term "5-membered heteroaryl" as used herein includes "heteroaryl" having 5 ring atoms.

The term "5- or 6-membered heteroarylene" as used herein includes divalent "5- or 6-membered heteroaryl" such as pyridinediyl, oxazolediyl, imidazolidinyl and the like.

The term "heterocycloalkyl" as used herein includes a monovalent group of a 4- to 10-membered non-aromatic heterocycle having one or more heteroatoms selected from the group consisting of a nitrogen, an oxygen and a sulfur atom, which may be fused with benzene and/or bridged. Its examples include azetidinyl, pyrrolidinyl, imidazolinyl, imidazolidinyl, pyrazolidinyl, pyrazolinyl, piperidinyl, azepinyl, piperazinyl, homopiperazinyl, morpholinyl, thiomorpholinyl, indolinyl, isoindolinyl, chromane, 8-azabicyo[3.2.1]octanyl, quinuclidinyl and the like.

The term "5-membered heterocycloalkyl" as used herein includes a monovalent group of a 5-membered "heterocycloalkyl" such as pyrrolidinyl, 2,3-dihydro-1H-pyrrolyl and the like.

The term "5-membered ring" as used herein includes ring having 5 atoms such as cyclopentane, imidazole, pyrazole, pyrrole.

The term "benzene ring which may be fused with 5-membered ring" as used herein includes benzene ring which may be fused with "5-membered ring" such as indole, dihydroindole, benzimidazole, indane, benzotriazole, benzpyrazole and the like. Removal of the two optional proton on ring atom of "benzene ring which may be fused with 5-membered ring" can be form divalent groups. The term "benzene ring which may be fused with 5-membered ring" may be substituted on any ring atom.

The term "halogen" as used herein means chloro, bromo, iodo and fluoro.

The terms "alkylsulfonyl" and "arylsulfonyl" as used herein denotes a group of formula $S(=O)_2R$ wherein R is "alkyl" or "aryl" respectively and alkyl and aryl are as defined herein.

The term "alkali metal" as used herein refers to a formula (I) including, but not limited to lithium ($Li^+$), sodium ($Na^+$), or potassium ($K^+$).

The compound of the present invention represented by the general formula (I) may comprise asymmetric carbon atoms depending on the kinds of substituent groups, and optical isomers based on the asymmetric carbon atom may exist. The compound of the present invention includes a mixture of these optical isomers or isolated ones. And, tautomers may exist in the compound of the present invention, and the compound of the present invention includes these isomers as a mixture or an isolated one. And, labeled compound, i.e., compounds wherein one or more atoms are labeled with radioisotopes or non-radioisotopes, are also included in the present invention.

In addition, the compound of the present invention may form a salt, which is included in the present invention as long as pharmaceutically acceptable. Examples of the salt include addition salts with a mineral acid such as HCl, hydrobromic acid, hydriodic acid, $H_2SO_4$, nitric acid, phosphoric acid, and the like; or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, p-toluenesulfonic acid, aspartic acid, glutamic acid, and the like; an inorganic base such as sodium salt, potassium salt, calcium salt, magnesium salt, and the like; or an organic base such as methylamine, ethylamine, ethanolamine, lysine, ornithine, and the like; and ammonium salts, and the like. And a hydrate and a solvate of the compound and its pharmaceutically acceptable salt of the present invention, and those having polymorphism are also included in the present invention.

In addition, the compound of the invention also includes a compound which is metabolized in a living body to be converted into the compound of the general formula (I) or its salt, a so-called "prodrug".

The "prodrug" means the derivatives of the compound (I) having chemically or metabolically degradable group, which became pharmaceutically after chemo- or biotransformation. As groups forming the prodrug, those described in Prog. Med., 1985, 5, pp. 2157-2161; and Hirokawa-Shoten, 1990, "Development of medicine" Vol. 7, Molecular Design, pp. 163-198 can be exemplified.

Suitable substituent in formula (I) is exemplified as follows: wherein

A: a group selected from the group consisting of (i), (ii) and (iii). The group of (i) or (ii) are preferred, (iii) is more preferred. {(i), (ii) or (iii) are defined in page 5 in this document.}

$X^1$: Each atom of [—CH=, —$CH_2$— or —N=] are preferred.

$X^2$: The groups are [—NH—, —N($C_1$-$C_6$ alkyl)-, —O— or —S—]. The groups of [—NH—, —N($CH_3$)—, —O— or —S—] are preferred. The groups of [—O— or —S—] are more preferred.

====: single bond or double bond. Double bond is preferred.

$Y^1$ and $Y^2$: [each $C_1$-$C_6$ alkylene or $C_2$-$C_6$ alkenylene, wherein each methylene unit may be replaced with —O—, —NH—, —N($C_1$-$C_6$ alkyl)-, —NHC(=O)—, —N{C(=O) ($C_1$-$C_6$ alkyl)}-, —S—, —S(=O)—, —S(=O)$_2$—, arylene, 5- or 6-membered heteroarylene or $C_3$-$C_{10}$ cycloalkylene] are preferred.

The groups of [$C_1$-$C_6$ alkylene or $C_2$-$C_6$ alkenylene, wherein each methylene unit may be replaced with —O—, —NH—, —N($CH_3$)—, —NHC(=O)—, —N{C(=O)$CH_3$}-, —S—, —S(=O)—, —S(=O)$_2$—, phenylene, pyridinediyl, oxazolediyl, imidazolidinyl or $C_3$-$C_{10}$ cycloalkylene] are preferred.

The groups of [$C_4$-$C_6$ alkylene or $C_4$-$C_6$ alkenylene, wherein each methylene unit may be replaced with —O—, —NH—, —N($CH_3$)—, —NHC(=O)—, —N{C(=O)$CH_3$}-, —S—, —S(=O)—, —S(=O)$_2$—, phenylene, pyridinediyl, oxazolediyl, imidazolidinyl or $C_3$-$C_{10}$ cycloalkylene] are more preferred.

$Y^2$: The group of [each $C_4$-$C_6$ alkylene or $C_4$-$C_6$ alkenylene, wherein each methylene unit may be replaced with —O—] is most preferred.

wherein each $C_1$-$C_6$ alkylene or $C_2$-$C_6$ alkenylene unit may be branched or unbranched. Each group is preferred.

$E^1$: The group of [—H or phenyl which may be substituted with one or more substituents selected from the group consisting of —$R^1$] is preferred. The group of [phenyl which may be substituted with one or more substituents selected from the group consisting of $R^1$] is more preferred.

$E^3$: The group of [benzene ring which may be fused with 5-membered ring,
wherein benzene ring which may be fused with 5-membered ring may be substituted by one or more substituents selected from the group consisting of —$R^3$] is preferred.
  The groups of [phenylene, indolediyl, dihydroindolediyl, benzimidazolediyl or indandiyl, wherein each ring may be substituted by one or more substituents selected from the group consisting of —$R^3$] is more preferred.
  The groups of [phenylene, indolediyl, dihydroindolediyl, benzimidazolediyl or indandiyl, wherein each ring may be substituted by one or more substituents selected from the group consisting of —$R^3$] is more preferred.
  The groups of [1,2-phenylene-(ortho-substituted, phenylene), 1,3-phenylene (meta-substituted phenylene), 1,3-indolediyl, 1,4-indolediyl, 1,4-dihydroindolediyl, 1,4-benzimidazolediyl or 2,4-indandiyl] are most preferred.

$R^1$: The groups of [halogen, $C_1$-$C_6$ alkyl or —O—($C_1$-$C_6$ alkyl) are each preferred. The groups of [halogen, —$CH_3$ or —$OCH_3$] are more preferred.

$R^2$: The groups of [$R^1$, aryl, —O-aryl or heteroaryl, wherein aryl, —O-aryl or heteroaryl may be substituted by one or more substituents selected from the group consisting of —$R^1$] are preferred. The groups of [$R^1$, phenyl, naphthyl, —O-phenyl, thienyl or quinolyl, each of which may be substituted with one or more substituents selected from —$R^1$] are more preferred.

$R^3$: The groups of [halogen or $C_1$-$C_6$ alkyl] are preferred. The groups of [halogen or —$CH_3$] are more preferred.

$R^4$: The groups of [—H, $C_1$-$C_6$ alkyl or alkali metal] are preferred. [—H or alkali metal] are more preferred.

$R^5$: The groups of [—H or halogen] are preferred. [—H] is more preferred.

$R^{61}$: Among the groups of [—H, $C_1$-$C_6$ alkyl or aryl], the groups of [—H, —$CH_3$ or phenyl] are preferred.

$R^{62}$ Among the groups of [—H, $C_1$-$C_6$— alkyl, aryl or absent], the groups of [—H, —$CH_3$ or phenyl] are preferred. The same group of $R^{61}$ and $R^{62}$ are more preferred.

$R^7$: The groups of [phenyl, —O-phenyl, 5- or 6-membered heteroaryl, $C_3$-$C_8$ cycloalkyl, $C_1$-$C_6$ alkyl or $C_2$-$C_6$ alkenyl, wherein each of which may be substituted by one or more substituent selected from the group consisting of —$R_{71}$] are preferred. The groups of [phenyl, —O-phenyl, pyridyl, thienyl, isooxazolyl, ethenyl, or cyclopentyl, each of which may be substituted with one or more substituents selected from the group consisting of $R^{71}$] are more preferred. The group of [phenyl which may be substituted with one or more substituents selected from the group consisting of —$R^{71}$] is more preferred.

$R^{71}$: The groups of [halogen, —OH, $C_1$-$C_6$ alkyl, —NHS($=$O)$_2$($C_1$-$C_6$ alkyl), —S($=$O)$_2$($C_1$-$C_6$ alkyl), —NHC($=$O) ($C_1$-$C_6$ alkyl), —C($=$O)OH, —O—($C_1$-$C_6$ alkyl), —O—($C_1$-$C_6$ alkyl)-aryl, —S($=$O)$_2$—$NH_2$ or —C($=$O) $NH_2$] are preferred. The groups of [halogen, —OH, —$CH_3$, —NHS($=$O)$_2CH_3$, —S($=$O)$_2CH_3$, —NHC($=$O)$CH_3$, —C($=$O)OH, —O—$CH_3$, —O—$CH_2$-phenyl, —S($=$O)$_2NH_2$ or —C($=$O)$NH_2$] are more preferred. The groups of [halogen, —OH, —$CH_3$, —NHS($=$O)$_2CH_3$, —S($=$O)$_2CH_3$, —NHC($=$O)$CH_3$, —C($=$O)OH, —O—$CH_3$, —S($=$O)$_2NH_2$ or —C($=$O) $NH_2$] are more preferred.

n: 0 or 1 are preferred. 1 is more preferred.
m: 1 or 2 are preferred. 2 is more preferred.
Each groups can be used in combination as aforesaid definition.

Preferred compound(s) of formula (I) is as follows (from [1] to [5c].):

[1].
$X^2$ is —NH—, —N($CH_3$)—, —O— or —S—;
$Y^1$ and $Y^2$ are each $C_1$-$C_6$ alkylene or $C_2$-$C_6$ alkenylene,
  wherein each methylene unit may be replaced with —O—, —NH—, —N($CH_3$)—, —NHC($=$O)—, —N{C($=$O)$CH_3$}-, —S—, —S($=$O)—, —S($=$O)$_2$—, phenylene, pyridinediyl, oxazolediyl, imidazolidinyl or $C_3$-$C_{10}$ cycloalkylene;
$E^3$ is a group selected from the group consisting of (a), (b), (c), (d) and (e),

(a)

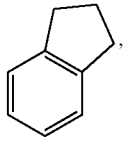
(b)

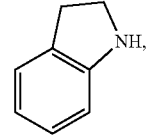
(c)

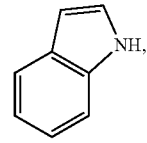
(d)

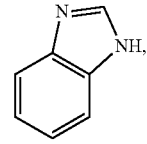
(e)

each of which may be substituted by one or more substituent (s) selected from the group consisting of —$R^3$;
$R^1$ is halogen, —$CH_3$ or —$OCH_3$;
$R^2$ is $R^1$, phenyl, naphthyl, —O-phenyl, thienyl or quinolyl, each of which may be substituted with one or more substituent(s) selected from $R^1$;
$R^3$ is halogen or —$CH_3$;
$R^{61}$ is —H, —$CH_3$ or phenyl;
$R^{62}$ is —H, —$CH_3$, phenyl or absent;
$R^7$ is phenyl, —O-phenyl, pyridyl, thienyl, isooxazolyl, ethenyl, or cyclopentyl,
  each of which may be substituted with one or more substituents selected from the group consisting of $R^{71}$;

$R^{71}$ is halogen, —OH, —CH$_3$, —NHS(=O)$_2$CH$_3$, —S(=O)$_2$CH$_3$, —NHC(=O)CH$_3$, —C(=O)OH, —O—CH$_3$, —O—CH$_2$-phenyl, —S(=O)$_2$NH$_2$ or —C(=O)NH$_2$;

n is 0 or 1; and m is 1 or 2;

or a pharmaceutically acceptable salt thereof, or prodrug thereof.

[2]. A compound of [1], wherein $Y^1$ is C$_1$-C$_6$ alkylene or C$_2$-C$_6$ alkenylene, wherein each methylene unit may be replaced with —O— or —S—; and $Y^2$ is C$_1$-C$_6$ alkylene or C$_2$-C$_6$ alkenylene, wherein each methylene unit may be replaced with —O—;

or a pharmaceutically acceptable salt thereof, or prodrug thereof.

[3]. A compound of [2], wherein $E^1$ is phenyl, which may be substituted with one or more substituent(s) selected from the group consisting of $R^1$;

$E^2$ is phenyl, which may be substituted with one or more substituent (s) selected from $R^2$; and $E^3$ is a group selected from the group consisting of (a) and (d), each of which may be substituted by one or more substituent(s) selected from the group consisting of $R^3$;

or a pharmaceutically acceptable salt thereof, or prodrug thereof.

[4]. A compound of [3], wherein $R^2$ is $R^1$, phenyl or naphthyl, wherein phenyl or naphthyl may be substituted with one or more substituent(s) selected from —$R^1$; and provided that when n is 1, $R^2$ is $R^1$;

or a pharmaceutically acceptable salt thereof, or prodrug thereof.

[5a]. A compound of [4], wherein

A is (i);

or a pharmaceutically acceptable salt thereof, or prodrug thereof.

[5b]. A compound of [4], wherein

A is (ii); and $X^2$ is —O—;

or a pharmaceutically acceptable salt thereof, or prodrug thereof.

[5c]. A compound of [4], wherein

A is (iii); and $R^7$ is phenyl, which may be substituted with one or more substituent (s) selected from the group consisting of $R^{71}$;

$R^{71}$ is halogen, —OH, —CH$_3$ or —NHS(=O)$_2$CH$_3$; and m is 2;

or a pharmaceutically acceptable salt thereof, or prodrug thereof.

Another preferred compound(s) of formula (I) is:

(1) (4-{3-[5-(Diphenylmethyl)-2-oxopyridin-1(2H)-yl]propyl}-1H-indol-1-yl)acetic acid, (2) (3-{3-[5-(Diphenylmethyl)-2-oxopyridin-1(2H)-yl]propyl}phenoxy)acetic acid, (3) 4-(3-{2-[3-(Diphenylmethyl)-6-oxopyridazin-1(6H)-yl]ethoxy}phenoxy)butanoic acid, (4) (2S)-2-(3-{3-[3-(Diphenylmethyl)-6-oxopyridazin-1(6H)-yl]propyl}phenoxy)propanoic acid, (5) 4-(3-{3-[3-(Diphenylmethyl)-6-oxopyridazin-1(6H)-yl]propyl}phenoxy)butanoic acid, (6) (3-{3-[(4S)-4-(Diphenylmethyl)-2-oxo-1,3-oxazolidin-3-yl]propyl}phenoxy)acetic acid, (7) 4-[3-({2-[3-(Diphenylmethyl)-6-oxopyridazin-1(6H)-yl]ethyl}sulfanyl)phenoxy]butanoic acid, (8) 4-(3-{3-[3-(Diphenylmethyl)-6-oxo-5,6-dihydropyridazin-1(4H)-yl]propyl}phenoxy)butanoic acid, (9) 4-(3-{3-[(4S)-4-(Diphenylmethyl)-2-oxo-1,3-oxazolidin-3-yl]propyl}phenoxy)butanoic acid,

(10) 4-[3-({2-[5-(Diphenylmethyl)-2-oxopyridin-1(2H)-yl]ethyl}sulfanyl)phenoxy]butanoic acid,

(11) (2S)-2-[3-({3-[3-(Diphenylmethyl)-6-oxopyridazin-1(6H)-yl]propyl}sulfanyl)phenoxy]propanoic acid,

(12) 4-[3-({3-[5-(Diphenylmethyl)-2-oxopyridin-1(2H)-yl]propyl}sulfanyl)phenoxy]butanoic acid,

(13) [3-{[3-(Aminosulfonyl)benzoyl](3,3-diphenylpropyl)amino}propyl)phenoxy]acetic acid,

(14) 4-[3-(3-{5-[Bis(4-fluorophenyl)methyl]-2-oxopyridin-1(2H)-yl}propyl)-4-fluorophenoxy]butanoic acid,

(15) 4-[3-(3-{3-[Bis(4-fluorophenyl)methyl]-6-oxopyridazin-1(6H)-yl}propyl)-4-fluorophenoxy]butanoic acid,

(16) 4-[3-(3-{3-[Bis(4-fluorophenyl)methyl]-6-oxopyridazin-1(6H)-yl}propyl)phenoxy]butanoic acid,

(17) 4-[3-(3-{5-[Bis(4-fluorophenyl)methyl]-2-oxopyridin-1(2H)-yl}propyl)phenoxy]butanoic acid,

(18) [3-(3-{5-[2-(1-Naphthyl)phenyl]-2-oxopyridin-1(2H)-yl}propyl)phenoxy]acetic acid,

(19) 4-(3-{3-[5-(2'-Methylbiphenyl-2-yl)-2-oxopyridin-1(2H)-yl]propyl}phenoxy)butanoic acid,

(20) 4-{3-[3-(2-Oxo-4,5-diphenyl-1,3-oxazol-3(2H)-yl)propyl]phenoxy}butanoic acid,

(21) 4-[3-({2-[(4S)-4-(Diphenylmethyl)-2-oxo-1,3-oxazolidin-3-yl]ethyl}sulfanyl)phenoxy]butanoic acid,

(22) (2S)-2-[3-({3-[(4S)-4-(Diphenylmethyl)-2-oxo-1,3-oxazolidin-3-yl]propyl}sulfanyl)phenoxy]propanoic acid,

(23) 4-[3-({2-[5-(2'-Methylbiphenyl-2-yl)-2-oxopyridin-1(2H)-yl]ethyl}sulfanyl)phenoxy]butanoic acid, and

(24) (3-{3-[3-(Diphenylmethyl)-6-oxopyridazin-1(6H)-yl]propyl}phenoxy)acetic acid, or a pharmaceutically acceptable salt thereof, or prodrug thereof.

<Abbreviations>

The abbreviations, symbols and terms used in this document have following meaning.

BES:N,N-bis(2-hydroxyethyl)-2-amino-ethane-sulfonic acid,

Burgess Reagent:(methoxycarbonylsulfamoyl)triethyl ammonium hydroxide, brine:saturated sodium chloride aqueous solution, CDI:carbonyldiimidazole, cs$_2$CO$_3$:cesium carbonate, DCC:dicyclohexylcarbodiimide, DCM:dichloromethane or methylene chloride, DEAD:diethyl azodicarboxylate, DIAD:diisopropyl azodicarboxylate, DIBAL:diisobutylaluminum hydride, DIPEA:diisopropylethylamine, DMAP:4-(N,N-dimethylamino)pyridine, DME:1,2-dimethoxyethane, DMF:N,N-dimethylformamide, DMSO:dimethylsulfoxide, EtOAc:ethyl acetate, EtOH:ethanol, HCl aqueous solution:hydrochloric acid aqueous solution, HCl/EtOAc:hydrogen chloride in EtOAc, HOBt:1-hydroxy-1H-1,2,3-benzotriazole, $^i$PrOH:isopropyl alcohol, $K_2CO_3$: potassium carbonate,
$KHCO_3$: potassium hydrogencarbonate,
$KOBu^t$: potassium tert-butoxide,
LiH: lithium hydride,
MEK: methyl ethyl ketone,
MeCN: acetonitrile,
MeOH: methanol,
$MgSO_4$: magnesium sulfate,
$N_2$ gas: nitrogen gas,
$Na_2CO_3$: sodium carbonate,
NaH: sodium hydride,
$NaHCO_3$: sodium hydrogencarbonate, sodium bicarbonate,
NaOH: sodium hydroxide,
NMM: N-methylmorpholine,
$Pd(PPh_3)_4$: tetrakis (triphenylphosphine) palladium,
$PPh_3$: triphenylphosphine,
Rochelle salt: potassium sodium (+)-tartrate tetrahydrate,
$H_2SO_4$: sulfuric acid
TEA: triethylamine,
TFA: trifluoroacetic acid,
THF: tetrahydrofuran,
TMAD: N,N,N',N'-tetramethylazodicarboxamide,
WSCD.HCl: 1-ethyl-3-(3-dimethylaminopropyl) carbodiimide hydrochloride, <Production Method>

The compound and its pharmaceutically acceptable salt of the present invention can be prepared by various known synthesis methods, using characteristics based on its basic backbone or the kinds of substituent groups. The object compound (I) of the present invention can be prepared by the following processes. And, according to the kinds of functional groups, it is advantageous in some cases in terms of preparation technique to substitute a functional group with a suitable protection group, that is to say, a group that can be easily converted into the functional group, in the starting material or intermediate step. Then, if necessary, the protection group is removed to obtain a desired compound. Examples of the functional group include hydroxy, carboxyl, amino group and the like, and examples of the protection group include those described in "Protective Groups in Organic Synthesis", third edition, edited by Greene and Wuts. It is preferable to suitably use them depending on reaction conditions.

Process 1

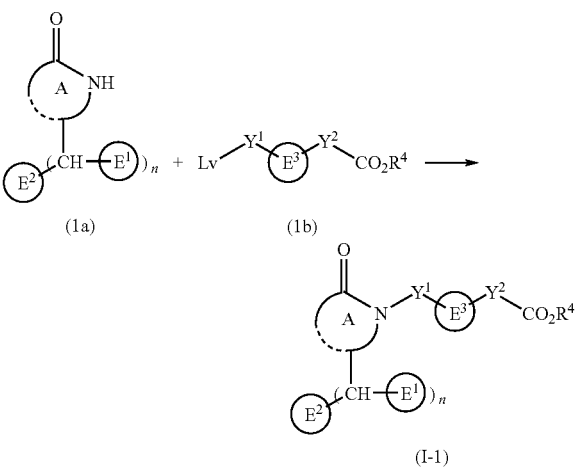

[wherein Lv is a leaving group; and A, $E^1$, $E^2$, $E^3$, $R^4$, $Y^1$, $Y^2$, n are as each defined in the foregoing.]

In this process, the compound (I-1) is prepared by N-alkylation reaction of (1a) with (1b). Examples of a leaving group include halogen, alkylsulfonyl substituted by one or more halogen, arylsulfonyl and the like.

The reaction is carried out in an inert organic solvent such as an aromatic hydrocarbon (e.g., toluene, xylene and the like); an ether (e.g., diethyl ether, THF, dioxane, diglyme and the like); an alcohol (e.g., MeOH, EtOH, $^i$PrOH and the like); a halogenated hydrocarbon (e.g., chloroform, DCM, dichloroethane and the like); MeCN, DMF, DMSO and the like; and their mixed solvents under cooling, cooling to ambient temperature, or ambient temperature to heating. Depending on the type of the reaction substrate and the reaction conditions, a suitable solvent may be selected for the reaction.

In order to progress the reaction smoothly, it is preferred in some cases to add a base. Specific examples of the base are alkali carbonates (e.g., $Na_2CO_3$, $K_2CO_3$, $Cs_2CO_3$ and the like); alkali hydroxide (e.g., KOH, NaOH and the like); alkali hydrogencarbonates (e.g., $NaHCO_3$, $KHCO_3$ and the like); alkali hydride (e.g., NaH, LiH and the like); alkali alkoxide (e.g., $KOBu^t$ and the like) and organic amines (e.g., TEA, DIPEA, pyridine and the like); NMM, N,N-dimethylaniline, DMAP, picoline, lutidine and the like.

Process 2

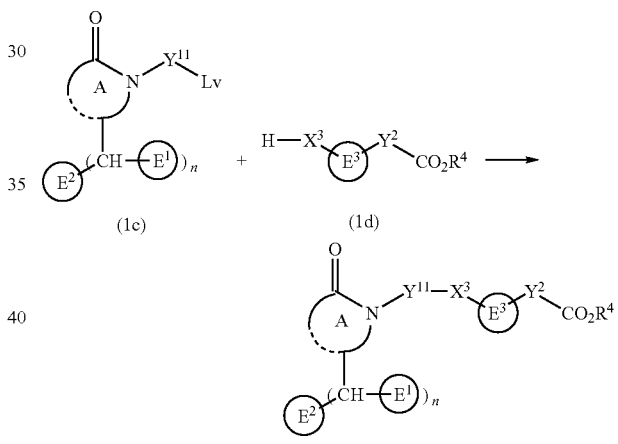

[wherein $X^3$ is —O— or —S—; $Y^{11}$—$X^3$ is $Y^1$; and Lv, A, $E^1$, $E^2$, $E^3$, $R^4$, n are as each defined in the foregoing.]

In this process, the compound (I-2) is prepared by O— or S-alkylation reaction of (1c) with (1d). Examples of a leaving group include halogen, alkylsulfonyl substituted by one or more halogen, arylsulfonyl and the like.

The reaction is carried out in an inert organic solvent such as an aromatic hydrocarbon (e.g., toluene, xylene and the like); a ketone (e.g., acetone, MEK and the like); an ether (e.g., including diethyl ether, THF, dioxane, diglyme and the like); an alcohol (e.g., MeOH, EtOH, $^i$PrOH and the like); a halogenated hydrocarbon (e.g., chloroform, DCM, dichloroethane and the like); MeCN, DMF, DMSO, water and the like; and their mixed solvents; under cooling, cooling to ambient temperature, or ambient temperature to heating. Depending on the type of the reaction substrate and the reaction conditions, a suitable solvent may be selected for the reaction.

In order to progress the reaction smoothly, it is advantageous in some cases to employ an excess amount of the compound (1c) or carry out the reaction in the presence of a base alkali carbonates (e.g., $Na_2CO_3$, $K_2CO_3$, $Cs_2CO_3$ and the like); alkali hydrogencarbonates (e.g., $NaHCO_3$, $KHCO_3$ and the like); alkali hydride (e.g., NaH, LiH and the like).

Process 3

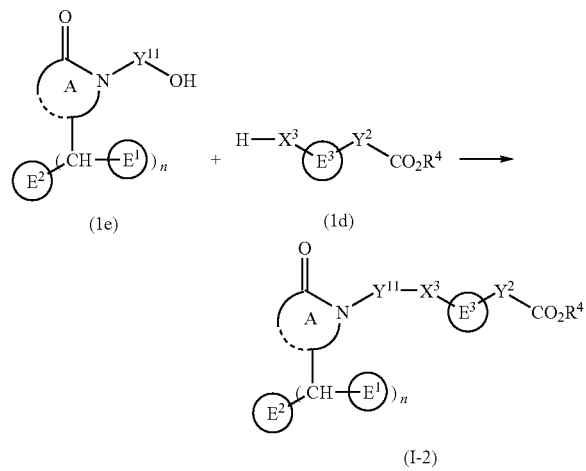

[wherein A, $E^1$, $E^2$, $E^3$, $R^4$, $X^3$, $Y^1$, $Y^{11}$, $Y^2$ or n are as each defined in the foregoing.]

In this process, the compound (I-2) is prepared by so-called Mitsunobu reaction of (1e) with (1d). At first, to the solution of the compound having hydroxy group (1e), compound (1d) and $PPh_3$ (or tributyl phosphine) was added DIAD, DEAD, TMAD or 1,1'-azobis(N,N-dimethylformamide) and the like.

The reaction is carried out in an inert organic solvent such as diisopropyl ether, THF, dioxane, toluene, preferably THF. The solvent employable in this process is not particularly limited so long as it is inactive in this reaction.

The temperature when adding the dehydrating agent (DIAD and the like) varies depending on the starting material, the solvent, and the like, but it is usually from $-10°$ C. to $50°$ C., preferably from $0°$ C. to $30°$ C.

In the above processes, functional group trans formation may be carried out on cue so long as the other sites of the compounds are not affected.

In addition to the processes as mentioned above, some of the compound (I) and salts thereof can be prepared, for example, according to the procedures as illustrated in Example(s) in the present specification or in a manner similar thereto. The starting compounds can be prepared, for example, according to the procedures as illustrated in Preparation(s) in the present specification or in a manner similar thereto.

Process 4

[wherein $X^3$—$Y^{21}$ is $Y^2$; wherein and Lv, A, $E^1$, $E^2$, $E^3$, $R^4$, $X^4$, $Y^1$, $Y^2$ or n are as each defined in the foregoing.]

In this process, the compound (I-3) is prepared by O— or S-alkylation reaction of (1g) with (1f). Examples of a leaving group include halogen, alkylsulfonyl substituted by one or more halogen, arylsulfonyl and the like.

The reaction is carried out in an inert organic solvent such as an aromatic hydrocarbon (e.g., toluene, xylene and the like);a ketone (e.g., acetone, MEK and the like); an ether (e.g., diethyl ether, THF, dioxane, diglyme and the like); an alcohol (e.g., MeOH, EtOH, $^iPrOH$ and the like); a halogenated hydrocarbon (e.g., chloroform, DCM, dichloroethane and the like); MeCN, DMF, DMSO, water and the like; and their mixed solvents; under cooling, cooling to ambient temperature, or ambient temperature to heating. Depending on the type of the reaction substrate and the reaction conditions, a suitable solvent may be selected for the reaction.

In order to progress the reaction smoothly, it is preferred in some cases to add a base. Specific examples of the base are alkali hydride such as NaH, LiH and the like; alkali carbonates such as $Na_2CO_3$, $K_2CO_3$, $Cs_2CO_3$ and the like; alkali hydrogencarbonates such as $NaHCO_3$, $KHCO_3$ and the like; alkali alcoxide such as $KOBu^t$ and the like, and organic amines such as TEA, DIPEA, pyridine, NMM, N,N-dimethylaniline, DMAP, picoline, lutidine and the like.

Process 5

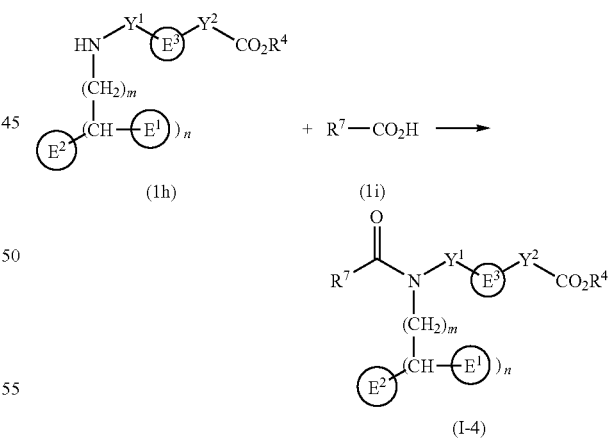

[wherein and $E^1$, $E^2$, $E^3$, $R^4$, $R^7$, $Y^1$, $Y^2$, n or rare as each defined in the foregoing.]

The compound (I-4) is obtained by reaction of the compound (1i) with (1h) in the presence of condensing reagents such as DCC, CDI, WSCD.HCl, HOBt and the like. The reaction is, although it varies depending on the reactive derivatives or condensing agent, carried out in an inert solvent such as a an inert organic solvent such as an aromatic hydrocarbon (e.g., toluene, xylene and the like); a ketone (e.g., acetone, MEK and the like); an ether (e.g., diethyl ether, THF, dioxane, diglyme and the like); a halogenated hydrocarbon (e.g., chloroform, DCM, dichloroethane and the like); DMF, DMSO and the like; and their mixed solvents; under cooling, cooling to ambient temperature, or ambient temperature to heating. In case (1i) is reacted in its acid halide form, to progress the reaction smoothly, it is advantageous in some cases to carry out the reaction in the presence of a base.

Intermediate is obtained according to the following processes or methods disclosed in the Preparation(s).

And, the thus-obtained compounds can be subjected to a process commonly used in the art such as alkylation, acylation, substitution, oxidation, reduction, hydrolysis, and the like to prepare some of the compounds of the general formula (I).

The thus-prepared compound of the present invention is isolated and purified as its free form or as a salt thereof. A salt of the compound (I) can be prepared by subjecting it to a usual salt formation reaction. The isolation and purification are carried out by usual chemical manipulations such as extraction, concentration, evaporation, crystallization, filtration, recrystallization, various types of chromatography and the like.

Various types of isomers can be separated by usual method using the difference in physicochemical properties among isomers. For example, a racemic mixture can be separated by a general racemic mixture resolution method, e.g., a method in which racemic mixture is converted into diastereomer salts with an optically active acid such as tartaric acid and the like and then subjected to optical resolution. And, diastereomers can be separated by fraction crystallization or various types of chromatography and the like. Also, optically active compounds can be prepared using appropriate optically active starting materials.

And, the thus-obtained compounds can be subjected to a process commonly used in the art such as alkylation, acylation, substitution, oxidation, reduction, hydrolysis, and the like to prepare some of the compounds of the general formula (I).

INDUSTRIAL APPLICABILITY

The compound of the invention and the salt thereof have a strong CRTH2 antagonistic activity. Accordingly, the compound of the invention is useful for treatment and/or prevention of various kind of diseases which relate to inflammatory cells.

The pharmacological activities of the compound of the invention were confirmed by the following pharmacological test.

Human CRTH2 Binding Assay

To evaluate CRTH2 binding activities of example compounds, $PGD_2$ binding assay was performed as modifications of former paper (Journal of pharmacology and experimental therapeutics, 2003, 306(2), pp. 463-470).

HEK293 cells stably transfected with human CRTH2 cDNA were suspended in assay buffer (10 mM BES, 1 mM EDTA, 10 mM $MnCl_2$, pH=7.0) and broken into pieces by strong mixture using injection needle. The membrane preparation at the concentration of 50 μg protein was mixed with various concentrations of compounds. Binding reaction was initiated by an addition of $^3$H-labeled $PGD_2$ to a final concentration of 2 nM and the reaction mixture was incubated at 4° C. for 120 minutes. The reaction was terminated by filtration using GF/B plate (PerkinElmer) which was washed with wash buffer (10 mM BES, 0.01% BSA). $^3$H-labeled $PGD_2$ which binds to CRTH2 were captured on this plate and the radioactivity was measured. The total and non-specific binding were determined in the absence and presence of 10 μM DK-PGD2. The binding activity of each compound was expressed as $IC_{50}$ value.

As a result of the human CRTH2 binding assay, the following Example compounds showed $IC_{50}$ values as follows:

TABLE 1 in vitro human CRTH2 binding assay

| Example No | $IC_{50}$ (nM) |
|---|---|
| Example 4 | 3.6 |
| Example 10 | 42 |
| Example 59 | 13 |
| Example 69 | 14 |
| Example 72 | 5.5 |
| Example 84 | 8.1 |
| Example 99 | 4.8 |
| Example 111 | 18 |
| Example 112 | 24 |
| Example 123 | 7.6 |

The result clearly suggests that the compound of the invention possesses CRTH2 binding activity.

Guinea Pig Antigen-Induced Hyper-Responsiveness Model

To evaluate anti asthma efficacy of the compounds, they were administered to Guinea Pig antigen-induced hyper-responsiveness model which is cited in the literature with minor modifications (Agents Actions, 1992, 37, pp. 162-164).

Male Hartley guinea pigs were actively sensitized to ovalbumin (OVA) by i.p. injection of 20 mg in 0.9% saline at day 0 and 1 mg at day 2. Animals were exposed for 10 minutes on days 14-21 to an aerosol of 0.5% OVA solution in 0.9% saline or saline alone generated from a nebulizer. All animals were treated with compound by p.o. administration 60 minutes prior to the aerosol and 1 mg/kg pyrilamine by i.p. injection 30 minutes prior to the aerosol. On day 22, animal was anesthetized with urethane (1.5 g/kg). The trachea was cannulated and the animal was mechanically ventilated (60 strokes/minute; 1 mL/100 g body weight) with a small animal respirator. Pulmonary inflation pressure (PIP) was monitored with a pressure transducer. Doses of methacholine (0-14 μg/kg) were administered sequentially (3 minutes intervals) by the right jugular vein to each animal. The area under the peak inflation pressure versus methacholine dose curve (AUC) was calculated for each animal.

As a result of the human CRTH2 binding assay, the following Example compounds showed inhibitory activity as follows:

TABLE 2

Guinea Pig antigen-induced hyper-responsiveness model

| Example No | dose (mg/kg) | inhibition (%) |
|---|---|---|
| Example 10 | 10 | 100 |
| Example 59 | 3 | 93 |
| Example 84 | 3 | 100 |
| Example 111 | 3 | 89 |
| Example 112 | 1 | 60 |

The present invention also provides a pharmaceutical composition comprising one or more compounds represented by the formula (I) as an active ingredient, which is useful as a CRTH2 antagonist, especially as a medicament for disorder that participates inflammatory cells including Th2 cells, eosinophils and basophils, for example, allergic disorder such as asthma, allergic rhinitis, allergic dermatitis, conjunctival inflammation, hives, eosinophilic bronchitis, food allergy, inflammation of the nasal sinuses, multiple sclerosis, angiitis, or chronic obstructive pulmonary disease (COPD) and the like.

The pharmaceutical composition that contains, as an active ingredient, one or more of the compounds and pharmaceutically acceptable salts thereof of the invention may be prepared by the use of a carrier, a vehicle and other additives generally used in formulating pharmaceutical compositions. It may be orally or parenterally administered in any form of tablets, powders, fine granules, granules, capsules, pills, liquids, injections, suppositories, ointments or poultices.

The clinical dose of the compound of the invention may be suitably determined, depending on the condition, the body weight, the age and the sex of the patients to which it is administered, but is favorable, in general, from 0.1 to 500 mg/adult/day for oral administration, and from 0.01 to 100 mg/adult/day for parenteral administration. This may be administered to the patients all at a time, or may be divided into a few portions for administration in a few times. Since the dose varies depending on various conditions, it may be smaller than the range mentioned above.

As a solid composition for oral administration of the compounds of the invention, tablets, powders, granules and the like are used. The solid composition of those types comprises one or more active substances mixed with at least one inert diluent, such as lactose, mannitol, glucose, hydroxypropyl cellulose, microcrystalline cellulose, starch, polyvinyl pyrrolidone, magnesium metasilicate aluminate. In an ordinary manner, the composition may contain any other additives except the inert diluents noted above, for example, a lubricant such as magnesium stearate, a disintegrator such as calcium cellulose glycolate, a stabilizer such as lactose, and a solubilizer or dissolution promoter such as glutamic acid or aspartic acid. If desired, the tablets and pills may be coated with a film of sugar or gastric or enteric substances such as sucrose, gelatin, hydroxypropyl cellulose, hydroxypropylmethyl cellulose phthalate.

A liquid composition for oral administration includes, for example, pharmaceutically-acceptable emulsions, solutions, suspensions, syrups, elixirs and the like, which contain ordinary inactive diluents such as pure water or ethyl alcohol. In addition to the inert diluents, those compositions may further contain pharmaceutical aids such as solubilizers, dissolution aids, wetting promoters, suspension promoters, and also sweeteners, flavorings, aromas and preservatives.

Injection for parenteral administration includes, for example, germ-free, aqueous or non-aqueous solutions, suspensions and emulsions. The diluent for the aqueous solutions and suspensions includes, for example, distilled water and physiological saline for injections. The diluent for the non-aqueous solutions and suspensions includes, for example, propylene glycol, polyethylene glycol, vegetable oils such as olive oil, alcohols such as ethyl alcohol, Polysolvate 80 (registered trademark)).

Those compositions may further contain additives such as isotonicity regulators, preservatives, wetting promoters, emulsifiers, dispersants, stabilizers (e.g., lactose), solubilizers, dissolution promoters. These are sterilized by filtering them through bacteria-trapping filters, or by adding microbicides thereto, or by exposing them to radiations. Germ-free, solid compositions may be produced previously, and they may be dissolved in germ-free water or in germ-free solvents for injection, before using them.

Pharmaceutical preparations of the CRTH2 receptor antagonist, such as the compound (I), either from alone or in combination with one or more additional agents which may include but are not limited to glucocorticosteroids (e.g., Adrenocorticoids, Corticosteroids, Glucocorticoids, Beclomethasone, hydrocortisone, Fluticasone, Budesonide and the like), Sodium cromoglycate (e.g., Cromolyn(registered trademark)) and the like), β2-agonists(e.g., Formoterol, Salmeterol, Salbutamol, Fenoterol and the like), Leukotriene antagonists (e.g., Montelukast, Pranlukast, Zafirlukast and the like), Immunomodulators (e.g., Omalizumab, Anti-IgE and the like), Anticholinergics (e.g., Ipratropium bromide, Oxitropium bromide, Tiotropium Bromide and the like), PDE4 Inhibitors(e.g., Roflumilast and the like), Antihistamine[e.g., ketotifen, mequitazine, azelastine, oxatomide fexofenadine{allegra(registered trademark)}, cetirizine{zyrtec(registered trademark)}, desloratadine {clarinex(registered trademark)} and the like], Theophylline, Aminophylline and the like, may be administrated as part of the same or separate dosage forms, via the same or different routes of administration, and on the same or different administration schedules according to standard pharmaceutical practice.

BEST MODE FOR CARRYING OUT OF THE INVENTION

The following describes the invention more illustratively with reference to Examples, but the present invention is not limited to these examples. In this connection, novel materials are included in the starting materials to be used in the Example(s), and production methods of the starting materials from known materials are described as Preparation(s).

Hereinafter the reaction each Preparation(s) and Example(s) for preparing the compound(I) of the present invention are explained in more detail. The invention should not be restricted by the following Preparation(s) and Example(s) in any way.

Preparation 1

To a solution of 5-(diphenylmethyl)-1-ethoxycarbonylmethyl-2(1H)-pyridinone (565 mg) in EtOH (11.3 mL) was added dropwise 1M NaOH aqueous solution (4.9 mL) at ambient temperature and the mixture was stirred at ambient temperature for 1 hour. The resulting mixture was diluted with water (25 mL) and acidified with 1M HCl aqueous solution (10 mL) The precipitate was collected by filtration and washed with water (10 mL) to give 5-(diphenylmethyl)-1-carboxylmethyl-2(1H)-pyridinone (472 mg) as colorless crystals.

MS (ESI, m/z):320 (M+H)$^+$.

Preparation 2

To a solution of diethyl (2E,2'E)-3,3'-(1,3-phenylene) bisacrylate (27.9 g) in a mixture of EtOH (300 mL) and THF (200 mL) was added 1M NaOH aqueous solution (92 mL) at 0° C. The reaction mixture was stirred at the same temperature for 5 hours. Organic solvents of the reaction mixture were evaporated in vacuo and the resultant liquid was washed with EtOAc. The aqueous layer was neutralized with 1M HCl aqueous solution (92 mL) and the precipitate was collected by filtration. The precipitate was recrystallized from EtOH-water twice to afford (2E)-3-{3-[(1E)-3-ethoxy-3-oxoprop-1-en-1-yl]phenyl}acrylic acid (10.5 g) as colorless crystals.

MS (ESI, m/z):245 (M−H)$^-$.

Preparation 3

To a suspension of LiH (45.6 mg) in DMF (6.0 mL) was added portionwise 5-(diphenylmethyl)-2(1H)-pyridinone (500 mg) at ambient temperature and the mixture was stirred at the same temperature for 15 minutes. Ethyl bromoacetate (255 μL) was added dropwise to the mixture. The mixture was stirred at ambient temperature for 14 hours. The reaction was quenched with 1M HCl aqueous solution (10.0 mL) and the mixture was extracted with EtOAc (30 mL). The organic layer was washed successively with saturated NaHCO$_3$ aqueous solution and brine, dried over anhydrous MgSO$_4$, filtered and evaporated in vacuo. The residue was purified by silica gel column chromatography (n-hexane:EtOAc=3:2) to afford 5-(diphenylmethyl)-1-ethoxycarbonylmethyl-2(1H)-pyridinone (574 mg) as a colorless amorphous.

$^1$H-NMR (CDCl$_3$) δ: 1.27 (3H, t, J=7.2 Hz), 4.21 (2H, q, J=7.2 Hz), 4.53 (2H, s), 5.26 (1H, s), 6.55 (1H, d, J=9.1 Hz), 6.67 (1H, d, J=1.8 Hz), 7.10-7.17 (4H, m), 7.19-7.38 (7H, m).

MS (ESI, m/z):348 (M+H)$^+$.

The following compound(s) was (were) obtained in a similar manner to that of Preparation 3.

Preparation 3-1

2-{2-[5-(Diphenylmethyl)-2-oxo-1(2H)-pyridinyl]ethyl}-1H-isoindole-1,3(2H)-dione.

$^1$H-NMR (DMSO-d$_6$) δ: 3.85-3.93 (2H, m), 3.97-4.05 (2H, m), 5.18 (1H, s), 6.35 (1H, d, J=9.1 Hz), 6.74 (1H, d, J=2.0 Hz), 6.82-6.91 (4H, m), 7.09-7.21 (7H, m), 7.83-7.93 (4H, m).

Preparation 4

To a solution of 5-(diphenylmethyl)-2(1H)-pyridone (232 mg) in DMF (2 mL) was added KOBu$^t$ (100 mg) at ambient temperature. After 5 minutes, tert-butyl 4-[(1E)-3-chloro-1-propen-1-yl]-1H-indole-1-carboxylate (200 mg) in DMF (1 mL) was added to the solution at ambient temperature and stirred for 5 hours. The resulting mixture was quenched with 1M HCl aqueous solution and diluted with EtOAc. The organic layer was washed successively with water and brine, dried over anhydrous MgSO$_4$, filtered and evaporated in vacuo. The residue was purified by silica gel column chromatography (chloroform:MeOH=100:0-97:3) to give a tert-butyl 4-{(1E)-3-[5-(diphenylmethyl)-2-oxo-1(2H)-pyridinyl]-1-propen-1-yl}-1H-indole-1-carboxylate.

$^1$H-NMR (CDCl$_3$) δ: 1.68 (9H, s), 4.70 (2H, d, J=6.5 Hz), 6.26 (1H, s), 6.35 (1H, dt, J=15.5, 6.5 Hz), 6.57 (1H, d, J=9.5 Hz), 6.62 (1H, d, J=3.5 Hz), 6.80 (1H, d, J=15.5 Hz), 6.89-6.88 (1H, m), 7.12-7.10 (4H, m), 7.31-7.17 (9H, m), 7.62 (1H, d, J=3.5 Hz), 8.08 (1H, d, J=6.5 Hz).

MS (ESI, m/z):517 (M+H)$^+$.

The following compound(s) was(were) obtained in a similar manner to that of Preparation 4.

Preparation 4-1 tert-Butyl 4-{[5-(diphenylmethyl)-2-oxo-1(2H)-pyridinyl]methyl}-1H-indole-1-carboxylate.

$^1$H-NMR (CDCl$_3$) δ: 1.69 (9H, s), 5.11 (1H, s), 5.28 (2H, s), 6.64-6.55 (3H, m), 7.01-6.95 (5H, m), 7.23-7.18 (8H, m), 7.56 (1H, d, J=3.5 Hz), 8.11 (1H, d, J=8.5 Hz).

MS (ESI, m/z):491 (M+H)$^+$.

Preparation 4-2

Ethyl {3-[(2-{[3-(diphenylmethyl)-6-oxopyridazin-1(6H)-yl]methyl}cyclohexyl)methyl]phenoxy}acetate.

MS (ESI, m/z):551 (M+H)$^+$.

The following compound(s) was (were) obtained in a similar manner to that of Example 170.

Preparation 5-1 tert-Butyl 3-{3-[5-(diphenylmethyl)-2-oxo-1(2H)-pyridinyl]propyl}-1H-indole-1-carboxylate.

$^1$H-NMR (CDCl$_3$): δ:1.67 (9H, s), 1.93-2.27 (2H, m), 2.68 (2H, t, J=7.6 Hz), 3.95 (2H, t, J=7.6 Hz), 5.21 (1H, s), 6.53 (1H, d, J=9.4 Hz), 6.72 (1H, d, J=2.2 Hz), 7.0-7.5 (15H, m), 8.12 (1H, d, J=7.9 Hz).

MS (ESI, m/z):519 (M+H)$^+$.

Preparation 5-2 tert-Butyl 4-(4-{[5-(diphenylmethyl)-2-oxo-1(2H)-pyridinyl]methyl}-1,3-oxazol-2-yl)-1H-indole-1-carboxylate.

$^1$H-NMR (CDCl$_3$) δ: 1.70 (9H, s), 5.03 (2H, s), 5.26 (1H, s), 6.53 (1H, d, J=9.2 Hz), 7.09-7.33 (13H, m), 7.39 (1H, dd, J=7.6, 8.2 Hz), 7.68 (1H, d, J=3.5 Hz), 7.78 (1H, s), 7.88 (1H, d, J=7.6 Hz), 8.29 (1H, d, J=8.2 Hz).

MS (ESI, m/z):558 (M+H)$^+$.

Preparation 5-3

5-(Diphenylmethyl)-1-[2-(tetrahydro-2H-pyran-2-yloxy)ethyl]-2(1H)-pyridinone.

$^1$H-NMR (CDCl$_3$) δ: 1.32-1.72 (6H, m), 3.36-3.48 (1H, m), 3.56-3.70 (2H, m), 3.88-4.00 (2H, m), 4.10-4.24 (1H, m), 4.44-4.52 (1H, m), 5.24 (1H, s),6.52 (1H, d, J=9.6 Hz), 6.92 (1H, d, J=2.5 Hz), 7.08-7.44 (11H, m).

MS (ESI, m/z):390 (M+H)$^+$.

Preparation 5-4 tert-Butyl 4-{3-[5-(diphenylmethyl)-2-oxo-1(2H)-pyridinyl]propyl}-1H-indole-1-carboxylate.

$^1$H-NMR (CDCl$_3$) δ: 1.67 (9H, s), 2.04-2.18 (2H, m), 2.85 (2H, t, J=7.3 Hz), 3.88 (2H, t, J=7.3 Hz), 5.22 (1H, s), 6.50-6.56 (2H, m), 6.70 (1H, d, J=2.6 Hz), 6.93 (1H, d, J=7.3 Hz), 7.05-7.37 (12H, m), 7.57 (1H, d, J=3.6 Hz), 8.00 (1H, d, J=8.20 Hz).

Preparation 5-5

Ethyl (3-{3-[5-(diphenylmethyl)-2-oxopyridin-1(2H)-yl]propoxy}phenoxy)acetate.

$^1$H-NMR (DMSO-d$_6$) δ: 1.20 (3H, t, J=7.1 Hz), 2.0-2.1 (2H, m), 3.88 (2H, t, J=5.9 Hz), 3.95 (2H, t, J=6.7 Hz), 4.16 (2H, q, J=7.1 Hz), 4.74 (2H, s), 5.28 (1H, s), 6.3-6.6 (4H, m), 7.0-7.3 (13H, m).

MS (ESI, m/z):520.

Preparation 5-6

5-(Diphenylmethyl)-1-[3-(tetrahydro-2H-pyran-2-yloxy)propyl]pyridin-2(1H)-one.

MS (ESI, m/z):426 (M+Na)$^+$.

Preparation 5-7

Ethyl 4-(3-{3-[5-(diphenylmethyl)-2-oxopyridin-1(2H)-yl]propyl}phenoxy)butanoate.

$^1$H-NMR (CDCl$_3$) δ: 1.26 (3H, t, J=7.1 Hz), 2.00-2.13 (4H, m), 2.51 (2H, t, J=7.3 Hz), 2.57 (2H, t, J=7.7 Hz), 3.85 (2H, t, J=7.2 Hz), 3.97 (2H, t, J=6.1 Hz), 4.14 (2H, q, J=7.1 Hz), 5.24 (1H, s), 6.56-6.74 (5H, m), 7.10-7.18 (5H, m), 7.23-7.34 (7H, m).

MS (ESI, m/z):532 (M+Na)$^+$.

Preparation 5-8

6-(Diphenylmethyl)-2-[2-(tetrahydro-2H-pyran-2-yloxy)ethyl]pyridazin-3(2H)-one.

$^1$H-NMR (DMSO-d$_6$) δ: 1.32-1.55 (6H, m), 3.28-3.33 (1H, m), 3.48-3.53 (1H, m), 3.66-3.71 (1H, m), 3.87-3.92 (1H, m), 4.13-4.22 (2H, m), 4.48 (1H, t, J=4.0 Hz), 5.55 (1H, s), 6.90 (1H, d, J=9.5 Hz), 7.21-7.34 (11H, m).

MS (ESI, m/z):413 (M+Na)$^+$.

Preparation 5-9

Methyl (2S)-2-(3-{3-[3-(diphenylmethyl)-6-oxo-5,6-dihydropyridazin-1(4H)-yl]propyl}phenoxy)propanoate.

$^1$H-NMR (CDCl$_3$) δ: 1.62 (3H, d, J=5.2 Hz), 1.87-1.95 (2H, m), 2.39-2.40 (4H, m), 2.54-2.58 (2H, m), 3.74-3.79 (5H, m), 4.74-4.79 (1H, m), 5.10 (1H, s), 6.65-6.76 (3H, m), 7.12-7.36 (11H, m).

Preparation 5-10

Ethyl 4-(3-{3-[3-(diphenylmethyl)-6-oxo-5,6-dihydropyridazin-1(4H)-yl]propyl}phenoxy)butanoate.

$^1$H-NMR (CDCl$_3$) δ: 1.25 (3H, t, J=7.1 Hz), 1.91-1.94 (2H, m), 2.04-2.12 (2H, m), 2.39-2.41 (4H, m), 2.50-2.59 (4H, m), 3.79 (2H, t, J=7.0 Hz), 3.98 (2H, t, J=6.0 Hz), 4.12-4.17 (2H, m), 5.10 (1H, s), 6.69-6.73 (3H, m), 7.12-7.35 (11H, m).

MS (ESI, m/z):513 (M+H)$^+$.

Preparation 5-11

Ethyl (3-{3-[3-(diphenylmethyl)-6-oxo-5,6-dihydropyridazin-1(4H)-yl]propyl}phenoxy)acetate.

¹H-NMR (CDCl₃) δ: 1.30 (3H, t, J=7.1 Hz), 1.90-1.94 (2H, m), 2.38-2.40 (4H, m), 2.57 (2H, t, J=7.8 Hz), 3.78 (2H, t, J=7.0 Hz), 4.27 (2H, q, J=7.1 Hz), 4.60 (2H, s), 5.10 (1H, s), 6.70-6.78 (3H, m), 7.14-7.36 (11H, m).

MS (ESI, m/z):507 (M+Na)⁺.

Preparation 5-12 tert-Butyl {2-[5-(diphenylmethyl)-2-oxopyridin-1(2H)-yl]ethyl}carbamate.

MS (ESI, m/z):405 (M+H)⁺.

Preparation 5-13

Methyl (2S)-2-(3-{3-[3-chloro-5-(diphenylmethyl)-2-oxopyridin-1(2H)-yl]propyl}phenoxy)propanoate.

¹H-NMR (CDCl₃) δ: 1.59-1.62 (3H, m), 2.00-2.06 (2H, m), 2.53-2.58 (2H, m), 3.74 (3H, s), 3.86-4.23 (2H, m), 4.72-4.78 (1H, m), 5.23, 5.30 (1H, s), 6.65-6.71 (4H, m), 7.09-7.36 (12H, m).

MS (ESI, m/z):516 (M)⁺.

Preparation 5-14

Ethyl (3-{3-[3-chloro-5-(diphenylmethyl)-2-oxopyridin-1(2H)-yl]propyl}phenoxy)acetate.

¹H-NMR (CDCl₃) δ: 1.30 (3H, t, J=7.1 Hz), 2.01-2.07 (2H, m), 2.58 (2H, t, J=7.6 Hz), 3.88 (2H, t, J=7.2 Hz), 4.27 (2H, q, J=7.1 Hz), 4.59 (2H, s), 5.23 (1H, s), 6.68-6.72 (4H, m), 7.08-7.18 (6H, m), 7.25-7.36 (6H, m).

MS (ESI, m/z):516 (M)⁺.

Preparation 5-15

Methyl (2S)-2-(3-{4-[5-(diphenylmethyl)-2-oxopyridin-1(2H)-yl]butyl}phenoxy)propanoate.

MS (ESI, m/z):518 (M+Na)⁺.

Preparation 5-16

Ethyl 4-(3-{3-[3-(diphenylmethyl)-6-oxopyridazin-1(6H)-yl]propyl}-4-fluorophenoxy)butanoate.

¹H-NMR (DMSO-d₆) δ: 1.16 (3H, t, J=7.1 Hz), 1.8-2.0 (4H, m), 2.44 (2H, t, J=7.3 Hz), 2.5-2.6 (2H, m), 3.93 (2H, t, J=6.4 Hz), 4.0-4.1 (4H, m), 5.55 (1H, brs), 6.7-7.4 (15H, m).

MS (ESI, m/z):551 (M+Na)⁺.

Preparation 5-17

Methyl (2S)-2-(3-{3-[3-(diphenylmethyl)-6-oxopyridazin-1(6H)-yl]propyl}-4-fluorophenoxy)propanoate.

¹H-NMR (DMSO-d₆) δ: 1.48 (3H, d, J=6.7 Hz), 1.8-2.0 (2H, m), 3.65 (3H, s), 4.02 (2H, t, J=7.1 Hz), 4.93 (1H, q, J=6.7 Hz), 5.55 (1H, brs),6.6-7.4 (15H, m).

MS (ESI, m/z):523 (M+Na)⁺.

Preparation 5-18

Methyl (2S)-2-(3-{3-[3-(diphenylmethyl)-6-oxopyridazin-1(6H)-yl]propyl}phenoxy)propanoate.

¹H-NMR (CDCl₃) δ: 1.61 (3H, d, J=6.8 Hz), 2.05-2.11 (2H, m), 2.59 (2H, t, J=7.8 Hz), 3.74 (3H, s), 4.15 (2H, t, J=7.2 Hz), 4.76 (1H, q, J=6.8 Hz), 5.46 (1H, s), 6.65-6.76 (3H, m), 6.84-6.8.6 (1H, m), 7.07-7.17 (6H, m), 7.24-7.35 (6H, m).

MS (ESI, m/z):483 (M+H)⁺.

Preparation 5-19

Methyl(2S)-2-(3-{4-[3-(diphenylmethyl)-6-oxopyridazin-1(6H)-yl]butyl}phenoxy)propanoate.

MS (ESI, m/z):519 (M+Na)⁺.

Preparation 5-20

Ethyl 4-(3-{3-[3-(diphenylmethyl)-6-oxopyridazin-1(6H)-yl]propyl}phenoxy)butanoate.

¹H-NMR (CDCl₃) δ: 1.25 (3H, t, J=7.1 Hz), 2.05-2.13 (4H, m), 2.51 (2H, t, J=7.3 Hz), 2.60 (2H, t, J=7.8 Hz), 3.97 (2H, t, J=6.1 Hz), 4.11-4.18 (4H, m),5.46 (1H, s), 6.70-6.73 (3H, m), 6.84-6.87 (1H, m), 7.07-7.17 (6H, m), 7.24-7.35 (6H, m).

MS (ESI, m/z): 533 (M+Na)⁺.

Preparation 5-21

Ethyl 4-(3-{3-[5-(diphenylmethyl)-2-oxopyridin-1(2H)-yl]propyl}-4-fluorophenoxy)butanoate.

¹H-NMR (DMSO-d₆) δ: 1.17 (3H, t, J=7.1 Hz), 1.8-2.0 (4H, m), 2.44 (2H, t, J=7.3 Hz), 2.5-2.6 (2H, m), 3.85 (2H, t, J=7.2 Hz), 3.93 (2H, t, J=6.3 Hz), 4.06 (2H, q, J=7.1 Hz), 5.36 (1H, brs),6.36 (1H, d, J=9.3 Hz), 6.7-7.4 (15H, m).

MS (ESI, m/z):528 (M+H)⁺.

Preparation 5-22

Methyl (2S)-2-(3-{3-[5-(diphenylmethyl)-2-oxopyridin-1(2H)-yl]propyl}-4-fluorophenoxy)propanoate.

¹H-NMR (DMSO-d₆) δ: 1.48 (3H, d, J=6.7 Hz), 1.8-1.9 (2H, m), 2.5-2.6 (2H, m), 3.65 (3H, s), 3.8-3.9 (2H, m), 4.94 (1H, q, J=6.7 Hz), 5.36 (1H, brs), 6.37 (1H, d, J=9.4 Hz), 6.7-7.4 (15H, m).

MS (ESI, m/z):500 (M+H)⁺.

Preparation 5-23

Ethyl (3-{3-[5-(diphenylmethyl)-2-oxopyridin-1(2H)-yl]propyl}-4-fluorophenoxy)acetate.

¹H-NMR (DMSO-d₆) δ: 1.19 (3H, t, J=7.1 Hz), 1.8-1.9 (2H, m), 2.4-2.6 (2H, m), 3.86 (2H, t, J=7.2 Hz), 4.15 (2H, q, J=7.1 Hz), 4.74 (2H, s), 5.36 (1H, s), 6.37 (1H, d, J=9.4 Hz), 6.7-7.4 (15H, m).

MS (ESI, m/z):522 (M+Na)⁺.

Preparation 5-24

Ethyl 4-(3-{3-[(4S)-4-(diphenylmethyl)-2-oxo-1,3-oxazolidin-3-yl]propyl}phenoxy)butanoate.

MS (ESI, m/z):502 (M+H)⁺.

Preparation 5-25

Ethyl (3-{3-[(4S)-4-(diphenylmethyl)-2-oxo-1,3-oxazolidin-3-yl]propyl}phenoxy)acetate.

MS (ESI, m/z):474 (M+H)⁺.

Preparation 5-26

Ethyl (3-{3-[(4R)-4-(diphenylmethyl)-2-oxo-1,3-oxazolidin-3-yl]propyl}phenoxy)acetate.

MS (ESI, m/z):474 (M+H)⁺.

Preparation 5-27

6-(Diphenylmethyl)-2-[3-(tetrahydro-2H-pyran-2-yloxy)propyl]pyridazin-3(2H)-one.

MS (ESI, m/z):427 (M+Na)⁺.

Preparation 5-28

Ethyl 3-(3-{3-[5-(diphenylmethyl)-2-oxopyridin-1(2H)-yl]propyl}phenyl)propanoate.

MS (ESI, m/z):502 (M+Na)⁺.

Preparation 5-29

Ethyl 3-(3-{3-[3-(diphenylmethyl)-6-oxopyridazin-1(6H)-yl]propyl}phenyl)propanoate.

MS (ESI, m/z):503 (M+Na)⁺.

Preparation 5-30

Ethyl (3-{4-[3-(diphenylmethyl)-6-oxopyridazin-1(6H)-yl]butyl}phenoxy)acetate.

MS (ESI, m/z):519 (M+Na)⁺.

Preparation 5-31

Ethyl (3-{3-[3-(diphenylmethyl)-6-oxopyridazin-1(6H)-yl]propyl}-4-fluorophenoxy)acetate.

¹H-NMR (DMSO-d₆) δ: 1.19 (3H, t, J=7.1 Hz), 1.8-2.0 (2H, m), 2.5-2.6 (2H, m), 4.0-4.1 (2H, m), 4.15 (2H, q, J=7.1 Hz), 4.73 (2H, s), 5.55 (1H, brs), 6.7-7.4 (15H, m).

MS (ESI, m/z):523 (M+Na)⁺.

Preparation 5-32

1-{3-[3-(Benzyloxy)phenyl]propyl}-5-(diphenylmethyl)pyridin-2(1H)-one.

MS (ESI, m/z):508 (M+Na)⁺.

Preparation 5-33
Methyl (2R)-2-(3-{3-[3-(diphenylmethyl)-6-oxopyridazin-1(6H)-yl]propyl}phenoxy)propanoate.
¹H-NMR (CDCl₃) δ: 1.61 (3H, d, J=6.8 Hz), 2.05-2.11 (2H, m), 2.59 (2H, t, J=7.8 Hz), 3.74 (3H, s), 4.15 (2H, t, J=7.2 Hz), 4.76 (1H, q, J=6.8 Hz), 5.46 (1H, s), 6.65-6.76 (3H, m), 6.84-6.86 (1H, m), 7.07-7.17 (6H, m), 7.24-7.35 (6H, m).
MS (ESI, m/z):483 (M+H)⁺.

Preparation 5-34
Ethyl {3-[3-(5-bromo-2-oxopyridin-1(2H)-yl)propyl]phenoxy}acetate.
MS (ESI, m/z): 394, 396 (M+H)⁺.

Preparation 5-35
Ethyl 4-{3-[3-(2-oxo-4,5-diphenyl-2,3-dihydro-1H-imidazol-1-yl)propyl]phenoxy}butanoate.
¹H-NMR (CDCl₃) δ: 1.26 (3H, t, J=7.1 Hz), 1.78-1.84 (2H, m), 2.04-2.11 (2H, m), 2.47-2.51 (4H, m), 3.66 (2H, t, J=7.4 Hz), 3.93 (2H, t, J=6.1 Hz), 4.14 (2H, q, J=7.1 Hz), 6.57-6.67 (3H, m), 7.07-7.44 (11H, m), 10.58 (1H, s).
MS (ESI, m/z):485 (M+H)⁺.

Preparation 5-36
Ethyl {3-[3-(2-oxo-4,5-diphenyl-2,3-dihydro-1H-imidazol-1-yl)propyl]phenoxy}acetate.
¹H-NMR (CDCl₃) δ: 1.28 (3H, t, J=7.1 Hz), 1.77-1.81 (2H, m), 2.48-2.52 (2H, m), 3.63-3.67 (2H, m), 4.26 (2H, q, J=7.1 Hz), 4.55 (2H, s), 6.61-6.69 (3H, m), 7.08-7.25 (6H, m), 7.30-7.32 (2H, m), 7.40-7.44 (3H, m), 10.44 (1H, s).
MS (ESI, m/z):457 (M+H)⁺.

Preparation 5-37
Ethyl 4-(3-{3-[2-oxo-5-(2-quinolin-8-ylphenyl)pyridin-1(2H)-yl]propyl}phenoxy)butanoate.
MS (ESI, m/z):569 (M+Na)⁺.

Preparation 5-38
Ethyl 4-(3-{3-[3-chloro-5-(2'-methylbiphenyl-2-yl)-2-oxopyridin-1(2H)-yl]propyl}phenoxy)butanoate.
MS (ESI, m/z):566 (M+Na)⁺.

Preparation 5-39
Ethyl (3-{3-[3-chloro-5-(2'-methylbiphenyl-2-yl)-2-oxopyridin-1(2H)-yl]propyl}phenoxy)acetate.
MS (ESI, m/z):538 (M+Na)⁺.

Preparation 5-40
Ethyl (3-{3-[2-oxo-5-(2-quinolin-8-ylphenyl)pyridin-1(2H)-yl]propyl}phenoxy)acetate.
MS (ESI, m/z):541 (M+H)⁺.

Preparation 5-41
Ethyl 4-[3-({2-[(4S)-4-benzyl-5,5-dimethyl-2-oxo-1,3-oxazolidin-3-yl]ethyl}sulfanyl)phenoxy]butanoate.
MS (ESI, m/z):472 (M+H)⁺.

Preparation 5-42
Ethyl (3-{3-[(4S)-4-benzyl-5,5-dimethyl-2-oxo-1,3-oxazolidin-3-yl]propyl}-4-fluorophenoxy)acetate.
MS (ESI, m/z):444 (M+H)⁺.

Preparation 5-43
Ethyl {4-fluoro-3-[3-(2-oxo-4,5-diphenyl-1,3-oxazol-3(2H)-yl)propyl]phenoxy}acetate.
¹H-NMR (DMSO-d₆) δ: 1.30 (3H, t, J=7.1 Hz), 1.76-1.80 (2H, m), 2.51 (2H, t, J=7.6 Hz), 3.52 (2H, t, J=7.5 Hz), 4.27 (2H, q, J=7.1 Hz), 4.55 (2H, s), 6.63-6.67 (2H, m), 6.83-6.88 (1H, m), 7.18-7.26 (5H, m), 7.36-7.38 (2H, m), 7.47-7.51 (3H, m).
MS (ESI, m/z):498 (M+Na)⁺.

Preparation 5-44
Ethyl {4-fluoro-3-[3-(2-oxo-4,5-diphenyl-1,3-thiazol-3(2H)-yl)propyl]phenoxy}acetate.
¹H-NMR (CDCl₃) δ: 1.30 (3H, t, J=7.1 Hz), 1.75-1.79 (2H, m), 2.45 (2H, t, J=7.6 Hz), 3.61 (2H, t, J=7.7 Hz), 4.27 (2H, q, J=7.1 Hz), 4.54 (2H, s), 6.59-6.67 (2H, m), 6.81-6.86 (1H, m), 6.98-7.01 (2H, m), 7.11-7.15 (3H, m), 7.23-7.26 (2H, m), 7.35-7.41 (3H, m).
MS (ESI, m/z):514 (M+Na)⁺.

Preparation 5-45
Ethyl 4-{3-[3-(2-oxo-4,5-diphenyl-1,3-thiazol-3(2H)-yl)propyl]phenoxy}butanoate.
¹H-NMR (CDCl₃) δ: 1.26 (3H, t, J=7.1 Hz), 1.76-1.80 (2H, m), 2.07-2.11 (2H, m), 2.43 (2H, t, J=7.7 Hz), 2.51 (2H, t, J=7.3 Hz), 3.61 (2H, t, J=7.7 Hz), 3.95 (2H, t, J=6.1 Hz), 4.15 (2H, q, J=7.1 Hz), 6.53-6.55 (2H, m), 6.65-6.67 (1H, m), 6.98-7.42 (11H, m).
MS (ESI, m/z):524 (M+Na)⁺.

Preparation 5-46
Methyl (2S)-2-[3-({3-[(4S)-4-benzyl-5,5-dimethyl-2-oxo-1,3-oxazolidin-3-yl]propyl}sulfanyl)phenoxy]propanoate.
MS (ESI, m/z):480 (M+Na)⁺.

Preparation 5-47
Methyl (2S)-2-[3-({3-[(4S)-4-(diphenylmethyl)-2-oxo-1,3-oxazolidin-3-yl]propyl}sulfanyl)phenoxy]propanoate.
MS (ESI, m/z):528 (M+Na)⁺.

Preparation 5-48
Methyl (2S)-2-[3-({3-[5-(2'-methylbiphenyl-2-yl)-2-oxopyridin-1(2H)-yl]propyl}sulfanyl)phenoxy]propanoate.
MS (ESI, m/z):536 (M+Na)⁺.

Preparation 5-49
Ethyl 4-[3-({2-[5-(2'-methylbiphenyl-2-yl)-2-oxopyridin-1(2H)-yl]ethyl}sulfanyl)phenoxy]butanoate.
MS (ESI, m/z):550 (M+Na)⁺.

Preparation 5-50
Ethyl 4-(3-{3-[(4S)-4-benzyl-5,5-dimethyl-2-oxo-1,3-oxazolidin-3-yl]propyl}phenoxy)butanoate.
MS (ESI, m/z):454 (M+H)⁺.

Preparation 5-51
Ethyl 4-{4-fluoro-3-[3-(2-oxo-4,5-diphenyl-1,3-oxazol-3(2H)-yl)propyl]phenoxy}butanoate.
¹H-NMR (CDCl₃) δ: 1.26 (3H, t, J=7.1 Hz), 1.58 (1H, s), 1.77-1.81 (2H, m), 2.06-2.10 (2H, m), 2.48-2.52 (3H, m), 3.53 (2H, t, J=7.5 Hz), 3.92 (2H, t, J=6.1 Hz), 4.15 (2H, q, J=7.1 Hz), 6.57-6.63 (2H, m), 6.81-6.86 (1H, m), 7.17-7.26 (5H, m), 7.36-7.38 (2H, m), 7.46-7.51 (3H, m).
MS (ESI, m/z):526 (M+Na)⁺.

Preparation 5-52
Ethyl (3-{3-[(4S)-4-benzyl-5,5-dimethyl-2-oxo-1,3-oxazolidin-3-yl]propyl}phenoxy)acetate.
MS (ESI, m/z):426 (M+H)⁺.

Preparation 5-53
Ethyl (3-{3-[(4R)-4-benzyl-5,5-dimethyl-2-oxo-1,3-oxazolidin-3-yl]propyl}phenoxy)acetate.
MS (ESI, m/z):426 (M+H)⁺.

Preparation 5-54
Ethyl 4-(3-{3-[5-(2'-methylbiphenyl-2-yl)-2-oxopyridin-1(2H)-yl]propyl}phenoxy)butanoate.
MS (ESI, m/z):532 (M+Na)⁺.

Preparation 5-55
Ethyl {3-[3-(2-oxo-4,5-diphenyl-1,3-oxazol-3(2H)-yl)propyl]phenoxy}acetate.
¹H-NMR (CDCl₃) δ: 1.30 (3H, t, J=7.1 Hz), 1.78-1.81 (2H, m), 2.49 (2H, t, J=7.7 Hz), 3.51 (2H, t, J=7.5 Hz), 4.27 (2H, q, J=7.1 Hz), 4.57 (2H, s), 6.61-6.70 (3H, m), 7.17-7.53 (11H, m).
MS (ESI, m/z):480 (M+Na)⁺.

Preparation 5-56
Ethyl 4-[3-({2-[(4S)-4-(diphenylmethyl)-2-oxo-1,3-oxazolidin-3-yl]ethyl}sulfanyl)phenoxy]butanoate.
MS (ESI, m/z):520 (M+H)⁺.

Preparation 5-57
Ethyl (3-{3-[(4S)-4-benzyl-2-oxo-1,3-oxazolidin-3-yl]propyl}phenoxy)acetate.
MS (ESI, m/z):398 (M+H)$^+$.

Preparation 5-58
Ethyl {3-[3-(2-oxo-4,5-diphenyl-1,3-thiazol-3(2H)-yl)propyl]phenoxy}acetate.
$^1$H-NMR (CDCl$_3$) δ: 1.30 (3H, t, J=7.1 Hz), 1.74-1.81 (2H, m), 2.44 (2H, t, J=7.7 Hz), 3.61 (2H, t, J=7.7 Hz), 4.27 (2H, q, J=7.1 Hz), 4.57 (2H, s), 6.58-6.61 (2H, m), 6.66-6.98 (1H, m), 6.98-7.00 (2H, m), 7.08-7.15 (4H, m), 7.23-7.25 (2H, m), 7.36-7.45 (3H, m).
MS (ESI, m/z):496 (M+Na.)$^+$.

Preparation 5-59
Ethyl (3-{3-[5-(2-bromophenyl)-2-oxopyridin-1(2H)-yl]propyl}phenoxy)acetate.
MS (ESI, m/z):492, 494 (M+Na)$^+$.

Preparation 5-60
Ethyl (3-{3-[6-oxo-3-(2-phenoxyphenyl)pyridazin-1(6H)-yl]propyl}phenoxy)acetate.
MS (ESI, m/z):485 (M+H)$^+$.

Preparation 5-61
Ethyl [3-(3-{5-[bis(4-methoxyphenyl)methyl]-2-oxopyridin-1(2H)-yl}propyl)phenoxy]acetate.
$^1$H-NMR (CDCl$_3$) δ: 1.29 (3H, t, J=7.1 Hz), 1.99-2.03 (2H, m), 2.58 (2H, t, J=7.7 Hz), 3.79 (6H, s), 3.84 (2H, t, J=7.3 Hz), 4.27 (2H, q, J=7.1 Hz), 4.59 (2H, s), 5.14 (1H, s), 6.53 (1H, d, J=9.4 Hz), 6.70-6.73 (4H, m), 6.84-6.87 (4H, m), 6.99-7.02 (4H, m), 7.13-7.17 (2H, m).
MS (ESI, m/z):564 (M+Na)$^+$.

Preparation 5-62
Ethyl [3-(3-{5-[bis(4-fluorophenyl)methyl]-2-oxopyridin-1(2H)-yl}propyl)phenoxy]acetate.
$^1$H-NMR (CDCl$_3$) δ: 1.30 (3H, t, J=7.1 Hz), 1.90-2.10 (2H, m), 2.59 (2H, t, J=7.6 Hz), 3.84 (2H, t, J=7.3 Hz), 4.27 (2H, q, J=7.1 Hz), 4.60 (2H, s), 5.21 (1H, s), 6.55 (1H, d, J=9.4 Hz), 6.67-6.73 (4H, m), 7.00-7.26 (10H, m).
MS (ESI, m/z):540 (M+Na)$^+$.

Preparation 5-63
Ethyl [3-(3-{5-[bis(4-chlorophenyl)methyl]-2-oxopyridin-1(2H)-yl}propyl)phenoxy]acetate.
$^1$H-NMR (CDCl$_3$) δ: 1.30 (3H, t, J=7.1 Hz), 1.98-2.05 (2H, m), 2.59 (2H, t, J=7.6 Hz), 3.84 (2H, t, J=7.3 Hz), 4.27 (2H, q, J=7.1 Hz), 4.59 (2H, s), 5.12 (1H, s), 6.56 (1H, d, J=9.4 Hz), 6.68-6.73 (4H, m), 7.01-7.35 (10H, m).
MS (ESI, m/z):572 (M+Na)$^+$.

Preparation 5-64
Ethyl [3-(3-{5-[bis(4-methoxyphenyl)methyl]-2-oxopyridin-1(2H)-yl}propoxy)phenoxy]acetate.
$^1$H-NMR (DMSO-d$_6$) δ:1.20 (3H, t, J=7.1 Hz), 2.0-2.1 (2H, m), 3.70 (6H, s), 3.89 (2H, t, J=5.9 Hz), 3.95 (2H, t, J=6.6 Hz), 4.15 (2H, q, J=7.1 Hz), 4.74 (2H, s), 5.14 (1H, s), 6.36 (1H, d, J=9.3 Hz), 6.4-6.6 (3H, m), 6.81 (4H, d, J=8.8 Hz), 6.94 (4H, d, J=8.8 Hz), 7.1-7.2 (3H, m).
MS (ESI, m/z):580 (M+Na)$^+$.

Preparation 5-65
Ethyl 4-[3-(3-{-3-[bis(4-fluorophenyl)methyl]-6-oxopyridazin-1(6H)-yl}propyl)phenoxy]butanoate.
$^1$H-NMR (DMSO-d$_6$) δ: 1.16 (3H, t, J=7.1 Hz), 1.8-2.0 (4H, m), 2.4-2.5 (4H, m), 3.95 (2H, t, J=6.3 Hz), 3.99 (2H, t, J=6.9 Hz), 4.06 (2H, q, J=7.1 Hz), 5.61 (1H, brs), 6.6-6.8 (3H, m), 6.90 (1H, d, J=9.5 Hz), 7.1-7.3 (9H, m), 7.30 (1H, d, J=9.5 Hz).
MS (ESI, m/z):569 (M+Na)$^+$.

Preparation 5-66
Ethyl 4-[3-(3-{3-[bis(4-fluorophenyl)methyl]-6-oxopyridazin-1(6H)-yl}propyl)-4-fluorophenoxy]butanoate.
$^1$H-NMR (DMSO-d$_6$) δ:1.16 (3H, t, J=7.1 Hz), 1.8-2.0 (4H, m), 2.44 (2H, t, J=7.3 Hz), 2.48-2.56 (2H, m), 3.93 (2H, t, J=6.3 Hz), 4.0-4.1 (4H, m), 5.60 (1H, brs), 6.7-7.4 (13H, m).
MS (ESI, m/z):563 (M–H)$^-$.

Preparation 5-67
Ethyl 4-[3-(3-{5-[bis(4-fluorophenyl)methyl]-2-oxopyridin-1(2H)-yl}propyl)phenoxy]butanoate.
$^1$H-NMR (DMSO-d$_6$) δ: 1.17 (3H, t, J=7.1 Hz), 1.8-2.0 (4H, m), 2.44 (2H, t, J=7.3 Hz), 2.47-2.55 (2H, m), 3.82 (2H, t, J=7.2 Hz), 3.95 (2H, t, J=6.3 Hz), 4.06 (2H, q, J=7.1 Hz), 5.40 (1H, brs), 6.37 (1H, d, J=9.3 Hz), 6.6-6.8 (3H, m), 7.1-7.3 (11H, m).
MS (ESI, m/z):568 (M+Na)$^+$.

Preparation 5-68
5-[Bis(4-fluorophenyl)methyl]-1-[2-(tetrahydro-2H-pyran-2-yloxy)ethyl]pyridin-2(1H)-one.
$^1$H-NMR (DMSO-d$_6$) δ: 1.2-1.5 (6H, m), 3.2-3.6 (3H, m), 3.7-3.8 (1H, m), 3.9-4.1 (2H, m), 4.47 (1H, brs), 5.42 (1H, brs), 6.38 (1H, d, J=9.3 Hz), 7.1-7.3 (10H, m).
MS (ESI, m/z):448 (M+Na)$^+$.

Preparation 5-69
Ethyl 4-[3-(3-{5-[bis(4-fluorophenyl)methyl]-2-oxopyridin-1(2H)-yl}propyl)-4-fluorophenoxy]butanoate.
$^1$H-NMR (DMSO-d$_6$) δ: 1.17 (3H, t, J=7.1 Hz), 1.8-2.0 (4H, m), 2.44 (2H, t, J=7.3 Hz), 2.5-2.6 (2H, m), 3.8-3.9 (2H, m), 3.93 (2H, t, J=6.3 Hz), 4.06 (2H, q, J=7.1 Hz), 5.39 (1H, brs), 6.37 (1H, d, J=9.3 Hz), 6.7-7.3 (13H, m).
MS (ESI, m/z):586 (M+Na)$^+$.

Preparation 5-70
Methyl (2S)-2-[3-(3-{5-[bis(4-methoxyphenyl)methyl]-2-oxopyridin-1(2H)-yl}propyl)phenoxy]propanoate.
$^1$H-NMR (CDCl$_3$) δ: 1.61 (3H, d, J=6.8 Hz), 1.96-2.04 (2H, m), 2.57 (2H, t, J=7.7 Hz), 3.75 (3H, s), 3.80 (6H, s), 3.84 (2H, t, J=7.2 Hz), 4.75 (1H, q, J=6.8 Hz), 5.14 (1H, s), 6.52-6.55 (1H, m), 6.65-6.71 (4H, m), 6.83-6.87 (4H, m), 6.99-7.02 (4H, m), 7.12-7.16 (2H, m).
MS (ESI, m/z):564 (M+Na)$^+$.

Preparation 5-71
Methyl (2S)-2-(3-{3-[2-oxo-5-(9H-xanthen-9-yl)pyridin-1(2H)-yl]propyl}phenoxy)propanoate.
$^1$H-NMR (CDCl$_3$) δ: 1.62 (3H, d, J=6.8 Hz), 2.06-2.12 (2H, m), 2.64 (2H, t, J=7.1 Hz), 3.76 (3H, s), 3.92 (2H, t, J=7.4 Hz), 4.78 (1H, q, J=6.8 Hz), 5.00 (1H, s), 6.49-6.51 (1H, m), 6.68-6.79 (3H, m), 7.02-7.27 (11H, m).
MS (ESI, m/z):518 (M+Na)$^+$.

Preparation 5-72
Methyl (2S)-2-[3-(3-{5-[bis(4-fluorophenyl)methyl]-2-oxopyridin-1(2H)-yl}propyl)phenoxy]propanoate.
$^1$H-NMR (CDCl$_3$) δ: 1.62 (3H, d, J=6.8 Hz), 1.96-2.04 (2H, m), 2.57 (2H, t, J=7.7 Hz), 3.75 (3H, s), 3.84 (2H, t, J=7.3 Hz), 4.75 (1H, q, J=6.8 Hz), 5.21 (1H, s), 6.53-6.55 (1H, m), 6.65-6.71 (4H, m), 6.99-7.17 (10H, m).
MS (ESI, m/z):540 (M+Na)$^+$.

Preparation 5-73
Ethyl (3-{3-[2-oxo-5-(9H-xanthen-9-yl)pyridin-1(2H)-yl]propyl}phenoxy)acetate.
$^1$H-NMR (CDCl$_3$) δ: 1.30 (3H, t, J=7.2 Hz), 2.09 (2H, p, J=7.5 Hz), 2.65 (2H, t, J=7.6 Hz), 3.92 (2H, t, J=7.4 Hz), 4.27 (2H, q, J=7.1 Hz), 4.62 (2H, s), 5.00 (1H, s), 6.52 (1H, d, J=9.2 Hz), 6.79-6.81 (3H, m), 7.04-7.26 (11H, m).
MS (ESI, m/z):518 (M+Na)$^+$.

Preparation 5-74

Ethyl [3-(3-{5-[bis(4-methylphenyl)methyl]-2-oxopyridin-1(2H)-yl}propyl)phenoxy]acetate.

$^1$H-NMR (CDCl$_3$) δ: 1.29 (3H, t, J=7.1 Hz),1.99-2.05 (2H, m), 2.33 (6H, s), 2.58 (2H, t, J=7.7 Hz), 3.84 (2H, t, J=7.2 Hz), 4.27 (2H, q, J=7.1 Hz), 4.60 (2H, s), 5.16 (1H, s), 6.53 (1H, d, J=9.4 Hz), 6.70-6.74 (4H, m), 6.97-7.01 (4H, m), 7.07-7.18 (6H, m).

MS (ESI, m/z): 532 (M+Na)$^+$.

Preparation 5-75

Ethyl 4-{3-[3-(2-oxo-4,5-diphenyl-1,3-oxazol-3(2H)-yl)propyl]phenoxy}butanoate.

MS (ESI, m/z): 508 (M+Na)$^+$.

Preparation 6

To a solution of 6-(diphenylmethyl)pyridazin-3(2H)-one (97.2 mg) in DMF (2.7 mL) was added LiH (5.89 mg) at ambient temperature. After 5-minutes, ethyl [(3'-{[(methylsulfonyl) oxy]methyl}biphenyl-3-yl)oxy]acetate (135 mg) in DMF (1 mL) and potassium iodide (12.3 mg) were added to the solution at ambient temperature and stirred for 5 hours. The resulting mixture was quenched with 1M HCl aqueous solution and diluted with EtOAc. The organic layer was washed successively with water and brine, dried over anhydrous MgSO$_4$, filtered and evaporated in vacuo. The residue was purified by silica gel column chromatography (chloroform:MeOH=100:0-97:3) to give ethyl [(3'-{[3-(diphenylmethyl)-6-oxopyridazin-1(6H)-yl]methyl}biphenyl-3-yl)oxy]acetate (187 mg) as a colorless gum.

MS (ESI, m/z):531 (M+H)$^+$.

The following compound(s) was (were) obtained in a similar manner to that of Preparation 6

Preparation 6-1

Ethyl [3-(6-{[3-(diphenylmethyl)-6-oxopyridazin-1(6H)-yl]methyl}pyridin-2-yl)phenoxy]acetate.

MS (ESI, m/z):532 (M+H)$^+$.

Preparation 6-2

Ethyl [3-(6-{[5-(diphenylmethyl)-2-oxopyridin-1(2H)-yl]methyl}pyridin-2-yl)phenoxy]acetate.

MS (ESI, m/z):531 (M+H)$^+$.

Preparation 7

To a solution of 6-(diphenylmethyl)pyridazin-3(2H)-one (158 mg) in DMF (2 mL) was added NaH (60% in oil, 26 mg) at 5° C. After stirring for an hour at ambient temperature, to the reaction mixture was added a solution of ethyl (3-{3-[(methylsulfonyl)oxy]propoxy}phenoxy)acetate (200 mg) in DMF (0.5 mL), and the resulting mixture was stirred at ambient temperature for 12 hours and then was stirred at 50° C. for 5 hours. After cooling, the reaction mixture was diluted with EtOAc (5 mL) and washed with water (5 mL) and brine (5 mL) two times. The organic layer was dried over anhydrous MgSO$_4$, filtered and evaporated in vacuo to give crude oil. The crude oil was purified by silica gel column chromatography (EtOAc:n-hexane=3:1) to give ethyl (3-{3-[3-(diphenylmethyl)-6-oxopyridazin-1(6H)-yl]propoxy}phenoxy)acetate (230 mg) as a pale yellow oil.

$^1$H-NMR (DMSO-d$_6$) δ: 1.20 (3H, t, J=7.1 Hz), 2.0-2.2 (2H, m), 3.92 (2H, t, J=6.1 Hz), 4.1-4.2 (4H, m), 4.73 (2H, s), 5.51 (1H, s), 6.4-6.5 (3H, m), 6.90 (1H, d, J=9.6 Hz), 7.1-7.4 (12H, m).

MS (ESI, m/z):521 (M+Na)$^+$.

Preparation 8

A mixture of bis(4-methylphenyl)methanol (5 g), and pyridin-2(1H)-one (6.72 g) was stirred at 180° C. To the solution was added concentrated H$_2$SO$_4$ (0.07 mL), and the mixture was stirred at 250° C. for 2 hours. Water (15 mL) and DCM (15 mL) were poured into the reaction mixture. The organic layer was washed with water and brine, dried over anhydrous MgSO$_4$, filtered and evaporated in vacuo. The residue was purified by silica gel column chromatography (n-hexane:EtOAc). The desired fractions were collected and evaporated in vacuo, and the residue was washed with MeCN and dried in vacuo to give 5-[bis(4-methylphenyl)methyl]pyridin-2(1H)-one (0.94 g) as white crystals.

$^1$H-NMR (CDCl$_3$) δ: 2.32 (6H, s), 5.19 (1H, s), 6.50 (1H, d, J=9.4 Hz), 6.86 (1H, d, J=2.6 Hz), 6.97 (4H, d, J=8.1 Hz), 7.10 (4H, d, J=8.0 Hz), 7.31-7.34 (1H, m).

MS (ESI, m/z):312 (M+Na)$^+$.

The following compound(s) was(were) obtained in a similar manner to that of Preparation 8.

Preparation 8-1

5-[Bis(4-chlorophenyl)methyl]pyridin-2(1H)-one.

$^1$H-NMR (CDCl$_3$) δ: 5.22 (1H, s), 6.54 (1H, d, J=9.4 Hz), 6.86-6.86 (1H, m), 6.99-7.03 (4H, m), 7.25-7.31 (5H, m).

MS (ESI, m/z): 352 (M+Na)$^+$.

Preparation 8-2

5-[Bis(4-fluorophenyl)methyl]pyridin-2(1H)-one.

$^1$H-NMR (CDCl$_3$) δ: 5.25 (1H, s), 6.54 (1H, d, J=9.3 Hz), 6.86 (1H, m), 6.97-7.06 (8H, m), 7.28-7.31 (1H, m).

MS (ESI, m/z): 320 (M+Na)$^+$.

Preparation 8-3

5-[Bis(4-methoxyphenyl)methyl]pyridin-2(1H)-one.

$^1$H-NMR (CDCl$_3$) δ: 3.79 (6H, s), 5.18 (1H, s), 6.52 (1H, d, J=9.3 Hz), 6.81-6.87 (5H, m), 6.98-7.01 (4H, m), 7.32-7.35 (2H, m).

MS (ESI, m/z):344 (M+Na)$^+$.

Preparation 8-4

5-(9H-Xanthen-9-yl)pyridin-2(1H)-one.

$^1$H-NMR (CDCl$_3$) δ: 5.05 (1H, s), 6.50 (1H, d, J=10.2 Hz), 7.03-7.29 (11H, m).

MS (ESI, m/z):298 (M+Na)$^+$.

Preparation 9

A mixture of 4-oxo-5,5-diphenylpentanoic acid (2.47 g) and hydrazine monohydrate (1.4 mL) in toluene (49 mL) was refluxed for 3.5 hours. Water and EtOAc were poured into the reaction mixture. The organic layer was separated, washed with saturated NaHCO$_3$ aqueous solution and brine, and dried over anhydrous MgSO$_4$, filtered and evaporated in vacuo. The residue was washed with MeCN to give 6-(diphenylmethyl)-4,5-dihydropyridazin-3(2H)-one (0.85 g) as white powder.

$^1$H-NMR (DMSO-d$_6$) δ:2.26-2.30 (2H, m), 2.37-2.42 (2H, m), 5.14 (1H, s), 7.19-7.24 (6H, m), 7.30-7.34 (4H, m), 10.60 (1H, s).

MS (ESI, m/z):265 (M+H)$^+$.

Preparation 10

To a solution of ethyl 5,5-bis(4-fluorophenyl)-2-hydroxy-4-oxopentanoate (796 mg) in 1-butanol (4 mL) was added hydrazine hydrate (137 mg) at ambient temperature. The reaction mixture was stirred at 130° C. for 12 hours. After cooling to ambient temperature, the reaction mixture was evaporated in vacuo. The resulting residue was stirred at 160° C. for 3 hours. After cooling, the reaction mixture was purified by silica gel column chromatography (EtOAc:n-hexane=2:1) and crystallized from solvent (EtOAc:n-hexane=1:2) to give 6-[bis(4-fluorophenyl)methyl]pyridazin-3(2H)-one (344 mg) as a pale brown solid.

$^1$H-NMR (DMSO-d$_6$) δ: 5.59 (1H, brs),6.84 (1H, d, J=9.8 Hz), 7.1-7.3 (9H, m),12.88 (1H, brs).

MS (ESI, m/z):321 (M+Na)$^+$.

Preparation 11

A mixture of 1-(2-phenoxyphenyl)ethanone (2.0 g) and glyoxylic acid (2.79 g) in DME (6 mL) was refluxed for 15 hours. After cooling to ambient temperature, the mixture was evaporated in vacuo and taken up EtOAc (20 mL) and water (20 mL). The separated organic layer was washed with water (20 mL) and evaporated in vacuo. The residue was suspended in 28% NH₃ aqueous solution (20 mL) and hydrazine monohydrate (2.51 mL). The mixture was refluxed for 7 hours. After cooling to ambient temperature, a separated solid was collected and washed with water. Crude solid was suspended in EtOH (4 mL) and water (1 mL) and collected to give 6-(2-phenoxyphenyl)pyridazin-3(2H)-one (1.02 g) as a pale yellow solid.

MS (ESI, m/z):287 (M+Na)⁺

The following compound(s) was (were) obtained in a similar manner to that of Preparation 11.

Preparation 11-1

6-(3-Phenoxyphenyl)pyridazin-3(2H)-one.
MS (ESI, m/z):287 (M+Na)⁺.

Preparation 12

To a suspension of ethyl N-[2-acetamido-3-(benzyloxy)phenyl]glycinate (2.82 g) in EtOH (28.2 mL) was added H₂SO₄ (1.62 g) at ambient temperature. The mixture was stirred at 70° C. for 1 hour. After cooling, the reaction mixture was added ice and alkalized with 2M NaOH aqueous solution (pH=8) under ice cooling. The formed precipitate was collected by filtration and washed with water to give ethyl [4-(benzyloxy)-2-methyl-1H-benzimidazol-1-yl]acetate (2.65 g) as a white solid.

¹H-NMR (DMSO-d₆) δ:1.22 (3H, t, J=7.1 Hz), 2.44 (3H, s), 4.17 (2H, q, J=7.1 Hz), 5.15 (2H, s), 5.32 (2H, s), 6.7-6.8 (1H, m), 7.0-7.1 (2H, m), 7.3-7.6 (5H, m).
MS (ESI, m/z):325 (M+H)⁺.

Preparation 13

To a solution of ethyl [3-(3-iodopropyl)phenoxy]acetate (2.5 g) in DMF (50 mL) was added (3,3-diphenylpropyl)amine (1.7 g) at ambient temperature. The reaction mixture was stirred for 8 hours at the same temperature. The resulting mixture was diluted with EtOAc and washed successively with saturated NaHCO₃ aqueous solution, water and brine. The organic layer was dried over anhydrous MgSO₄, filtered and evaporated in vacuo. The residue was purified by silica gel column chromatography (chloroform:MeOH=100:0-95:5) to give ethyl (3-{3-[(3,3-diphenylpropyl)amino]propyl}phenoxy)acetate (1.25 g).

¹H-NMR (CDCl₃) δ: 1.29 (3H, t, J=7.0 Hz), 1.79-1.69 (2H, m), 2.23 (2H, dd, J=7.5, 7.5 Hz), 2.60-2.53 (6H, m), 3.99 (1H, t, J=7.5 Hz), 4.26 (2H, q, J=7.0 Hz), 4.59 (2H, s), 6.80-6.69 (3H, m), 7.30-7.15 (11H, m).
MS (ESI, m/z):432 (M+H)⁺.

The following compound(s) was (were) obtained in a similar manner to that of Preparation 13.

Preparation 13-1 tert-Butyl 4-(4-{[(3,3-diphenylpropyl-)amino]methyl}-1,3-oxazol-2-yl)-1H-indole-1-carboxylate ¹H-NMR (CDCl₃) δ: 1.69 (9H, s), 2.25-2.35 (2H, m), 2.68 (2H, t, J=7.8 Hz), 3.76 (2H, s), 4.05 (1H, t, J=7.8 Hz), 7.13-7.30 (10H, m), 7.38 (1H, dd, J=7.7, 8.1 Hz), 7.42 (1H, d, J=3.8 Hz), 7.54 (1H, s), 7.70 (1H, d, J=3.8 Hz), 7.94 (1H, d, J=7.7 Hz), 8.28 (1H, d, J=8.1 Hz).
MS (ESI, m/z):508 (M+H)⁺.

Preparation 13-2

Ethyl[(2-{[(3,3-diphenylpropyl)amino]methyl}-2,3-dihydro-1H-inden-4-yl)oxy]acetate.

¹H-NMR (CDCl₃) δ: 1.28 (3H, t, J=7.1 Hz), 2.2-2.35 (2.5H, m), 2.55-2.75 (7H, m), 2.95-3.35 (2.5H, m), 3.9-4.05 (1H, m), 4.25 (2H, q, J=7.1 Hz), 4.61 (2H, s), 6.52 (1H, d, J=8.1 Hz), 6.83 (1H, d, J=7.4 Hz), 7.07 (1H, dd, J=8.1, 7.4 Hz), 7.15-7.35 (10H, m).

Preparation 13-3 tert-Butyl {2-[(3,3-diphenylpropyl)amino]ethyl}carbamate.

¹H-NMR (CDCl₃) δ: 1.45 (9H, s), 2.22 (2H, dt, J=7.2, 7.8 Hz), 2.56 (2H, t, J=7.2 Hz), 2.65 (2H, t, J=5.8 Hz), 3.09-3.20 (2H, m), 4.01 (1H, t, J=7.8 Hz), 4.82-4.91 (1H, brs),7.13-7.33 (10H, m).
MS (ESI, m/z):355 (M+H)⁺.

Preparation 13-4

Ethyl (5-{3-[(3,3-diphenylpropyl)amino]propyl}-2-fluorophenoxy)acetate.

¹H-NMR (CDCl₃) δ: 1.28 (3H, t, J=7.4 Hz), 1.70 (2H, m), 2.23 (2H, q, J=7.2 Hz), 2.48-2.60 (6H, m), 3.99 (1H, t, J=7.7 Hz), 4.25 (2H, q, J=7.4 Hz), 6.66 (2H, s), 6.68-6.76 (2H, m), 6.92-7.02 (1H, m), 7.13-7.32 (10H, m).
MS (ESI, m/z):450 (M+H)⁺.

Preparation 13-5 tert-Butyl 3-{3-[(3,3-diphenylpropyl)amino]propyl}-1H-indole-1-carboxylate.

¹H-NMR (CDCl₃) δ: 1.66 (9H, s), 1.78-1.92 (2H, m), 2.20-2.30 (2H, m), 2.5-2.8 (6H, m), 4.0 (1H, t, J=7.8 Hz), 7.1-7.4 (13H, m), 7.49 (1H, d, J=7.6 Hz), 8.06-8.16 (1H, m).
MS (ESI, m/z):469 (M+H)⁺.

Preparation 13-6 tert-Butyl 4-{(1E)-3-[(3,3-diphenylpropyl)amino]-1-propen-1-yl}-1H-indole-1-carboxylate.

¹H-NMR (CDCl₃) δ: 1.67 (9H, s), 2.34-2.26 (2H, m), 2.67 (2H, t, J=7.5 Hz), 3.42 (2H, d, J=6.0 Hz), 4.04 (1H, t, J=7.5 Hz), 6.41-6.31 (1H, m), 6.71 (1H, d, J=3.5 Hz), 6.80 (1H, d, J=15.5 Hz), 7.32-7.14 (12H, m), 7.60 (1H, d, J=3.5 Hz), 8.05-8.03 (1H, m).
MS (ESI, m/z):467 (M+H)⁺.

Preparation 13-7

N-{3-[2-(Benzyloxy)phenyl]propyl}-3,3-diphenyl-1-propanamine.

¹H-NMR (CDCl₃) δ: 1.81-1.71 (2H, m), 2.21-2.14 (2H, m), 2.59-2.49 (4H, m),2.68 (2H, t, J=7.5 Hz), 3.95 (1H, t, J=7.5 Hz), 5.06 (2H, s), 6.91-6.86 (2H, m), 7.43-7.11 (16H, m), 8.01 (1H, s).
MS (ESI, m/z):436 (M+H)⁺.

Preparation 14

To a mixture of N-[2-amino-6-(benzyloxy)phenyl]acetamide (2.95 g) and ethyl bromoacetate (2.11 g) in DMF (29.5 mL) were added sodium iodide (1.73 g) and K₂CO₃ (1.91 g) at ambient temperature. The mixture was stirred at 80° C. for 6 hours. After cooling, the reaction mixture was added water (50 mL). The formed precipitate was collected by filteration and washed with water and recrystallized from solvent (EtOAc and n-hexane) to give ethyl N-[2-acetamido-3-(benzyloxy)phenyl]glycinate (2.86 g) as a white solid.

¹H-NMR (DMSO-d₆) δ: 1.20 (3H, t, J=7.1 Hz), 2.02 (3H, s), 3.89 (2H, d, J=5.9 Hz), 4.12 (2H, q, J=7.1 Hz), 5.04 (2H, brs),5.32 (1H, t, J=5.9 Hz), 6.11 (1H, d, J=7.9 Hz), 6.37 (1H, d, J=7.6 Hz), 6.98 (1H, t, J=8.2 Hz), 7.2-7.5 (5H, m), 8.83 (1H, brs).
MS (ESI, m/z):365 (M+Na)⁺.

Preparation 15

To a solution of ethyl {3-[({2-[5-(diphenylmethyl)-2-oxopyridin-1(2H)-yl]ethyl}amino)methyl]phenoxy}acetate (90 mg) in EtOH (3 mL) was added sodium triacetoxyborohydride (326 mg) at ambient temperature and the resulting mixture was stirred at ambient temperature for 18 hours. And then the reaction mixture was evaporated in vacuo and partitioned between EtOAc and water. The organic layer was washed with brine, dried over anhydrous MgSO₄, filtered and evaporated in vacuo. The residue was purified by silica gel column chromatography (chloroform:MeOH=20:1) to give ethyl (3-{[{2-[5-(diphenylmethyl)-2-oxopyridin-1(2H)-yl]ethyl}(methyl)amino]methyl}phenoxy)acetate (61.9 mg) as a colorless oil.

MS (ESI, m/z):511 (M+H)⁺.

Preparation 16

To a solution of 1-(2-aminoethyl)-5-(diphenylmethyl)pyridin-2(1H)-one hydrochloride (350 mg), ethyl (3-formylphenoxy)acetate (214 mg) and TEA (114 mg) in DCM (10 mL) was added sodium triacetoxyborohydride (326 mg) on ice bath temperature and the resulting mixture was stirred for 4 hours at ambient temperature. And then the reaction mixture was partitioned between DCM and saturated NaHCO$_3$ aqueous solution The organic layer was washed with brine, dried over sodium sulfate and filtered and evaporated in vacuo. The residue was purified by silica gel column chromatography (chloroform:MeOH=99:1-90:10) to give ethyl {3-[({2-[5-(diphenylmethyl)-2-oxopyridin-1(2H)-yl]ethyl}amino)methyl]phenoxy}acetate (321 mg).

MS (ESI, m/z):497 (M+H)$^+$.

Preparation 17

Under an inert gas atmosphere, to a solution of ethyl 4-{3-[3-(2-oxo-4,5-diphenyl-2,3-dihydro-1H-imidazol-1-yl)propyl]phenoxy}butanoate (100 mg) in DMF (2 mL) was added portionwise NaH(60% in mineral oil, 9 mg) at ice-cooled temperature. After 1.5 hours, iodomethane (35 mg) in DMF (0.2 mL) was added dropwise to the solution at ambient temperature and stirred for 14 hours. The resulting mixture was poured into ice-water, and extracted with EtOAc. The organic layer was washed with brine, dried over anhydrous MgSO$_4$, filtered and evaporated in vacuo. The residue was purified by silica gel column chromatography (n-hexane:EtOAc=1:1) to give a ethyl 4-{3-[3-(3-methyl-2-oxo-4,5-diphenyl-2,3-dihydro-1H-imidazol-1-yl)propyl]phenoxy}butanoate (71 mg) as a colorless oil.

$^1$H-NMR (CDCl$_3$) δ: 1.26 (3H, t, J=7.1 Hz), 1.77-1.85 (2H, m), 2.05-2.12 (2H, m), 2.46-2.52 (4H, m), 3.25 (3H, s), 3.75 (2H, t, J=7.5 Hz), 3.94 (2H, t, J=6.1 Hz), 4.14 (2H, q, J=7.1 Hz), 6.57-6.68 (3H, m), 7.08-7.15 (5H, m), 7.23-7.30 (6H, m).

MS (ESI, m/z):499 (M+H)$^+$.

The following compound(s) was (were) obtained in a similar manner to that of Example 177.

Preparation 18-1

Ethyl (4-nitro-1H-indol-1-yl)acetate.

$^1$H-NMR (CDCl$_3$) δ: 1.29 (3H, t, J=7.0 Hz), 4.25 (2H, q, J=7.0 Hz), 4.95 (2H, s), 7.20-7.40 (3H, m), 7.60 (1H, d, J=8.0 Hz), 8.19 (1H, d, J=7.3 Hz).

MS (ESI, m/z):249 (M+H)$^+$.

Preparation 18-2

Ethyl (4-{[tert-butyl(dimethyl)silyl]oxy}-1H-indol-1-yl)acetate.

$^1$H-NMR (CDCl$_3$) δ: 0.23 (6H, s), 1.05 (9H, s), 1.25 (3H, t, J=7.0 Hz), 4.20 (2H, q, J=7.0 Hz), 4.80 (2H, s), 6.53 (1H, d, J=8.0 Hz), 6.59 (1H, d, J=3.5 Hz), 6.87 (1H, d, J=8.0 Hz), 6.98 (1H, d, J=3.5 Hz), 7.06 (1H, dd, J=8.0, 8.0 Hz).

MS (ESI, m/z):334 (M+H)$^+$.

Preparation 19

To a solution of 3-(3-hydroxypropyl)phenol (100 g) in MeCN (750 mL) was added K$_2$CO$_3$ (109 g) at ambient temperature. Ethyl bromoacetate (87.4 mL) was added dropwise to the mixture at 0° C. over 30 minutes, and then the mixture was stirred at ambient temperature for 20 hours and at 60° C. for 7 hours. Water (800 mL) was added to the mixture at ambient temperature and the resulting mixture was extracted with EtOAc(1 L) two times. The organic layer was washed with brine, dried over anhydrous MgSO$_4$, filtered and evaporated in vacuo. The residue was purified by silica gel column chromatography (n-hexane:EtOAc=1:1) to afford ethyl [3-(3-hydroxypropyl)phenoxy]acetate (121 g) as a colorless oil.

$^1$H-NMR (CDCl$_3$) δ: 1.30 (3H, t, J=7.1 Hz), 1.82-1.93 (2H, m), 2.69 (2H, t, J=7.9 Hz), 3.67 (2H, t, J=6.4 Hz), 4.27 (2H, q, J=7.1 Hz), 4.61 (2H, s), 6.72 (1H, dd, J=2.0, 7.9 Hz), 6.77-6.80 (1H, m), 6.84 (1H, d, J=7.9 Hz), 7.20 (1H, t, J=7.9 Hz).

MS (ESI, m/z):239 (M+H)$^+$.

The following compound(s) was (were) obtained in a similar manner to that of Preparation 19.

Preparation 19-1

Ethyl {3-[(1E)-3-hydroxy-1-propen-1-yl]phenoxy}acetate.

$^1$H-NMR (CDCl$_3$) δ: 1.31 (3H, t, J=7.0 Hz), 4.33-4.25 (4H, m), 4.63 (2H, s), 6.35 (1H, dt, J=15.8, 5.5 Hz), 6.58 (1H, d, J=15.8 Hz), 6.81-6.78 (1H, m), 6.95 (1H, s), 7.03 (1H, d, J=8.0 Hz), 7.23 (1H, d, J=8.0 Hz).

Preparation 19-2

Ethyl [2-(3-hydroxypropyl)phenoxy]acetate.

$^1$H-NMR (CDCl$_3$) δ: 1.32 (3H, t, J=7.0 Hz), 1.93-1.84 (2H, m), 2.84 (2H, t, J=7.0 Hz), 3.60 (2H, t, J=7.0 Hz), 4.30 (2H, q, J=7.0 Hz), 4.63 (2H, s), 6.75 (1H, d, J=8.0 Hz), 6.99-6.94 (1H, m), 7.21-7.15 (2H, m).

MS (ESI, m/z):239 (M+H)$^+$.

Preparation 19-3

Ethyl [3-(4-hydroxybutyl)phenoxy]acetate.

$^1$H-NMR (CDCl$_3$) δ: 1.30 (3H, t, J=7.0 Hz), 1.72-1.56 (4H, m), 2.62 (2H, t, J=7.0 Hz), 3.67-3.64 (2H, m), 4.28 (2H, q, J=7.0 Hz), 4.61 (2H, s), 6.84-6.70 (3H, m), 7.20 (1H, t, J=7.5 Hz).

MS (ESI, m/z):275 (M+Na)$^+$.

Preparation 19-4

Ethyl {[2-(hydroxymethyl)-2,3-dihydro-1H-inden-4-yl]oxy}acetate.

$^1$H-NMR (CDCl$_3$) δ: 1.29 (3H, t, J=7.1 Hz), 2.6-2.85 (3H, m), 3.00-3.20 (2H, m), 3.55-3.75 (2H, m), 4.26 (2H, q, J=7.1 Hz), 4.62 (2H, s), 6.53 (1H, d, J=8.1 Hz), 6.86 (1H, d, J=7.4 Hz), 7.09 (1H, dd, J=8.1, 7.4 Hz).

Preparation 19-5

Ethyl [2-fluoro-5-(3-hydroxypropyl)phenoxy]acetate.

$^1$H-NMR (CDCl$_3$) δ: 1.24-1.38 (4H, m), 1.78-1.90 (2H, m), 2.65 (2H, t, J=7.8 Hz), 3.65 (2H, dt, J=6.2, 5.2 Hz), 4.27 (2H, q, J=7.3 Hz), 4.68 (2H, s), 6.73-6.82 (2H, m), 6.93-7.06 (1H, m).

MS (ESI, m/z):257 (M+H)$^+$.

Preparation 19-6

Ethyl [4-fluoro-3-(3-hydroxypropyl)phenoxy]acetate.

$^1$H-NMR (DMSO-d$_6$) δ: 1.20 (3H, t, J=7.1 Hz), 1.6-1.8 (2H, m), 2.5-2.7 (2H, m), 3.3-3.5 (2H, m), 4.16 (2H, q, J=7.1 Hz), 4.50 (1H, t, J=5.2 Hz), 4.73 (2H, s), 6.7-7.1 (3H, m).

MS (ESI, m/z):279 (M+Na)$^+$.

Preparation 19-7

Ethyl 4-[3-(3-hydroxypropyl)phenoxy]butanoate.

$^1$H-NMR (CDCl$_3$) δ: 1.26 (3H, t, J=7.1 Hz), 1.47 (1H, s), 1.85-1.92 (2H, m), 2.05-2.14 (2H, m), 2.51 (2H, t, J=7.3 Hz), 2.68 (2H, t, J=7.7 Hz), 3.67 (2H, t, J=6.4 Hz), 3.99 (2H, t, J=6.1 Hz), 4.15 (2H, q, J=7.1 Hz), 6.71-6.80 (3H, m), 7.19 (1H, t, J=7.8 Hz).

MS (ESI, m/z):289 (M+Na)$^+$.

Preparation 19-8

Ethyl 4-[4-fluoro-3-(3-hydroxypropyl)phenoxy]butanoate.

$^1$H-NMR (DMSO-d$_6$) δ: 1.18 (3H, t, J=7.1 Hz), 1.6-1.8 (2H, m), 1.9-2.0 (2H, m), 2.44 (2H, t, J=7.3 Hz), 2.5-2.7 (2H, m), 3.3-3.5 (2H, m), 3.93 (2H, t, J=6.4 Hz), 4.06 (2H, q, J=7.1 Hz), 4.49 (1H, t, J=5.1 Hz), 6.7-7.1 (3H, m).

MS (ESI, m/z):307 (M+Na)$^+$.

Preparation 19-9

Ethyl 4-{3-[(2-hydroxyethyl)sulfanyl]phenoxy}butanoate.

MS (ESI, m/z):307 (M+Na)$^+$.

Preparation 19-10

Ethyl (3-{[2-(hydroxymethyl)cyclohexyl]methyl}phenoxy)-acetate.

MS (ESI, m/z):307 (M+H)$^+$.

Preparation 20

To a solution of ethyl (4-hydroxy-1H-indol-1-yl)acetate (160 mg) in DMF (3.5 mL) was added K$_2$CO$_3$ (151 mg) and 2-(3-bromopropoxy)tetrahydro-2H-pyran (488 mg) at ambient temperature. The reaction mixture was stirred at 100° C. for 15 hours. The resulting mixture was cooled to ambient temperature. The mixture was diluted with EtOAc and washed with 5% citric acid solution, saturated NaHCO$_3$ solution and brine. The organic layer was dried over anhydrous MgSO$_4$, filtered and evaporated in vacuo. The residue was purified by silica gel column chromatography (n-hexane:EtOAc=80:20-50:50) to give a ethyl {4-[3-(tetrahydro-2H-pyran-2-yloxy)propoxy]-1H-indol-1-yl}acetate.

$^1$H-NMR (CDCl$_3$) δ: 1.25 (3H, t, J=7.0 Hz), 1.56-1.51 (4H, m), 1.85-1.68 (2H, m), 2.21-2.12 (2H, m), 3.53-3.46 (1H, m), 3.69-3.62 (1H, m), 3.90-3.83 (1H, m), 4.03-3.95 (1H, m), 4.23 (2H, q, J=7.0 Hz), 4.63-4.61 (1H, m), 4.81 (2H, s), 6.56 (1H, d, J=8.0 Hz), 6.66 (1H, d, J=3.0 Hz), 6.86 (1H, d, J=8.0 Hz), 6.98 (1H, d, J=3.0 Hz), 7.13 (1H, dd, J=8.0, 8.0 Hz).

MS (ESI, m/z):362 (M+H)$^+$.

The following compound(s) was(were) obtained in a similar manner to that of Preparation 20.

Preparation 20-1

Ethyl {3-[3-(tetrahydro-2H-pyran-2-yloxy)propoxy]phenoxy}acetate.

$^1$H-NMR (DMSO-d$_6$) δ:1.21 (3H, t, J=7.1 Hz), 1.3-1.8 (6H, m), 1.9-2.0 (2H, m), 3.3-3.5 (2H, m), 3.6-3.8 (2H, m), 4.02 (2H, t, J=6.3 Hz), 4.16 (2H, q, J=7.1 Hz), 4.5-4.6 (1H, m), 4.75 (2H, s), 6.4-6.6 (3H, m), 7.17 (1H, t, J=8.5 Hz-).

MS (ESI, m/z):361 (M+Na)$^+$.

Preparation 21

To a solution of 3-(3-{[tert-butyl(dimethyl)silyl]oxy}propyl)phenol (1.78 g) in MeCN (10 mL) were added methyl propiolate (0.667 mL) and NMM (0.0441 mL) at ambient temperature and the mixture was stirred at the same temperature for 3 hours. The solvent was evaporated in vacuo. The residue was purified by silica gel column chromatography (n-hexane:EtOAc=97:3) to afford methyl (2E)-3-[3-(3-{[tert-butyl(dimethyl)silyl]oxy}propyl)phenoxy]-acrylate (1.80 g) as a colorless oil.

$^1$H-NMR (CDCl$_3$) δ: 0.05 (6H, s), 0.91 (9H, s), 1.78-1.88 (2H, m), 2.69 (2H, t, J=8.1 Hz), 3.63 (2H, t, J=6.2 Hz), 3.73 (3H, s), 5.55 (1H, d, J=12.2 Hz), 6.86-6.91 (2H, m), 7.02 (1H, d, J=7.7 Hz), 7.27 (1H, dt, J=1.1, 7.7 Hz), 7.80 (1H, d, J=12.2 Hz).

Preparation 22

To a mixture of 4-fluoro-3-(3-hydroxypropyl)phenol (1.5 g), methyl (2R)-2-chloropropanoate (1.30 g) in DMSO (7.5 mL) was added Cs$_2$CO$_3$ (3.45 g) at ambient temperature. The mixture was stirred at 60° C. for 3 hours. After cooling to ambient temperature, the reaction mixture was diluted with EtOAc (50 mL) and washed successively with water (30 mL) two times and brine (30 mL). The organic layer was dried over anhydrous MgSO$_4$, filtered and evaporated in vacuo to give crude oil. The crude oil was purified by silica gel column chromatography (n-hexane:EtOAc=4:1-2:1) to give methyl (2S)-2-[4-fluoro-3-(3-hydroxypropyl)phenoxy]propanoate (1.51 g) as a colorless oil.

$^1$H-NMR (DMSO-d$_6$) δ: 1.48 (3H, d, J=6.7 Hz), 1.6-1.7 (2H, m), 2.5-2.6 (2H, m), 3.3-3.5 (2H, m), 3.67 (3H, s), 4.50 (1H, t, J=5.2 Hz), 4.93 (1H, q, J=6.7 Hz), 6.6-7.1 (3H, m).

MS (ESI, m/z):279 (M+Na)$^+$.

The following compound(s) was(were) obtained in a similar manner to that of Preparation 22.

Preparation 22-1

Methyl (2R)-2-[3-(3-hydroxypropyl)phenoxy]propanoate.

$^1$H-NMR (CDCl$_3$) δ: 1.40-1.52 (1H, m), 1.62 (3H, d, J=6.8 Hz), 1.84-1.91 (2H, m), 2.64-2.69 (2H, m), 3.61-3.68 (2H, m), 3.76 (3H, s), 4.77 (1H, q, J=6.8 Hz), 6.67-6.71 (1H, m), 6.74-6.75 (1H, m), 6.81-6.83 (1H, m), 7.18 (1H, t, J=7.9 Hz).

MS (ESI, m/z):261 (M+Na)$^+$.

Preparation 22-2

Methyl (2S)-2-[3-({2-[3-(diphenylmethyl)-6-oxopyridazin-1(6H)-yl]ethyl}sulfanyl)phenoxy]propanoate.

$^1$H-NMR (DMSO-d$_6$) δ: 1.49 (3H, d, J=6.7 Hz), 3.29 (2H, t, J=6.8 Hz), 3.65 (3H, s), 4.19 (2H, t, J=6.8 Hz), 5.01 (1H, q, J=6.7 Hz), 5.53 (1H, s), 6.71 (1H, d, J=8.4 Hz), 6.86-6.91 (3H, m), 7.16-7.34 (12H, m).

MS (ESI, m/z):523 (M+Na)$^+$.

Preparation 22-3

Methyl (2S)-2-[3-({2-[5-(diphenylmethyl)-2-oxopyridin-1(2H)-yl]ethyl}sulfanyl)phenoxy]propanoate.

$^1$H-NMR (DMSO-d$_6$) δ: 1.49 (2H, d, J=6.8 Hz), 3.27 (2H, t, J=6.6 Hz), 3.65 (3H, s), 3.96 (2H, t, J=6.6 Hz), 5.03 (1H, q, J=6.8 Hz), 5.32 (1H, s), 6.37 (1H, d, J=9.3 Hz), 6.68-6.71 (1H, m), 6.82-6.85 (3H, m), 7.11-7.34 (13H, m).

MS (ESI, m/z):522 (M+Na)$^+$.

Preparation 22-4

Methyl (2S)-2-[3-(3-hydroxypropyl)phenoxy]propanoate.

$^1$H-NMR (CDCl$_3$) δ: 1.40-1.53 (1H, m), 1.61 (3H, d, J=6.8 Hz), 1.83-1.91 (2H, m), 2.64-2.69 (2H, m), 3.61-3.68 (2H, m), 3.76 (3H, s), 4.77 (1H, q, J=6.8 Hz), 6.65-6.71 (1H, m), 6.74-6.75 (1H, m), 6.81-6.83 (1H, m), 7.18 (1H, t, J=7.9 Hz).

MS (ESI, m/z):261 (M+Na)$^+$.

Preparation 23

A mixture of 2-[3-(diphenylmethyl)-6-oxopyridazin-1(6H)-yl]ethyl methanesulfonate (200 mg), ethyl 4-(3-hydroxyphenoxy)butanoate (140 mg), K$_2$CO$_3$ (93 mg), sodium iodide (94 mg), and DMF (2 mL) was stirred at 80° C. for 2 hours. After cooling, the reaction mixture was diluted with EtOAc (50 mL) and washed with water (30 mL) and brine (30 mL) two times. The organic layer was dried over anhydrous MgSO$_4$, filtered and evaporated in vacuo to give crude oil. The crude oil was purified by silica gel column chromatography (n-hexane:EtOAc=1:1) to give ethyl 4-(3-{2-[3-(diphenylmethyl)-6-oxopyridazin-1(6H)-yl]ethoxy}phenoxy)butanoate (87 mg) as a pale yellow oil.

$^1$H-NMR (DMSO-d$_6$) δ: 1.16 (3H, t, J=7.1 Hz), 1.8-2.0 (2H, m), 2.44 (2H, t, J=7.3 Hz), 3.93 (2H, t, J=6.4 Hz), 4.05 (2H, q, J=7.1 Hz), 4.2-4.4 (4H, m), 5.53 (1H, s), 6.4-6.6 (3H, m), 6.92 (1H, d, J=9.7 Hz), 7.1-7.4 (12H, m).

MS (ESI, m/z):535 (M+Na)$^+$.

The following compound(s) was (were) obtained in a similar manner to that of Preparation 23.

Preparation 23-1

Ethyl (4-{2-[5-(diphenylmethyl)-2-oxopyridin-1(2H)-yl]ethoxy}-2-methyl-1H-benzimidazol-1-yl)acetate.

$^1$H-NMR (DMSO-d$_6$) δ: 1.21 (3H, t, J=7.1 Hz), 2.40 (3H, s), 4.17 (2H, q, J=7.1 Hz), 4.22 (2H, t, J=5.0 Hz), 4.49 (2H, t, J=5.0 Hz), 5.16 (2H, s), 5.33 (1H, s), 6.38 (1H, d, J=9.4 Hz), 6.56 (1H, d, J=7.6 Hz), 6.9-7.4 (14H, m).

MS (ESI, m/z):522 (M+H)$^+$.

Preparation 24

To a solution of 5-(diphenylmethyl)-1-[3-(3-hydroxyphenyl)propyl]pyridin-2(1H)-one (200 mg) in MeCN (3 mL) was added K$_2$CO$_3$ (84 mg) at ambient temperature. Ethyl 2-bromopropanoate (78 μL) was added dropwise to the mixture and then the mixture was stirred at 60° C. for 14 hours. Water was added to the mixture at ambient temperature and the resulting mixture was extracted with EtOAc. The organic layer was washed with brine, dried over anhydrous MgSO$_4$, filtered and evaporated in vacuo. The residue was purified by silica gel column chromatography (n-hexane:EtOAc=1:1) to afford ethyl 2-(3-{3-[5-(diphenylmethyl)-2-oxopyridin-1(2H)-yl]propyl}phenoxy) propanoate (238 mg) as a colorless oil.

MS (ESI, m/z):518 (M+Na)$^+$.

The following compound(s) was (were) obtained in a similar manner to that of Preparation 24.

Preparation 24-1

Methyl(2S)-2-(3-{3-[5-(diphenylmethyl)-2-oxopyridin-1(2H)-yl]propyl}phenoxy)propanoate.

MS (ESI, m/z):504 (M+Na)$^+$.

Preparation 24-2

Methyl (2S)-2-[3-({3-[3-(diphenylmethyl)-6-oxopyridazin-1(6H)-yl]propyl}sulfanyl)phenoxy]propanoate.

MS (ESI, m/z):515 (M+H)$^+$.

Preparation 24-3

Ethyl [3-({3-[3-(diphenylmethyl)-6-oxopyridazin-1(6H)-yl]propyl}sulfanyl)phenoxy]acetate.

MS (ESI, m/z):515 (M+H)$^+$.

Preparation 24-4

Methyl (2S)-2-[3-(4-hydroxybutyl)phenoxy]propanoate.

MS (ESI, m/z):275 (M+Na)$^+$.

Preparation 24-5

Ethyl 2-[3-({3-[5-(diphenylmethyl)-2-oxopyridin-1(2H)-yl]propyl}sulfanyl)phenoxy]propanoate.

MS (ESI, m/z):550 (M+Na)$^+$.

Preparation 24-6

Ethyl [3-({3-[5-(diphenylmethyl)-2-oxopyridin-1(2H)-yl]propyl}sulfanyl)phenoxy]acetate.

MS (ESI, m/z):536 (M+Na)$^+$.

Preparation 24-7

Methyl (2R)-2-(3-{3-[5-(diphenylmethyl)-2-oxopyridin-1(2H)-yl]propyl}phenoxy)propanoate.

MS (ESI, m/z):504 (M+Na)$^+$.

Preparation 24-8

Ethyl 4-[3-({2-[3-(diphenylmethyl)-6-oxopyridazin-1(6H)-yl]ethyl}sulfanyl)phenoxy]butanoate.

$^1$H-NMR (DMSO-d$_6$) δ: 1.16 (3H, t, J=7.2 Hz),1.91-1.98 (2H, m), 2.43 (2H, t, J=7.3 Hz), 3.29-3.33 (2H, m), 3.97 (2H, t, J=6.3 Hz), 4.05 (2H, q, J=7.2 Hz), 4.19 (2H, t, J=6.8 Hz), 5.52 (1H, s), 6.75 (1H, dd, J=8.2, 2.4 Hz), 6.84-6.90 (3H, m), 7.16-7.33 (12H, m).

MS (ESI, m/z):551 (M+Na)$^+$.

Preparation 24-9

Ethyl 4-[3-({2-[5-(diphenylmethyl)-2-oxopyridin-1(2H)-yl]ethyl}sulfanyl)phenoxy]butanoate.

$^1$H-NMR (DMSO-d$_6$) δ: 1.16 (3H, t, J=7.1 Hz),1.9-1.98 (2H, m), 2.43 (2H, t, J=7.3 Hz), 3.28 (2H, t, J=6.5 Hz), 3.95-3.99 (4H, m), 4.05 (2H, q, J=7.1 Hz), 5.31 (1H, s), 6.36 (1H, d, J=9.3 Hz), 6.72-6.86 (3H, m), 7.10-7.33 (13H, m).

MS (ESI, m/z):550 (M+Na)$^+$.

Preparation 24-10

Ethyl(3-{3-[5-(diphenylmethyl)-2-oxopiperidin-1-yl]propyl} phenoxy)acetate.

MS (ESI, m/z):508 (M+Na)$^+$.

Preparation 24-11

Ethyl 4-{3-[(2-hydroxyethyl)sulfanyl]phenoxy}butanoate.

MS (ESI, m/z):307 (M+Na)$^+$.

Preparation 24-12

Methyl(2S)-2-(3-{[3-(tetrahydro-2H-pyran-2-yloxy)propyl]sulfanyl}phenoxy)propanoate.

MS (ESI, m/z): 377 (M+Na)$^+$.

Preparation 25

To a solution of 3-hydroxythiophenol (222 mg) in DMF (15 mL) were added K$_2$CO$_3$ (243 mg) and 3-[5-(diphenylmethyl)-2-oxopyridin-1(2H)-yl]propyl methanesulfonate (700 mg) at ambient temperature and the mixture was stirred for 7 hours. Water was added to the mixture at ambient temperature and the resulting mixture was extracted with EtOAc. The organic layer was washed with brine, dried over anhydrous MgSO$_4$, filtered and evaporated in vacuo. The residue was purified by silica gel column chromatography (n-hexane:EtOAc=1:1) to afford 5-(diphenylmethyl)-1-{3-[(3-hydroxyphenyl)sulfanyl]propyl}pyridin-2(1H)-one (610 mg) as a colorless oil.

MS (ESI, m/z):450 (M+Na)$^+$.

The following compound(s) was(were) obtained in a similar manner to that of Preparation 25.

Preparation 25-1

6-(Diphenylmethyl)-2-{3-[(3-hydroxyphenyl)sulfanyl]propyl}pyridazin-3(2H)-one.

MS (ESI, m/z):451 (M+Na)$^+$.

Preparation 25-2

5-(Diphenylmethyl)-1-{2-[(3-hydroxyphenyl)sulfanyl]ethyl}pyridin-2(1H)-one.

$^1$H-NMR (DMSO-d$_6$) δ: 3.23 (2H, t, J=6.5 Hz), 3.95 (2H, t, J=6.5 Hz), 5.32 (1H, s), 6.36 (1H, d, J=9.4 Hz), 6.58-6.71 (3H, m), 7.04-7.33 (13H, m), 9.54 (1H, s).

MS (ESI, m/z):436 (M+Na)$^+$.

Preparation 25-3

Ethyl 4-[(3-methoxyphenyl)sulfanyl]butanoate.

$^1$H-NMR (DMSO-d$_6$) δ: 1.17 (3H, t, J=7.1 Hz), 1.81 (2H, tt, J=7.2, 7.2 Hz), 2.43 (2H, t, J=7.2 Hz), 2.98 (2H, t, J=7.2 Hz), 3.75 (3H, s), 4.05 (2H, q, J=7.1 Hz), 6.73-6.76 (1H, m), 6.86-6.89 (2H, m), 7.23 (1H, dd, J=7.9, 8.0 Hz).

MS (ESI, m/z):277 (M+Na)$^+$.

Preparation 25-4

3-{[3-(Tetrahydro-2H-pyran-2-yloxy)propyl]sulfanyl}phenol.

MS (ESI, m/z):291 (M+Na)$^+$.

Preparation 25-5

3-[(2-Hydroxyethyl)sulfanyl]phenol.

MS (ESI, m/z):169 (M−H)$^−$.

Preparation 26

To a solution of 5-(diphenylmethyl)-1-(2-hydroxyethyl)pyridin-2(1H)-one (300 mg) in toluene (4.0 mL) were added 1,1'-azobis(N,N-dimethylformamide) (203 mg) and tributylphosphine (291 μL) at ambient temperature. And then to the mixture was added a solution of ethyl 4-[(3-hydroxyphenyl)sulfanyl]butanoate (378 mg) in toluene (2.0 mL) at 0° C. After stirring at ambient temperature for an hour, the reaction mixture was diluted with EtOAc (10 mL). The mixture was washed with water (10 mL) and brine (10 mL). The organic layer was dried over anhydrous MgSO$_4$, filtered and evaporated in vacuo to give crude oil. The oil was purified by silica gel column chromatography(n-hexane:EtOAc=4:1-1:1) to give ethyl 4-[(3-{2-[5-(diphenylmethyl)-2-oxopyridin-1(2H)-yl]ethoxy}phenyl)sulfanyl]butanoate (436 mg) as a colorless oil.

$^1$H-NMR (DMSO-d$_6$) δ: 1.15 (3H, t, J=7.2 Hz), 1.79 (2H, tt, J=7.2, 7.2 Hz), 2.42 (2H, t, J=7.2 Hz), 2.96 (2H, t, J=7.1 Hz), 4.03 (2H, q, J=7.2 Hz), 4.17 (4H, s), 5.37 (1H, s), 6.38 (1H, d, J=9.2 Hz), 6.60 (1H, d, J=8.2 Hz), 6.74 (1H, s), 6.90 (1H, d, J=7.9 Hz), 7.12-7.34 (13H, m).

MS (ESI, m/z):550 (M+Na)$^+$.

The following compound(s) was (were) obtained in a similar manner to that of Preparation 26.

Preparation 26-1

Ethyl 4-[(3-{2-[3-(diphenylmethyl)-6-oxopyridazin-1(6H)-yl]ethoxy}phenyl)sulfanyl]butanoate.

$^1$H-NMR (DMSO-$d_6$) δ: 1.15 (3H, t, J=7.2 Hz), 1.79 (2H, tt, J=7.2, 7.2 Hz), 2.41 (2H, t, J=7.2 Hz), 2.97 (2H, t, J=7.1 Hz), 4.03 (2H, q, J=7.2 Hz), 5.53 (1H, s), 6.67 (1H, dd, J=2.3, 8.1 Hz), 6.80 (1H, dd, J=1.7, 2.0 Hz), 6.89-6.93 (2H, m), 7.16-7.34 (12H, m).

MS (ESI, m/z):551 (M+Na)$^+$.

Preparation 27

To a mixture of 6-(diphenylmethyl)-2-(2-hydroxyethyl)pyridazin-3(2H)-one (100 mg), 3-sulfanylphenol (33.3 μL), 1,1-azobis(N,N-dimethylformamide) (62 mg) and toluene (2.0 mL) was added tributylphosphine (89 μL) at ambient temperature. The mixture was stirred for 3 hours at ambient temperature. The mixture was diluted with EtOAc (10 mL) and washed with water (10 mL) and brine (10 mL). The organic layer was dried over anhydrous MgSO$_4$, filtered and evaporated in vacuo to give a crude oil. The crude oil was purified by preparative thin-layer chromatography(n-hexane:EtOAc=1:1) to give 6-(diphenylmethyl)-2-{2-[(3-hydroxyphenyl)sulfanyl]ethyl}pyridazin-3(2H) one (86 mg) as a white solid.

$^1$H-NMR (DMSO-$d_6$) δ: 3.26 (2H, t, J=6.8 Hz), 4.19 (2H, t, J=6.8 Hz), 5.53 (1H, s), 6.61 (1H, dd, J=8.1, 1.5 Hz), 6.70-6.74 (2H, m), 6.89 (1H, d, J=9.5 Hz), 7.08 (1H, dd, J=7.9, 7.9 Hz), 7.21-7.33 (11H, m), 9.55 (1H, s).

MS (ESI, m/z):437 (M+Na)$^+$.

Preparation 28

To a mixture of ethyl (4-hydroxy-2-methyl-1H-benzimidazol-1-yl)acetate (476 mg), 5-[bis(4-fluorophenyl)methyl]-1-(2-hydroxyethyl)pyridin-2(1H)-one (694 mg), 1,1'-azobis(N,N-dimethylformamide) (385 mg) and toluene (9.5 mL) was added tributylphosphine (452 mg) at ambient temperature. The mixture was stirred at ambient temperature for 20 hours. The reaction mixture was diluted with a mixture of EtOAc (50 mL) and THF (20 mL), and washed with water (30 mL) and brine (30 mL). The organic layer was dried over anhydrous MgSO$_4$, filtered and evaporated in vacuo to give crude oil. The crude oil was crystallized from solvent(EtOAc and n-hexane) to give ethyl[4-(2-{5-[bis(4-fluorophenyl)methyl]-2-oxopyridin-1(2H)-yl}ethoxy)-2-methyl-1H-benzimidazol-1-yl]acetate (1.07 g) as a white powder.

$^1$H-NMR (DMSO-$d_6$) δ: 1.21 (3H, t, J=7.1 Hz), 2.39 (3H, s), 4.16 (2H, q, J=7.1 Hz), 4.23 (2H, t, J=4.8 Hz), 4.47 (2H, t, J=4.8 Hz), 5.17 (2H, s), 5.38 (1H, brs),6.39 (1H, d, J=9.3 Hz), 6.57 (1H, d, J=7.0 Hz), 7.0-7.3 (12H, m).

MS (ESI, m/z):558 (M+H)$^+$.

Preparation 29

To a solution of tert-butyl 4-formyl-1H-indole-1-carboxylate (812 mg) in THF (8 mL) was added ethyl (triphenylphosphoranylidene)acetate (1.15 g) at ambient temperature. The reaction mixture was stirred for 7 hours at the same temperature. The resulting mixture was evaporated in vacuo. The residue was dissolved in EtOAc and washed successively with water and brine. The organic layer was dried over anhydrous MgSO$_4$, filtered and evaporated in vacuo. The residue was purified by silica gel column chromatography (n-hexane:EtOAc=90:10-70:30) to give a tert-butyl 4-[(1E)-3-ethoxy-3-oxo-1-propen-1-yl]-1H-indole-1-carboxylate.

$^1$H-NMR (CDCl$_3$) δ: 1.36 (3H, t, J=7.0 Hz), 1.68 (9H, s), 4.30 (2H, q, J=7.0 Hz), 6.57 (1H, d, J=15.0 Hz), 6.86 (1H, d, J=3.5 Hz), 7.32 (1H, t, J=7.5 Hz), 7.50 (1H, d, J=7.5 Hz), 7.69 (1H, d, J=3.5 Hz), 8.06 (1H, d, J=15.0 Hz), 8.21 (1H, d, J=7.5 Hz).

MS (ESI, m/z):316 (M+H)$^+$.

The following compound(s) was (were) obtained in a similar manner to that of Preparation 29.

Preparation 29-1 tert-Butyl 4-[(1E)-3-methoxy-3-oxo-1-propen-1-yl]-1H-indole-1-carboxylate.

$^1$H-NMR (CDCl$_3$) δ: 1.68 (9H, s), 3.84 (3H, s), 6.57 (1H, d, J=16.0 Hz), 6.85 (1H, d, J=4.1 Hz), 7.33 (1H, dd, J=8.2, 7.5 Hz), 7.50 (1H, d, J=7.5 Hz), 7.69 (1H, d, J=4.1 Hz), 8.08 (1H, d, J=16.0 Hz), 8.21 (1H, d, J=8.2 Hz).

MS (ESI, m/z):302 (M+H)$^+$.

Preparation 29-2

Methyl (2E)-3-[3-(benzyloxy)-4-fluorophenyl]acrylate.

$^1$H-NMR (CDCl$_3$) δ:3.8 (3H, s), 5.17 (2H, s), 6.29 (1H, d, J=16.1 Hz), 7.06-7.18 (3H, m), 7.30-7.50 (5H, m), 7.59 (1H, d, J=16.1 Hz).

Preparation 29-3

Ethyl (2E)-3-(2-fluoro-5-methoxyphenyl)acrylate.

$^1$H-NMR (DMSO-$d_6$) δ: 1.27 (3H, t, J=7.1 Hz), 3.79 (3H, s), 4.21 (2H, q, J=7.1 Hz), 6.76 (1H, d, J=16.1 Hz), 7.0-7.5 (3H, m), 7.67 (1H, d, J=16.1 Hz). MS (ESI, m/z):247 (M+Na)$^+$.

Preparation 30

To a solution of ethyl (3-bromophenoxy)acetate (488 mg) in DME (10 mL) was added 3-(hydroxymethyl)phenylboronic acid (429 mg), 1,1'-bis(diphenylphosphino)ferrocenepalladium (II) dichloride (77 mg) and 2M Na$_2$CO$_3$ aqueous solution (5 mL) at ambient temperature. The reaction mixture was stirred at 80° C. for 7 hours. The resulting mixture was cooled to ambient temperature and diluted with EtOAc. The mixture was washed successively with water and brine. The organic layer was dried over anhydrous MgSO$_4$, filtered and evaporated in vacuo. The residue was purified by silica gel column chromatography (chloroform:MeOH=100:0-97:3) to give ethyl {[3'-(hydroxymethyl)-3-biphenylyl]oxy}acetate.

$^1$H-NMR (CDCl$_3$) δ: 1.31 (3H, t, J=7.0 Hz), 1.74 (1H, t, J=6.0 Hz), 4.29 (2H, q, J=7.0 Hz), 4.68 (2H, s), 4.77 (2H, d, J=5.5 Hz), 6.89 (1H, d, J=8.0 Hz), 7.16 (1H, s), 7.25-7.22 (1H, m), 7.39-7.34 (2H, m), 7.43 (1H, dd, J=7.5, 7.5 Hz), 7.50 (1H, d, J=7.5 Hz), 7.58 (1H, s).

Preparation 31

To a solution of (6-bromopyridin-2-yl)methanol (811 mg) in DME (20 mL) was added Pd(PPh$_3$)$_4$ (453 mg) at ambient temperature under N$_2$ gas atmosphere. After stirring for 20 minutes, ethyl [3-(4,4,5,5-tetramethyl-1,3,2-dioxaborolan-2-yl)phenoxy]acetate (1.20 g) and a solution of 2M Na$_2$CO$_3$ aqueous solution (5.88 mL) were added and the mixture was refluxed for 7 hours. The mixture was cooled to ambient temperature and partitioned between EtOAc (40 mL) and water. The organic layer was washed with saturated NaHCO$_3$ aqueous solution, water and then brine, dried over anhydrous MgSO$_4$, filtered and evaporated in vacuo. The residue was purified by silica gel column chromatography (n-hexane:EtOAc=10:1) to give ethyl {3-[6-(hydroxymethyl)pyridin-2-yl]phenoxy}acetate (297 mg) as a colorless oil.

MS (ESI, m/z):288 (M+H)$^+$.

Preparation 32

A mixture of ethyl {3-[3-(5-bromo-2-oxopyridin-1(2H)-yl) propyl]phenoxy}acetate (187.5 mg), 2-biphenylboronic acid (104 mg), Na$_2$CO$_3$(504 mg), Pd(PPh$_3$)$_4$ (27 mg), water (4 mL) and toluene (8 mL) were stirred under N$_2$ gas atmosphere at 100° C. for 3 hours. The reaction mixture was cooled to ambient temperature, diluted with 5% aqueous sodium chloride solution and extracted with EtOAc. The organic layer was washed with brine, dried over anhydrous MgSO$_4$, filtered and evaporated in vacuo. The residue was purified by silica gel column chromatography (n-hexane:

EtOAc=70:30-50:50). to give ethyl {3-[3-(5-biphenyl-2-yl-2-oxopyridin-1(2H)-yl)propyl]phenoxy}acetate (184 mg) as a colorless oil.
MS (ESI, m/z):490 (M+Na)+.

The following compound(s) was (were) obtained in a similar manner to that of Preparation 32.

Preparation 32-1
Ethyl [3-(3-{2-oxo-5-[2-(3-thienyl)phenyl]pyridin-1(2H)-yl}propyl)phenoxy]acetate.
MS (ESI, m/z):496 (M+Na)+.

Preparation 32-2
Ethyl(3-{3-[2-oxo-5-(2-phenoxyphenyl)pyridin-1(2H)-yl]propyl}phenoxy)acetate.
MS (ESI, m/z):506 (M+Na)+.

Preparation 32-3
Ethyl(3-{3-[5-(3'-methylbiphenyl-2-yl)-2-oxopyridin-1(2H)-yl]propyl}phenoxy)acetate.
MS (ESI, m/z):504 (M+Na)+.

Preparation 32-4
Ethyl(3-{3-[5-(4'-methoxybiphenyl-2-yl)-2-oxopyridin-1(2H)-yl]propyl}phenoxy)acetate.
MS (ESI, m/z):520 (M+Na)+.

Preparation 32-5
Ethyl(3-{3-[5-(3',4'-dimethylbiphenyl-2-yl)-2-oxopyridin-1(2H)-yl]propyl}phenoxy)acetate.
MS (ESI, m/z):518 (M+Na)+.

Preparation 32-6
8-[2-(6-Methoxypyridin-3-yl)phenyl]quinoline.
MS (ESI, m/z):313 (M+H)+.

Preparation 32-7
Ethyl(3-{3-[5-(2',5'-dimethylbiphenyl-2-yl)-2-oxopyridin-1(2H)-yl]propyl}phenoxy)acetate.
MS (ESI, m/z):518 (M+Na)+.

Preparation 32-8
Ethyl(3-{3-[5-(2',3'-dimethylbiphenyl-2-yl)-2-oxopyridin-1(2H)-yl]propyl}phenoxy)acetate.
MS (ESI, m/z):518 (M+Na)+.

Preparation 32-9
Ethyl(3-{3-[5-(2',4'-dimethylbiphenyl-2-yl)-2-oxopyridin-1(2H)-yl]propyl}phenoxy)acetate.
MS (ESI, m/z):518 (M+Na)+.

Preparation 32-10
Ethyl (3-{3-[5-(2'-methylbiphenyl-2-yl)-2-oxopyridin-1(2H)-yl]propyl}phenoxy)acetate.
MS (ESI, m/z):504 (M+Na)+.

Preparation 32-11
Ethyl[3-(3-{5-[2-(1-naphthyl)phenyl]-2-oxopyridin-1(2H)-yl}propyl)phenoxy]acetate.
MS (ESI, m/z):518 (M+H)+.

Preparation 32-12
Ethyl(3-{3-[5-(3',5'-dimethylbiphenyl-2-yl)-2-oxopyridin-1(2H)-yl]propyl}phenoxy)acetate.
MS (ESI, m/z):496 (M+H)+.

Preparation 32-13
Ethyl(3-{3-[5-(4'-tert-butylbiphenyl-2-yl)-2-oxopyridin-1(2H)-yl]propyl}phenoxy)acetate.
MS (ESI, m/z):546 (M+Na)+.

Preparation 32-14
Ethyl (3-{3-[5-(4'-fluorobiphenyl-2-yl)-2-oxopyridin-1(2H)-yl]propyl}phenoxy)acetate.
MS (ESI, m/z):508 (M+Na)+.

Preparation 32-15
2-Methoxy-5-(2'-methylbiphenyl-2-yl)pyridine.
MS (ESI, m/z):276 (M+H)+.

Preparation 32-16
5-(2-Bromophenyl)-2-methoxypyridine.
MS (ESI, m/z):264, 266 (M+H)+.

Preparation 32-17
Ethyl (3-{3-[5-(4'-methylbiphenyl-2-yl)-2-oxopyridin-1(2H)-yl]propyl}phenoxy)acetate.
MS (ESI, m/z):482 (M+H)+.

Preparation 32-18
Ethyl (3-{3-[5-(4'-chlorobiphenyl-2-yl)-2-oxopyridin-1(2H)-yl]propyl}phenoxy)acetate.
MS (ESI, m/z):524 (M+Na)+.

Preparation 33
A mixture of ethyl (3-{3-[5-(2-bromophenyl)-2-oxopyridin-1(2H)-yl]propyl}phenoxy)acetate (235 mg), (2-methoxyphenyl)boronic acid (114 mg), Na$_2$CO$_3$(159 mg), Pd(PPh$_3$)$_4$ (29 mg) in toluene (8 mL) and water (4 mL) was stirred under N$_2$ gas atmosphere at 98° C. for 30 hours and cooled to ambient temperature. The reaction mixture was extracted with EtOAc. The organic layer was washed with brine, dried over anhydrous MgSO$_4$, filtered and evaporated in vacuo. The aqueous layer of the reaction mixture was acidified with 1M HCl aqueous solution and extracted with EtOAc and the organic layer was washed with brine, dried over anhydrous MgSO$_4$, filtered and evaporated in vacuo. The filtrate and the residue of the first extract was combined and evaporated in vacuo. The residue was dissolved in EtOH (20 mL). To the solution was added concentrated H$_2$SO$_4$ (1.5 mL) at ambient temperature and refluxed for 1 hour. The reaction mixture was cooled to ambient temperature, neutralized with saturated NaHCO$_3$ aqueous solution and extracted with EtOAc. The organic layer was washed with brine, dried over anhydrous MgSO$_4$, filtered and evaporated in vacuo. The residue was purified by silica gel column chromatography (n-hexane:EtOAc=60:40) to afford ethyl (3-{3-[5-(2'-methoxybiphenyl-2-yl)-2-oxopyridin-1(2H)-yl]propyl}phenoxy)acetate (75 mg) as a colorless oil.
MS (ESI, m/z):520 (M+Na)+.

Preparation 34
A mixture of ethyl (3-{3-[5-(2-bromophenyl)-2-oxopyridin-1(2H)-yl]propyl}phenoxy)acetate (255 mg), (2,6-dimethylphenyl)boronic acid (122 mg), 2'-(dicyclohexylphosphino)-N,N-dimethylbiphenyl-2-amine (26 mg), tripotassium phosphate (345 mg) and palladium (II) acetate (4 mg) in toluene (10 mL) was stirred under N$_2$ gas atmosphere at 100° C. for 40 hours and cooled to ambient temperature. To the mixture was added 2'-(dicyclohexylphosphino)-N,N-dimethylbiphenyl-2-amine (26 mg), (2,6-dimethylphenyl)boronic acid (50 mg) and palladium (II) acetate (4 mg) and the mixture was stirred under N$_2$ gas atmosphere at 100° C. for 60 hours and cooled to ambient temperature. The reaction mixture was acidified with 1M HCl aqueous solution and extracted with EtOAc. The organic layer was washed with brine, dried over anhydrous MgSO$_4$, filtered and evaporated in vacuo. The residue was dissolved in EtOH (10 mL). To the solution was added concentrated H$_2$SO$_4$(1.5 mL) and the mixture was refluxed for 1.5 hours and cooled to ambient temperature. The reaction mixture was neutralized with saturated aqueous NaHCO$_3$ solution and extracted with EtOAc. The organic layer was washed with brine, dried over anhydrous MgSO$_4$, filtered and evaporated in vacuo. The residue was purified by silica gel column chromatography (n-hexane:EtOAc=70:30) to give ethyl (3-{3-[5-(2',6'-dimethylbiphenyl-2-yl)-2-oxopyridin-1(2H)-yl]propyl}phenoxy)acetate (55.1 mg) as a colorless oil.
MS (ESI, m/z):518 (M+Na)+.

Preparation 35
To a solution of 1-(2-aminoethyl)-5-(diphenylmethyl)-2(1H)-pyridinone (75.0 mg), a mixture of indole-4-carboxylic acid (39.7 mg), HOBt (36.6 mg) and DMF (3.0 mL) was added WSCD. HCl (52.0 mg) at ambient temperature and the mixture was stirred at the same temperature for 18 hours. The resulting mixture was diluted with water (10.0 mL) and extracted with EtOAc (15 mL). The organic layer was washed successively with 1M HCl aqueous solution, saturated NaHCO$_3$ aqueous solution and brine, dried over anhydrous MgSO$_4$, filtered and evaporated in vacuo. The residue was purified by preparative thin-layer chromatography (chloroform:MeOH=90:10) to afford N-{2-[5-(diphenylmethyl)-2-oxo-1(2H)-pyridinyl]ethyl}-1H-indole-4-carboxamide (65 mg) as a yellow amorphous powder.

$^1$H-NMR (CDCl$_3$) δ: 3.83 (2H, dt, J=5.1, 5.8 Hz), 4.21 (2H, t, J=5.8 Hz), 5.16 (1H, s), 6.55 (1H, d, J=9.4 Hz), 6.85 (1H, d, J=2.1 Hz), 6.97-7.04 (4H, m), 7.15-7.28 (10H, m), 7.31 (1H, t, J=2.8 Hz), 7.46 (1H, d, J=7.4 Hz), 7.52 (1H, d, J=8.1 Hz), 8.41-8.48 (1H, brs).

MS (ESI, m/z):448 (M+H)$^+$.

The following compound(s) was (were) obtained in a similar manner to that of Preparation 35.

Preparation 35-1

N-{2-[Benzoyl(3,3-diphenylpropyl)amino]ethyl}-1H-indole-4-carboxamide.

$^1$H-NMR (CDCl$_3$) δ: 2.24-2.37 (2H, m), 3.20-3.30 (2H, m), 3.64-3.72 (1H, m), 3.76-3.90 (2H, m), 6.98-7.40 (21H, m), 7.48-7.57 (2H, m), 8.38-8.47 (1H, brs).

MS (ESI, m/z) 502 (M+H)$^+$.

Preparation 35-2 tert-Butyl 3-[({2-[benzoyl(3,3-diphenylpropyl)amino]ethyl}amino)carbonyl]-1H-indole-1-carboxylate.

$^1$H-NMR (CDCl$_3$) δ: 1.20 (9H, s), 2.24-2.36 (2H, m), 3.20-3.30 (2H, m), 3.64-3.88 (5H, m), 6.96-7.40 (17H, m), 8.04-8.24 (3H, m).

MS (ESI, m/z):602 (M+H)$^+$.

Preparation 35-3 tert-Butyl 4-[({2-[5-(diphenylmethyl)-2-oxo-1(2H)-pyridinyl]ethyl}amino)carbonyl]-1-indolinecarboxylate.

$^1$H-NMR (CDCl$_3$) δ: 1.56 (9H, s), 3.31-3.40 (2H, m), 3.67-3.75 (2H, m), 3.90-4.00 (2H, m), 4.12-4.19 (2H, m), 5.22 (1H, s), 6.55 (1H, d, J=9.4 Hz), 6.80 (1H, d, J=1.8 Hz), 7.03-7.13 (5H, m), 7.15-7.32 (9H, m), 7.38-7.45 (1H, brs).

MS (ESI, m/z):550 (M+H)$^+$.

Preparation 35-4 tert-Butyl 4-[({2-[benzoyl(3,3-diphenylpropyl)amino]ethyl}amino)carbonyl]-1-indolinecarboxylate.

$^1$H-NMR (CDCl$_3$) δ: 1.56 (9H, s), 2.23-2.34 (2H, m), 3.18-3.27 (2H, m), 3.36-3.45 (2H, m), 3.63-3.72 (3H, m), 3.75-3.83 (2H, m), 3.92-4.01 (2H, m), 6.98-7.05 (4H, m), 7.10-7.40 (14H, m).

MS (ESI, m/z):604 (M+H)$^+$.

Preparation 35-5

3-[({2-[5-(Diphenylmethyl)-2-oxo-1(2H)-pyridinyl]ethyl}amino)carbonyl]phenyl acetate.

$^1$H-NMR (CDCl$_3$) δ: 2.31 (3H, s), 3.68-3.77 (2H, m), 4.13-4.20 (2H, m), 5.23 (1H, s), 6.57 (1H, d, J=9.4 Hz), 6.78 (1H, d, J=1.6 Hz), 7.03-7.11 (4H, m), 7.18-7.34 (8H, m), 7.43 (1H, t, J=7.9 Hz), 7.59 (1H, s), 7.64 (1H, d, J=7.9 Hz), 7.85-7.90 (1H, brs).

MS (ESI, m/z):467 (M+H)$^+$.

Preparation 36

To a solution of 3-hydroxybenzylamine (40.0 mg), 5-(diphenylmethyl)-1-carboxylmethyl-2(1H)-pyridinone (103.7 mg) and HOBt (48.3 mg) in DMF (1.6 mL) was added WSCD.HCl (68.5 mg) at ambient temperature and the mixture was stirred at the same temperature for 20 hours. The resulting mixture was diluted with water (10.0 mL) and extracted with EtOAc (15 mL) The organic layer was washed successively with 1M HCl aqueous solution, saturated NaHCO$_3$ aqueous solution and brine, dried over anhydrous MgSO$_4$, filtered and evaporated in vacuo. The residue was purified by preparative thin-layer chromatography (chloroform:MeOH=9:1) to afford 2-[5-(diphenylmethyl)-2-oxo-1(2H)-pyridinyl]-N-(3-hydroxybenzyl)acetamide (137 mg) as an off-white amorphous powder.

$^1$H-NMR (CDCl$_3$) δ: 4.32 (2H, d, J=5.1 Hz), 4.63 (2H, s), 5.28 (1H, s), 6.33 (1H, d, J=9.4 Hz), 6.47 (1H, s), 6.64 (1H, dd, J=1.8, 8.3 Hz), 6.67 (1H, d, J=8.3 Hz), 6.95 (1H, d, J=1.8 Hz), 7.06 (1H, t, J=7.8 Hz), 7.13-7.22 (5H, m), 7.25-7.38 (6H, m), 7.53-7.63 (1H, br),8.15 (1H, t, J=4.8 Hz).

MS (ESI, m/z):425 (M+H)$^+$.

Preparation 37

To a solution of methyl (2S)-2-amino-3-hydroxypropanoate hydrochloride (1.25 g), 1-(tert-butoxycarbonyl)-1H-indole-4-carboxylic acid (2.10 g) and N-ethyl-N-isopropyl-2-propanamine (2.94 mL) in DMF (25.0 mL) was added dropwise DPPA (1.91 mL) at 0° C. and the mixture was stirred at ambient temperature for 3 days. The resulting mixture was diluted with water (50.0 mL) and extracted with EtOAc (75 mL). The organic layer was washed successively with 1M HCl aqueous solution, saturated NaHCO$_3$ aqueous solution. and brine, dried over anhydrous MgSO$_4$, filtered and evaporated in vacuo. The residue was purified by silica gel column chromatography (chloroform:MeOH=99:1) to afford tert-butyl 4-({[(1S)-1-(hydroxymethyl)-2-methoxy-2-oxoethyl]amino}carbonyl)-1H-indole-1-carboxylate (2.12 g) as a colorless syrup.

$^1$H-NMR (CDCl$_3$) δ: 1.68 (9H, s), 2.56-2.63 (1H, m), 3.85 (3H, s), 4.08-4.15 (2H, m), 4.93-4.99 (1H, m), 7.10-7.17 (1H, m), 7.14 (1H, d, J=3.5 Hz), 7.36 (1H, dd, J=7.5, 8.0 Hz), 7.62 (1H, d, J=7.5 Hz), 7.70 (1H, d, J=3.5 Hz), 8.36 (1H, d, J=8.0 Hz).

MS (ESI, m/z):363 (M+H)$^+$.

The following compound(s) was (were) obtained in a similar manner to that of Example 193.

Preparation 38-1

Ethyl (3-{3-[(3,3-diphenylpropyl)(2-thienylcarbonyl)amino]propyl}phenoxy)acetate.

$^1$H-NMR (CDCl$_3$) δ: 1.29 (3H, t, J=7.1 Hz), 1.62-1.92 (2H, m), 2.35-2.55 (4H, m), 3.37-3.47 (5H, m), 4.27 (2H, q, J=7.1 Hz), 4.59, 4.63 (2H, s), 6.72-6.90 (3H, m), 6.90-7.38 (13H, m), 8.52-8.53 (1H, m).

MS (ESI, m/z):564 (M+Na)$^+$.

Preparation 38-2

Ethyl (3-{3-[(3,3-diphenylpropyl)(3-thienylcarbonyl)amino]propyl}phenoxy)acetate.

$^1$H-NMR (CDCl$_3$) δ: 1.29 (3H, t, J=7.1 Hz), 1.70-1.95 (2H, m), 2.20-2.70 (4H, m), 3.15-4.10 (5H, m), 4.27 (2H, q, J=7.1 Hz), 4.59, 4.61 (2H, s), 6.50-6.90 (3H, m), 7.00-7.35 (14H, m).

MS (ESI, m/z):564 (M+Na)$^+$.

Preparation 38-3

Ethyl (3-{3-[(3-acetamidobenzoyl)(3,3-diphenylpropyl)amino]propyl}phenoxy)acetate.

$^1$H-NMR (CDCl$_3$) δ: 1.31 (3H, t, J=6.9 Hz), 1.71-1.89 (2H, m), 2.15 (3H, s), 2.32-4.00 (9H, m), 4.29 (2H, q, J=7.1 Hz), 4.58, 4.60 (2H, s), 6.52-8.26 (19H, m).

MS (ESI, m/z):593 (M+H)$^+$.

Preparation 38-4

Ethyl [3-(3-{(3,3-diphenylpropyl)[3-(methylsulfonyl)benzoyl]amino}propyl)phenoxy]acetate.

$^1$H-NMR (CDCl$_3$) δ: 1.30 (3H, t, J=7.1 Hz), 1.72-1.74 (1H, m), 1.95-1.97 (1H, m), 2.18-2.20 (1H, m), 2.34-2.36 (1H, m), 2.42-2.44 (1H, m), 2.64-2.67 (1H, m), 3.01 (3H, s), 3.03-3.09 (2H, m), 3.42-3.55 (2H, m), 3.63-4.05 (1H, m), 4.27 (2H, q,

J=7.1 Hz), 4.57, 4.61 (2H, s), 6.57-6.85 (3H, m), 7.00-7.02 (2H, m), 7.10-7.29 (9H, m), 7.46-7.55 (2H, m), 7.85-7.94 (2H, m).

MS (ESI, m/z):614 (M+H)$^+$.

Preparation 38-5

Ethyl (3-{3-[(3,3-diphenylpropyl)(3-[(methylsulfonyl)amino]benzoyl}amino]propyl)phenoxy)acetate.

$^1$H-NMR (CDCl$_3$) δ: 1.29 (3H, t, J=7.1 Hz), 1.65-1.72 (1H, m), 1.90-1.95 (1H, m), 2.10-2.20 (1H, m), 2.34-2.42 (2H, m), 2.62-2.64 (1H, m), 2.90, 2.94 (3H, s), 3.03-3.09 (2H, m), 3.39-3.52 (2H, m), 3.60-4.05 (1H, m), 4.25-4.31 (2H, m), 4.57-4.60 (2H, m), 6.51-6.78 (3H, m), 7.00-7.41 (16H, m).

MS (ESI, m/z):629 (M+H)$^+$.

Preparation 38-6

Ethyl [3-(3-{[3-(aminosulfonyl)benzoyl](3,3-diphenylpropyl)amino}propyl)phenoxy]acetate.

$^1$H-NMR (CDCl$_3$) δ: 1.26 (3H, t, J=7.2 Hz), 1.65-1.70 (1H, m), 1.92-1.96 (1H, m), 2.16-2.18 (1H, m), 2.32-2.43 (2H, m), 2.63-2.66 (1H, m), 3.00-3.10 (2H, m), 3.41-4.05 (3H, m), 4.24-4.29 (2H, m), 4.56, 4.59 (2H, s), 6.46-6.84 (3H, m), 7.00-7.48 (15H, m), 7.75-7.87 (2H, m).

MS (ESI, m/z):615 (M+H)$^+$.

Preparation 38-7

Methyl 3-[(3,3-diphenylpropyl){3-[3-(2-ethoxy-2-oxoethoxy)phenyl]propyl}carbamoyl]benzoate.

$^1$H-NMR (CDCl$_3$) δ: 1.30 (3H, t, J=7.2 Hz), 1.72-1.96 (2H, m), 2.18-2.67 (4H, m), 3.10-3.20 (2H, m), 3.43-3.63 (3H, m), 3.93 (3H, s), 4.27 (2H, q, J=7.1 Hz), 4.56, 4.61 (2H, s), 6.56-6.85 (3H, m), 6.98-7.00 (2H, m), 7.11-7.45 (11H, m), 7.95-8.05 (2H, m).

MS (ESI, m/z):594 (M+H)$^+$.

Preparation 38-8

Ethyl [3-(3-{(3,3-diphenylpropyl)[(5-methylisoxazol-3-yl)carbonyl]amino}propyl)phenoxy]acetate.

MS (ESI, m/z):563 (M+Na)$^+$.

Preparation 38-9

Ethyl (3-{3-[(4-carbamoylbenzoyl)(3,3-diphenylpropyl)amino]propyl}phenoxy)acetate.

$^1$H-NMR (CDCl$_3$) δ: 1.30 (3H, t, J=7.1 Hz), 1.68-1.72 (1H, m), 1.92-1.95 (1H, m), 2.16-2.17 (1H, m), 2.32-2.44 (2H, m), 2.62-2.66 (1H, m), 3.05-3.11 (2H, m), 3.41-4.00 (3H, m), 4.27 (2H, q, J=7.1 Hz), 4.56, 4.60 (2H, s),6.51-6.84 (3H, m), 6.98-7.30 (15H, m), 7.72-7.74 (2H, m).

MS (ESI, m/z):601 (M+Na)$^+$.

Preparation 38-10

Ethyl [3-(3-{[4-(benzyloxy)benzoyl](3,3-diphenylpropyl)amino}propyl)phenoxy]acetate.

$^1$H-NMR (CDCl$_3$) δ: 1.29 (3H, t, J=7.1 Hz), 1.65-1.94 (2H, m), 2.15-2.65 (4H, m), 3.10-4.00 (5H, m), 4.26 (2H, q, J=7.1 Hz), 4.58 (2H, s), 5.08 (2H, s), 6.55-6.95 (5H, m), 7.00-7.46 (18H, m).

MS (ESI, m/z):664 (M+Na)$^+$.

The following compound(s) was (were) obtained in a similar manner to that of Example 194.

Preparation 39-1 tert-Butyl 4-(4-{[benzoyl(3,3-diphenylpropyl)amino]methyl}-1,3-oxazol-2-yl)-1H-indole-1-carboxylate.

$^1$H-NMR (CDCl$_3$) δ: 1.70 (9H, s), 2.39-2.55 (2H, br),3.31-3.40 (1H, br), 3.48-3.57 (1H, m), 3.69-3.78 (1H, m), 4.35-4.41 (1H, m), 4.70-4.75 (1H, m), 7.02-7.45 (16H, m), 7.60-7.78 (3H, m), 7.88-7.97 (1H, m), 8.30 (1H, d, J=8.2 Hz).

MS (ESI, m/z):612 (M+H)$^+$.

Preparation 39-2 tert-Butyl {2-[benzoyl(3,3-diphenylpropyl)amino]ethyl}carbamate.

$^1$H-NMR (CDCl$_3$) δ: 1.42 (9H, s), 2.20-2.31 (2H, m), 3.15-3.24 (2H, m), 3.35-3.43 (2H, m), 3.58-3.68 (2H, m), 5.03-5.11 (1H, br),6.98-7.40 (15H, m).

MS (ESI, m/z):459 (M+H)$^+$.

Preparation 39-3 tert-Butyl 3-{3-[benzoyl(3,3-diphenylpropyl)amino]propyl}-1H-indole-1-carboxylate.

$^1$H-NMR (CDCl$_3$) δ: 1.67 (9H, s), 1.73-1.88 (1H, m), 1.96-2.10 (1H, m), 2.12-2.28 (1H, m), 2.33-2.51 (2H, m), 2.66-2.81 (1H, m), 3.04-3.29 (2H, m), 3.37-3.50 (1H, m), 3.51-3.68 (1.5H, m), 3.91-4.06 (0.5H, m), 6.85-7.05 (2H, m), 7.05-7.6 (17H, m), 8.05-8.2 (1H, m).

MS (ESI, m/z):573 (M+H)$^+$.

Preparation 39-4 tert-Butyl 4-{(1E)-3-[benzoyl(3,3-diphenylpropyl)amino]-1-propen-1-yl}-1H-indole-1-carboxylate.

$^1$H-NMR (CDCl$_3$) δ: 1.68 (9H, s), 2.52-2.29 (2H, m), 3.24-3.22 (1H, m), 3.53-3.52 (1H, m), 4.01-3.99 (2H, m), 4.36-3.35 (1H, m), 6.13-6.08 (1H, m),6.38-6.33 (1H, m), 7.45-7.03 (18H, m), 7.63 (1H, d, J=3.5 Hz), 8.09-8.07 (1H, m)$^+$.

MS (ESI, m/z):571 (M+H)$^+$.

Preparation 39-5

N-{3-[2-(Benzyloxy)phenyl]propyl}-N-(3,3-diphenylpropyl)benzamide.

$^1$H-NMR (CDCl$_3$) δ: 1.76-1.75 (1H, m), 1.95-1.93 (1H, m), 2.13-2.11 (1H, m),2.42-2.34 (3H, m), 2.75-2.73 (1H, m), 3.16-3.09 (2H, m), 3.57-3.55 (1H, m), 3.79-3.68 (1H, m), 5.05, 4.98 (2H, s), 7.01-6.83 (5H, m), 7.46-7.44 (19H, m).

MS (ESI, m/z):540 (M+H)$^+$.

Preparation 39-6

Ethyl (3-{3-[(3,3-diphenylpropyl)(4-fluorobenzoyl)amino]propyl}phenoxy)acetate.

$^1$H-NMR (CDCl$_3$) δ: 1.30 (3H, t, J=7.1 Hz), 1.65-1.75 (1H, m), 1.85-1.95 (1H, m), 2.15-2.25 (1H, m), 2.28-2.45 (2H, m), 2.58-2.70 (1H, m), 3.10-3.20 (2H, m), 3.38-4.10 (3H, m), 4.27 (2H, q, J=7.1 Hz), 4.59 (2H, s), 6.58-6.83 (3H, m), 6.98-7.00 (4H, m), 7.15-7.28 (11H, m).

MS (ESI, m/z):576 (M+Na)$^+$.

Preparation 39-7

Ethyl (3-{3-[(3,3-diphenylpropyl)(4-methoxybenzoyl)amino]propyl}phenoxy)acetate.

$^1$H-NMR (CDCl$_3$) δ: 1.29 (3H, t, J=7.1 Hz), 1.73-1.95 (2H, m), 2.20-2.65 (4H, m), 3.10-4.00 (5H, m), 3.83 (3H, s), 4.27 (2H, q, J=7.1 Hz), 4.58, 4.60 (2H, s), 6.60-6.85 (5H, m), 7.00-7.31 (13H, m).

MS (ESI, m/z):588 (M+Na)$^+$.

Preparation 39-8

Ethyl {3-[(acetyl{2-[5-(diphenylmethyl)-2-oxopyridin-1(2H)-yl]ethyl}amino)methyl]phenoxy}acetate.

MS (ESI, m/z):539 (M+H)$^+$.

Preparation 40

1.59M n-Butyllithium solution in n-hexane (25 mL) was added dropwise to a stirred solution of 1,1'-methylenedibenzene (6.73 g) in THF (75 mL) below 35° C. under N$_2$ gas atmosphere. The reaction mixture was added dropwise to a solution of dihydrofuran-2,5-dione(2 g) in THF (50 mL) below 25° C. After stirring for 4 hours. 1M HCl aqueous solution (45 mL) and EtOAc were poured into the reaction mixture. The organic layer was separated and was washed with water and brine, and dried over anhydrous MgSO$_4$, filtered and evaporated in vacuo. The residue was purified by silica gel column chromatography (DCM:MeOH). The desired fractions were collected and evaporated in vacuo to give 4-oxo-5,5-diphenylpentanoic acid (2.48 g) as a yellow solid.

$^1$H-NMR (CDCl$_3$) δ: 2.62 (2H, t, J=7.1 Hz), 2.86 (2H, t, J=6.5 Hz), 5.16 (1H, s),7.12-7.37 (10H, m).

Preparation 41

To a stirring solution of 3-(1H-indol-3-yl)propanoic acid (0.3 g) in MeCN (9 mL) was added K$_2$CO$_3$ (0.33 g) at ambient temperature followed by addition of iodomethane (0.15 mL). After 3 hours, water was added and the mixture was extracted with EtOAc. The organic layer was washed with brine, dried over anhydrous sodium sulfate, filtered and evaporated in vacuo. The residue was purified by column chromatography (n-hexane:EtOAc=3:1) to give methyl 3-(1H-indol-3-yl)propanoate (0.32 g).

$^1$H-NMR (CDC$_3$) δ: 2.73 (2H, t, J=8.0 Hz), 3.11 (2H, t, J=8.0 Hz), 3.67 (3H, s), 6.96-7.02 (1H, m), 7.12 (1H, t, J=7.2 Hz), 7.19 (1H, t, J=7.2 Hz), 7.60 (1H, d, J=7.2 Hz), 7.99 (1H, brs).

Preparation 42

To a solution of 3-(3-hydroxyphenyl)propanoic acid (135 g) in EtOH (670 mL) was added concentrated H$_2$SO$_4$ (34.7 mL) at ambient temperature and the mixture was refluxed for 24 hours. After cooled to ambient temperature, the mixture was evaporated in vacuo. Water (400 mL) was added to the mixture and the mixture was extracted with EtOAc (600 mL). The organic layer was washed with brine, dried over anhydrous MgSO$_4$, filtered and evaporated in vacuo to afford ethyl 3-(3-hydroxyphenyl)propanoate (163 g) as a slightly yellow oil.

$^1$H-NMR (CDCl$_3$) δ: 1.24 (3H, t, J=7.1 Hz), 2.61 (2H, t, J=7.5 Hz), 2.90 (2H, t, J=7.5 Hz), 4.13 (2H, q, J=7.1 Hz), 4.32-4.58 (1H, brs),6.65-6.72 (2H, m), 6.76 (1H, d, J=7.7 Hz), 7.15-7.18 (1H, m).

The following compound(s) was (were) obtained in a similar manner to that of Preparation 42.

Preparation 42-1

Ethyl 3-(2-hydroxyphenyl)propanoate.

$^1$H-NMR (CDCl$_3$) δ: 1.23 (3H, t, J=7.0 Hz), 2.71 (2H, t, J=7.0 Hz), 2.90 (2H, t, J=7.0 Hz), 4.14 (2H, q, J=7.0 Hz), 6.86 (2H, t, J=8.0 Hz), 7.15-7.07 (2H, m).

MS (ESI, m/z):195 (M+H)$^+$.

Preparation 43

The mixture of 4-benzyl 1-tert-butyl 1H-indole-1,4-dicarboxylate (6.37 g) and 10% palladium on carbon (964 mg) in MeOH (95.6 mL) and water (3.2 mL) was hydrogenated at 3.5 atm of hydrogen for 3.5 hours. The resulting mixture was filtered through a bed of celite and the filtrate was evaporated in vacuo. The residue was dissolved in chloroform (100 mL) and the solution was dried over anhydrous MgSO$_4$, filtered and evaporated in vacuo. The residue was triturated with cold MeOH (20 mL) to give 1-(tert-butoxycarbonyl)-1H-indole-4-carboxylic acid (2.90 g) as a colorless crystals. The above filtrate was evaporated in vacuo and the residue was triturated with solvent (n-hexane:EtOAc=5:1, 12 mL) to afford 1-(tert-butoxycarbonyl)-1H-indole-4-carboxylic acid (1.31 g) as colorless crystals.

$^1$H-NMR (DMSO-d$_6$) δ: 1.64 (9H, s), 7.23 (1H, d, J=3.9 Hz), 7.43 (1H, dd, J=7.2, 8.3 Hz), 7.82 (1H, d, J=3.9 Hz), 7.88 (1H, d, J=7.2 Hz), 8.33 (1H, d, J=8.3 Hz).

MS (ESI, m/z):279 (M+H$_2$O)$^+$.

Preparation 44

To a solution of ethyl [3-(3-hydroxypropyl)phenoxy]acetate (107.4 g) in DCM (1.07 L) was added TEA (113 mL) at ambient temperature. Methanesulfonyl chloride (45.4 mL) was added dropwise to the mixture at 0° C. The mixture was stirred for 1 hour at ambient temperature and water (1 L) was added to the mixture at the same temperature. The organic layer was washed with brine, dried over anhydrous MgSO$_4$, filtered and evaporated in vacuo to afford ethyl (3-{3-[(methylsulfonyl)oxy]propyl}phenoxy)acetate (155.5 g) as a yellow oil.

$^1$H-NMR (CDCl$_3$) δ: 1.30 (3H, t, J=7.1 Hz), 2.00-2.12 (2H, m), 2.73 (2H, t, J=7.7 Hz), 3.00 (3H, s), 4.22 (2H, t, J=6.2 Hz), 4.27 (2H, q, J=7.1 Hz), 4.62 (2H, s), 6.72-6.78 (2H, m), 6.83 (1H, d, J=7.7 Hz), 7.22 (1H, t, J=7.7 Hz).

The following compound(s) was(were) obtained in a similar manner to that of Preparation 44.

Preparation 44-1

Ethyl [(2-{[(methylsulfonyl)oxy]methyl}-2,3-dihydro-1H-inden-4-yl)oxy]acetate.

Preparation 44-2

Ethyl [(3'-{[(methylsulfonyl)oxy]methyl}-3-biphenylyl)oxy]acetate.

$^1$H-NMR (CDCl$_3$) δ: 1.31 (3H, t, J=7.0 Hz), 2.96 (3H, s), 4.29 (2H, q, J=7.0 Hz), 4.69 (2H, s), 5.30 (2H, s), 6.91 (1H, dd, J=8.0, 2.5 Hz), 7.16 (1H, s), 7.23 (1H, d, J=8.0 Hz), 7.42-7.35 (2H, m), 7.49 (1H, dd, J=8.0, 8.0 Hz), 7.61-7.59 (2H, m).

MS (ESI, m/z):365 (M+H)$^+$.

Preparation 44-3

Ethyl (2-{3-[(methylsulfonyl)oxy]propyl}phenoxy)acetate.

$^1$H-NMR (CDCl$_3$) δ: 1.30 (3H, t, J=7.0 Hz), 2.17-2.08 (2H, m), 2.82 (2H, t, J=7.0 Hz), 3.00 (3H, s), 4.31-4.23 (4H, m), 4.65 (2H, s), 6.72 (1H, d, J=8.5 Hz), 6.95 (1H, d, J=8.5 Hz), 7.21-7.16 (2H, m).

Preparation 44-4

Ethyl (3-{4-[(methylsulfonyl)oxy]butyl}phenoxy)acetate.

$^1$H-NMR (CDCl$_3$) δ: 1.30 (3H, t, J=7.0 Hz), 1.77-1.74 (4H, m), 2.64 (2H, t, J=7.0 Hz), 2.99 (3H, s), 4.31-4.21 (4H, m), 4.61 (2H, s), 6.83-6.71 (3H, m), 7.21 (1H, t, J=8.0 Hz).

Preparation 44-5

3-[2-(Benzyloxy)phenyl]propyl methanesulfonate.

$^1$H-NMR (CDCl$_3$) δ: 2.12-2.03 (2H, m), 2.80 (2H, t, J=7.5 Hz), 2.91 (3H, s), 4.22 (2H, dd, J=6.5, 6.5 Hz), 5.08 (2H, s), 6.94-6.89 (2H, m), 7.22-7.15 (2H, m), 7.45-7.33 (5H, m).

Preparation 44-6

Methyl 3-(3-{3-[(methylsulfonyl)oxy]propyl}phenoxy)propanoate.

$^1$H-NMR (CDCl$_3$) δ: 2.02-2.12 (2H, m), 2.72 (2H, t, J=7.3 Hz), 2.81 (2H, t, J=6.4 Hz), 3.00 (3H, s), 3.73 (3H, s), 4.22 (2H, t, J=6.4 Hz), 4.24 (2H, t, J=6.4 Hz), 6.73-6.81 (3H, m), 7.18-7.24 (1H, m).

Preparation 44-7

Ethyl (4-{3-[(methylsulfonyl)oxy]propoxy}-1H-indol-1-yl)acetate.

Preparation 44-8

2-[5-(Diphenylmethyl)-2-oxopyridin-1(2H)-yl]ethyl methanesulfonate.

$^1$H-NMR (DMSO-d$_6$) δ: 2.29 (3H, s), 4.87 (2H, t, J=9.4 Hz), 5.04 (2H, t, J=9.4 Hz), 5.83 (1H, s), 7.15-7.40 (13H, m).

Preparation 44-9

2-[3-(Diphenylmethyl)-6-oxopyridazin-1(6H)-yl]ethyl methanesulfonate.

$^1$H-NMR (CDCl$_3$) δ: 2.81 (3H, s), 4.4-4.7 (4H, m), 5.44 (1H, s), 6.87 (1H, d, J=9.8 Hz), 7.1-7.4 (1H, m).

Preparation 44-10

Ethyl (4-fluoro-3-{3-[(methylsulfonyl)oxy]propyl}phenoxy)acetate.

$^1$H-NMR (CDCl$_3$) δ: 1.30 (3H, t, J=7.1 Hz), 2.0-2.1 (2H, m) 2.7-2.8 (2H, m), 3.01 (3H, s), 4.2-4.3 (4H, m), 4.58 (2H, s), 6.6-7.0 (3H, m).

MS (ESI, m/z):357 (M+Na)$^+$.

Preparation 44-11

Methyl (2S)-2-(4-fluoro-3-{3-[(methylsulfonyl)oxy]propyl}phenoxy)propanoate.

$^1$H-NMR (CDCl$_3$) δ: 1.60 (3H d, J=6.8 Hz), 2.0-2.1 (2H, m), 2.7-2.8 (2H, m), 3.01 (3H, s), 3.76 (3H, s), 4.22 (2H, t, J=6.3 Hz), 4.70 (1H, q, J=6.8 Hz), 6.6-7.0 (3H, m).

MS (ESI, m/z):357 (M+Na)$^+$.

Preparation 44-12

Methyl (2S)-2-(3-{3-[(methylsulfonyl)oxy]propyl}phenoxy) propanoate.

MS (ESI, m/z):339 (M+Na)$^+$.

Preparation 44-13

Methyl (2R)-2-(3-{3[(methylsulfonyl)oxy]propyl}phenoxy)propanoate.

MS (ESI, m/z):339 (M+Na)$^+$.

Preparation 44-14

Ethyl 4-(3-{3-[(methylsulfonyl)oxy]propyl}phenoxy)butanoate.

$^1$H-NMR (CDCl$_3$) δ: 1.27 (3H, t, J=7.1 Hz), 2.04-2.14 (4H, m), 2.52 (2H, t, J=7.3 Hz), 2.72 (2H, t, J=7.5 Hz), 3.00 (3H, s), 4.00 (2H, t, J=6.1 Hz), 4.15 (2H, q, J=7.1 Hz), 4.23 (2H, t, J=6.3 Hz), 6.73-6.78 (3H, m), 7.20 (1H, t, J=7.7 Hz).

MS (ESI, m/z):367 (M+Na)$^+$.

Preparation 44-15

Ethyl [3-(6-{[(methylsulfonyl)oxy]methyl}pyridin-2-yl)phenoxy]acetate.

$^1$H-NMR (CDCl$_3$) δ: 1.32 (3H, t, J=7.1 Hz), 3.12 (3H, s), 4.30 (2H, q, J=7.1 Hz), 4.72 (2H, s), 5.45 (2H, s), 6.98-7.90 (7H, m).

Preparation 44-16

3-[5-(Diphenylmethyl)-2-oxopyridin-1(2H)-yl]propyl methanesulfonate.

$^1$H-NMR (CDCl$_3$) δ: 2.43-2.51 (2H, m), 2.67 (3H, s), 4.76-4.87 (4H, m), 5.71 (1H, s), 7.08-7.36 (13H, m).

Preparation 44-17

Ethyl (3-{3-[(methylsulfonyl)oxy]propoxy}phenoxy)acetate.

$^1$H-NMR (DMSO-d$_6$) δ:1.21 (3H, t, J=7.1 Hz), 2.0-2.2 (2H, m), 3.18 (3H, s), 4.04 (2H, t, J=6.1 Hz), 4.16 (2H, q, J=7.1 Hz), 4.35 (2H, t, J=6.3 Hz), 4.75 (2H, s), 6.4-6.6 (3H, m), 7.18 (1H, t, J=8.5 Hz).

MS (ESI, m/z):355 (M+Na)$^+$.

Preparation 44-18

3-[3-(Diphenylmethyl)-6-oxopyridazin-1(6H)-yl]propyl methanesulfonate.

MS (ESI, m/z):421 (M+Na)$^+$.

Preparation 44-19

Methyl (2S)-2-(3-{4-[(methylsulfonyl)oxy]butyl}phenoxy)propanoate.

MS (ESI, m/z):353 (M+Na)$^+$.

Preparation 44-20

Ethyl 4-(4-fluoro-3-{3-[(methylsulfonyl)oxy]propyl}phenoxy)butanoate.

$^1$H-NMR (CDCl$_3$) δ: 1.26 (3H, t, J=7.1 Hz), 2.0-2.2 (4H, m), 2.50 (2H, t, J=7.3 Hz), 2.7-2.8 (2H, m), 3.01 (3H, s), 3.96 (2H, t, J=6.1 Hz), 4.15 (2H, q, J=7.1 Hz), 4.24 (2H, t, J=6.3 Hz), 6.6-7.0 (3H, m).

MS (ESI, m/z):385 (M+Na)$^+$.

Preparation 44-21

Ethyl 4-[3-({2-[(methylsulfonyl)oxy]ethyl}sulfanyl)phenoxy]butanoate.

MS (ESI, m/z):385 (M+Na)$^+$.

Preparation 44-22

Ethyl {[3'-(chloromethyl)-3-biphenylyl]oxy}acetate.

$^1$H-NMR (CDCl$_3$) δ: 1.31 (3H, t, J=7.0 Hz), 4.29 (2H, q, J=7.0 Hz), 4.65 (2H, s), 4.68 (2H, s), 6.90 (1H, dd, J=8.0, 2.0 Hz), 7.15 (1H, s), 7.22 (1H, d, J=8.0 Hz), 7.46-7.34 (3H, m), 7.52 (1H, d, J=7.5 Hz), 7.59 (1H, s).

MS (ESI, m/z):305 (M+H)$^+$.

Preparation 45

To a stirring solution of [3-(benzyloxy)-4-fluorophenyl]methanol (14 mg) in DCM (0.7 mL) was added manganese dioxide (140 mg) at ambient temperature. After 22 hours, the reaction mixture was filtered through a bed of Celite and evaporated in vacuo. The residue was purified by silica gel column chromatography (n-hexane:EtOAc=10:1) to give 3-(benzyloxy)-4-fluorobenzaldehyde (13 mg).

$^1$H-NMR (CDCl$_3$) δ: 5.21 (2H, s), 7.20-7.30 (1H, m), 7.31-7.50 (6H, m), 7.55-7.60 (1H, m), 9.90 (1H, s).

Preparation 46

To a solution of 2-[3-(benzyloxy)phenyl]ethanol (700 mg) in DCM (10 mL) was added Dess-Martin periodinane (1.43 g) at 0° C. The reaction mixture was stirred for 5 hours at ambient temperature. The mixture was diluted with diethylether (25 mL), and the resulting suspension was added to saturated NaHCO$_3$ aqueous solution (15 mL) and saturated sodium thiosulfate aqueous solution (15 mL). After the mixture was stirred for 10 minutes, the organic layer was washed with brine. The organic layer was dried over anhydrous MgSO$_4$, filtered and evaporated in vacuo. The residue was purified by silica gel column chromatography (n-hexane:EtOAc=90:10-70:30) to give a [3-(benzyloxy)phenyl]acetaldehyde.

$^1$H-NMR (CDCl$_3$) δ: 3.65 (2H, d, J=2.0 Hz), 5.06 (2H, s), 6.85-6.81 (2H, m), 6.92 (1H, d, J=8.5 Hz), 7.45-7.25 (6H, m), 9.73 (1H, t, J=2.0 Hz).

Preparation 47

To a solution of ethyl [3-({3-[5-(diphenylmethyl)-2-oxopyridin-1(2H)-yl]propyl}sulfanyl)phenoxy]acetate (320 mg) in DCM (7 mL) was added 3-chloroperoxybenzoic acid (307 mg) at 0° C. The reaction mixture was stirred at ambient temperature for 2 days. The resulting mixture was extracted with EtOAc. The organic layer was washed with saturated NaHCO$_3$ aqueous solution and brine, dried over anhydrous MgSO$_4$, filtered and evaporated in vacuo. The residue was purified by silica gel column chromatography (n-hexane:EtOAc=1:1-1:2) to afford ethyl [3-({3-[5-(diphenylmethyl)-2-oxopyridin-1(2H)-yl]propyl}sulfonyl)phenoxy]acetate (236 mg) as a colorless oil.

MS (ESI, m/z):568 (M+Na)$^+$.

The following compound(s) was (were) obtained in a similar manner to that of Preparation 47.

Preparation 47-1

Ethyl 2-[3-({3-[5-(diphenylmethyl)-2-oxopyridin-1(2H)-yl]propyl]sulfonyl)phenoxy}propanoate.

MS (ESI, m/z):582 (M+Na)$^+$.

Preparation 48

To a solution of ethyl 2-[3-({3-[5-(diphenylmethyl)-2-oxopyridin-1(2H)-yl]propyl}sulfanyl)phenoxy]propanoate (175 mg) in DCM (5 mL) was added 3-chloroperoxybenzoic acid (82 mg) at 0° C. for 20 minutes. The resulting mixture was extracted with EtOAc. The organic layer was washed with saturated NaHCO$_3$ aqueous solution and brine, dried over anhydrous MgSO$_4$, filtered and evaporated in vacuo. The residue was purified by silica gel column chromatography (n-hexane: EtOAc=1:1-1:10) to afford ethyl 2-[3-({3-[5-(diphenylmethyl)-2-oxopyridin-1(2H)-yl]propyl}sulfinyl)phenoxy]propanoate (170 mg) as a colorless oil.

MS (ESI, m/z):566 (M+Na)$^+$.

Preparation 49

To the mixture of ethyl [3-({3-[3-(diphenylmethyl)-6-oxopyridazin-1(6H)-yl]propyl}sulfanyl)phenoxy]acetate (90 mg) and tetra-n-butylammonium hydrogensulfate (8.90 mg) in EtOAc (5 mL) were added water (3 mL) and 2 $KHSO_5 \cdot KHSO_4 \cdot K_2SO_4$ (OXONE (registered trademark)) (323 mg). And then, the mixture was stirred at ambient temperature for 15 hours. The mixture was extracted with EtOAc. The organic layer was washed with water and brine, dried over anhydrous $MgSO_4$, filtered and evaporated in vacuo. The residue was purified by silica gel column chromatography (n-hexane:EtOAc=1:1) to give ethyl [3-({3-[3-(diphenylmethyl)-6-oxopyridazin-1(6H)-yl]propyl}sulfonyl)phenoxy]acetate (89.7 mg).

MS (ESI, m/z):547 (M+H)$^+$.

The following compound(s) was (were) obtained in a similar manner to that of Preparation 49.

Preparation 49-1

Methyl (2S)-2-[3-({3-[3-(diphenylmethyl)-6-oxopyridazin-1(6H)-yl]propyl}sulfonyl)phenoxy]propanoate.

MS (ESI, m/z):547 (M+H)$^+$.

Preparation 50

To a solution of ethyl 3-(3-hydroxyphenyl)propanoate (54.5 g) in DCM (926 mL) was added dropwise 1.0 M DIBAL in DCM (926 mL) at 0° C. over 1 hour under $N_2$ gas atmosphere. 30% Rochelle salt aqueous solution (1.34 L) was added to the reaction mixture with dropping funnel at the same temperature. The resulting mixture was stirred for 7 hours at ambient temperature and the organic layer was separated. The aqueous layer was stand for 2 days and extracted with chloroform(1.5 L) 4 times. The combined organic layer was washed with brine, dried over anhydrous $MgSO_4$, filtered and evaporated in vacuo to afford 3-(3-hydroxypropyl)phenol (40.2 g) as a yellow oil.

$^1$H-NMR (CDCl$_3$) δ: 1.31-1.42 (1H, brs),1.84-1.94 (2H, m), 2.67 (2H, t, J=8.1 Hz), 3.68 (2H, t, J=6.4 Hz), 5.02-5.06 (1H, brs),6.63-6.70 (2H, m), 6.77 (1H, d, J=7.5 Hz), 7.15 (1H, t, J=7.5 Hz).

The following compound(s) was (were) obtained in a similar manner to that of Preparation 50.

Preparation 50-1

3-[(1E)-3-Hydroxy-1-propen-1-yl]phenol.

$^1$H-NMR (DMSO-d$_6$) δ: 4.12-4.08 (2H, m), 4.86 (1H, t, J=5.5 Hz), 6.31-6.26 (1H, m), 6.45 (1H, d, J=16.0 Hz), 6.64-6.61 (1H, m), 6.84-6.78 (2H, m), 7.11 (1H, t, J=7.5 Hz), 9.37 (1H, s).

Preparation 50-2

2-(3-Hydroxypropyl)phenol.

$^1$H-NMR (CDCl$_3$) δ: 1.92-1.84 (2H, m), 2.78 (2H, t, J=7. Hz), 3.64 (2H, t, J=7.0 Hz), 6.89-6.82 (2H, m), 7.13-7.07 (2H, m).

Preparation 50-3

(2E)-4-[3-(Benzyloxy)phenyl]-2-buten-1-ol.

$^1$H-NMR (CDCl$_3$) δ: 3.36 (2H, d, J=6.0 Hz), 4.12 (2H, brs),5.05 (2H, s), 5.89-5.65 (2H, m), 6.84-6.78 (3H, m), 7.24-7.19 (1H, m), 7.45-7.32 (5H, m).

Preparation 50-4

4-Fluoro-3-(3-hydroxypropyl)phenol.

$^1$H-NMR (DMSO-d$_6$): 1.6-1.7 (2H, m), 2.4-2.6 (2H, m), 3.3-3.5 (2H, m), 4.48 (1H, brs),6.5-7.0 (3H, m), 9.22 (1H, s).

MS (ESI, m/z):169 (M−H)$^-$.

Preparation 51

To a solution of tert-butyl 4-[(1E)-3-ethoxy-3-oxo-1-propen-1-yl]-1H-indole-1-carboxylate (1.2 g) in DCM (12 mL) was added 1M DIBAL in DCM (4 mL) at 0° C. The reaction mixture was stirred at 0° C. for 8 hours. The resulting mixture was quenched with Roschelle salt aqueous solution and the organic layer was washed successively with water and brine. The organic layer was dried over anhydrous $MgSO_4$, filtered and evaporated in vacuo. The residue was purified by silica gel column chromatography (n-hexane:EtOAc=80:20-50:50) to give a tert-butyl 4-[(1E)-3-hydroxy-1-propen-1-yl]-1H-indole-1-carboxylate.

$^1$H-NMR (CDCl$_3$) δ: 1.68 (9H, s), 4.40 (2H, d, J=6.0 Hz), 6.49 (1H, dt, J=15.0, 6.0 Hz), 6.76 (1H, d, J=3.5 Hz), 6.98 (1H, d, J=15.0 Hz), 7.28 (1H, t, J=7.5 Hz), 7.37 (1H, d, J=7.5 Hz), 7.62 (1H, d, J=3.5 Hz), 8.07 (1H, d, J=7.5 Hz).

MS (ESI, m/z):529 (M+H)$^+$.

The following compound(s) was (were) obtained in a similar manner to that of Preparation 51.

Preparation 51-1 tert-Butyl 4-(hydroxymethyl)-1H-indole-1-carboxylate.

$^1$H-NMR (CDCl$_3$) δ: 1.67 (9H, s), 4.93 (2H, s), 6.71 (1H, d, J=4.0 Hz), 7.32-7.21 (2H, m), 7.62 (1H, d, J=4.0 Hz), 8.11 (1H, d, J=8.0 Hz).

MS (ESI, m/z):477 (M+H)$^+$.

Preparation 51-2

(2E)-3-[3-(Benzyloxy)-4-fluorophenyl]-2-propen-1-ol.

$^1$H-NMR (CDCl$_3$) δ: 1.45 (1H, t, J=5.8 Hz), 4.27-4.34 (2H, m), 5.15 (2H, s), 6.23 (1H, ddd, J=15.8, 5.8, 5.2 Hz), 6.53 (1H, d, J=15.8 Hz), 6.88-7.95 (1H, m), 7.00-7.08 (2H, m), 7.10-7.48 (5H, m).

Preparation 52

To a stirring solution of tert-butyl 3-(3-methoxy-3-oxopropyl)-1H-indole-1-carboxylate (50 mg) was added lithium aluminum hydride (6 mg) at 0° C. After 1 hour, to the mixture was added water, and the resulting mixture was extracted with EtOAc. The organic layer was washed with brine, dried over anhydrous sodium sulfate, filtered and evaporated in vacuo. The residue was purified by silica gel column chromatography (n-hexane:EtOAc=5:1) to give tert-butyl 3-(3-hydroxypropyl)-1H-indole-1-carboxylate (45 mg).

$^1$H-NMR (CDCl$_3$) δ: 1.67 (9H, s), 1.92-2.04 (2H, m), 2.79 (2H, t, J=7.5 Hz), 3.68-3.78 (2H, m), 7.2-7.4 (3H, m), 7.53 (1H, d, J=7.6 Hz), 8.12 (1H, d, J=7.6 Hz).

MS (ESI, m/z):276 (M+H)$^+$

The following compound(s) was (were) obtained in a similar manner to that of Preparation 52.

Preparation 52-1

[3-(Benzyloxy)-4-fluorophenyl]methanol.

$^1$H-NMR (CDCl$_3$) δ: 4.61 (2H, s), 5.14 (2H, s), 6.87 (1H, m), 7.02-7.12 (2H, m), 7.28-7.48 (5H, m).

Preparation 52-2 tert-Butyl 4-(3-hydroxypropyl)-1H-indole-1-carboxylate.

$^1$H-NMR (CDCl$_3$) δ: 1.30 (1H, t, J=5.3 Hz), 1.67 (9H, s), 2.96 (2H, t, J=7.5 Hz), 3.79 (2H, dt, J=6.5, 5.3 Hz), 6.64 (1H, d, J=3.6 Hz), 7.06 (1H, d, J=7.3 Hz), 7.24 (1H, dd, J=8.4, 7.3 Hz), 7.60 (1H, d, J=3.6 Hz), 8.01 (1H, d, J=8.4 Hz).

Preparation 53

To a solution of tert-butyl 4-[4-(methoxycarbonyl)-1,3-oxazol-2-yl]-1H-indole-1-carboxylate (512 mg) in DCM (10.2 mL) was added dropwise 1M DIBAL in DCM solution (4.2 mL) at 0° C. and the mixture was stirred at the same temperature for 1.5 hours. 1M DIBAL in DCM solution (0.60 mL) was added dropwise to the mixture. The mixture was stirred at 0° C. for 1.5 hours. To the resulting solution was added dropwise 1M Rochelle salt aqueous solution (25.0 mL) and the suspension was stirred at ambient temperature for overnight. The suspension was diluted with chloroform (50.0 mL) and filtered through a bed of celite. The layers were separated and the organic layer was washed with 0.5 M Rochelle salt solution, dried over anhydrous $MgSO_4$, filtered and evaporated in vacuo. The residue was purified by silica gel column chromatography (n-hexane:EtOAc=2:1) to give tert-butyl 4-[4-(hydroxymethyl)-1,3-oxazol-2-yl]-1H-indole-1-carboxylate.

$^1$H-NMR (CDCl$_3$) δ: 1.69 (9H, s), 2.17 (1H, t, J=6.0 Hz), 4.72 (2H, d, J=6.0 Hz), 7.39 (1H, dd, J=7.6, 8.2 Hz), 7.43 (1H, d, J=3.8 Hz), 7.71 (1H, d, J=3.8 Hz), 7.72 (1H, s), 7.96 (1H, d, J=7.6 Hz), 8.30 (1H, d, J=8.2 Hz).

MS (ESI, m/z):315 (M+H)$^+$.

Preparation 54

To a solution of 3-[3-(3-ethoxy-3-oxopropyl)phenyl]propanoic acid (10.7 g) and TEA (6.28 mL) in THF (100 mL) was added isobutyl chloroforamate (5.82 mL) dropwise at 0° C. The reaction mixture was stirred at the same temperature for 5 minutes and filtered. And the precipitate was and rinsed with THF (50 mL). The filtrate and the rinse liquid were combined and the resultant mixture was cooled at 0° C. To the resultant mixture was added sodium borohydride (2.43 g) followed by adding water (1.21 mL) dropwise at the same temperature. The reaction mixture was quenched and extracted with EtOAc. The organic layer was washed with brine, dried over anhydrous MgSO$_4$, filtered and evaporated in vacuo. The residue was purified by silica gel column chromatography (n-hexane:EtOAc=7:3) to afford ethyl 3-[3-(3-hydroxypropyl)phenyl]propanoate (5.60 g) a colorless oil.

MS (ESI, m/z):259 (M+Na)$^+$.

Preparation 55

To a solution of {3-[3-(benzyloxy)phenyl]propoxy}(tert-butyl)dimethylsilane (2.90 g) in MeOH (30 mL) was added 10% palladium on carbon (300 mg) and the mixture was stirred at ambient temperature for 3 hours under hydrogen atmosphere (3 atm). The mixture was filtered through a bed of Celite. The filtrate was evaporated in vacuo to afford 3-(3-{[tert-butyl(dimethyl)silyl]oxy}propyl)phenol (1.78 g) as a colorless oil.

$^1$H-NMR (DMSO-d$_6$) δ: 0.07 (6H, s), 0.92 (9H, s), 1.68-1.80 (2H, m), 2.52-2.56 (2H, m), 3.61 (2H, t, J=6.4 Hz), 6.57-6.64 (3H, m), 7.08 (1H, t, J=8.2 Hz).

Preparation 56

To a solution of methyl (2E)-3-[3-(3-hydroxypropyl)phenoxy]acrylate (300 mg) in MeOH (4.0 mL) was added 10% palladium on carbon (50 mg) at ambient temperature and the mixture was stirred at ambient temperature for 4 hours under hydrogen atmosphere (3 atms). The mixture was filtered through a bed of celite. The filtrate was evaporated in vacuo to afford methyl 3-[3-(3-hydroxypropyl)phenoxy]propanoate (275 mg) as a colorless oil.

$^1$H-NMR (CDCl$_3$) δ: 1.84-1.94 (2H, m), 2.68 (2H, t, J=7.9 Hz), 2.80 (2H, t, J=6.4 Hz), 3.47-3.51 (1H, brs),3.63-3.71 (2H, m), 3.73 (3H, s), 4.24 (2H, t, J=6.4 Hz), 6.71-6.83 (3H, m), 7.20 (1H, t, J=7.5 Hz).

Preparation 57

To a solution of ethyl [4-(benzyloxy)-2-methyl-1H-benzimidazol-1-yl]acetate (2.57 g) in a mixture of EtOH (25.7 mL) and THF (12.9 mL) was added 10% palladium on carbon (50% wet, 0.78 g) at ambient temperature, and the resultant mixture was hydrogenated under atmospheric pressure of hydrogen for 2 hours. The catalyst was removed by filtration and evaporated in vacuo to give crude solid. The crude solid was recrystallized from solvent (EtOAc:n-hexane) to give ethyl (4-hydroxy-2-methyl-1H-benzimidazol-1-yl)acetate (1.73 g) as a white solid.

$^1$H-NMR (DMSO-d$_6$) δ: 1.21 (3H, t, J=7.1 Hz), 2.43 (3H, s), 4.17 (2H, q, J=7.1 Hz), 5.10 (2H, s), 6.51 (1H, dd, J=0.9, 7.7 Hz), 6.84 (1H, dd, J=0.8, 8.1 Hz), 6.94 (1H, t, J=7.9 Hz), 9.67 (1H, brs).

MS (ESI, m/z):235 (M+H)$^+$.

Preparation 58

To a solution of (2E)-4-[3-(benzyloxy)phenyl]-2-buten-1-ol (650 mg) in EtOH (6 mL) was added 10% palladium on carbon (70 mg) at ambient temperature. The reaction mixture was stirred for 5 hours under hydrogen atmosphere (3 atm). The resulting mixture was filtered through a bed of Celite. The filtrate was evaporated in vacuo and the residue was purified by silica gel column chromatography (n-hexane:EtOAc=90:10-70:30) to give a 3-(4-hydroxybutyl)phenol.

$^1$H-NMR (CDCl$_3$) δ: 1.76-1.57 (4H, m), 2.59 (2H, t, J=7.0 Hz), 3.67 (2H, t, J=6.5 Hz), 5.60 (1H, brs),6.67-6.64 (2H, m), 6.74 (1H, d, J=7.5 Hz), 7.16-7.11 (1H, m).

The following compound(s) was (were) obtained in a similar manner to that of Preparation 58.

Preparation 58-1

1-(tert-Butoxycarbonyl)-1H-indole-3-carboxylic acid.

$^1$H-NMR (CDCl$_3$) δ: 1.70 (9H, s), 7.32-7.44 (2H, m), 8.16-8.24 (2H, m), 8.39 (1H, s).

Preparation 58-2 tert-Butyl 4-(3-methoxy-3-oxopropyl)-1H-indole-1-carboxylate.

$^1$H-NMR (CDCl$_3$) δ: 1.67 (9H, s), 2.71 (2H, t, J=7.9 Hz), 3.20 (2H, t, J=7.9 Hz), 3.67 (3H, s), 6.63 (1H, d, J=4.0 Hz), 7.05 (1H, d, J=7.3 Hz), 7.24 (1H, dd, J=8.2, 7.3 Hz), 7.61 (1H, d, J=4.0 Hz), 8.02 (1H, d, J=8.2 Hz).

Preparation 58-3

2-Fluoro-5-(3-hydroxypropyl)phenol.

$^1$H-NMR (CDCl$_3$-CD$_3$OD (10:1), δ):1.76-1.88 (2H, m), 2.60 (2H, t, J=7.4 Hz), 3.60 (2H, t, J=6.6 Hz), 6.60 (1H, ddd, J=8.0, 4.5, 2.2 Hz), 6.77 (1H, dd, J=8.5, 2.2 Hz), 6.93 (1H, dd, J=11.0, 8.0 Hz).

Preparation 58-4

N-(3,3-Diphenylpropyl)-N-[3-(2-hydroxyphenyl)propyl]benzamide.

$^1$H-NMR (CDCl$_3$) δ: 1.70-1.75 (1H, m), 1.96-1.93 (1H, m), 2.21-2.19 (1H, m),2.43-2.34 (2H, m), 2.70-2.67 (1H, m), 3.18-3.17 (2H, m), 3.45-3.42 (1H, m), 3.56-3.52 (1H, m), 3.64, 3.99 (1H, t, J=7.5 Hz), 5.28, 6.27 (1H, brs),7.38-6.64 (19H, m).

MS (ESI, m/z):450 (M+H)$^+$.

Preparation 59

To a solution of (2E)-3-{3-[(1E)-3-ethoxy-3-oxo-1-propen-1-yl]phenyl}acrylic acid (10.40 g) in a mixed solvent (THF:EtOAc=150 mL:100 mL) was added 10% Palladium on activated carbon (50% wet, 1.6 g) at ambient temperature. The reaction mixture was stirred under hydrogen atmosphere at ambient temperature for 5 hours and was filtered through celite. The filtrate was evaporated in vacuo to afford 3-[3-(3-ethoxy-3-oxopropyl)phenyl]propanoic acid (10.57 g) as a colorless oil.

MS (ESI, m/z):249 (M−H)$^-$.

The following compound(s) was (were) obtained in a similar manner to that of Preparation 59.

Preparation 59-1

Ethyl 3-(2-fluoro-5-methoxyphenyl)propanoate.

$^1$H-NMR (DMSO-d$_6$) δ: 1.15 (3H, t, J=7.1 Hz), 2.60 (2H, t, J=7.6 Hz), 2.83 (2H, t, J=7.6 Hz), 3.71 (3H, s), 4.05 (2H, q, J=7.1 Hz), 6.7-7.1 (3H, m).

MS (ESI, m/z):249 (M+Na)$^+$.

Preparation 60

5-(Diphenylmethyl)-1-[3-(3-hydroxyphenyl)propyl]pyridin-2(1H)-one (1 g) in EtOH (20 mL) was added dioxoplatinum (70 mg) at ambient temperature and the mixture was stirred at ambient temperature for 1 day under hydrogen atmosphere. The mixture was filtered through a bed of celite. The filtrate was evaporated in vacuo. The residue was purified by silica gel column chromatography (n-hexane:EtOAc=1:3)

to afford 5-(diphenylmethyl)-1-[3-(3-hydroxyphenyl)propyl]piperidin-2-one (550 mg) as a yellow oil.

MS (ESI, m/z):422 (M+Na)+

Preparation 61

To the mixture of 1-{3-[3-(benzyloxy)phenyl]propyl}-5-(diphenylmethyl)pyridin-2(1H)-one (200 mg) and TFA (3.0 mL) was added 1,2,3,4,5-pentamethylbenzene (305 mg) at ambient temperature. After stirring for 12 hours, the resulting mixture was evaporated in vacuo and 10% $K_2CO_3$ aqueous solution was added to the residue. The aqueous solution was extracted with EtOAc The organic layer was washed with brine, dried over anhydrous $MgSO_4$, filtered and evaporated in vacuo. The residue was purified by silica gel column chromatography (n-hexane:EtOAc=1:1-1:2) to give a 5-(diphenylmethyl)-1-[3-(3-hydroxyphenyl) propyl]pyridin-2(1H)-one (147 mg) as a colorless oil.

MS (ESI, m/z):418 (M+Na)+.

Preparation 62

To a solution of tert-butyl 4-[(1E)-3-hydroxy-1-propen-1-yl]-1H-indole-1-carboxylate (300 mg) and TEA (167 mg) in DCM (6 mL) was added methanesulfonyl chloride (138 mg) at 0° C. The reaction mixture was stirred for 7 hours at ambient temperature. The resulting mixture was diluted with EtOAc and washed successively with water and brine. The organic layer was dried over anhydrous $MgSO_4$, filtered and evaporated in vacuo to give a tert-butyl 4-[(1E)-3-chloro-1-propen-1-yl]-1H-indole-1-carboxylate.

$^1$H-NMR (CDCl$_3$) δ: 1.68 (9H, s), 4.32 (2H, d, J=7.0 Hz), 6.44 (1H, dt, J=15.5, 7.0 Hz), 6.74 (1H, d, J=3.5 Hz), 7.00 (1H, d, J=15.5 Hz), 7.30 (1H, t, J=7.5 Hz), 7.37 (1H, d, J=7.5 Hz), 7.63 (1H, d, J=3.5 Hz), 8.07 (1H, d, J=7.5 Hz).

The following compound(s) was (were) obtained in a similar manner to that of Preparation 62.

Preparation 62-1 tert-Butyl 4-(chloromethyl)-1H-indole-1-carboxylate.

$^1$H-NMR (CDCl$_3$) δ: 1.68 (9H, s), 4.86 (2H, s), 6.74 (1H, d, J=3.5 Hz), 7.31-7.22 (2H, m), 7.67 (1H, d, J=3.5 Hz), 8.15 (1H, d, J=8.0 Hz).

Preparation 62-2

1-(2-Chloroethyl)-5-(diphenylmethyl)-2(1H)-pyridinone.

$^1$H-NMR (CDCl$_3$) δ: 3.84 (2H, t, J=5.6 Hz), 4.12 (2H, t, J=5.6 Hz), 5.26 (1H, s), 6.53 (1H, d, J=9.0 Hz), 6.80 (1H, d, J=2.5 Hz), 7.08-7.40 (11H, m).

MS (ESI, m/z):324 (M+H)+.

Preparation 62-3

Ethyl {3-[(1E)-3-chloro-1-propen-1-yl]phenoxy}acetate.

$^1$H-NMR (CDCl$_3$) δ: 1.3 (3H, t, J=7.0 Hz), 4.32-4.23 (4H, m), 4.63 (2H, s), 6.30 (1H, dt, J=15.0, 7.0 Hz), 6.62 (1H, d, J=15.0 Hz), 6.87-6.80 (1H, m), 6.94 (1H, s), 7.03 (1H, d, J=7.0 Hz), 7.28-7.23 (1H, m).

Preparation 63

To a solution of tert-butyl 4-[4-(hydroxymethyl)-1,3-oxazol-2-yl]-1H-indole-1-carboxylate (330 mg) and PPh$_3$ (330 mg) in DCM (6.6 mL) was added portionwise carbon tetrabromide (418 mg) at ambient temperature and the mixture was stirred at the same temperature for 4 hours. The resulting mixture was evaporated in vacuo and the residue was purified by silica gel column chromatography(n-hexane:EtOAc=5:1) to afford tert-butyl 4-[4-(bromomethyl)-1,3-oxazol-2-yl]-1H-indole-1-carboxylate (396 mg) as a white solid.

$^1$H-NMR (CDCl$_3$) δ: 1.69 (9H, s), 4.50 (2H, s), 7.39 (1H, dd, J=7.6, 8.3 Hz), 7.44 (1H, d, J=3.7 Hz), 7.72 (1H, d, J=3.7 Hz), 7.78 (1H, s), 7.96 (1H, d, J=7.6 Hz), 8.31 (1H, d, J=8.3 Hz).

MS (ESI, m/z):377 (M+H)+.

Preparation 64

To a solution of ethyl (3-{3-[(methylsulfonyl)oxy]propyl}phenoxy)acetate (155 g) in acetone (1.55 L) was added sodium iodide (293.7 g) at ambient temperature and the mixture was stirred at the same temperature for 18 hours. EtOAc (1 L) was added to the mixture at ambient temperature and the resulting mixture was washed successively with water and brine. The organic layer was dried over anhydrous MgSO$_4$, filtered and evaporated in vacuo to afford ethyl [3-(3-iodopropyl)phenoxy]acetate (142 g) as a red oil.

$^1$H-NMR (CDCl$_3$) δ: 1.31 (3H, t, J=7.1 Hz), 2.05-2.17 (2H, m), 2.71 (2H, t, J=7.3 Hz), 3.16 (2H, t, J=6.8 Hz), 4.28 (2H, q, J=7.1 Hz), 4.62 (2H, s), 6.70-6.80 (2H, m), 6.84 (1H, d, J=7.7 Hz), 7.21 (1H, t, J=7.7 Hz).

MS (ESI, m/z):349 (M#H)+.

The following compound(s) was (were) obtained in a similar manner to that of Preparation 64.

Preparation 64-1

Ethyl {[2-(iodomethyl)-2,3-dihydro-1H-inden-4-yl]oxy}acetate.

$^1$H-NMR (CDCl$_3$) δ: 1.29 (3H, t, J=7.1 Hz), 2.6-2.9 (3H, m), 3.05-3.25 (2H, m), 3.25-3.45 (2H, m), 4.26 (2H, q, J=7.1 Hz), 4.63 (2H, s), 6.54 (1H, d, J=8.1 Hz), 6.84 (1H, d, J=7.5 Hz), 7.1 (1H, dd, J=8.1, 7.5 Hz).

Preparation 64-2

Methyl 3-[3-(3-iodopropyl)phenoxy]propanoate.

$^1$H-NMR (CDCl$_3$) δ: 2.12 (2H, quint, J=7.4 Hz), 2.70 (2H, t, J=7.4 Hz), 2.81 (2H, t, J=6.4 Hz), 3.17 (2H, t, J=7.4 Hz), 3.74 (3H, s), 4.25 (2H, t, J=6.4 Hz), 6.74-6.82 (3H, m), 7.20 (1H, dd, J=7.5, 8.8 Hz).

Preparation 64-3

1-(Benzyloxy)-3-(3-iodopropyl)benzene.

$^1$H-NMR (CDCl$_3$) δ: 2.07-2.16 (2H, m), 2.70 (2H, t, J=7.2 Hz), 3.15 (2H, t, J=7.2 Hz), 5.05 (2H, s), 6.77-6.85 (3H, m), 7.17-7.46 (6H, m).

Preparation 64-4

Ethyl [3-(3-iodopropoxy)phenoxy]acetate.

$^1$H-NMR (DMSO-d$_6$) δ:1.21 (3H, t, J=7.1 Hz), 2.1-2.2 (2H, m), 3.37 (2H, t, J=6.8 Hz), 4.00 (2H, t, J=5.9 Hz), 4.16 (2H, q, J=7.1 Hz), 4.75 (2H, s), 6.4-6.6 (3H, m), 7.18 (1H, t, J=8.5 Hz).

MS (ESI, m/z):387 (M+Na)+.

Preparation 64-5

Ethyl [4-fluoro-3-(3-iodopropyl)phenoxy]acetate.

$^1$H-NMR (DMSO-d$_6$) δ:1.21 (3H, t, J=7.1 Hz),1.9-2.1 (2H, m), 2.6-2.7 (2H, m), 3.25 (2H, t, J=6.8 Hz), 4.16 (2H, q, J=7.1 Hz), 4.75 (2H, s), 6.7-7.1 (3H, m).

MS (ESI, m/z):389 (M+Na)+.

Preparation 64-6

Methyl (2S)-2-[4-fluoro-3-(3-iodopropyl)phenoxy]propanoate.

$^1$H-NMR (DMSO-d$_6$) δ: 1.48 (3H, d, J=6.7 Hz), 1.9-2.1 (2H, m), 2.6-2.7 (2H, m), 3.2-3.3 (2H, m), 3.67 (3H, s), 4.95 (1H, q, J=6.7 Hz), 6.7-7.1 (3H, m).

MS (ESI, m/z):389 (M+Na)+.

Preparation 64-7

Ethyl 4-[4-fluoro-3-(3-iodopropyl)phenoxy]butanoate.

$^1$H-NMR (DMSO-d$_6$) δ: 1.18 (3H, t, J=7.1 Hz),1.9-2.1 (4H, m), 2.44 (2H, t, J=7.3 Hz), 2.6-2.7 (2H, m), 3.26 (2H, t, J=6.8 Hz), 3.94 (2H, t, J=6.3 Hz), 4.06 (2H, q, J=7.1 Hz), 6.7-7.1 (3H, m).

MS (ESI, m/z):417 (M+Na)+.

Preparation 64-8

Methyl (2S)-2-[3-(4-iodobutyl)phenoxy]propanoate.

MS (ESI, m/z):385 (M+Na)+.

Preparation 64-9

Methyl (2R)-2-[3-(3-iodopropyl)phenoxy]propanoate.

MS (ESI, m/z):371 (M+Na)$^+$.

Preparation 64-10

Ethyl 4-[3-(3-iodopropyl)phenoxy]butanoate.

$^1$H-NMR (CDCl$_3$) δ: 1.26 (3H, t, J=7.1 Hz), 2.04-2.15 (4H, m), 2.52 (2H, t, J=7.3 Hz), 2.69 (2H, t, J=7.3 Hz), 3.17 (2H, t, J=6.8 Hz), 4.00 (2H, t, J=6.1 Hz), 4.15 (2H, q, J=7.1 Hz), 6.73-6.79 (3H, m), 7.17-7.22 (1H, m).

MS (ESI, m/z):399 (M+Na)$^+$.

Preparation 64-11

Methyl (2S)-2-[3-(3-iodopropyl)phenoxy]propanoate.

$^1$H-NMR (CDCl$_3$) δ: 1.62 (3H, d, J=6.8 Hz), 2.04-2.14 (2H, m), 2.66-2.73 (2H, m), 3.11-3.18 (2H, m), 3.76 (3H, s), 4.77 (1H, q, J=6.8 Hz), 6.67-6.75 (2H, m), 6.81-6.83 (1H, m), 7.20 (1H, t, J=7.9 Hz).

MS (ESI, m/z):371 (M+Na)$^+$.

Preparation 64-12

Ethyl [3-(4-iodobutyl)phenoxy]acetate.

MS (ESI, m/z):385 (M+Na)$^+$.

Preparation 64-13

Ethyl 4-{3-[(2-iodoethyl)sulfanyl]phenoxy}butanoate.

MS (ESI, m/z):417 (M+Na)$^+$.

Preparation 65

To a solution of ethyl 3-[3-(3-hydroxypropyl)phenyl]propanoate (5.20 g) in DCM (100 mL) was added TEA (4.3 mL) at ambient temperature. Methanesulfonyl chloride (2.0 mL) was added dropwise to the mixture at 0° C. The mixture was stirred at the same temperature for 1 hour. To the reaction mixture was added water and was extracted with EtOAc. The organic layer was washed with brine, dried over anhydrous MgSO$_4$, filtered and evaporated in vacuo. The residue was azeotropized with toluene and the crude methanesulfonate was dissolved in acetone (120 mL). To a solution of the methanesulfonate in acetone was added sodium iodide (13.2 g) at ambient temperature. The reaction mixture was stirred at the same temperature for 14 hours. The reaction mixture was evaporated in vacuo, diluted with water and extracted with EtOAc. The organic layer was washed with brine, dried over anhydrous MgSO$_4$, filtered and evaporated in vacuo. The residue was purified by silica gel column chromatography (n-hexane:EtOAc=9:1) to afford ethyl 3-[3-(3-iodopropyl)phenyl]propanoate (5.79 g) as a colorless oil.

MS (ESI, m/z):369 (M+Na)$^+$.

The following compound(s) was (were) obtained in a similar manner to that of Preparation 65.

Preparation 65-1

Methyl (2S)-2-{3-[(3-iodopropyl)sulfanyl]phenoxy}propanoate.

MS (ESI, m/z):403 (M+Na)$^+$.

Preparation 66

To a stirring solution of tert-butyl 3-(3-hydroxypropyl)-1H-indole-1-carboxylate in MeCN were added imidazole (44 mg), PPh$_3$ (129 mg) and iodine (124 mg) at ambient temperature. After 3 hours, water was added and the mixture was extracted with EtOAc. The organic layer was washed with brine, dried over anhydrous sodium sulfate, filtered and evaporated in vacuo. The residue was purified by silica gel column chromatography (n-hexane:EtOAc=15:1) to give tert-butyl 3-(3-iodopropyl)-1H-indole-1-carboxylate (63 mg).

$^1$H-NMR (CDCl$_3$) δ: 1.67 (9H, s), 1.93-2.27 (2H, m), 2.82 (2H, t, J=7.2 Hz), 3.24 (2H, t, J=6.8 Hz), 7.2-7.35 (2H, m), 7.41 (1H, brs),7.53 (1H, d, J=7.7 Hz), 8.12 (1H, d, J=7.7 Hz).

The following compound(s) was(were) obtained in a similar manner to that of Preparation 66.

Preparation 66-1 tert-Butyl 4-(3-iodopropyl)-1H-indole-1-carboxylate.

$^1$H-NMR (CDCl$_3$) δ:1.67 (9H, s), 2.15-2.26 (2H, m), 2.98 (2H, t, J=7.4 Hz), 3.19 (2H, t, J=7.4 Hz), 6.65 (1H, d, J=3.6 Hz), 7.06 (1H, d, J=7.3 Hz), 7.24 (1H, t, J=8.3, 7.3 Hz), 7.61 (1H, d, J=3.6 Hz), 8.02 (1H, d, J=8.3 Hz).

Preparation 66-2

Ethyl [2-fluoro-5-(3-iodopropyl)phenoxy]acetate.

$^1$H-NMR (CDCl$_3$) δ: 1.30 (3H, t, J=7.3 Hz), 2.07 (2H, m), 2.67 (2H, t, J=6.5 Hz), 3.14 (2H, t, J=6.5 Hz), 4.28 (2H, q, J=7.3 Hz), 4.69 (2H, s), 6.75-6.82 (2H, m), 6.96-7.05 (1H, m).

Preparation 67

To a stirring solution of methyl 3-(1H-indol-3-yl)propionate (320 mg) in MeCN (6.4 mL) was added di-t-butyl dicarbonate (0.412 g) and DMAP (0.02 g) at ambient temperature. After 3 hours, water was added to the mixture and the resulting mixture was extracted with EtOAc. The combined organic layer was washed with brine, dried over anhydrous sodium sulfate, filtered and evaporated in vacuo. The residue was purified by silica gel column chromatography (n-hexane:EtOAc=5:1) to give tert-butyl 3-(3-methoxy-3-oxopropyl)-1H-indole-1-carboxylate.

$^1$H-NMR (CDCl$_3$) δ: 1.67 (9H, s), 2.73 (2H, t, J=8.2 Hz), 3.04 (2H, t, J=8.2 Hz), 3.70 (3H, s), 7.2-7.4 (3H, m), 7.53 (1H, d, J=7.6 Hz), 8.12 (1H, d, J=7.6 Hz).

Preparation 68

To a solution of 4-formylindole (1.0 g) and DMAP (841 mg) in MeCN (20 mL) was added di-tert-butyl dicarbonate (1.5 g) at ambient temperature. The reaction mixture was stirred for 18 hours at ambient temperature. The resulting mixture was evaporated in vacuo. The residue was dissolved in EtOAc. The solution was washed successively with water and brine. The organic layer was dried over anhydrous MgSO$_4$, filtered and evaporated in vacuo to give a tert-butyl 4-formyl-1H-indole-1-carboxylate.

$^1$H-NMR (CDCl$_3$) δ: 1.69 (9H, s), 7.40 (1H, d, J=3.5 Hz), 7.47 (1H, t, J=7.5 Hz), 7.77 (1H, d, J=3.5 Hz), 8.48 (1H, d, J=7.5 Hz), 10.24 (1H, s).

MS (ESI, m/z):246 (M+H)$^+$.

The following compound(s) was (were) obtained in a similar manner to that of Preparation 68.

Preparation 68-1

3-Benzyl 1-tert-butyl 1H-indole-1,3-dicarboxylate.

$^1$H-NMR (CDCl$_3$) δ: 1.68 (9H, s), 5.40 (2H, s), 7.28-7.52 (7H, m), 8.12-8.20 (2H, m), 8.31 (1H, s).

Preparation 69

The mixture of tert-butyl 4-[({2-[5-(diphenylmethyl)-2-oxo-1(2H)-pyridinyl]ethyl}amino)carbonyl]-1-indolinecarboxylate (142 mg) and TFA (4.0 mL) was stood at ambient temperature for 10 minutes. The resulting mixture was evaporated in vacuo and saturated NaHCO$_3$ aqueous solution (5.0 mL) was added to the residue. The aqueous solution was extracted with EtOAc (10 mL). The organic layer was washed with brine, dried over anhydrous MgSO$_4$, filtered and evaporated in vacuo to afford N-{2-[5-(diphenylmethyl)-2-oxo-1(2H)-pyridinyl]ethyl}-4-indolinecarboxamide (96 mg) as an yellow amorphous.

$^1$H-NMR (CDCl$_3$) δ: 3.32 (2H, t, J=8.4 Hz), 3.57 (2H, t, J=8.4 Hz), 3.68-3.76 (2H, m), 4.08-4.19 (2H, m), 5.22 (1H, s), 6.55 (1H, d, J=9.4 Hz), 6.71 (1H, d, J=7.7 Hz), 6.81 (1H, d, J=1.5 Hz), 6.87 (1H, d, J=7.7 Hz), 6.99-7.10 (5H, m), 7.17-7.33 (9H, m).

MS (ESI, m/z):450 (M+H)$^+$.

The following compound(s) was (were) obtained in a similar manner to that of Preparation 69.

Preparation 69-1

N-{2-[Benzoyl-(3,3-diphenylpropyl)amino]ethyl}-4-indolinecarboxamide.

$^1$H-NMR (CDCl$_3$) δ: 2.22-2.34 (2H, m), 3.17-3.28 (2H, m), 3.31-3.40 (2H, m), 3.52-3.61 (2H, m), 3.62-3.73 (3H, m), 3.75-3.83 (2H, m), 6.70 (1H, d, J=8.2 Hz), 6.95 (1H, d, J=8.3 Hz), 6.99-7.07 (4H, m), 7.10-7.42 (14H, m).

MS (ESI, m/z):504 (M+H)$^+$.

Preparation 70

To a suspension of tert-butyl {2-[benzoyl-(3,3-diphenylpropyl)amino]ethyl}carbamate (225 mg) in EtOAc (675 µL) was added 4M HCl/EtOAc (1.23 mL) at ambient temperature and the mixture was stirred at the same temperature for 1 hour. The resulting mixture was diluted with n-hexane (5.0 mL) and the precipitate was collected by filtration followed by washing with n-hexane (10 mL) to afford N-(2-aminoethyl)-N-(3,3-diphenylpropyl)benzamide hydrochloride (166 mg) as colorless crystals.

$^1$H-NMR (DMSO-d$_6$) δ: 2.20-2.33 (2H, m), 2.98-3.14 (4H, m), 3.55-3.74 (3H, m), 7.03-7.45 (15H, m), 7.95-8.07 (2H, brs).

MS (ESI, m/z):359 (M+H)$^+$.

The following compound(s) was (were) obtained in a similar manner to that of Preparation 70.

Preparation 70-1

1-(2-Aminoethyl)-5-(diphenylmethyl)pyridin-2(1H)-one hydrochloride.

MS (ESI, m/z):305 (M+H)$^+$.

Preparation 71

To a solution of tert-butyl 4-{(1E)-3-[5-(diphenylmethyl)-2-oxo-1(2H)-pyridinyl]-1-propen-1-yl}-1H-indole-1-carboxylate (247 mg) in MeOH (5 mL) was added 1M NaOH aqueous solution (1.5 mL) at ambient temperature. The reaction mixture was stirred for 17 hours at ambient temperature. The resulting mixture was diluted with EtOAc (15 mL) and washed successively with water and brine. The organic layer was dried over anhydrous MgSO$_4$, filtered and evaporated in vacuo. The residue was purified by silica gel column chromatography (n-hexane:EtOAc=80:20-50:50) to give 5-(diphenylmethyl)-1-[(2E)-3-(1H-indol-4-yl)-2-propen-1-yl]-2(1H)-pyridinone.

$^1$H-NMR (CDCl$_3$) δ: 4.77 (2H, d, J=6.5 Hz), 5.24 (1H, s), 6.40 (1H, dt, J=15.5, 6.5 Hz), 6.57 (1H, d, J=9.5 Hz), 6.64 (1H, m), 6.87 (1H, d, J=15.5 Hz), 6.94-6.93 (1H, m), 7.35-7.09 (15H, m), 8.34 (1H, brs).

MS (ESI, m/z):417 (M+H)$^+$.

The following compound(s) was (were) obtained in a similar manner to that of Preparation 71.

Preparation 71-1

N-{2-[Benzoyl(3,3-diphenylpropyl)amino]ethyl}-1H-indole-3-carboxamide.

$^1$H-NMR (CDCl$_3$) δ: 2.20-2.36 (2H, m), 3.16-3.32 (2H, m), 3.60-3.88 (5H, m), 6.96-7.40 (18H, m), 7.60-7.65 (1H, m), 8.16-8.24 (1H, m), 8.86-8.96 (1H, m).

MS (ESI, m/z):502 (M+H)$^+$.

Preparation 71-2

5-(Diphenylmethyl)-1-(1H-indol-4-ylmethyl)-2(1H)-pyridinone.

$^1$H-NMR (CDCl$_3$) δ: 5.11 (1H, s), 5.35 (2H, s), 6.48 (1H, m), 6.58 (1H, d, J=9.5 Hz), 6.77-6.76 (1H, m), 6.88 (1H, d, J=7.0 Hz), 6.99-6.96 (4H, m), 7.25-7.08 (8H, m), 7.34 (1H, d, J=8.0 Hz), 8.38 (1H, brs).

MS (ESI, m/z):391 (M+H)$^+$.

Preparation 71-3

5-(Diphenylmethyl)-1-[3-(1H-indol-3-yl)propyl]-2(1H)-pyridinone.

$^1$H-NMR (CDCl$_3$) δ: 2.08-2.20 (2H, m), 2.75 (2H, t, J=7.3 Hz), 3.90 (2H, t, J=7.0 Hz), 5.22 (1H, s), 6.53 (1H, d, J=9.4 Hz), 6.72-6.76 (1H, m), 6.84-6.88 (1H, m), 7.05-7.4 (14H, m), 7.52 (1H, d, J=7.8 Hz), 8.14 (1H, brs).

MS (ESI, m/z):419 (M+H)$^+$.

Preparation 71-4

5-(Diphenylmethyl)-1-[3-(1H-indol-4-yl)propyl]-2(1H)-pyridinone.

$^1$H-NMR (CDCl$_3$) δ: 2.10-2.24 (2H, m), 2.90 (2H, t, J=7.7 Hz), 3.90 (2H, t, J=7.7 Hz), 5.22 (1H, s), 6.47-6.51 (1H, m), 6.53 (1H, d, J=9.6 Hz), 6.74 (1H, d, J=2.9 Hz), 6.81 (1H, d, J=7.4 Hz), 7.04-7.36 (14H, m), 8.24-8.30 (1H, m).

MS (ESI, m/z):419 (M+H)$^+$.

Preparation 71-5

N-(3,3-Diphenylpropyl)-N-[3-(1H-indol-3-yl)propyl]benzamide.

$^1$H-NMR (CDCl$_3$) δ: 1.74-1.92 (1H, m), 1.95-2.25 (2H, m), 2.35-2.6 (2H, m), 2.73-2.88 (1H, m), 3.05-3.3 (2H, m), 3.35-3.5 (1H, m), 3.5-3.75 (1.5H, m), 3.9-4.05 (0.5H, m), 6.60-6.70 (0.5H, m), 6.9-7.65 (19.5H, m), 7.83-8.08 (1H, m).

MS (ESI, m/z):473 (M+H)$^+$.

Preparation 71-6

N-(3,3-Diphenylpropyl)-N-[(2E)-3-(1H-indol-4-yl)-2-propen-1-yl]benzamide.

$^1$H-NMR (CDCl$_3$) δ: 2.31-2.29 (1H, m), 2.55-2.49 (2H, m), 3.25-3.22 (1H, m), 3.56-3.52 (1H, m), 4.04-4.00, 3.68-3.65 (1H, m), 4.40-4.38 (1H, m), 6.19-6.15 (0.5H, m), 6.42-6.38 (0.5H, m), 6.72-6.64 (2H, m), 7.02-6.84 (2H, m), 7.43-7.16 (16H, m), 8.30 (1H, brs).

MS (ESI, m/z):471 (M+H)$^+$.

Preparation 71-7

5-(Diphenylmethyl)-1-{[2-(1H-indol-4-yl)-1,3-oxazol-4-yl]methyl}-2(1H)-pyridinone.

$^1$H-NMR (DMSO-d$_6$) δ: 5.04 (2H, s), 5.42 (1H, s), 6.41 (1H, d, J=9.4 Hz), 7.02 (1H, d, J=2.3 Hz), 7.15-7.35 (12H, m), 7.48 (1H, d, J=2.3 Hz), 7.52 (1H, t, J=2.3 Hz), 7.58 (1H, d, J=8.1 Hz), 7.64 (1H, d, J=7.4 Hz), 8.11 (1H, s), 11.46 (1H, s).

MS (ESI, m/z):458 (M+H)$^+$.

Preparation 71-8

N-(3,3-Diphenylpropyl)-N-{[2-(1H-indol-4-yl)-1,3-oxazol-4-yl]methyl}benzamide.

$^1$H-NMR (CDCl$_3$) δ: 2.38-2.55 (2H, m), 3.31-3.41 (1H, m), 3.48-3.58 (1H, m), 3.94-4.05 (1H, m), 4.34-4.43 (1H, brs),4.70-4.77 (1H, brs),7.00-7.44 (16H, m), 7.50 (1H, d, J=8.4 Hz), 7.62-7.69 (1H, m), 7.74-7.90 (2H, m), 8.38-8.47 (1H, m).

MS (ESI, m/z):512 (M+H)$^+$.

Preparation 71-9

3-{[2-(hydroxymethyl)cyclohexyl]methyl}phenol.

$^1$H-NMR (CDCl$_3$) δ: 0.80-1.80 (10H, m), 2.20 (1H, m), 2.50 (1H, m), 3.56-3.80 (2H, m), 6.60-6.80 (3H, m), 7.05-7.20 (1H, m).

Preparation 72

To a solution of ethyl (4-{3-[(tert-butoxycarbonyl)amino]propyl}phenoxy)acetate (2.5 g) in EtOAc (7.5 mL) was added 4 M HCl/EtOAc (10 mL) at ambient temperature. After stirring for 5 hours at ambient temperature, the mixture was evaporated in vacuo to give a ethyl [4-(3-aminopropyl)phenoxy]acetate hydrochloride.

$^1$H-NMR (DMSO-d$_6$) δ: 1.21 (3H, t, J=7.0 Hz), 1.87-1.77 (2H, m), 2.58 (2H, t, J=7.5 Hz), 2.74 (2H, t, J=7.5 Hz), 4.16 (2H, q, J=7.0 Hz), 4.74 (2H, s), 6.85 (2H, d, J=9.0 Hz), 7.13 (2H, d, J=9.0 Hz), 7.99 (2H, brs).

Preparation 73

To a solution of 3-(3-hydroxypropyl)phenol (1.27 g) in MeCN (12.7 mL) were added $K_2CO_3$ (1.73 g) and benzyl bromide (1.05 mL) at ambient temperature and the mixture was stirred at 60° C. for 16 hours. Water (15 mL) was added to the mixture at ambient temperature and the resulting mixture was extracted with EtOAc (20 mL, two times). The organic layer was washed with brine, dried over anhydrous $MgSO_4$, filtered and evaporated in vacuo. The residue was purified by silica gel column chromatography (n-hexane: EtOAc=3:1) to afford 3-[3-(benzyloxy)phenyl]-1-propanol (1.77 g) as a colorless oil.

$^1$H-NMR (DMSO-$d_6$) δ: 1.64-1.75 (2H, m), 2.57 (2H, t, J=7.7 Hz), 3.40 (2H, q, J=6.0 Hz), 4.46 (1H, t, J=5.2 Hz), 5.07 (2H, s), 6.75-6.86 (3H, m), 7.18 (1H, t, J=7.9 Hz), 7.29-7.48 (5H, m).

Preparation 74

To a solution of 3-(2-hydroxyethyl)phenol (1.0 g) and $K_2CO_3$ (1.5 g) in acetone (20 mL) was added (bromomethyl) benzene (1.49 g) at ambient temperature. The reaction mixture was stirred at the same temperature for 17 hours. The resulting mixture was evaporated in vacuo. The residue was diluted with EtOAc and washed successively with water and brine. The organic layer was dried over anhydrous $MgSO_4$, filtered and evaporated in vacuo. The residue was purified by silica gel column chromatography (n-hexane:EtOAc=90:10-70:30) to give 2-[3-(benzyloxy)phenyl]ethanol.

$^1$H-NMR (CDCl$_3$) δ: 2.85 (2H, t, J=7.0 Hz), 3.86 (2H, brs),5.07 (2H, s), 6.89-6.83 (3H, m), 7.25-7.22 (1H, m), 7.46-7.33 (5H, m).

MS (ESI, m/z):229 (M+H)$^+$.

The following compound(s) was(were) obtained in a similar manner to that of Preparation 74.

Preparation 74-1

3-[2-(Benzyloxy)phenyl]-1-propanol.

$^1$H-NMR (CDCl$_3$) δ: 1.63 (1H, t, J=6.0 Hz),1.91-1.82 (2H, m), 2.78 (2H, dd, J=7.0, 7.0 Hz), 3.59 (2H, q, J=6.0 Hz), 5.09 (2H, s), 6.94-6.90 (2H, m), 7.20-7.15 (2H, m), 7.46-7.33 (5H, m).

MS (ESI, m/z):243 (M+H)$^+$.

Preparation 74-2

Benzyl 3-(benzyloxy)-4-fluorobenzoate.

$^1$H-NMR (CDCl$_3$) δ: 5.17 (2H, s), 5.34 (2H, s), 7.13 (1H, dd, J=10.6, 8.4 Hz), 7.34-7.46 (10H, m), 7.68 (1H, ddd, J=8.4, 4.5, 2.2 Hz), 7.74 (1H, dd, J=8.0, 1.7 Hz).

Preparation 75

To a solution of 2-{2-[5-(diphenylmethyl)-2-oxo-1(2H)-pyridinyl]ethyl}-1H-isoindole-1,3(2H)-dione (295 mg) in mixed solvent (EtOH:THF=4.4 mL:2.2 mL) was added hydrazine hydrate (329 µL) and the mixture was stirred at ambient temperature for 1 hour. The resulting mixture was evaporated in vacuo and the residue was diluted with chloroform (10 mL). The mixture was filtered and the filtrate was evaporated in vacuo. The residue was purified by silica gel column chromatography (chloroform:MeOH=99:1-96:4) to afford 1-(2-aminoethyl)-5-(diphenylmethyl)-2(1H)-pyridinone (154 mg) as colorless crystals.

$^1$H-NMR (DMSO-$d_6$) δ:2.72 (2H, t, J=6.4 Hz), 3.76 (2H, t, J=6.4 Hz), 5.35 (1H, s), 6.36 (1H, d, J=9.4 Hz), 7.05-7.40 (12H, m).

Preparation 76

To a solution of 3-[({2-[5-(diphenylmethyl)-2-oxo-1(2H)-pyridinyl]ethyl}amino)carbonyl]phenyl acetate (77.0 mg) in MeOH (2.3 mL) was added portionwise $K_2CO_3$ (68.4 mg) at ambient temperature and the mixture was stirred at the same temperature for 15 minutes. The resulting mixture was diluted with water (5.0 mL) and the aqueous solution was extracted with EtOAc (10.0 mL). The organic layer was washed successively with 1M HCl aqueous solution, saturated NaHCO$_3$ aqueous solution and brine, dried over anhydrous $MgSO_4$, filtered and evaporated in vacuo to give N-{2-[5-(diphenylmethyl)-2-oxo-1(2H)-pyridinyl]ethyl}-3-hydroxybenzamide (70 mg) as a off-white amorphous powder.

$^1$H-NMR (CDCl$_3$) δ: 3.68-3.77 (2H, m), 4.11-4.20 (2H, m), 5.22 (1H, s), 6.59 (1H, d, J=9.4 Hz), 6.83 (1H, d, J=1.8 Hz), 6.98-7.08 (5H, m), 7.18-7.34 (9H, m), 7.40 (1H, s), 7.72 (1H, t, J=4.8 Hz), 8.36-8.44 (1H, brs).

MS (ESI, m/z):425 (M+H)$^+$.

Preparation 77

To a stirring solution of 5-(diphenylmethyl)-1-[2-(tetrahydro-2H-pyran-2-yloxy)ethyl]-2(1H)-pyridinone (46 mg) in MeOH (1.38 mL) was added pyridium p-toluenesulfonate (9 mg) at ambient temperature. After 48 hours, water was added and the mixture was extracted with EtOAc. The organic layer was washed with brine, dried over anhydrous sodium sulfate, filtered and evaporated in vacuo. The residue was purified by preparative thin-layer chromatography (chloroform: EtOAc=1:2) to give 5-(diphenylmethyl)-1-(2-hydroxyethyl)-2(1H)-pyridinone (20 mg).

$^1$H-NMR (CDCl$_3$) δ: 3.72-3.80 (1H, m), 3.83-3.92 (2H, m), 4.02 (2H, t, J=4.4 Hz), 5.25 (1H, s), 6.53 (1H, d, J=9.5 Hz), 6.83 (1H, d, J=2.7 Hz), 7.08-7.36 (11H, m).

MS (ESI, m/z):306 (M+H)$^+$.

The following compound(s) was (were) obtained in a similar manner to that of Preparation 77.

Preparation 77-1

Ethyl [4-(3-hydroxypropoxy)-1H-indol-1-yl]acetate.

$^1$H-NMR (CDCl$_3$) δ: 1.25 (3H, t, J=7.2 Hz), 1.98 (1H, t, J=5.5 Hz), 2.13 (2H, quint, J=5.8 Hz), 3.93 (2H, q, J=5.5 Hz), 4.20 (2H, q, J=7.2 Hz), 4.29 (2H, t, J=5.8 Hz), 4.81 (2H, s), 6.56 (1H, d, J=8.0 Hz), 6.63 (1H, d, J=3.3 Hz), 6.88 (1H, d, J=8.0 Hz), 7.00 (1H, d, J=3.3 Hz), 7.13 (1H, t, J=8.0 Hz).

MS (ESI, m/z):278 (M+H)$^+$.

Preparation 77-2

Methyl (2S)-2-{3-[(3-hydroxypropyl)sulfanyl]phenoxy}propanoate.

MS (ESI, m/z):293 (M+Na)$^+$.

Preparation 78

To a solution of ethyl {3-[3-(tetrahydro-2H-pyran-2-yloxy)propoxy]phenoxy}acetate (3.54 g. crude) in EtOH (34.5 mL) was added 1M HCl aqueous solution (20.4 mL) at ambient temperature. The mixture was stirred for an hour at ambient temperature. The reaction mixture was neutralized with saturated NaHCO$_3$ aqueous solution and evaporated in vacuo. The resulting residue was dissolved in EtOAc (50 mL) and washed with brine (30 mL). The organic layer was dried over anhydrous $MgSO_4$, filtered and evaporated in vacuo to give crude oil. The crude oil was purified by silica gel column chromatography (n-hexane:EtOAc=2:1-1:1) to give ethyl [3-(3-hydroxypropoxy)phenoxy]acetate (2.1 g) as a colorless oil.

$^1$H-NMR (CDCl$_3$) δ: 1.30 (3H, t, J=7.1 Hz), 2.0-2.1 (2H, m), 3.86 (2H, t, J=6.0 Hz), 4.10 (2H, t, J=6.0 Hz), 4.27 (2H, q, J=7.1 Hz), 4.60 (2H, s), 6.4-6.6 (3H, m), 7.18 (1H, t, J=8.1 Hz).

MS (ESI, m/z):277 (M+Na)$^+$.

The following compound(s) was (were) obtained in a similar manner to that of Preparation 78.

Preparation 78-1

6-(Diphenylmethyl)-2-(2-hydroxyethyl)pyridazin-3(2H)-one.

$^1$H-NMR (DMSO-$d_6$) δ:3.64-3.68 (2H, m), 4.06 (2H, t, J=6.2 Hz), 4.78 (1H, t, J=5.8 Hz), 5.53 (1H, s), 6.88 (1H, d, J=9.5 Hz), 6.87-7.35 (11H, m).

MS (ESI, m/z):329 (M+Na)$^+$.

Preparation 78-2

6-(Diphenylmethyl)-2-(3-hydroxypropyl)pyridazin-3(2H)-one.

MS (ESI, m/z):343 (M+Na)$^+$.

Preparation 78-3

5-(Diphenylmethyl)-1-(3-hydroxypropyl)pyridin-2(1H)-one.

MS (ESI, m/z):342 (M+Na)$^+$.

Preparation 78-4

5-[Bis(4-fluorophenyl)methyl]-1-(2-hydroxyethyl)pyridin-2(1H)-one.

$^1$H-NMR (DMSO-$d_6$) δ: 3.5-3.6 (2H, m), 3.85 (2H, t, J=5.4 Hz), 4.83 (1H, t, J=5.1 Hz), 5.40 (1H, brs),6.3-6.4 (1H, m), 7.1-7.3 (10H, m).

MS (ESI, m/z):364 (M+Na)$^+$.

Preparation 79

To a solution of 1H-indole-4-ol (2.4 g) in DMF (50 mL) was added tert-butyldimethylchlorosilane (2.7 g) and 1H-imidazole (1.5 g) at ambient temperature. The reaction mixture was stirred for 17 hours at ambient temperature. The resulting mixture was evaporated in vacuo and diluted with EtOAc. The organic layer was washed with water and brine and then dried over anhydrous MgSO$_4$, filtered and evaporated in vacuo. The residue was purified by silicagel column chromatography (n-hexane:EtOAc=80:20-60:40) to give 4-{[tert-butyl(dimethyl)silyl]oxy}-1H-indole.

$^1$H-NMR (CDCl$_3$) δ: 0.24 (6H, s), 1.06 (9H, s), 6.54-6.52 (1H, m), 6.60-6.58 (1H, m), 7.04-7.02 (2H, m), 7.11-7.09 (1H, m), 8.11 (1H, brs).

MS (ESI, m/z):248 (M+H)$^+$.

Preparation 80

To a solution of 3-[3-(benzyloxy)phenyl]-1-propanol (1.73 g) in DMF (20 mL) were added imidazole (1.07 g) and tert-butyldimethylchlorosilane (1.83 g) at ambient temperature and the mixture was stirred at the same temperature for 2 hours. Water (20 mL) was added to the mixture at ambient temperature and the mixture was extracted with EtOAc (20 mL) two times. The organic layer was washed successively with 12% NaCl aqueous solution and brine, dried over anhydrous MgSO$_4$, filtered and evaporated in vacuo to afford {3-[3-(benzyloxy)phenyl]propoxy}(tert-butyl)dimethylsilane (2.96 g) as a colorless oil.

$^1$H-NMR (CDCl$_3$) δ: 0.06 (6H, s), 0.90 (9H, s), 1.77-1.88 (2H, m), 2.64 (2H, t, J=7.7 Hz), 3.62 (2H, t, J=6.4 Hz), 5.04 (2H, s), 6.76-6.85 (3H, m), 7.18 (1H, t, J=7.7 Hz), 7.30-7.45 (5H, m).

Preparation 81

To a solution of methyl (2E)-3-[3-(3-{[tert-butyl (dimethyl)silyl]oxy}propyl)phenoxy]acrylate (1.77 g) in THF (17.7 mL) was added 1.0 M tetrabutylammonium fluoride in THF (5.05 mL) at ambient temperature under N$_2$ gas atmosphere and the mixture was stirred at ambient temperature for 1.5 hours.

1M HCl aqueous solution (15 mL) was added to the mixture at ambient temperature. The organic layer was washed successively with water and brine, dried over anhydrous MgSO$_4$, filtered and evaporated in vacuo. The residue was purified by silica gel column chromatography (n-hexane: EtOAc=2:1) to afford methyl (2E)-3-[3-(3-hydroxypropyl)phenoxy]acrylate (1.02 g) as a colorless oil.

$^1$H-NMR (DMSO-$d_6$) δ: 1.71 (2H, m), 2.63 (2H, t, J=7.9 Hz), 3.40 (2H, q, J=6.1 Hz), 3.65 (3H, s), 4.48 (1H, t, J=6.1 Hz), 5.59 (1H, d, J=12.1 Hz), 7.04 (3H, m), 7.33 (1H, t, J=7.9 Hz), 7.85 (1H, d, J=12.1 Hz).

Preparation 82

To a solution of ethyl (4-{[tert-butyl(dimethyl)silyl]oxy}-1H-indol-1-yl)acetate (3.7 g) in THF (74 mL) was added tetra n-butylammomium fluoride (3.5 g) at ambient temperature. The reaction mixture was stirred at the same temperature for 7 hours. The resulting mixture was evaporated in vacuo and diluted with EtOAc. The organic solution was washed successively with water and brine. The organic layer was dried over anhydrous MgSO$_4$, filtered and evaporated in vacuo. The residue was purified by silica gel column chromatography (n-hexane:EtOAc=80:20-60:40) to give ethyl (4-hydroxy-1H-indol-1-yl)acetate.

$^1$H-NMR (CDCl$_3$) δ: 1.28 (3H, t, J=7.0 Hz), 4.21 (2H, q, J=7.0 Hz), 4.82 (2H, s), 5.21 (1H, s), 6.53 (1H, d, J=8.0 Hz), 6.61 (1H, d, J=3.5 Hz), 6.85 (1H, d, J=8.0 Hz), 7.03 (1H, d, J=3.5 Hz), 7.08 (1H, dd, J=8.0, 8.0 Hz).

MS (ESI, m/z):220 (M+H)$^+$.

The following compound(s) was (were) obtained in a similar manner to that of Preparation 82.

Preparation 82-1

2-(Hydroxymethyl)-4-indanol.

$^1$H-NMR (CDCl$_3$) δ: 2.60-2.85 (3H, m), 2.90-3.15 (2H, m), 3.60-3.75 (2H, m), 4.90-5.10 (1H, m), 6.61 (1H, d, J=8.0 Hz), 6.80 (1H, d, J=7.4 Hz), 7.04 (1H, dd, J=8.0, 7.4 Hz).

Preparation 83

To a solution of ethyl 3-(2-fluoro-5-methoxyphenyl) propanoate (100 mg) in DCM (0.5 mL) was added dropwise borane tribromide (1M solution in DCM, 1.33 mL) under ice cooling. After stirring for an hour at 5° C., the reaction mixture was added EtOH (5 mL) and then water (30 mL) and extracted with EtOAc (40 mL). The organic layer was washed with water (20 mL) and brine (20 mL). The organic layer was dried over anhydrous MgSO$_4$, filtered and evaporated in vacuo to give ethyl 3-(2-fluoro-5-hydroxyphenyl)propanoate (93 mg) as a colorless oil.

$^1$H-NMR (DMSO-$d_6$) δ:1.15 (3H, t, J=7.1 Hz), 2.55 (2H, t, J=7.5 Hz), 2.77 (2H, t, J=7.5 Hz), 4.04 (2H, q, J=7.1 Hz), 6.5-7.0 (3H, m), 9.27 (1H, brs).

MS (ESI, m/z):235 (M+Na)$^+$.

The following compound(s) was (were) obtained in a similar manner to that of Preparation 83.

Preparation 83-1

Ethyl 4-[(3-hydroxyphenyl)sulfanyl]butanoate.

$^1$H-NMR (DMSO-$d_6$) δ: 1.17 (3H, t, J=7.1 Hz), 1.80 (2H, tt, J=7.2, 7.3 Hz), 2.42 (2H, t, J=7.3 Hz), 2.92 (2H, t, J=7.1 Hz), 4.05 (2H, q, J=7.1 Hz), 6.56-6.59 (1H, m), 6.69-6.74 (2H, m), 7.10 (1H, dd, J=7.9, 7.9 Hz),9.53 (1H, s).

MS (ESI, m/z):263 (M+Na)$^+$.

Preparation 84

To a solution of 5-(2-bromophenyl)-2-methoxypyridine (7.2 g) in 1,2-dichloroethane (75 mL) was added aluminum chloride (9.09 g) at ambient temperature. The reaction mixture was stirred at 50° C. for 3 hours. The reaction mixture was poured into ice and was extracted with a mixed solvent (THF:EtOAc=3:1) and the organic layer was washed with brine, dried over anhydrous MgSO$_4$, filtered and evaporated in vacuo. The residue was added silica gel (150 g), and the mixture of the filtrate and silica gel was evaporated in vacuo. The residue was purified by silica gel column chromatography (chloroform:MeOH=97:3) to afford 5-(2-bromophenyl) pyridin-2(1H)-one (4.72 g) as yellow crystals.

MS (ESI, m/z):248, 250 (M−H)

Preparation 85

To a solution of 2-methoxy-5-(2'-methylbiphenyl-2-yl)pyridine (2.20 g) in DCM (50 mL) was added iodo(trimethyl)silane (5.0 g) at ambient temperature. The reaction mixture was stirred at ambient temperature for 4 days. To the reaction mixture was added brine (50 mL). The mixture was extracted with EtOAc and the organic layer was dried over anhydrous $MgSO_4$, filtered and evaporated in vacuo. The residue was purified by silica gel column chromatography (EtOAc:chloroform=3:7) to afford 5-(2'-methylbiphenyl-2-yl)pyridin-2-ol (1.35 g) as pale yellow crystals.

MS (ESI, m/z):260 (M−H)$^+$.

The following compound(s) was (were) obtained in a similar manner to that of Preparation 85.

Preparation 85-1

5-(2-quinolin-8-ylphenyl)pyridin-2-ol.

MS (ESI, m/z):321 (M+Na)$^+$.

Preparation 86

To a solution of tert-butyl 4-({[(1S)-1-(hydroxymethyl)-2-methoxy-2-oxoethyl]amino}carbonyl)-1H-indole-1-carboxylate (2.09 g) in THF (21.0 mL) was added Burgess Reagent (1.44 g) at ambient temperature and the mixture was stirred at 70° C. for 45 minutes. The resulting mixture was diluted with EtOAc (60 mL) and washed successively with saturated $NaHCO_3$ aqueous solution and brine. The organic layer was dried over anhydrous $MgSO_4$, filtered and evaporated in vacuo. The residue was purified by silica gel column chromatography (n-hexane:EtOAc=2:1) to afford tert-butyl 4-[(4S)-4-(methoxycarbonyl)-4,5-dihydro-1,3-oxazol-2-yl]-1H-indole-1-carboxylate (1.35 g) as a colorless amorphous.

$^1$H-NMR (CDCl$_3$) δ: 1.68 (9H, s), 3.84 (3H, s), 4.63 (1H, dd, J=8.7, 10.5H z), 4.73 (1H, dd, J=7.9, 8.7 Hz), 5.03 (1H, dd, J=7.9, 10.5 Hz), 7.30 (1H, d, J=3.7 Hz), 7.34 (1H, d, J=8.0 Hz), 7.67 (1H, d, J=3.7 Hz), 7.88 (1H, d d, J=8.0, 8.3 Hz), 8.33 (1H, d, J=8.3 Hz).

MS (ESI, m/z):345 (M+H)$^+$.

Preparation 87

A solution of tert-butyl 4-[(4S)-4-(methoxycarbonyl)-4,5-dihydro-1,3'-oxazol-2-yl]-1H-indole-1-carboxylate (750 mg) in DCM (22.5 mL) was cooled to 0° C. and 2,3,4,6,7,8,9,10-octahydropyrimido[1,2-a]azepine (358 μL) was added to the mixture. Bromotrichloromethane (235 μL) was then added dropwise to the above mixture over 5 minutes. The mixture was stirred at the same temperature for 3.5 hours and at ambient temperature for 16.5 hours. The resulting mixture was diluted with EtOAc (100 mL) and washed with saturated ammonium chloride aqueous solution (50 mL). The organic layer was dried over anhydrous $MgSO_4$, filtered and evaporated in vacuo. The residual solid was triturated with EtOAc (2.0 mL) to give tert-butyl 4-[4-(methoxycarbonyl)-1,3-oxazol-2-yl]-1H-indole-1-carboxylate (520 mg) as a colorless solid.

$^1$H-NMR (CDCl$_3$) δ: 1.69 (9H, s), 3.98 (3H, s), 7.41 (1H, t, J=8.0 Hz), 7.45 (1H, d, J=3.7 Hz), 7.73 (1H, d, J=3.7 Hz), 8.04 (1H, d, J=8.0 Hz), 8.35 (1H, d, J=8.0 Hz), 8.36 (1H, s).

MS (ESI, m/z):343 (M+H)$^+$.

Preparation 88

A mixture of 1,1-bis(4-fluorophenyl)acetone (2.4 g) and ethyl glyoxylate (47% solution in toluene, 2.1 g) was stirred at 130° C. for 3 days. The reaction mixture was cooled to ambient temperature. The mixture was purified by silica gel column chromatography (n-hexane:EtOAc=4:1) to give ethyl 5,5-bis(4-fluorophenyl)-2-hydroxy-4-oxopentanoate (800 mg) as a brown oil.

$^1$H-NMR (DMSO-d$_6$) δ: 1.14 (3H, t, J=7.1 Hz), 2.7-3.0 (2H, m), 4.05 (2H, q, J=7.1 Hz), 4.3-4.5 (1H, m), 5.46 (1H, brs),5.62 (1H, d, J=6.0 Hz), 7.1-7.3 (8H, m).

MS (ESI, m/z):371 (M+Na)$^+$.

Preparation 89

A mixture of 5-(diphenylmethyl)pyridin-2(1H)-one (0.3 g) and N-chlorosuccinimide(0.184 g) in DMF (3 mL) was stirred at ambient temperature for 23 hours. The reaction mixture was poured into saturated $NaHCO_3$ aqueous solution and the resulting precipitates were collected by filtration and washed with water to afford 3-chloro-5-(diphenylmethyl)pyridin-2(1H)-one (0.31 g) as white powder.

$^1$H-NMR (DMSO-d$_6$) δ: 5.42 (1H, s), 6.86 (1H, m), 7.09-7.55 (11H, m), 12.01 (1H, s).

MS (ESI, m/z):296 (M+H)$^+$.

The following compound(s) was (were) obtained in a similar manner to that of Preparation 89.

Preparation 89-1

3-Chloro-5-(2'-methylbiphenyl-2-yl)pyridin-2-ol.

MS (ESI, m/z):318 (M+Na)$^+$.

Preparation 90

Under $N_2$ gas atmosphere, to a stirred mixture of lithium aluminum hydride (0.703 g) in THF (9 mL) was added 2-(3-methoxybenzyl)cyclohexanecarboxylic acid (2.3 g) in THF (9 mL) dropwise at 0° C. The reaction mixture was stirred at 0° C. for an hour, at ambient temperature for an hour, at 60° C. for 4 hours. The reaction mixture was cooled to 0° C. and was added mixed solution (1M HCl aqueous solution:THF=10:90) dropwise. The resulting mixture was diluted with water and was extracted with diethylether two times. The organic layer was dried over anhydrous $MgSO_4$, filtered and evaporated in vacuo. The mixture was purified by thin-layer chromatography (n-hexane:EtOAc=5:1) to give [2-(3-methoxybenzyl)cyclohexyl]methanol (1.74 g) as a pale yellow oil.

MS (ESI, m/z):235 (M+H)$^+$.

Preparation 91

To a solution of [2-(3-methoxybenzyl)cyclohexyl]methanol (1.5 g) in pyridine (7.5 mL) was added acetic anhydride (4.1 mL) at 0° C. The reaction mixture was stirred at 0° C. for 1 hour and at ambient temperature for 1 hour. The reaction mixture was added 1M HCl aqueous solution and was extracted with EtOAc. The organic layer was washed with 1M HCl aqueous solution and saturated $NaHCO_3$ aqueous solution, and brine. The organic layer was dried over anhydrous $MgSO_4$, filtered and evaporated in vacuo to afford [2-(3-methoxybenzyl)cyclohexyl]methyl acetate (1.57 g) as a colorless oil.

MS (ESI, m/z):277 (M+H)$^+$.

Preparation 92

The reaction mixture of [2-(3-methoxybenzyl)cyclohexyl]methyl acetate (66 mg), DL-methionine (357 mg), and methanesulfonic acid (1.55 mL) was stirred at ambient temperature for 18 hours. To the reaction mixture was added diethylether and water. The reaction mixture was stirred. The organic layer was washed with water, brine, dried over anhydrous $MgSO_4$, filtered and evaporated in vacuo. The mixture was purified by silica gel column chromatography (n-hexane:EtOAc=5:1) to afford [2-(3-hydroxybenzyl)cyclohexyl]methyl acetate (42 mg) as colorless oil.

MS (ESI, m/z):263 (M+H)$^+$.

EXAMPLE 1

To a solution of methyl 3-(3-{3-[5-(diphenylmethyl)-2-oxo-1(2H)-pyridinyl]propyl}phenoxy)propanoate (155 mg) in MeOH (2.0 mL) was added 1M NaOH aqueous solution (0.482 mL) at ambient temperature and the mixture was stirred at ambient temperature for overnight. The mixture was acidified to pH=3 with 1M HCl aqueous solution and extracted with chloroform (4.0 mL). The organic layer was washed with brine, dried over anhydrous MgSO$_4$, filtered and evaporated in vacuo. The residue was purified by preparative thin-layer chromatography (chloroform:MeOH=9:1) to afford 3-(3-{3-[5-(diphenylmethyl)-2-oxo-1(2H)-pyridinyl]propyl}phenoxy)propanoic acid (27.8 mg) as white crystals.

$^1$H-NMR (DMSO-d$_6$) δ: 2.02 (2H, quint, J=7.3 Hz), 2.59 (2H, t, J=7.3 Hz), 2.82 (2H, t, J=6.4 Hz), 3.83 (2H, t, J=7.3 Hz), 4.30 (2H, t, J=6.4 Hz), 5.25 (1H, s), 6.58 (1H, d, J=9.3 Hz), 6.67 (1H, d, J=7.5 Hz), 6.72-6.80 (3H, m), 7.08-7.17 (5H, m), 7.20 (1H, dd, J=2.6, 9.3 Hz), 7.25-7.35 (6H, m).

MS (ESI, m/z):468 (M+H)$^+$.

EXAMPLE 2

To a solution of ethyl (4-{(1E)-3-[5-(diphenylmethyl)-2-oxo-1(2H)-pyridinyl]-1-propen-1-yl}-1H-indol-1-yl)acetate (70 mg) in MeOH (1.5 mL) was added 1M NaOH aqueous solution (0.2 mL) at ambient temperature. The reaction mixture was stirred at the same temperature for 5 hours. The reaction was quenched with 1M HCl aqueous solution (0.2 mL). The mixture was extracted with EtOAc and washed successively with water and brine. The organic layer was dried over anhydrous MgSO$_4$, filtered and evaporated in vacuo. The residue was purified by silica gel column chromatography (chloroform:MeOH=100:0-97:3) to give (4-{(1E)-3-[5-(diphenylmethyl)-2-oxo-1(2H)-pyridinyl]-1-propen-1-yl}-1H-indol-1-yl)acetic acid.

$^1$H-NMR (DMSO-d$_6$) δ:4.70 (2H, d, J=6.0 Hz), 5.02 (2H, s), 5.41 (1H, s), 6.47-6.38 (2H, m), 6.50 (1H, d, J=3.5 Hz), 6.78 (1H, d, J=15.5 Hz), 7.33-7.09 (14H, m), 7.43-7.39 (2H, m).

MS (ESI, m/z):475 (M+H)$^+$.

The following compound(s) was (were) obtained in a similar manner to that of Example 2.

EXAMPLE 3

(4-{(1E)-3-[Benzoyl(3,3-diphenylpropyl)amino]-1-propen-1-yl}-1H-indol-1-yl)acetic acid.

$^1$H-NMR (DMSO-d$_6$) δ:2.42-2.31 (2H, m), 2.89-2.83 (0.5H, m), 3.11-3.07 (1H, m), 3.74-3.72 (0.5H, m), 4.02-3.99 (2H, m), 4.30-4.28 (1H, m), 5.01 (2H, s), 6.34-6.22 (1H, m), 6.72-6.57 (2H, m), 7.42-7.06 (19H, m).

MS (ESI, m/z):529 (M+H)$^+$.

EXAMPLE 4

(4-{3-[5-(diphenylmethyl)-2-oxopyridin-1(2H)-yl]propyl}-1H-indol-1-yl)acetic acid.

$^1$H-NMR (DMSO-d$_6$) δ: 1.90-2.04 (2H, m), 2.76 (2H, t, J=7.0 Hz), 3.91 (2H, t, J=7.0 Hz), 4.99 (2H, s), 5.39 (1H, s), 6.35 (1H, d, J=3.0 Hz), 6.39 (1 H, d, J=9.4 Hz), 6.78 (1H, d, J=7.3 Hz), 7.01 (1H, dd, J=8.0, 7.3 Hz), 7.11-7.38 (14H, m).

MS (ESI, m/z):477 (M+H)$^+$.

EXAMPLE 5

(3-{3-[Benzoyl(3,3-diphenylpropyl)amino]propyl}-1H-indol-1-yl)acetic acid.

$^1$H-NMR (CDCl$_3$) δ: 1.70-2.00 (2H, m), 2.05-2.25 (1H, m), 2.30-2.55 (2H, m),2.60-2.80 (1H, m), 3.00-3.25 (2H, m), 3.35-3.65 (2.5H, m), 3.90-4.05 (0.5H, m), 4.53 (2H, brs), 6.30-6.80 (2.5H, m), 6.85-7.55 (17.5H, m).

MS (ESI, m/z):531 (M+H)$^+$.

EXAMPLE 6

{3-[({2-[Benzoyl(3,3-diphenylpropyl)amino]ethyl}amino)carbonyl]-1H-indol-1-yl}acetic acid.

$^1$H-NMR (DMSO-d$_6$) δ: 2.20-2.52 (2H, m), 3.04-3.76 (7H, m), 5.06 (2H, s), 7.00-7.48 (17H, m), 7.80-8.24 (3H, m).

MS (ESI, m/z):560 (M+H)$^+$.

EXAMPLE 7

(4-{3-[5-(Diphenylmethyl)-2-oxo-1(2H)-pyridinyl]propoxy}-1H-indol-1-yl)acetic acid.

$^1$H-NMR (DMSO-d$_6$) δ: 2.08-2.20 (2H, m), 3.96-4.40 (4H, m), 4.98 (2H, s), 5.20 (1H, s), 6.36-6.43 (2H, m), 6.44-6.52 (1H, m), 6.95-7.08 (6H, m), 7.10-7.28 (9H, m).

MS (ESI, m/z):493 (M+H)$^+$.

EXAMPLE 8

(4-{2-[5-(Diphenylmethyl)-2-oxo-1(2H)-pyridinyl]ethoxy}-1H-indol-1-yl)acetic acid.

$^1$H-NMR (DMSO-d$_6$) δ: 4.25 (4H, m), 4.93 (2H, brs),5.38 (1H, s), 6.08 (1H, d, J=3.4 Hz), 6.37 (1H, d, J=9.1 Hz), 6.45 (1H, dd, J=5.6, 2.6 Hz), 6.90-7.00 (2H, m), 7.08-7.35 (12H, m), 7.38-7.42 (1H, m).

MS (ESI, m/z):479 (M+H)$^+$.

EXAMPLE 9

(4-{[5-(Diphenylmethyl)-2-oxo-1(2H)-pyridinyl]methyl}-1H-indol-1-yl)acetic acid.

$^1$H-NMR (DMSO-d$_6$) δ: 5.02 (2H, s), 5.29 (2H, s), 5.33 (2H, s), 6.45-6.41 (2H, m), 6.75 (1H, d, J=7.0 Hz), 7.08-7.02 (5H, m), 7.34-7.18 (10H, m).

MS (ESI, m/z):449 (M+H)$^+$.

EXAMPLE 10

To a solution of ethyl (3-{3-[5-(diphenylmethyl)-2-oxo-1(2H)-pyridinyl]propyl}phenoxy)acetate (113 g) in MeOH (1.01) was added 1M NaOH aqueous solution (352 mL) at 0° C. and the mixture was stirred at ambient temperature for 1 hour. The mixture was evaporated in vacuo and 1M HCl aqueous solution (360 mL) was added to the mixture at 0° C. The mixture was extracted with chloroform (3 L). The organic layer was washed successively with water and brine, dried over anhydrous MgSO$_4$, filtered and evaporated in vacuo. The residue was crystallized from EtOH.

The crystals (100 g) were suspended with mixed solvent (EtOH:water=1:2) at ambient temperature for 3 hours, and collected by filtration and washed with water (100 mL) two times. The crystals (92 g) were recrystallized from $^a$PrOH (1.25 L) to afford (3-{3-[5-(diphenylmethyl)-2-oxopyridin-1(2H)-yl]propyl}phenoxy)acetic acid (69.7 g) as colorless crystals.

$^1$H-NMR (CDCl$_3$) δ:2.01 (2H, quint, J=7.3 Hz), 2.58 (2H, t, J=7.3 Hz), 3.84 (2H, t, J=7.3 Hz), 4.64 (2H, s), 5.26 (1H, s), 6.66 (1H, d, J=9.5 Hz), 6.70 (1H, d, J=7.3 Hz), 6.75-6.81 (3H, m), 7.08-7.35 (12H, m).

MS (ESI, m/z):454 (M+H)$^+$.

The following compound(s) was (were) obtained in a similar manner to that of Example 10.

EXAMPLE 11

{4-[({2-[Benzoyl(3,3-diphenylpropyl)amino]ethyl}amino)carbonyl]-1H-indol-1-yl}acetic acid.

$^1$H-NMR (DMSO-d$_6$) δ: 2.21-2.33 (2H, m), 3.06-3.17 (2H, m), 3.28-3.45 (2H, m), 3.52-3.59 (1H, m), 3.62-3.74 (2H, m), 5.07 (2H, s), 6.88 (1H, s), 7.02-7.45 (18H, m), 7.55 (1H, d, J=8.2 Hz), 8.35-8.45 (1H, brs).

MS (ESI, m/z):560 (M+H)$^+$.

EXAMPLE 12

(3-{4-[5-(Diphenylmethyl)-2-oxo-1(2H)-pyridinyl]butyl}phenoxy)acetic acid.

$^1$H-NMR (CDCl$_3$) δ: 1.62-1.60 (4H, m), 2.61-2.60 (2H, m), 3.83-3.82 (2H, m), 4.64 (2H, s), 5.25 (1H, s), 6.63 (1H, d, J=9.5 Hz), 6.80-6.73 (4H, m), 7.09-7.07 (4H, m), 7.33-7.14 (8H, m).

MS (ESI, m/z):468 (M+H)$^+$.

EXAMPLE 13

(3-{3-[(2E)-2-Butenoyl)(3,3-diphenylpropyl)amino]propyl}phenoxy)acetic acid.

$^1$H-NMR (DMSO-d$_6$) δ:1.78-1.70 (5H, m), 2.27-2.18 (2H, m), 2.45-2.42 (2H, m), 3.26-3.17 (4H, m), 3.93-3.91 (1H, m), 4.63 (2H, s), 6.18, 5.92 (1H, d, J=14.5 Hz), 6.74-6.56 (4H, m), 7.21-7.14 (3H, m), 7.35-7.29 (8H, m).

MS (ESI, m/z):427 (M+H)$^+$.

EXAMPLE 14

{3-[({2-[5-(Diphenylmethyl)-2-oxo-1(2H)-pyridinyl]ethyl}amino)carbonyl]phenoxy}acetic acid.

$^1$H-NMR (DMSO-d$_6$) δ: 3.46-3.58 (2H, m), 3.87-3.99 (2H, m), 4.72 (2H, s), 5.23 (1H, s), 6.38 (1H, d, J=9.5 Hz), 6.86 (1H, d, J=2.0 Hz), 6.92-7.02 (5H, m), 7.05-7.22 (6H, m), 7.30-7.45 (4H, m), 8.55-8.65 (1H, m).

MS (ESI, m/z):483 (M+H)$^+$.

EXAMPLE 15

(3-{(1E)-3-[5-(Diphenylmethyl)-2-oxo-1(2H)-pyridinyl]-1-propen-1-yl}phenoxy)acetic acid.

$^1$H-NMR (CDCl$_3$) δ: 4.61-4.60 (4H, m), 5.27 (1H, s), 6.30-6.20 (1H, m), 6.42 (1H, d, J=15.0 Hz), 6.92-6.69 (6H, m), 7.11-7.08 (5H, m), 7.32-7.17 (6H, m).

MS (ESI, m/z):452 (M+H)$^+$.

EXAMPLE 16

(3-{3-[(Cyclopentylcarbonyl)(3,3-diphenylpropyl)amino]propyl}phenoxy)acetic acid.

$^1$H-NMR (DMSO-d$_6$) δ: 1.71-1.23 (11H, m), 2.27-2.15 (2H, m), 2.46-2.40 (2H, m), 3.25-3.09 (4H, m), 3.94-3.87 (1H, m), 4.62 (2H, s), 6.77-6.69 (3H, m), 7.20-7.13 (3H, m), 7.36-7.27 (8H, m).

MS (ESI, m/z):500 (M+H)$^+$.

EXAMPLE 17

(3-{3-[(3,3-Diphenylpropyl)(isonicotinoyl)amino]propyl}phenoxy)acetic acid.

$^1$H-NMR (DMSO-d$_6$) δ: 1.70-1.65 (1H, m), 1.85-1.81 (1H, m), 2.36-2.21 (3H, m), 2.59-2.54 (1H, m), 3.05-2.96 (2H, m), 3.50-3.45 (2H, m), 3.74, 4.02 (1H, t, J=7.5 Hz), 4.64, 4.61 (2H, s), 6.82-6.55 (4H, m), 7.37-7.11 (12H, m), 8.57-8.52 (2H, m).

MS (ESI, m/z):509 (M+H)$^+$.

EXAMPLE 18

{4-[({2-[5-(Diphenylmethyl)-2-oxo-1(2H)-pyridinyl]ethyl}amino)carbonyl]-1H-indol-1-yl}acetic acid.

$^1$H-NMR (DMSO-d$_6$) δ: 3.54-3.64 (2H, m), 3.95-4.03 (2H, m), 5.07 (2H, s), 5.22 (1H, s), 6.39 (1H, d, J=9.4 Hz), 6.89 (1H, d, J=3.1 Hz), 6.93-7.05 (5H, m), 7.07-7.21 (8H, m), 7.37-7.44 (2H, m), 7.55 (1H, d, J=8.2 Hz), 8.38 (1H, t, J=5.4 Hz).

MS (ESI, m/z):506 (M+H)$^+$.

EXAMPLE 19

{3-[({[5-(Diphenylmethyl)-2-oxo-1(2H)-pyridinyl]acetyl}amino)methyl]phenoxy}acetic acid.

$^1$H-NMR (DMSO-d$_6$) δ: 4.26 (2H, d, J=5.7 Hz), 4.55 (2H, s), 4.66 (2H, s), 5.36 (1H, s), 6.38 (1H, d, J=9.3 Hz), 6.77 (1H, d, J=8.6 Hz), 6.82-6.88 (2H, m), 7.12-7.37 (13H, m), 8.67 (1H, t, J=5.7 Hz).

MS (ESI, m/z):483 (M+H)$^+$.

EXAMPLE 20

(3-{3-[5-(Diphenylmethyl)-2-oxo-1(2H)-pyridinyl]propyl}-1H-indol-1-yl)acetic acid.

$^1$H-NMR (DMSO-d$_6$) δ: 1.88-2.04 (2H, m), 2.62 (2H, t, J=7.5 Hz), 3.91 (2H, t, J=6.9 Hz), 4.92 (2H, s), 5.37 (1H, s), 6.38 (1H, d, J=9.4 Hz), 6.9-7.5 (17H, m).

MS (ESI, m/z):477 (M+H)$^+$.

EXAMPLE 21

(2-{3-[Benzoyl(3,3-diphenylpropyl)amino]propyl}phenoxy)acetic acid.

$^1$H-NMR (DMSO-d$_6$) δ: 1.82-1.70 (2H, m), 2.33-2.20 (0.3H, m), 2.62-2.60 (1H, m), 3.14-3.06 (3H, m), 3.49-3.47 (1H, m), 4.02, 3.72 (1H, t, J=7.5H z), 4.64, 4.59 (2H, s), 6.90-6.79 (3H, m), 7.37-7.10 (16H, m).

MS (ESI, m/z):508 (M+H)$^+$.

EXAMPLE 22

[(2-{[Benzoyl(3,3-diphenylpropyl)amino]methyl}-2,3-dihydro-1H-inden-4-yl)oxy]acetic acid.

$^1$H-NMR (CDCl$_3$) δ: 2.1-3.1 (7H, m), 3.15-3.35 (2H, m), 3.4-3.75 (2.5H, m), 4.0-4.1 (0.5H, m), 4.55-4.7 (2H, m), 6.45-7.7 (18H, m).

MS (ESI, m/z):520 (M+H)$^+$.

The following compound(s) was(were) obtained in a similar manner to that of Example 206.

EXAMPLE 23

Sodium (5-{3-[Benzoyl(3,3-diphenylpropyl)amino]propyl}-2-fluorophenoxy)acetate.

$^1$H-NMR (DMSO-d$_6$) δ: 1.50-1.84 (2H, m), 2.08-2.52 (4H, m), 2.95-3.80 (4.5H, m), 3.96-4.20 (2.5H, m), 6.30-7.48 (18H, m).

MS (ESI, m/z):526 (M+H)$^+$.

The following compound(s) was (were) obtained in a similar manner to that of Example 10.

EXAMPLE 24

(3-{3-[Acetyl(3,3-diphenylpropyl)amino]propyl}phenoxy)acetic acid.

$^1$H-NMR (CDCl$_3$) δ: 1.80-1.72 (2H, m), 1.90, 1.84 (3H, s), 2.30-2.23 (2H, m), 2.55-2.46 (2H, m), 3.16-3.07 (2H, m), 3.30-3.20 (2H, m), 3.89-3.80 (1H, m), 4.59 (2H, s), 6.74-6.69 (3H, m), 7.31-7.12 (11H, m).

MS (ESI, m/z):446 (M+H)$^+$.

EXAMPLE 25

[4-(4-{[N-Benzoyl-N-(3,3-diphenylpropyl)amino]methyl}-1,3-oxazol-2-yl)-1H-indol-1-yl]acetic acid.

$^1$H-NMR (DMSO-d$_6$) δ:2.36-2.47 (2H, m), 3.21-3.45 (2H, m), 3.97-4.05 (1H, m), 4.35-4.44 (1H, m), 4.67-4.74 (1H, m), 5.11 (2H, s), 7.05-7.67 (18H, m), 7.73 (1H, d, J=8.4 Hz), 7.93-7.99 (1H, m), 8.10-8.16 (1H, m).

MS (ESI, m/z):570 (M+H)$^+$.

EXAMPLE 26

[4-({2-[5-(Diphenylmethyl)-2-oxo-1(2H)-pyridinyl]ethyl}amino)-1H-indol-1-yl]acetic acid.

$^1$H-NMR (DMSO-d$_6$) δ: 3.90-4.08 (4H, m), 4.73 (2H, s), 5.2 (1H, s), 5.80-5.92 (1H, m), 6.05 (1H, d, J=6.6 Hz), 6.37 (1H, d, J=9.4 Hz), 6.45-6.53 (1H, m), 6.57 (1H, d, J=7.8 Hz), 6.76-6.88 (1H, m), 6.92-7.30 (12H, m), 8.3 (1H, s).

MS (ESI, m/z):478 (M+H)$^+$.

EXAMPLE 27

(3-{3-[3-(Diphenylmethyl)-6-oxo-1(6H)-pyridazinyl]propyl}phenoxy)acetic acid.

$^1$H-NMR (DMSO-d$_6$) δ: 1.95-1.91 (2H, m), 2.48-2.46 (2H, m), 4.01 (2H, t, J=7.5 Hz), 4.62 (2H, s), 5.67 (1H, s), 6.72-6.69 (3H, m), 6.90 (1H, d, J=10.0 Hz), 7.36-7.12 (12H, m).

MS (ESI, m/z):455 (M+H)$^+$.

EXAMPLE 28

(3-{3-[(3,3-Diphenylpropyl)(3-pyridinylcarbonyl)amino]propyl}phenoxy)acetic acid.

$^1$H-NMR (DMSO-d$_6$) δ:1.68-1.67 (1H, m), 1.84-1.82 (1H, m), 2.35-2.21 (3H, m), 2.58-2.56 (1H, m), 3.10-3.01 (3H, m), 3.51-3.46 (1H, m), 4.03, 3.74 (1H, t, J=7.5 Hz), 4.64, 4.61 (2H, s), 6.83-6.55 (5H, m), 7.35-7.12 (10H, m), 7.68 (1H, d, J=7.5 Hz), 8.49 (1H, s), 8.57 (1H, d, J=4.5 Hz).

MS (ESI, m/z):509 (M+H)$^+$.

EXAMPLE 29

(3-{3-[(3,3-Diphenylpropyl)(2-pyridinylcarbonyl)amino]propyl}phenoxy)acetic acid.

$^1$H-NMR (DMSO-d$_6$) δ: 1.83-1.72 (2H, m), 2.36-2.24 (3H, m), 2.59-2.54 (1H, m), 3.20-3.07 (3H, m), 3.49-3.44 (1H, m), 4.02, 3.74 (1H, t, J=7.5H z), 4.64, 4.60 (2H, s), 6.57 (1H, d, J=9.5 Hz), 6.82-6.65 (2H, m), 7.18-7.09 (8H, m), 7.46-7.27 (5H, m), 7.86-7.81 (1H, m), 8.49-8.44 (1H, m).

MS (ESI, m/z):509 (M+H)$^+$.

EXAMPLE 30

(2-{3-[5-(Diphenylmethyl)-2-oxo-1(2H)-pyridinyl]propyl}phenoxy)acetic acid.

$^1$H-NMR (CDCl$_3$) δ: 2.11-2.01 (2H, m), 2.68 (2H, t, J=7.0 Hz), 3.91 (2H, t, J=7.0 Hz), 4.59 (2H, s), 5.24 (1H, s), 6.56 (1H, d, J=9.5 Hz), 6.73 (1H, d, J=8.0 Hz), 6.88-6.84 (2H, m), 7.18-7.01 (8H, m), 7.34-7.22 (5H, m).

MS (ESI, m/z) 454 (M+H)$^+$.

EXAMPLE 31

[(3'-{[5-(Diphenylmethyl)-2-oxo-1(2H)-pyridinyl]methyl}-3-biphenylyl)oxy]acetic acid.

$^1$H-NMR (DMSO-d$_6$) δ: 4.76 (2H, s), 5.13 (2H, s), 5.39 (1H, s), 6.43 (1H, d, J=9.5 Hz), 6.94 (1H, dd, J=8.0, 2.0 Hz), 7.14-7.12 (5H, m), 7.33-7.21 (9H, m), 7.42-7.39 (2H, m), 7.46 (1H, s), 7.51 (1H, d, J=2.0 Hz), 7.56 (1H, d, J=7.5 Hz).

MS (ESI, m/z):502 (M+H)$^+$.

EXAMPLE 32

(3-{3-[Benzoyl(3,3-diphenylpropyl)amino]propyl}phenoxy)acetic acid.

$^1$H-NMR (CDCl$_3$) δ: 1.95-1.67 (2H, m), 2.69-2.18 (4H, m), 3.18-3.12 (2H, m), 3.52-3.40 (2H, m), 3.91-3.88, 3.66-3.61 (4H, m), 4.60, 4.58 (2H, s), 6.83-6.55 (4H, m), 7.01-6.96 (2H, m), 7.36-7.10 (13H, m).

MS (ESI, m/z):508 (M+H)$^+$.

EXAMPLE 33

[3-(3-{(3,3-Diphenylpropyl)[(2E)-3-(4-pyridinyl)-2-propenoyl]amino}propyl)phenoxy]acetic acid.

$^1$H-NMR (DMSO-d$_6$) δ: 1.80-1.72 (2H, m), 2.38-2.24 (2H, m), 2.56-2.51 (2H, m), 3.48-3.27 (4H, m), 3.99-3.95 (1H, m), 4.64 (2H, s), 6.78-6.70 (3H, m), 7.19-7.16 (3H, m), 7.44-7.24 (9H, m), 7.58 (1H, brs), 7.71 (1H, brs), 8.70 (1H, brs).

MS (ESI, m/z):534 (M+H)$^+$.

EXAMPLE 34

(2E)-3-(2-{3-[Benzoyl(3,3-diphenylpropyl)amino]propyl}phenoxy)acrylic acid.

$^1$H-NMR (DMSO-d$_6$) δ: 1.79-1.63 (2H, m), 2.32-2.20 (4H, m), 2.58-2.56 (1H, m), 3.11-3.04 (2H, m), 3.49-3.46 (1H, m), 4.01, 3.71 (1H, t, J=7.5 Hz), 5.32-5.23 (1H, m), 7.37-7.11 (19H, m), 7.73, 7.63 (1H, d, J=12.0 Hz).

MS (ESI, m/z):520 (M+H)$^+$.

EXAMPLE 35

(3-{3-[(3,3-Diphenylpropyl)(phenoxycarbonyl)amino]propyl}phenoxy)acetic acid.

$^1$H-NMR (DMSO-d$_6$) δ: 1.84-1.77 (2H, m), 2.41-2.31 (2H, m), 2.57-2.50 (2H, m), 3.27-3.18 (4H, m), 3.98-3.96 (1H, m), 4.62 (2H, s), 6.79-6.70 (3H, m), 7.07 (2H, d, J=8.0 Hz), 7.40-7.15 (14H, m).

MS (ESI, m/z):524 (M+H)$^+$.

EXAMPLE 36

[4-(4-{[5-(Diphenylmethyl)-2-oxo-1(2H)-pyridinyl]methyl}-oxazol-2-yl)-1H-indol-1-yl]acetic acid.

$^1$H-NMR (DMSO-d$_6$) δ: 5.05 (2H, s), 5.12 (2H, s), 5.42 (1H, s), 6.41 (1H, d, J=9.4 Hz), 7.03 (1H, d, J=3.1 Hz), 7.15-7.35 (12H, m), 7.48 (1H, d, J=2.1 Hz), 7.54 (1H, d, J=3.1 Hz), 7.60 (1H, d, J=8.2 Hz), 7.68 (1H, d, J=7.4 Hz), 8.12 (1H, s).

MS (ESI, m/z):516 (M+H)$^+$.

EXAMPLE 37

(4-{2-[5-(Diphenylmethyl)-2-oxopyridin-1(2H)-yl]ethoxy}-2-methyl-1H-benzimidazol-1-yl)acetic acid.

$^1$H-NMR (DMSO-d$_6$) δ: 2.40 (3H, s), 4.22 (2H, t, J=5.0 Hz), 4.49 (2H, t, J=5.0 Hz), 5.02 (2H, s), 5.34 (1H, s), 6.38 (1H, d, J=9.3 Hz), 6.55 (1H, d, J=7.0 Hz), 6.9-7.4 (14H, m), 13.3 (1H, brs).

MS (ESI, m/z):492 (M−H)$^-$.

EXAMPLE 38

(3-{3-[3-(Diphenylmethyl)-6-oxopyridazin-1(6H)-yl]propoxy}phenoxy)acetic acid.

$^1$H-NMR (DMSO-d$_6$) δ: 2.0-2.2 (2H, m), 3.92 (2H, t, J=6.0 Hz), 4.16 (2H, t, J=6.7 Hz), 4.62 (2H, s), 5.51 (1H, s), 6.3-6.5 (3H, m), 6.90 (1H, d, J=9.8 Hz), 7.1-7.4 (12H, m), 12.97 (1H, brs).

MS (ESI, m/z):469 (M−H)$^-$.

EXAMPLE 39

4-(3-{2-[3-(Diphenylmethyl)-6-oxopyridazin-1(6H)-yl]ethoxy}phenoxy)butanoic acid.

$^1$H-NMR (DMSO-d$_6$) δ: 1.8-2.0 (2H, m), 2.37 (2H, t, J=7.3 Hz), 3.93 (2H, t, J=6.4 Hz), 4.2-4.4 (4H, m), 5.53 (1H, s), 6.4-6.6 (3H, m), 6.92 (1H, d, J=9.4 Hz), 7.1-7.4 (12H, m), 12.18 (1H, brs).

MS (ESI, m/z):483 (M−H)$^-$.

EXAMPLE 40

(3-{3-[5-(Diphenylmethyl)-2-oxopyridin-1(2H)-yl]propoxy}phenoxy)acetic acid.

$^1$H-NMR (DMSO-d$_6$) δ: 2.0-2.1 (2H, m), 3.88 (2H, t, J=5.9 Hz), 3.95 (2H, t, J=6.7 Hz), 4.63 (2H, s), 5.28 (1H, s), 6.3-6.6 (4H, m), 7.0-7.3 (13H, m), 12.98 (1H, brs).

MS (ESI, m/z):468 (M−H)$^-$.

EXAMPLE 41

(2R)-2-(3-{3-[5-(Diphenylmethyl)-2-oxopyridin-1(2H)-yl]propyl}phenoxy)propanoic acid.

$^1$H-NMR (CDCl$_3$) δ: 1.65 (3H, d, J=6.7 Hz),1.90-2.08 (2H, m), 2.48-2.63 (2H, m), 3.72-3.88 (2H, m), 4.78 (1H, q, J=6.7 Hz), 5.27 (1H, s), 6.63-6.68 (2H, m), 6.72-6.80 (3H, m), 7.16-7.36 (12H, m).

MS (ESI, m/z):490 (M+Na)$^+$.

EXAMPLE 42

2-[3-({3-[5-(Diphenylmethyl)-2-oxopyridin-1(2H)-yl]propyl}sulfanyl)phenoxy]propanoic acid.

$^1$H-NMR (CDCl$_3$) δ: 1.67 (3H, d, J=6.8 Hz), 1.75-1.87 (1H, m), 1.93-2.06 (1H, m), 2.60-2.68 (1H, m), 2.97-3.07 (1H, m), 3.54-3.63 (1H, m), 4.24-4.33 (1H, m), 4.71 (1H, q, J=6.8 Hz), 5.26 (1H, s), 6.66-6.91 (4H, m), 7.05-7.35 (13H, m).

MS (ESI, m/z):522 (M+Na)$^+$.

EXAMPLE 43

(3-{3-[(4-Carbamoylbenzoyl)(3,3-diphenylpropyl)amino]propyl}phenoxy)acetic acid.

$^1$H-NMR (DMSO-d$_6$) δ: 1.60-1.70 (1H, m), 1.83-1.84 (1H, m), 2.27-2.36 (3H, m), 2.57-2.29 (1H, m), 3.01-3.09 (3H, m), 3.45-3.48 (1H, m), 3.74, 4.02 (1H, t, J=7.1 Hz), 4.59, 4.63 (2H, s), 6.55-6.82 (3H, m), 7.06-7.45 (14H, m), 7.84-8.04 (3H, m), 13.00 (1H, brs).

MS (ESI, m/z):573 (M+Na)$^+$.

EXAMPLE 44

(3-{3-[(3,3-Diphenylpropyl)(4-fluorobenzoyl)amino]propyl}phenoxy).acetic acid.

$^1$H-NMR (DMSO-d$_6$) δ: 1.65-1.90 (2H, m), 2.15-2.40 (3H, m), 2.55-2.63 (1H, m), 3.00-3.15 (3H, m), 3.45-3.55 (1H, m), 3.70-4.05 (1H, m), 4.63 (2H, s), 6.55-6.85 (3H, m), 7.13-7.34 (15H, m), 12.95 (1H, brs).

MS (ESI, m/z):548 (M+Na)$^+$.

EXAMPLE 45

(3-{3-[(3,3-Diphenylpropyl)(3-thienylcarbonyl)amino]propyl}phenoxy)acetic acid.

$^1$H-NMR (CDCl$_3$) δ: 1.75-2.61 (5H, m), 3.26-4.00 (6H, m), 4.60 (2H, s), 6.66-6.74 (3H, m), 6.99-7.52 (14H, m).

MS (ESI, m/z):536 (M+Na)$^+$.

EXAMPLE 46

4-(3-{3-[5-(Diphenylmethyl)-2-oxopyridin-1(2H)-yl]propyl}-4-fluorophenoxy)butanoic acid.

$^1$H-NMR (DMSO-d$_6$) δ:1.8-2.0 (4H, m), 2.36 (2H, t, J=7.3 Hz), 3.85 (2H, t, J=7.2 Hz), 3.92 (2H, t, J=6.4 Hz), 5.36 (1H, s), 6.37 (1H, d, J=9.4 Hz), 6.7-7.4 (15H, m), 12.19 (1H, brs).

MS (ESI, m/z):498 (M−H)$^-$.

EXAMPLE 47

[3-({3-[5-(Diphenylmethyl)-2-oxopyridin-1(2H)-yl]propyl}sulfonyl)phenoxy]acetic acid.

$^1$H-NMR (CDCl$_3$) δ: 2.00-2.11 (2H, m), 3.06-3.12 (2H, m), 3.87-3.94 (2H, m),4.73 (2H, s), 5.29 (1H, s), 6.70-6.84 (2H, m), 7.06-7.112 (4H, m), 7.24-7.54 (11H, m).

MS (ESI, m/z):540 (M+Na)$^+$.

EXAMPLE 48

4-(3-{3-[5-(Diphenylmethyl)-2-oxopyridin-1(2H)-yl]propyl}phenoxy)butanoic acid.

$^1$H-NMR (CDCl$_3$) δ:2.03 (2H, m), 2.11 (2H, m), 2.52-2.59 (4H, m), 3.86 (2H, t, J=7.4 Hz), 4.04 (2H, t, J=6.1 Hz), 5.26 (1H, s), 6.65-6.85 (5H, m), 6.98-7.34 (12H, m).

MS (ESI, m/z):504 (M+Na)$^+$.

EXAMPLE 49

2-[3-({3-[5-(Diphenylmethyl)-2-oxopyridin-1(2H)-yl]propyl}sulfinyl)phenoxy]propanoic acid.

$^1$H-NMR (CDCl$_3$) δ: 1.67 (1.5H, d, J=6.6 Hz), 1.68 (1.5H, d, J=6.6 Hz), 1.80-2.08 (2H, m), 2.56-2.98 (2H, m), 3.68-4.08 (2H, m), 4.77 (0.5H, q, J=7.0 Hz), 4.87 (0.5H, q, J=7.0 Hz), 5.26 (0.5H, s), 5.27 (0.5H, s), 6.62-6.82 (4H, m), 7.07-7.46 (13H, m).

MS (ESI, m/z):538 (M+Na)$^+$.

EXAMPLE 50

2-[3-({3-[5-(Diphenylmethyl)-2-oxopyridin-1(2H)-yl]propyl}sulfonyl)phenoxy]propanoic acid.

$^1$H-NMR (CDCl$_3$) δ: 1.68 (3H, d, J=6.7 Hz), 1.88-2.11 (2H, m), 2.96-3.17 (2H, m), 3.78-3.92 (2H, m), 4.83 (1H, q, J=6.7 Hz), 5.28 (1H, s), 6.62-6.80 (2H, m), 7.06-7.12 (4H, m), 7.21-7.53 (11H, m).

MS (ESI, m/z):554 (M+Na)$^+$.

EXAMPLE 51

[3-(6-{[5-(Diphenylmethyl)-2-oxopyridin-1(2H)-yl]methyl}pyridin-2-yl)phenoxy]acetic acid.

$^1$H-NMR (DMSO-d$_6$) δ:4.63 (2H, s), 5.18 (2H, s), 5.60 (1H, s), 6.41 (1H, d, J=9.4 Hz), 6.95-7.90 (19H, m).

MS (ESI, m/z):503 (M+H)$^+$.

EXAMPLE 52

[3-(3-{(3,3-Diphenylpropyl)[(5-methylisoxazol-3-yl)carbonyl]amino}propyl)phenoxy]acetic acid.

$^1$H-NMR (CDCl$_3$) δ: 1.77-1.96 (2H, m), 2.29-2.54 (6H, m), 2.60 (1H, t, J=7.6 Hz), 3.32-3.55 (4H, m), 3.82 (0.5H, t, J=7.6 Hz), 3.95 (0.5H, t, J=7.6 Hz), 4.64 (2H, s), 6.14 (0.5H, s), 6.23 (0.5H, s), 6.65-6.86 (3H, m), 7.11-7.33 (11H, m).

MS (ESI, m/z):511 (M−H)$^−$.

EXAMPLE 53

[3-(6-{[3-(Diphenylmethyl)-6-oxopyridazin-1(6H)-yl]methyl}pyridin-2-yl)phenoxy]acetic acid.

$^1$H-NMR (DMSO-d$_6$) δ: 4.65 (2H, s), 5.39 (2H, s), 5.56 (1H, s), 6.90-7.95 (19H, m), 13.10 (1H, brs).

MS (ESI, m/z):504 (M+H)$^+$.

EXAMPLE 54

[(3'-{[3-(Diphenylmethyl)-6-oxopyridazin-1(6H)-yl]methyl}biphenyl-3-yl)oxy]acetic acid.

$^1$H-NMR (DMSO-d$_6$) δ: 4.73 (2H, s), 5.24 (2H, s), 5.57 (1H, s), 6.90-7.70 (20H, m), 13.1 (1H, brs).

MS (ESI, m/z):503 (M+H)$^+$.

EXAMPLE 55

3-(3-{3-[3-(Diphenylmethyl)-6-oxopyridazin-1(6H)-yl]propyl}phenyl)propanoic acid.

$^1$H-NMR (CDCl$_3$) δ: 2.02-2.18 (2H, m), 2.56-2.67 (4H, m), 2.92 (2H, t, J=7.6 Hz), 4.12 (2H, t, J=7.3 Hz), 5.47 (1H, s), 6.85-7.41 (16H, m).

MS (ESI, m/z):451 (M−H)$^−$.

EXAMPLE 56

3-(3-{3-[5-(Diphenylmethyl)-2-oxopyridin-1(2H)-yl]propyl}phenyl)propanoic acid.

$^1$H-NMR (CDCl$_3$) δ: 1.96-2.06 (2H, m), 2.56-2.68 (4H, m), 2.93 (2H, t, J=7.5 Hz), 3.79 (2H, t, J=7.6 Hz), 5.25 (1H, s), 6.59 (1H, d, J=9.3 Hz), 6.78 (1H, d, J=2.4 Hz), 6.92 (1H, d, J=7.5 Hz), 7.00-7.40 (14H, m).

MS (ESI, m/z):450 (M−H)$^−$.

EXAMPLE 57

(3-{3-[(3,3-Diphenylpropyl){3-[(methylsulfonyl)amino]benzoyl}amino]propyl}phenoxy)acetic acid.

$^1$H-NMR (CDCl$_3$) δ: 1.66-1.70 (1H, m), 1.92-1.95 (1H, m), 2.17-2.21 (1H, m), 2.32-2.35 (1H, m), 2.39-2.45 (1H, m), 2.61-2.65 (1H, m), 2.87 (3H, s), 3.03-3.11 (2H, m), 3.40-3.44 (1H, m), 3.48-3.52 (1H, m), 3.62-4.01 (1H, m), 4.55, 4.58 (2H, s), 6.49-6.80 (3H, m), 6.97-7.06 (4H, m), 7.11-7.96 (12H, m).

MS (ESI, m/z):601 (M+H)$^+$.

EXAMPLE 58

(3-{4-[3-(Diphenylmethyl)-6-oxopyridazin-1(6H)-yl]butyl}phenoxy)acetic acid.

$^1$H-NMR (DMSO-d$_6$) δ: 1.42-1.52 (2H, m), 1.60-1.70 (2H, m), 2.44-2.50 (2H, m), 4.00 (2H, t, J=6.8 Hz), 4.28 (2H, s), 5.53 (1H, s), 6.60-6.70 (2H, m), 6.86-6.90 (1H, m), 7.00-7.40 (13H, m).

MS (ESI, m/z):491 (M+Na)$^+$.

EXAMPLE 59

(2S)-2-(3-{3-[3-(Diphenylmethyl)-6-oxopyridazin-1(6H)-yl]propyl}phenoxy)propanoic acid.

$^1$H-NMR (CDCl$_3$) δ: 1.64 (3H, d, J=6.8 Hz), 2.01-2.14 (2H, m), 2.59 (2H, t, J=7.5 Hz), 4.07-4.21 (2H, m), 4.77 (1H, q, J=6.8 Hz), 5.46 (1H, s), 6.72-6.76 (3H, m), 6.91-6.93 (1H, m), 7.09-7.20 (6H, m), 7.24-7.34 (6H, m

MS (ESI, m/z):491 (M+Na)$^+$.

EXAMPLE 60

(3-{3-[3-(Diphenylmethyl)-6-oxopyridazin-1(6H)-yl]propyl}-4-fluorophenoxy)acetic acid.

$^1$H-NMR (DMSO-d$_6$) δ: 1.8-2.0 (2H, m), 4.0-4.1 (2H, m), 4.63 (2H, s), 5.56 (1H, s), 6.7-7.4 (15H, m), 13.02 (1H, brs).

MS (ESI, m/z):471 (M−H)$^−$.

EXAMPLE 61

4-(3-{3-[3-(Diphenylmethyl)-6-oxopyridazin-1(6H)-yl]propyl}-4-fluorophenoxy)butanoic acid.

$^1$H-NMR (DMSO-d$_6$) δ: 1.8-2.0 (4H, m), 2.37 (2H, t, J=7.3 Hz), 3.92 (2H, t, J=6.4 Hz), 4.03 (2H, t, J=6.9 Hz) 5.55 (1H, s), 6.7-7.4 (15H, m), 12.17 (1H, brs).

MS (ESI, m/z):499 (M−H)$^−$.

EXAMPLE 62

(2S)-2-(3-{3-[3-(Diphenylmethyl)-6-oxopyridazin-1(6H)-yl]propyl}-4-fluorophenoxy)propanoic acid.

$^1$H-NMR (DMSO-d$_6$) δ:1.47 (3H, d, J=6.7 Hz), 1.8-2.0 (2H, m), 4.02 (2H, t, J=6.9 Hz), 4.77 (1H, q, J=6.7 Hz), 5.56 (1H, s), 6.6-7.4 (15H, m), 13.02 (1H, brs).

MS (ESI, m/z):485 (M−H)$^−$.

EXAMPLE 63

(2S)-2-(3-{4-[5-(Diphenylmethyl)-2-oxopyridin-1(2H)-yl]butyl}phenoxy)propanoic acid.

$^1$H-NMR (CDCl$_3$) δ: 1.65 (3H, d, J=6.6 Hz), 1.48-1.70 (4H, m), 2.50-2.69 (2H, m), 3.60-3.70 (1H, m), 3.90-3.99 (1H, m), 4.75 (1H, q, J=6.6 Hz), 5.25 (1H, s), 6.57-6.82 (5H, m), 7.04-7.34 (12H, m).

MS (ESI, m/z):504 (M+Na)$^+$.

EXAMPLE 64

[3-(3-{(3,3-Diphenylpropyl)[3-(methylsulfonyl)benzoyl]amino}propyl)phenoxy]acetic acid.

¹H-NMR (CDCl₃) δ: 1.69-1.71 (1H, m), 1.94-1.97 (1H, m), 2.18-2.22 (1H, m), 2.32-2.36 (1H, m), 2.42-2.46 (1H, m), 2.64-2.67 (1H, m), 3.00 (3H, s), 3.04-3.09 (2H, m), 3.42-3.46 (1H, m), 3.51-3.54 (1H, m), 3.63, 3.99 (1H, t, J=7.8 Hz), 4.59, 4.62 (2H, s), 6.52-6.86 (3H, m), 7.00-7.02 (2H, m), 7.09-7.29 (9H, m), 7.45-7.53 (2H, m), 7.83-7.92 (2H, m).

MS (ESI, m/z):584 (M−H)⁻.

EXAMPLE 65

(2S)-2-(3-{4-[3-(Diphenylmethyl)-6-oxopyridazin-1(6H)-yl]butyl}phenoxy)propanoic acid.

¹H-NMR (DMSO-d₆) δ: 1.41 (3H, d, J=6.7 Hz), 1.42-1.52 (2H, m), 1.60-1.70 (2H, m), 2.42-2.52 (2H, m), 4.00 (2H, t, J=6.7 Hz), 4.54 (1H, q, J=6.7 Hz), 5.49 (1H, s), 6.60-6.66 (3H, m), 6.88 (1H, d, J=9.8 Hz), 7.04-7.35 (12H, m).

MS (ESI, m/z):505 (M+Na)⁺.

EXAMPLE 66

3-[{3-[3-(Carboxymethoxy)phenyl]propyl}(3,3-diphenylpropyl)carbamoyl]benzoic acid.

¹H-NMR (CDCl₃) δ: 1.70-1.75 (1H, m), 1.96-1.98 (1H, m), 2.17-2.19 (1H, m), 2.32-2.35 (1H, m), 2.44-2.46 (1H, m), 2.63-2.65 (1H, m), 3.06-3.10 (2H, m), 3.43-3.47 (1H, m), 3.51-3.54 (1H, m), 3.62, 4.01 (1H, t, J=7.8 Hz), 4.55, 4.63 (2H, s), 6.49-7.30 (14H, m), 7.35-7.52 (2H, m), 7.91-8.05 (4H, m).

MS (ESI, m/z):574 (M+Na)⁺.

EXAMPLE 67

(3-{3-[(3-Acetamidobenzoyl)(3,3-diphenylpropyl)amino]propyl}phenoxy)acetic acid.

¹H-NMR (CDCl₃) δ: 1.64-1.88 (2H, m), 2.00 (3H, s), 2.08-2.59 (4H, m), 3.01-3.47 (4H, m), 3.61-3.98 (1H, m), 4.51, 4.57 (2H, s), 6.36-7.63 (19H, m), 8.80 (1H, s).

MS (ESI, m/z):565 (M+H)⁺.

EXAMPLE 68

(2S)-2-(3-{3-[5-(Diphenylmethyl)-2-oxopyridin-1(2H)-yl]propyl}-4-fluorophenoxy)propanoic acid.

¹H-NMR (DMSO-d₆) δ: 1.47 (3H, d, J=6.8 Hz), 1.8-2.0 (2H, m), 3.85 (2H, t, J=7.4 Hz), 4.78 (1H, q, J=6.8 Hz), 5.36 (1H, s), 6.37 (1H, d, J=9.3 Hz), 6.6-7.4 (15H, m), 13.02 (1H, brs).

MS (ESI, m/z):484 (M−H)⁻.

EXAMPLE 69

4-(3-{3-[3-(Diphenylmethyl)-6-oxopyridazin-1(6H)-yl]propyl}phenoxy)butanoic acid.

¹H-NMR (CDCl₃) δ: 2.06-2.14 (4H, m), 2.54-2.61 (4H, m), 4.02 (2H, t, J=6.0 Hz), 4.16 (2H, t, J=7.2 Hz), 5.46 (1H, s), 6.69-6.72 (3H, m), 6.90-6.94 (1H, m), 7.09-7.20 (6H, m), 7.23-7.52 (6H, m).

MS (ESI, m/z):505 (M+Na)⁺.

EXAMPLE 70

(3-{3-[5-(Diphenylmethyl)-2-oxopyridin-1(2H)-yl]propyl}-4-fluorophenoxy)acetic acid.

¹H-NMR (DMSO-d₆) δ:1.8-2.0 (2H, m), 2.4-2.6 (2H, m), 3.86 (2H, t, J=7.3 Hz), 4.63 (2H, s), 5.36 (1H, s), 6.37 (1H, d, J=9.3 Hz), 6.7-7.4 (15H, m), 13.02 (1H, brs).

MS (ESI, m/z):470 (M−H)⁻.

EXAMPLE 71

(3-{3-[5-(Diphenylmethyl)-2-oxopiperidin-1-yl]propyl}phenoxy)acetic acid.

¹H-NMR (CDCl₃) δ: 1.30-1.43 (1H, m), 1.69-1.81 (2H, m), 2.27-2.40 (1H, m), 2.47-2.65 (4H, m), 2.89-2.96 (1H, m), 3.06-3.13 (1H, m), 3.24-3.32 (2H, m), 3.57-3.63 (1H, m), 4.65 (2H, s), 6.71-6.82 (3H, m), 7.15-7.33 (11H, m).

MS (ESI, m/z):458 (M+H)⁺.

EXAMPLE 72

(3-{3-[(4S)-4-(Diphenylmethyl)-2-oxo-1,3-oxazolidin-3-yl]propyl}phenoxy)acetic acid.

¹H-NMR ((DMSO-d₆) δ: 1.40-1.75 (2H, m), 2.00-2.45 (3H, m), 3.07 (1H, m), 3.78 (1H, m), 4.22 (2H, m), 4.62 (2H, s), 4.93 (1H, m), 6.60-7.55 (14H, m), 13.00 (1H, brs).

MS (ESI, m/z):468 (M+Na)⁺.

EXAMPLE 73

(3-{3-[(4R)-4-(Diphenylmethyl)-2-oxo-1,3-oxazolidin-3-yl]propyl}phenoxy)acetic acid.

¹H-NMR (DMSO-d₆) δ: 1.40-1.75 (2H, m), 2.00-2.45 (3H, m), 3.07 (1H, m), 3.78 (1H, m), 4.22 (2H, m), 4.64 (2H, s), 4.93 (1H, m), 6.60-7.55 (14H, m), 13.02 (1H, brs).

MS (ESI, m/z):468 (M+Na)⁺.

EXAMPLE 74

(2S)-2-[3-({2-[3-(Diphenylmethyl)-6-oxopyridazin-1(6H)-yl]ethyl}sulfanyl)phenoxy]propanoic acid.

¹H-NMR (DMSO-d₆) δ: 1.48 (3H, d, J=6.7 Hz), 3.29 (2H, t, J=6.9 Hz), 4.19 (2H, t, J=6.9 Hz), 4.85 (1H, q, J=6.8 Hz), 5.54 (1H, s), 6.68-6.71 (1H, m), 6.84-6.91 (3H, m), 7.16-7.34 (12H, m).

MS (ESI, m/z):485 (M−H)⁻.

EXAMPLE 75

4-[3-({2-[3-(Diphenylmethyl)-6-oxopyridazin-1(6H)-yl]ethyl}sulfanyl)phenoxy]butanoic acid.

¹H-NMR (DMSO-d₆) δ:1.88-1.95 (2H, m), 2.36 (2H, t, J=7.3 Hz), 3.27-3.32 (2H, m), 3.97 (2H, t, J=6.4 Hz), 4.19 (2H, t, J=6.8 Hz), 5.52 (1H, s), 6.76 (1H, dd, J=8.2, 2.4 Hz), 6.84 (1H, d, J=7.6 Hz), 6.88-6.90 (2H, m), 7.15-7.33 (12H, m), 12.12 (1H, brs).

MS (ESI, m/z):499 (M−H)⁻.

EXAMPLE 76

{3-[(Acetyl{2-[5-(diphenylmethyl)-2-oxopyridin-1(2H)-yl]ethyl}amino)methyl]phenoxy}acetic acid.

¹H-NMR (DMSO-d₆) δ: 1.86 (3H, s), 3.48 (2H, m), 4.01 (2H, m), 4.40 (2H, s), 4.63 (2H, s), 5.34 (1H, s), 6.30-7.40 (17H, m), 13.02 (1H, brs).

MS (ESI, m/z):533 (M+Na)⁺.

EXAMPLE 77

(3-{[{2-[5-(Diphenylmethyl)-2-oxopyridin-1(2H)-yl]ethyl}(methyl)amino]methyl}phenoxy)acetic acid.
$^1$H-NMR (DMSO-d$_6$) δ: 2.09 (3H, s), 2.55 (2H, m), 3.42 (2H, s), 3.92 (2H, m), 4.60 (2H, s), 5.37 (1H, s), 6.33 (1H, d, J=10.1 Hz), 6.60-7.40 (16H, m), 13.00 (1H, brs).
MS (ESI, m/z):483 (M+H)$^+$.

EXAMPLE 78

(2S)-2-[3-({2-[5-(Diphenylmethyl)-2-oxopyridin-1(2H)-yl]ethyl}sulfanyl)phenoxy]propanoic acid.
$^1$H-NMR (DMSO-d$_6$) δ: 1.47 (3H, d, J=6.8 Hz), 3.26 (2H, t, J=6.5 Hz), 3.96 (2H, t, J=6.5 Hz), 4.83 (1H, q, J=6.8 Hz), 5.33 (1H, s), 6.37 (1H, d, J=9.3 Hz), 6.68 (1H, d, J=5.9 Hz), 6.79-6.82 (2H, m), 7.12-7.34 (13H, m).
MS (ESI, m/z):484 (M−H)$^-$.

EXAMPLE 79

{3-[({2-[5-(Diphenylmethyl)-2-oxopyridin-1(2H)-yl]ethyl}amino)methyl]phenoxy}acetic acid.
$^1$H-NMR (DMSO-d$_6$) δ: 2.79 (2H, m), 3.33 (2H, brs),3.91 (2H, m), 4.60 (2H, s), 5.34 (1H, s), 6.36 (1H, d, J=9.4 Hz), 6.70-7.40 (16H, m).
MS (ESI, m/z):469 (M+H)$^+$.

EXAMPLE 80

4-(3-{3-[3-(Diphenylmethyl)-6-oxo-5,6-dihydropyridazin-1(4H)-yl]propyl}phenoxy)butanoic acid.
$^1$H-NMR (CDCl$_3$) δ: 1.89-1.97 (2H, m), 2.05-2.13 (2H, m), 2.35-2.45 (4H, m), 2.55-2.60 (4H, m), 3.78 (2H, t, J=7.0 Hz), 4.01 (2H, t, J=6.0 Hz), 5.10 (1H, s), 6.69-6.73 (3H, m), 7.12-7.35 (11H, m).
MS (ESI, m/z):485 (M+H)$^+$.

EXAMPLE 81

4-[(3-{2-[3-(Diphenylmethyl)-6-oxopyridazin-1(6H)-yl]ethoxy}phenyl)sulfanyl]butanoic acid.
$^1$H-NMR (DMSO-d$_6$) δ: 1.77 (2H, tt, J=7.2, 7.2 Hz), 2.34 (2H, t, J=7.2 Hz), 2.96 (2H, t, J=7.1 Hz), 4.32-4.35 (4H, m), 5.53 (1H, s), 6.66 (1H, dd, J=2.3, 8.2 Hz), 6.81 (1H, s), 6.89-6.93 (2H, m), 7.16-7.34 (12H, m).
MS (ESI, m/z):499 (M−H)$^-$.

EXAMPLE 82

4-[(3-{2-[5-(Diphenylmethyl)-2-oxopyridin-1(2H)-yl]ethoxy}phenyl)sulfanyl]butanoic acid.
$^1$H-NMR (DMSO-d$_6$) δ: 1.76 (2H, tt, J=7.2, 7.2 Hz), 2.34 (2H, t, J=7.2 Hz), 2.96 (2H, t, J=7.1 Hz), 4.17 (4H, s), 5.38 (1H, s), 6.38 (1H, d, J=9.2 Hz), 6.58 (1H, d, J=8.1 Hz), 6.74 (1H, s), 6.90 (1H, d, J=8.2 Hz), 7.12-7.34 (13H, m).
MS (ESI, m/z):498 (M−H)$^-$.

EXAMPLE 83

4-(3-{3-[(4S)-4-(Diphenylmethyl)-2-oxo-1,3-oxazolidin-3-yl]propyl}phenoxy)butanoic acid.
$^1$H-NMR (DMSO-d$_6$) δ:1.40-1.70 (2H, m), 1.93 (2H, m), 2.05-2.45 (5H, m), 3.08 (1H, m), 3.79 (1H, m), 3.96 (2H, m), 4.22 (2H, m), 4.92 (1H, m), 6.60-7.60 (14H, m), 12.10 (1H, brs).
MS (ESI, m/z):496 (M+Na)$^+$.

EXAMPLE 84

4-[3-({2-[5-(Diphenylmethyl)-2-oxopyridin-1(2H)-yl]ethyl}sulfanyl)phenoxy]butanoic acid.
$^1$H-NMR (DMSO-d$_6$) δ: 1.88-1.95 (2H, m), 2.36 (2H, t, J=7.3 Hz), 3.27-3.34 (2H, m), 3.95-3.98 (4H, m), 5.32 (1H, s), 6.37 (1H, d, J=9.3 Hz), 6.73-6.86 (3H, m), 7.10-7.33 (13H, m).
MS (ESI, m/z):498 (M−H)$^-$.

EXAMPLE 85

(2S)-2-[3-({3-[3-(Diphenylmethyl)-6-oxopyridazin-1(6H)-yl]propyl}sulfonyl)phenoxy]propanoic acid.
$^1$H-NMR (DMSO-d$_6$) δ: 1.52 (3H, d, J=6.8 Hz),1.93 (2H, m), 3.30 (2H, m), 4.04 (2H, t, J=7.1 Hz), 5.01 (1H, q, J=6.8 Hz), 5.51 (1H, s), 6.88 (1H, d, J=9.6 Hz), 7.10-7.60 (15H, m), 13.20 (1H, brs).
MS (ESI, m/z):555 (M+Na)$^+$.

EXAMPLE 86

[3-({3-[3-(Diphenylmethyl)-6-oxopyridazin-1(6H)-yl]propyl}sulfonyl)phenoxy]acetic acid.
$^1$H-NMR (DMSO-d$_6$) δ: 1.93 (2H, m), 3.33 (2H, m), 4.04 (2H, t, J=6.9 Hz), 4.81 (2H, s), 5.51 (1H, s), 6.88 (1H, d, J=9.6 Hz), 7.10-7.60 (15H, m), 13.15 (1H, brs).
MS (ESI, m/z):541 (M+Na)$^+$.

EXAMPLE 87

(3-{3-[3-(Diphenylmethyl)-6-oxo-5,6-dihydropyridazin-1(4H)-yl]propyl}phenoxy)acetic acid.
$^1$H-NMR (CDCl$_3$) δ: 1.89-1.97 (2H, m), 2.33-2.43 (4H, m), 2.58 (2H, t, J=7.5 Hz), 3.76 (2H, t, J=6.9 Hz), 4.64 (2H, s), 5.09 (1H, s), 6.72-6.78 (3H, m), 7.12-7.35 (11H, m).
MS (ESI, m/z):479 (M+Na)$^+$.

EXAMPLE 88

(2S)-2-[3-({3-[3-(Diphenylmethyl)-6-oxopyridazin-1(6H)-yl]propyl}sulfanyl)phenoxy]propanoic acid.
$^1$H-NMR (DMSO-d$_6$): 1.47 (3H, d, J=6.7 Hz),1.94 (2H, m), 2.90 (2H, t, J=7.2 Hz), 4.10 (2H, t, J=6.7 Hz), 4.82 (1H, q, J=6.7 Hz), 5.54 (1H, s), 6.60-7.40 (16H, m), 13.05 (1H, brs).
MS (ESI, m/z):523 (M+Na)$^+$.

EXAMPLE 89

[3-({3-[3-(Diphenylmethyl)-6-oxopyridazin-1(6H)-yl]propyl}sulfanyl)phenoxy]acetic acid.
$^1$H-NMR (DMSO-d$_6$) δ: 1.94 (2H, m), 2.91 (2H, t, J=7.2 Hz), 4.11 (2H, t, J=6.7 Hz), 4.66 (2H, s), 5.54 (1H, s), 6.70-7.40 (16H, m), 13.02 (1H, brs).
MS (ESI, m/z):509 (M+Na)$^+$.

EXAMPLE 90

(3-{3-[3-Chloro-5-(diphenylmethyl)-2-oxopyridin-1(2H)-yl]propyl}phenoxy)acetic acid.
$^1$H-NMR (CDCl$_3$) δ: 1.99-2.08 (2H, m), 2.58 (2H, t, J=7.5 Hz), 3.89 (2H, t, J=7.3 Hz), 4.65 (2H, s), 5.24 (1H, s), 6.71-6.78 (4H, m), 7.08-7.35 (12H, m).
MS (ESI, m/z):488 (M+H)$^+$.

EXAMPLE 91

4-[3-({3-[5-(Diphenylmethyl)-2-oxopyridin-1(2H)-yl]propyl}sulfanyl)phenoxy]butanoic acid.
$^1$H-NMR (CDCl$_3$) δ: 2.00-2.12 (4H, m), 2.53 (2H, t, J=6.9 Hz), 2.83-2.88 (2H, m), 3.95-4.05 (4H, m), 5.24 (1H, s), 6.60-6.87 (4H, m), 7.05-7.33 (13H, m).
MS (ESI, m/z):536 (M+Na)$^+$.

EXAMPLE 92

[3-({3-[5-(Diphenylmethyl)-2-oxopyridin-1(2H)-yl]propyl}sulfanyl)phenoxy]acetic acid.
$^1$H-NMR (CDCl$_3$) δ: 1.90-2.00 (2H, m), 2.81-2.87 (2H, m), 3.92-3.98 (2H, m), 4.65 (2H, s), 5.26 (1H, s), 6.64-6.92 (4H, m), 7.05-7.36 (13H, m).
MS (ESI, m/z):508 (M+Na)$^+$.

EXAMPLE 93

(3-{3-[(3,3-Diphenylpropyl)(4-methoxybenzoyl)amino]propyl}phenoxy)acetic acid.
$^1$H-NMR (DMSO-d$_6$) δ:1.60-1.90 (2H, m), 2.15-2.60 (4H, m), 3.00-3.50 (4H, m), 3.78 (3H, s), 3.70-4.10 (1H, m), 4.62 (2H, s), 6.55-6.90 (5H, m), 7.10-7.50 (13H, m), 12.98 (1H, brs).
MS (ESI, m/z):560 (M+Na)$^+$.

EXAMPLE 94

[3-(3-{[4-(Benzyloxy)benzoyl](3,3-diphenylpropyl)amino}propyl)phenoxy]acetic acid.
$^1$H-NMR (DMSO-d$_6$) δ:1.65-2.50 (5H, m), 2.50-2.60 (1H, m), 3.00-4.10 (5H, m), 4.62 (2H, s), 5.13 (2H, s), 6.60-6.96 (5H, m), 7.14-7.49 (18H, m), 13.01 (1H, brs).
MS (ESI, m/z):612 (M−H)$^-$.

EXAMPLE 95

(3-{3-[(3,3-Diphenylpropyl)(2-thienylcarbonyl)amino]propyl}phenoxy)acetic acid.
$^1$H-NMR (DMSO-d$_6$) δ: 1.76-1.84 (2H, m), 2.30-2.36 (3H, m), 3.15-3.50 (5H, m), 3.88-4.00 (1H, m), 4.63 (2H, s), 6.71-6.74 (3H, m), 7.11-7.31 (13H, m), 7.65-7.67 (1H, m), 13.00 (1H, brs).
MS (ESI, m/z):536 (M+Na)$^+$.

EXAMPLE 96

(2S)-2-(3-{3-[5-(Diphenylmethyl)-2-oxopyridin-1(2H)-yl]propyl}phenoxy)propanoic acid.
$^1$H-NMR (CDCl$_3$) δ: 1.65 (3H, d, J=6.7 Hz), 1.90-2.08 (2H, m), 2.48-2.63 (2H, m), 3.72-3.88 (2H, m), 4.78 (1H, q, J=6.7 Hz), 5.27 (1H, s), 6.63-6.68 (2H, m), 6.72-6.80 (3H, m), 7.16-7.36 (12H, m).
MS (ESI, m/z):490 (M+Na)$^+$.

EXAMPLE 97

2-(3-{3-[5-(Diphenylmethyl)-2-oxopyridin-1(2H)-yl]propyl}phenoxy)propanoic acid.
$^1$H-NMR (CDCl$_3$) δ: 1.65 (3H, d, J=6.7 Hz), 1.90-2.08 (2H, m), 2.48-2.63 (2H, m), 3.72-3.88 (2H, m), 4.78 (1H, q, J=6.7 Hz), 5.27 (1H, s), 6.63-6.68 (2H, m), 6.72-6.80 (3H, m), 7.16-7.36 (12H, m).
MS (ESI, m/z):490 (M+Na)$^+$.

EXAMPLE 98

(2S)-2-(3-{3-[3-Chloro-5-(diphenylmethyl)-2-oxopyridin-1(2H)-yl]propyl}phenoxy)propanoic acid.
$^1$H-NMR (CDCl$_3$) δ: 1.64-1.67 (3H, m), 1.98-2.05 (2H, m), 2.54-2.58 (2H, m), 3.82-3.88 (2H, m), 4.76-4.81 (1H, m), 5.24, 5.30 (1H, s), 6.68-6.76 (4H, m), 7.08-7.38 (12H, m).
MS (ESI, m/z):502 (M+H)$^+$.

EXAMPLE 99

[3-(3-{[3-(Aminosulfonyl)benzoyl](3,3-diphenylpropyl)amino}propyl)phenoxy]acetic acid.
$^1$H-NMR (CDCl$_3$) δ: 1.65-1.67 (1H, m), 1.93-1.96 (1H, m), 2.17-2.18 (1H, m),2.30-2.34 (1H, m), 2.42-2.43 (1H, m), 2.60-2.62 (1H, m), 3.03-3.10 (2H, m), 3.40-3.50 (2H, m), 3.62, 3.98 (1H, t, J=7.6 Hz), 4.49, 4.54 (2H, s), 6.38-6.81 (3H, m), 6.99-7.34 (15H, m), 7.76-7.86 (2H, m).
MS (ESI, m/z):585 (M−H)$^-$.

EXAMPLE 100

(2R)-2-(3-{3-[3-(Diphenylmethyl)-6-oxopyridazin-1(6H)-yl]propyl}phenoxy)propanoic acid.
$^1$H-NMR (CDCl$_3$) δ: 1.64 (3H, d, J=6.8 Hz), 2.01-2.14 (2H, m), 2.59 (2H, t, J=7.5 Hz), 4.07-4.14 (2H, m), 4.77 (1H, q, J=6.8 Hz), 5.30, 5.46 (1H, s), 6.72-6.76 (3H, m), 6.91-6.93 (1H, m), 7.09-7.20 (6H, m), 7.24-7.36 (6H, m).
MS (ESI, m/z):491 (M+Na)$^+$.

EXAMPLE 101

[3-(3-{5-[Bis(4-chlorophenyl)methyl]-2-oxopyridin-1(2H)-yl}propyl)phenoxy]acetic acid.
$^1$H-NMR (CDCl$_3$) δ: 2.00-2.06 (2H, m), 2.60 (2H, t, J=7.4 Hz), 3.85 (2H, t, J=7.4 Hz), 4.64 (2H, s), 5.21 (1H, s), 6.70-6.78 (5H, m), 6.99-7.03 (4H, m), 7.15-7.18 (2H, m), 7.23-7.31 (4H, m).
MS (ESI, m/z):545 (M+Na)$^+$.

EXAMPLE 102

[3-(3-{5-[Bis(4-methoxyphenyl)methyl]-2-oxopyridin-1(2H)-yl}propyl)phenoxy]acetic acid.
$^1$H-NMR (CDCl$_3$) δ: 1.94-2.20 (2H, m), 2.59 (2H, t, J=7.4 Hz), 3.79 (6H, s), 3.85 (2H, t, J=7.3 Hz), 4.64 (2H, s), 5.17 (1H, s), 6.70-7.24 (15H, m).
MS (ESI, m/z):536 (M+Na)$^+$.

EXAMPLE 103

[3-(3-{5-[Bis(4-methylphenyl)methyl]-2-oxopyridin-1(2H)-yl}propyl)phenoxy]acetic acid.
$^1$H-NMR (CDCl$_3$) δ: 1.96-2.10 (2H, m), 2.33 (6H, s), 2.58 (2H, t, J=7.4 Hz), 3.86 (2H, t, J=7.3 Hz), 4.64 (2H, s), 5.18 (1H, s), 6.68-6.80 (5H, m), 6.95-6.97 (4H, m), 7.10-7.24 (6H, m).
MS (ESI, m/z):504 (M+Na)$^+$.

EXAMPLE 104

[3-(3-{5-[Bis(4-fluorophenyl)methyl]-2-oxopyridin-1(2H)-yl}propyl)phenoxy]acetic acid.
$^1$H-NMR (CDCl$_3$) δ: 1.97-2.10 (2H, m), 2.59 (2H, t, J=7.4 Hz), 3.85 (2H, t, J=7.4 Hz), 4.64 (2H, s), 5.23 (1H, s), 6.68-6.79 (5H, m), 6.99-7.03 (8H, m), 7.13-7.18 (2H, m).
MS (ESI, m/z):512 (M+Na)$^+$.

EXAMPLE 105

(3-{3-[2-Oxo-5-(9H-xanthen-9-yl)pyridin-1(2H)-yl]propyl}phenoxy)acetic acid.

$^1$H-NMR (CDCl$_3$) δ: 2.00-2.15 (2H, m), 2.62 (2H, t, J=7.4 Hz), 3.90 (2H, t, J=7.6 Hz), 4.64 (2H, s), 4.95 (1H, s), 6.61 (1H, d, J=9.2 Hz), 6.74-6.83 (3H, m), 7.01-7.27 (11H, m).

MS (ESI, m/z):466 (M−H)$^−$.

EXAMPLE 106

[3-(3-{5-[Bis(4-methoxyphenyl)methyl]-2-oxopyridin-1(2H)-yl}propoxy)phenoxy]acetic acid.

$^1$H-NMR (DMSO-d$_6$) δ: 2.0-2.1 (2H, m), 3.70 (6H, s), 3.8-4.0 (4H, m), 4.63 (2H, s), 5.14 (1H, s), 6.3-6.6 (4H, m), 6.81 (4H, d, J=8.7 Hz), 6.94 (4H, d, J=8.7 Hz), 7.1-7.2 (3H, m), 12.98 (1H, brs).

MS (ESI, m/z):528 (M−H)$^−$.

EXAMPLE 107

(2S)-2-[3-(3-{5-[Bis(4-methoxyphenyl)methyl]-2-oxopyridin-1(2H)-yl}propyl)phenoxy]propanoic acid.

$^1$H-NMR (CDCl$_3$) δ: 1.65 (3H, d, J=6.8 Hz), 1.93-2.02 (2H, m), 2.53-2.57 (2H, m), 3.76-3.85 (2H, m), 3.79 (6H, s), 4.77 (1H, q, J=6.8 Hz), 5.16, 5.30 (1H, s), 6.62-6.67 (2H, m), 6.72-6.77 (3H, m), 6.83-6.86 (4H, m), 6.98-7.00 (4H, m), 7.09-7.13 (1H, m), 7.18-7.21 (1H, m).

MS (ESI, m/z):528 (M+H)$^+$.

EXAMPLE 108

(2S)-2-(3-{3-[2-Oxo-5-(9H-xanthen-9-yl)pyridin-1(2H)-yl]propyl}phenoxy)propanoic acid.

$^1$H-NMR (DMSO-d$_6$) δ:1.49 (3H, d, J=6.8 Hz),1.91-1.99 (2H, m), 2.57 (2H, t, J=7.7 Hz), 3.89 (2H, t, J=7.3 Hz), 4.82 (1H, q, J=6.7 Hz), 5.21 (1H, s), 6.28 (1H, d, J=9.4 Hz), 6.68-6.70 (2H, m), 6.75-6.80 (1H, m), 6.91-6.94 (2H, m), 7.06-7.34 (8H, m), 7.76-7.77 (1H, m), 13.03 (1H, s).

MS (ESI, m/z):504 (M+Na)$^+$.

EXAMPLE 109

4-[3-(3-{5-[Bis(4-fluorophenyl)methyl]-2-oxopyridin-1(2H)-yl}propyl)-4-fluorophenoxy]butanoic acid.

$^1$H-NMR (DMSO-d$_6$) δ: 1.8-2.0 (4H, m), 2.38 (2H, t, J=7.3 Hz), 2.4-2.6 (2H, m), 3.86 (2H, t, J=7.2 Hz), 3.93 (2H, t, J=6.4 Hz), 5.39 (1H, s), 6.37 (1H, d, J=9.3 Hz), 6.7-6.9 (2H, m), 7.0-7.3 (11H, m), 12.18 (1H, brs).

MS (ESI, m/z):534 (M−H)$^−$.

EXAMPLE 110

4-[3-(3-{3-[Bis(4-fluorophenyl)methyl]-6-oxopyridazin-1(6H)-yl}propyl)-4-fluorophenoxy]butanoic acid.

$^1$H-NMR (DMSO-d$_6$) δ:1.8-2.0 (4H, m), 2.37 (2H, t, J=7.3 Hz), 2.4-2.6 (2H, m), 3.92 (2H, t, J=6.4 Hz), 4.01 (2H, t, J=6.9 Hz), 5.60 (1H, s), 6.7-6.8 (2H, m), 6.90 (1H, d, J=9.5 Hz), 7.0-7.4 (10H, m), 12.14 (1H, brs).

MS (ESI, m/z):535 (M−H)$^−$.

EXAMPLE 111

4-[3-(3-{3-[Bis(4-fluorophenyl)methyl]-6-oxopyridazin-1(6H)-yl}propyl)phenoxy]butanoic acid.

$^1$H-NMR (DMSO-d$_6$) δ:1.8-2.0 (4H, m), 2.37 (2H, t, J=7.3 Hz), 2.42-2.55 (2H, m), 3.94 (2H, t, J=6.4 Hz), 3.99 (2H, t, J=6.9 Hz), 5.61 (1H, s), 6.6-6.8 (3H, m), 6.90 (1H, d, J=9.5 Hz), 7.1-7.4 (10H, m), 12.15 (1H, brs).

MS (ESI, m/z):517 (M−H)$^−$.

EXAMPLE 112

4-[3-(3-{5-[Bis(4-fluorophenyl)methyl]-2-oxopyridin-1(2H)-yl}propyl)phenoxy]butanoic acid.

$^1$H-NMR (DMSO-d$_6$) δ:1.8-2.0 (4H,m), 2.37 (2H, t, J=7.3 Hz), 2.46-2.55 (2H, m), 3.82 (2H, t, J=7.2 Hz), 3.94 (2H, t, J=6.4 Hz), 5.40 (1H, s), 6.37 (1H, d, J=9.3 Hz), 6.6-6.8 (3H, m), 7.1-7.3 (11H, m), 12.16 (1H, brs).

MS (ESI, m/z):516 (M−H)$^−$.

EXAMPLE 113

(2S)-2-(3-{3-[3-(Diphenylmethyl)-6-oxo-5,6-dihydropyridazin-1(4H)-yl]propyl}phenoxy)propanoic acid.

$^1$H-NMR (CDCl$_3$) δ: 1.64 (3H, d, J=6.8 Hz), 1.65-1.95 (2H, m), 2.31-2.39 (4H, m), 2.56 (2H, t, J=7.5 Hz), 3.70-3.77 (2H, m), 4.77 (1H, q, J=6.8 Hz), 5.09 (1H, s), 6.70-6.74 (3H, m), 7.09-7.35 (11H, m).

MS (ESI, m/z):471 (M+H)$^+$.

EXAMPLE 114

[4-(2-{5-[Bis(4-fluorophenyl)methyl]-2-oxopyridin-1(2H)-yl}ethoxy)-2-methyl-1H-benzimidazol-1-yl]acetic acid.

$^1$H-NMR (DMSO-d$_6$) δ: 2.39 (3H, s), 4.23 (2H, t, J=4.7 Hz), 4.47 (2H, t, J=4.7 Hz), 5.04 (2H, s), 5.38 (1H, s), 6.38 (1H, d, J=9.4 Hz), 6.56 (1H, d, J=7.6 Hz), 7.0-7.4 (12H, m), 13.28 (1H, brs).

MS (ESI, m/z):528 (M−H)$^−$.

EXAMPLE 115

(2S)-2-[3-(3-{5-[Bis(4-fluorophenyl)methyl]-2-oxopyridin-1(2H)-yl}propyl)phenoxy]propanoic acid.

$^1$H-NMR (CDCl$_3$) δ: 1.65 (3H, d, J=6.8 Hz),1.90-2.03 (2H, m), 2.50-2.59 (2H, m), 3.74-3.86 (2H, m), 4.77 (1H, q, J=6.8 Hz), 5.23, 5.30 (1H, s), 6.63-6.66 (2H, m), 6.71-6.78 (3H, m), 6.98-7.30 (10H, m).

MS (ESI, m/z):526 (M+Na)$^+$.

EXAMPLE 116

(3-{3-[5-(4'-1-Methylbiphenyl-2-yl)-2-oxopyridin-1(2H)-yl]propyl}phenoxy)acetic acid.

$^1$H-NMR (CDCl$_3$) δ: 1.79-1.90 (2H, m), 2.23 (3H, s), 2.51 (2H, t, J=7.4 Hz), 3.81 (2H, t, J=7.3 Hz), 4.66 (2H, s), 6.66 (1H, d, J=9.3 Hz), 6.72-6.82 (3H, m), 6.97 (1H, d, J=2.3 Hz), 7.20-7.43 (10H, m).

MS (ESI, m/z):452 (M−H)$^−$.

EXAMPLE 117

{3-[3-(5-Biphenyl-2-yl-2-oxopyridin-1(2H)-yl)propyl]phenoxy}acetic acid.

$^1$H-NMR (DMSO-d$_6$) δ: 1.68-1.79 (2H, m), 2.44 (2H, t, J=7.8 Hz), 3.81 (2H, t, J=7.4 Hz), 4.05 (2H, s), 6.21 (1H, d, J=9.4 Hz), 6.71-6.79 (3H, m), 7.03-7.46 (12H, m).

MS (ESI, m/z):438 (M−H)$^−$.

EXAMPLE 118

(3-{3-[2-Oxo-5-(2-phenoxyphenyl)pyridin-1(2H)-yl]propyl}phenoxy)acetic acid.
$^1$H-NMR (CDCl$_3$) δ:2.00-2.15 (2H, m), 2.63 (2H, t, J=7.4 Hz), 3.93 (2H, t, J=7.6 Hz), 4.65 (2H, s), 6.69-7.37 (14H, m), 7.50 (1H, d, J=2.5 Hz), 7.61 (1H, dd, J=2.4, 9.3 Hz).
MS (ESI, m/z):454 (M−H)$^-$.

EXAMPLE 119

4-{3-[3-(2-Oxo-4,5-diphenyl-2,3-dihydro-1H-imidazol-1-yl)propyl]phenoxy}butanoic acid.
$^1$H-NMR (DMSO-d$_6$) δ:1.57-1.64 (2H, m), 1.88-1.95 (2H, m), 2.35-2.39 (4H, m), 3.42-3.46 (2H, m), 3.89-3.97 (2H, m), 6.55-6.69 (2H, m), 6.73-6.80 (1H, m), 7.07-7.21 (6H, m), 7.35-7.37 (2H, m), 7.42-7.52 (3H, m), 10.77 (1H, s), 12.16 (1H, brs).
MS (ESI, m/z):457 (M+H)$^+$.

EXAMPLE 120

(3-{3-[6-Oxo-3-(2-phenoxyphenyl)pyridazin-1(6H)-yl]propyl}phenoxy)acetic acid.
$^1$H-NMR (DMSO-d$_6$) δ:1.98 (2H, m), 2.56 (2H, t, J=3.9 Hz), 4.08 (2H, t, J=3.6 Hz), 4.63 (2H, s), 6.65-7.80 (15H, m), 12.98 (1H, brs).
MS (ESI, m/z):457 (M+H)$^+$.

EXAMPLE 121

(3-{3-[5-(4'-Chlorobiphenyl-2-yl)-2-oxopyridin-1(2H)-yl]propyl}phenoxy)acetic acid.
$^1$H-NMR (CDCl$_3$) δ: 1.81-1.95 (2H, m), 2.57 (2H, t, J=7.3 Hz), 3.82 (2H, t, J=7.6 Hz), 4.66 (2H, s), 6.65 (1H, d, J=9.3 Hz), 6.74-6.82 (3H, m), 6.97 (1H, d, J=2.4 Hz), 7.07-7.45 (10H, m).
MS (ESI, m/z):472 (M−H)$^-$.

EXAMPLE 122

(3-{3-[5-(3'-Methylbiphenyl-2-yl)-2-oxopyridin-1(2H)-yl]propyl}phenoxy)acetic acid.
$^1$H-NMR (CDCl$_3$) δ: 1.77-1.88 (2H, m), 2.26 (3H, s), 2.50 (2H, t, J=7.5 Hz), 3.80 (2H, t, J=7.6 Hz), 4.66 (2H, s), 6.65 (1H, d, J=9.3 Hz), 6.72-6.83 (3H, m), 6.90-7.21 (4H, m), 7.13-7.43 (7H, m).
MS (ESI, m/z):452 (M−H)$^-$.

EXAMPLE 123

[3-(3-{5-[2-(1-Naphthyl)phenyl]-2-oxopyridin-1(2H)-yl}propyl)phenoxy]acetic acid.
$^1$H-NMR (CDCl$_3$) δ: 1.40-1.51 (2H, m), 2.17-2.34 (2H, m), 3.47-3.64 (2H, m), 4.65 (2H, s), 6.59-6.70 (3H, m), 6.76-6.88 (2H, m), 7.16-7.56 (11H, m), 7.70-7.78 (2H, m).
MS (ESI, m/z):488 (M−H)$^-$.

EXAMPLE 124

[3-(3-{2-Oxo-5-[2-(3-thienyl)phenyl]pyridin-1(2H)-yl}propyl)phenoxy]acetic acid.
$^1$H-NMR (CDCl$_3$) δ: 1.88-1.99 (2H, m), 2.59 (2H, t, J=7.5 Hz), 3.84 (2H, t, J=7.4 Hz), 4.66 (2H, s), 6.68 (1H, d, J=5.2 Hz), 6.74-6.82 (4H, m), 7.03 (1H, d, J=2.4 Hz), 7.09-7.44 (8H, m).
MS (ESI, m/z):444 (M−H)$^-$.

EXAMPLE 125

(3-{3-[(4S)-4-Benzyl-2-oxo-1,3-oxazolidin-3-yl]propyl}phenoxy)acetic acid.
$^1$H-NMR (DMSO-d$_6$) δ: 1.70-1.90 (2H, m), 2.40-3.50 (6H, m), 3.90-4.20 (3H, m), 4.63 (2H, s), 6.60-6.90 (3H, m), 7.10-7.40 (6H, m), 13.0 (1H, brs).
MS (ESI, m/z):370/392 (M+Na)$^+$.

EXAMPLE 126

(3-{3-[5-(2',6'-Dimethylbiphenyl-2-yl)-2-oxopyridin-1(2H)-yl]propyl}phenoxy)acetic acid.
$^1$H-NMR (CDCl$_3$) δ: 1.69-1.79 (2H, m), 1.91 (6H, s), 2.48 (2H, t, J=7.4 Hz), 3.71 (2H, t, J=7.4 Hz), 4.66 (2H, s), 6.59 (1H, d, J=9.3 Hz), 6.74-6.83 (4H, m), 6.98-7.09 (3H, m), 7.14-7.30 (3H, m), 7.35-7.45 (3H, m).
MS (ESI, m/z):466 (M−H)$^-$.

EXAMPLE 127

(3-{3-[5-(2'-Methoxybiphenyl-2-yl)-2-oxopyridin-1(2H)-yl]propyl}phenoxy)acetic acid.
$^1$H-NMR (CDCl$_3$) δ: 1.66-1.82 (2H, m), 2.48 (2H, t, J=7.5 Hz), 3.47 (3H, s), 3.55-4.02 (2H, m), 4.66 (2H, s), 6.65 (1H, d, J=9.2 Hz), 6.70-6.99 (5H, m), 7.15-7.70 (9H, m).
MS (ESI, m/z):468 (M−H)$^-$.

EXAMPLE 128

(3-{3-[5-(2',4'-Dimethylbiphenyl-2-yl)-2-oxopyridin-1(2H)-yl]propyl}phenoxy)acetic acid.
$^1$H-NMR (CDCl$_3$) δ: 1.70-1.83 (2H, m), 1.85 (3H, s), 2.20 (3H, s), 2.48 (2H, t, J=7.5 Hz), 3.62-3.72 (1H, m), 3.76-3.85 (1H, m), 4.65 (2H, s), 6.63 (1H, d, J=9.3 Hz), 6.72-6.82 (3H, m), 6.87-7.03 (4H, m), 7.18 (1H, t, J=7.9 Hz), 7.24-7.44 (5H, m).
MS (ESI, m/z):466 (M−H)$^-$.

EXAMPLE 129

(3-{3-[5-(2',5'-Dimethylbiphenyl-2-yl)-2-oxopyridin-1(2H)-yl]propyl}phenoxy)acetic acid.
$^1$H-NMR (CDCl$_3$) δ: 1.69-1.83 (2H, m), 1.83 (3H, s), 2.26 (3H, s), 2.48 (2H, t, J=7.5 Hz), 3.62-3.72 (1H, m), 3.76-3.85 (1H, m), 4.65 (2H, s), 6.64 (1H, d, J=9.3 Hz), 6.72-6.83 (3H, m), 6.88-7.02 (4H, m), 7.19 (1H, t, J=7.6 Hz), 7.24-7.44 (5H, m).
MS (ESI, m/z):466 (M−H).

EXAMPLE 130

(3-{3-[5-(2',3'-Dimethylbiphenyl-2-yl)-2-oxopyridin-1(2H)-yl]propyl}phenoxy)acetic acid.
$^1$H-NMR (CDCl$_3$) δ: 1.58-1.84 (2H, m), 1.76 (3H, s), 2.13 (3H, s), 2.39-2.54 (2H, m), 3.53-3.65 (1H, m), 3.77-3.91 (1H, m), 4.66 (2H, s), 6.63 (1H, d, J=9.2 Hz), 6.72-6.87 (4H, m), 6.97-7.12 (3H, m), 7.16-7.45 (6H, m). MS (ESI, m/z):466 (M−H)$^-$.

EXAMPLE 131

(3-{3-[5-(2'-Methylbiphenyl-2-yl)-2-oxopyridin-1(2H)-yl]propyl}phenoxy)acetic acid.
$^1$H-NMR (CDCl$_3$) δ: 1.66-1.84 (2H, m), 1.89 (3H, s), 2.48 (2H, t, J=7.4 Hz), 3.61-3.70 (1H, m), 3.74-3.82 (1H, m), 4.66 (2H, s), 6.67 (1H, d, J=9.3 Hz), 6.71-6.83 (3H, m), 6.87 (1H, d, J=2.4 Hz), 7.08-7.22 (5H, m), 7.25-7.46 (5H, m).
MS (ESI, m/z):452 (M−H)$^-$.

EXAMPLE 132

(3-{3-[5-(3',5'-Dimethylbiphenyl-2-yl)-2-oxopyridin-1(2H)-yl]propyl}phenoxy)acetic acid.
$^1$H-NMR (CDCl$_3$) δ: 1.78-1.87 (2H, m), 2.21 (6H, s), 2.49 (2H, t, J=7.5 Hz), 3.82 (2H, t, J=7.3 Hz), 4.66 (2H, s), 6.68-6.83 (7H, m), 6.98 (1H, d, J=2.4 Hz), 7.19 (1H, t, J=7.9 Hz), 7.26-7.42 (5H, m).
MS (ESI, m/z):466 (M−H)$^-$.

EXAMPLE 133

(3-{3-[5-(3',4'-Dimethylbiphenyl-2-yl)-2-oxopyridin-1(2H)-yl]propyl}phenoxy)acetic acid.
$^1$H-NMR (CDCl$_3$) δ: 1.78-1.89 (2H, m), 2.13 (3H, s), 2.17 (3H, s), 2.49 (2H, t, J=7.5 Hz), 3.81 (2H, t, J=7.2 Hz), 4.66 (2H, s), 6.66 (1H, d, J=9.3H z), 6.71-6.88 (4H, m), 6.94-7.05 (3H, m), 7.14-7.43 (6H, m).
MS (ESI, m/z):466 (M−H)$^-$.

EXAMPLE 134

4-(3-{3-[3-Chloro-5-(2'-methylbiphenyl-2-yl)-2-oxopyridin-1(2H)-yl]propyl}phenoxy)butanoic acid.
$^1$H-NMR (CDCl$_3$) δ: 1.66-1.84 (2H, m), 1.90 (3H, s), 2.08-2.16 (2H, m), 2.47 (2H, t, J=7.4 Hz), 2.57 (2H, t, J=7.1 Hz), 3.64-3.73 (1H, m), 3.74-3.83 (1H, m), 4.03 (2H, t, J=6.0 Hz) 6.68-6.81 (4H, m), 7.09-7.51 (10H, m).
MS (ESI, m/z):514 (M−H)$^-$.

EXAMPLE 135

(3-{3-[3-Chloro-5-(2'-methylbiphenyl-2-yl)-2-oxopyridin-1(2H)-yl]propyl}phenoxy)acetic acid.
$^1$H-NMR (CDCl$_3$) δ: 1.64-1.83 (2H, m), 1.90 (3H, s), 2.47 (2H, t, J=7.5 Hz), 3.63-3.73 (1H, m), 3.75-3.84 (1H, m), 4.66 (2H, s), 6.71-6.80 (4H, m), 7.08-7.46 (9H, m), 7.50 (1H, d, J=2.4 Hz).
MS (ESI, m/z):486 (M−H)$^-$.

EXAMPLE 136

4-(3-{3-[2-Oxo-5-(2-quinolin-8-ylphenyl)pyridin-1(2H)-yl]propyl}phenoxy)butanoic acid.
$^1$H-NMR (CDCl$_3$) δ: 1.68-1.81 (2H, m), 1.99-2.12 (2H, m), 2.34-2.45 (4H, m), 3.53-3.76 (2H, m), 3.98-4.16 (2H, m), 6.16 (1H, d, J=9.4 Hz), 6.60-6.82 (3H, m), 6.94-7.80 (11H, m), 8.12 (1H, d, J=7.4 Hz), 8.82 (1H, brs).
MS (ESI, m/z):517 (M−H)$^-$.

EXAMPLE 137

(3-{3-[2-Oxo-5-(2-quinolin-8-ylphenyl)pyridin-1(2H)-yl]propyl}phenoxy)acetic acid.
$^1$H-NMR (CDCl$_3$) δ: 1.44-1.88 (2H, m), 2.17-2.54 (2H, m), 3.30-3.88 (2H, m), 4.56 (1.9H, s), 4.81 (0.1H, s), 6.21 (0.95H, d, J=9.2 Hz), 6.27 (0.05H, d, J=9.2 Hz), 6.58-7.81 (14H, m), 8.01 (0.05H, d, J=7.6 Hz), 8.17 (0.95H, d, J=7.6 Hz), 8.75 (0.05H, brs),8.92 (0.95H, brs).
MS (ESI, m/z):489 (M−H)$^-$.

EXAMPLE 138

(3-{3-[(4S)-4-Benzyl-5,5-dimethyl-2-oxo-1,3-oxazolidin-3-yl]propyl}-4-fluorophenoxy)acetic acid.
$^1$H-NMR (DMSO-d$_6$) δ: 1.17 (3H, s), 1.27 (3H, s), 1.57 (2H, m), 2.20-2.50 (2H, m), 2.70-3.40 (4H, m), 3.90 (1H, t),4.59 (2H, s, J=3.5 Hz), 6.70-7.40 (8H, m), 13.0 (1H, brs).
MS (ESI, m/z):438 (M+Na)$^+$.

EXAMPLE 139

{4-Fluoro-3-[3-(2-oxo-4,5-diphenyl-1,3-oxazol-3(2H)-yl)propyl]phenoxy}acetic acid.
$^1$H-NMR (CDCl$_3$) δ: 1.72-1.84 (2H, m), 2.51 (2H, t, J=7.5 Hz), 3.51 (2H, t, J=7.5 Hz), 4.62 (2H, s), 6.68-6.71 (2H, m), 6.85-7.00 (1H, m), 7.18-7.24 (5H, m), 7.36-7.38 (2H, m), 7.49-7.51 (3H, m).
MS (ESI, m/z):470 (M+Na)$^+$.

EXAMPLE 140

{4-Fluoro-3-[3-(2-oxo-4,5-diphenyl-1,3-thiazol-3(2H)-yl)propyl]phenoxy}acetic acid.
$^1$H-NMR (CDCl$_3$) δ: 1.75-1.85 (2H, m), 2.46 (2H, t, J=7.5 Hz), 3.61 (2H, t, J=7.7 Hz), 4.62 (2H, s), 6.65-6.69 (2H, m), 6.83-6.88 (1H, m), 6.98-7.00 (2H, m), 7.12-7.14 (3H, m), 7.23-7.26 (2H, m), 7.38-7.40 (3H, m).
MS (ESI, m/z):486 (M+Na)$^+$.

EXAMPLE 141

{3-[3-(2-Oxo-4,5-diphenyl-1,3-thiazol-3(2H)-yl)propyl]phenoxy}acetic acid.
$^1$H-NMR (DMSO-d$_6$) δ: 1.60-1.68 (2H, m), 2.34-2.37 (2H, m), 3.51 (2H, t, J=7.6 Hz), 4.60 (2H, s), 6.55-6.59 (2H, m), 6.65-6.67 (1H, m), 6.98-7.22 (6H, m), 7.39-7.51 (5H, m), 12.90 (1H, brs).
MS (ESI, m/z):468 (M+Na)$^+$.

EXAMPLE 142

4-{3-[3-(2-Oxo-4,5-diphenyl-1,3-thiazol-3(2H)-yl)propyl]phenoxy}butanoic acid.
$^1$H-NMR (DMSO-d$_6$) δ: 1.61-1.68 (2H, m), 1.88-1.95 (2H, m), 2.34-2.39 (4H, m), 3.50 (2H, t, J=7.6 Hz), 3.91 (2H, t, J=6.4 Hz), 6.52-6.57 (2H, m), 6.67-6.69 (1H, m), 6.98-7.26 (6H, m), 7.38-7.50 (5H, m), 12.20 (1H, brs).
MS (ESI, m/z):496 (M+Na)$^+$.

EXAMPLE 143

4-(3-{3-[(4S)-4-Benzyl-5,5-dimethyl-2-oxo-1,3-oxazolidin-3-yl]propyl}phenoxy)butanoic acid.
$^1$H-NMR (DMSO-d) δ:1.18 (3H, s), 1.26 (3H, s), 1.56 (2H, m), 1.93 (2H, m), 2.20-2.40 (4H, m), 2.70-3.40 (4H, m), 3.89 (1H, t, J=3.5 Hz), 3.94 (2H, t, J=3.2 Hz), 6.60-6.80 (3H, m), 7.10-7.40 (6H, m).
MS (ESI, m/z):448 (M+Na)$^+$.

EXAMPLE 144

(3-{3-[(4S)-4-Benzyl-5,5-dimethyl-2-oxo-1,3-oxazolidin-3-yl]propyl}phenoxy)acetic acid.
$^1$H-NMR (DMSO-d$_6$) δ: 1.19 (3H, s), 1.26 (3H, s), 1.56 (2H, m), 2.20-2.40 (2H, m), 2.70-3.40 (4H, m), 3.89 (1H, t, J=3.5 Hz), 4.61 (2H, s), 6.60-6.80 (3H, m), 7.10-7.40 (6H, m), 12.95 (1H, brs).
MS (ESI, m/z):420 (M+Na)$^+$.

EXAMPLE 145

(3-{3-[(4R)-4-Benzyl-5,5-dimethyl-2-oxo-1,3-oxazolidin-3-yl]propyl}phenoxy)acetic acid.
1H-NMR (DMSO-d$_6$) δ: 1.19 (3H, s), 1.26 (3H, s), 2.20-2.40 (2H, m), 2.70-3.40 (4H, m), 3.89 (1H, t, J=3.5 Hz), 4.62 (2H, s), 6.60-6.80 (3H, m), 7.10-7.40 (6H, m), 12.90 (1H, brs)
MS (ESI, m/z):420 (M+Na)$^+$.

EXAMPLE 146

4-(3-{3-[5-(2'-Methylbiphenyl-2-yl)-2-oxopyridin-1(2H)-yl]propyl}phenoxy)butanoic acid.
$^1$H-NMR (CDCl$_3$) δ: 1.68-1.86 (2H, m), 1.90 (3H, s), 2.07-2.16 (2H, m), 2.47 (2H, t, J=7.4 Hz), 2.55 (2H, t, J=7.1 Hz), 3.61-3.71 (1H, m), 3.72-3.82 (1H, m), 4.05 (2H, t, J=6.1 Hz), 6.51 (1H, d, J=9.4 Hz), 6.67-6.76 (3H, m), 6.84 (1H, d, J=2.5 Hz), 7.08-7.21 (5H, m), 7.24-7.45 (5H, m).
MS (ESI, m/z):480 (M−H)$^-$.

EXAMPLE 147

{3-[3-(2-Oxo-4,5-diphenyl-1,3-oxazol-3(2H)-yl)propyl]phenoxy}acetic acid.
$^1$H-NMR (DMSO-d$_6$) δ: 1.61-1.69 (2H, m), 2.41 (2H, t, J=7.6 Hz), 3.43 (2H, t, J=7.3 Hz), 4.60 (2H, s), 6.60-6.68 (3H, m), 7.09-7.30 (6H, m), 7.52-7.60 (5H, m), 13.00 (1H, brs).
MS (ESI, m/z):452 (M+Na)$^+$.

EXAMPLE 148

4-{3-[3-(2-Oxo-4,5-diphenyl-1,3-oxazol-3(2H)-yl)propyl]phenoxy}butanoic acid.
$^1$H-NMR (DMSO-d$_6$) δ: 1.62-1.69 (2H, m), 1.88-1.95 (2H, m), 2.35-2.43 (4H, m), 3.42 (2H, t, J=7.3 Hz), 3.91 (2H, t, J=6.4 Hz), 6.57-6.70 (3H, m), 7.07-7.30 (6H, m), 7.51-7.58 (5H, m), 12.15 (1H, brs).
MS (ESI, m/z):480 (M+Na)$^+$.

EXAMPLE 149

4-{4-Fluoro-3-[3-(2-oxo-4,5-diphenyl-1,3-oxazol-3(2H)-yl)propyl]phenoxy}butanoic acid.
$^1$H-NMR (CDCl$_3$) δ: 1.77-1.83 (2H, m), 2.06-2.13 (2H, m), 2.50 (2H, t, J=7.5 Hz), 2.57 (2H, t, J=7.2 Hz), 3.52 (2H, t, J=7.5 Hz), 3.95 (2H, t, J=6.1 Hz), 6.61-6.64 (2H, m), 6.82-6.86 (1H, m), 7.17-7.26 (5H, m), 7.36-7.38 (2H, m), 7.46-7.52 (3H, m).
MS (ESI, m/z):498 (M+Na)$^+$.

EXAMPLE 150

4-[3-({2-[(4S)-4-(Diphenylmethyl)-2-oxo-1,3-oxazolidin-3-yl]ethyl}sulfanyl)phenoxy]butanoic acid.
$^1$H-NMR (DMSO-d$_6$) δ: 1.85-2.00 (2H, m), 2.37 (2H, t),2.75-3.40 (4H, m), 3.75-4.30 (5H, m), 4.90 (1H, m), 6.70-6.90 (3H, m), 7.15-7.50 (11H, m MS (ESI, m/z):514 (M+Na)$^+$.

EXAMPLE 151

4-[3-({2-[(4S)-4-Benzyl-5,5-dimethyl-2-oxo-1,3-oxazolidin-3-yl]ethyl}sulfanyl)phenoxy]butanoic acid.
$^1$H-NMR (DMSO-d$_6$) δ: 1.18 (3H, s), 1.26 (3H, s), 1.90 (2H, m), 2.35 (2H, t, J=6.8 Hz), 2.75-3.50 (6H, m), 3.85-4.05 (3H, m), 6.70-6.90 (3H, m), 7.15-7.40 (6H, m).
MS (ESI, m/z):466 (M+Na)$^+$.

EXAMPLE 152

(2S)-2-[3-({3-[(4S)-4-(Diphenylmethyl)-2-oxo-1,3-oxazolidin-3-yl]propyl}sulfanyl)phenoxy]propanoic acid
$^1$H-NMR (DMSO-d$_6$) δ:1.48 (3H, d, J=6.7 Hz), 1.45-1.69 (2H, m), 2.47-2.55 (2H, m), 2.56-2.70 (2H, m), 3.14-3.22 (1H, m), 3.83 (1H, dd, J=5.1, 8.8 Hz), 4.25 (1H, d, J=9.3 Hz), 4.29 (1H, d, J=8.7 Hz), 4.80-4.91 (2H, m), 6.69 (1H, d, J=8.2 Hz), 6.74 (1H, t, J=2.0 Hz), 6.82 (1H, d, J=7.9 Hz), 7.18-7.25 (3H, m), 7.27-7.38 (6H, m), 7.43 (2H, d, J=7.3 Hz), 13.15 (1H, brs).
MS (ESI, m/z):514 (M+Na)$^+$.

EXAMPLE 153

(2S)-2-[3-({3-[5-(2'-Methylbiphenyl-2-yl)-2-oxopyridin-1(2H)-yl]propyl}sulfanyl)phenoxy]propanoic acid.
$^1$H-NMR (DMSO-d$_6$) δ: 1.48 (3H, d, J=6.7 Hz), 1.67-1.75 (2H, m), 1.88 (3H, s), 2.68-2.82 (2H, m), 3.77-3.92 (2H, m), 4.84 (1H, q, J=6.8 Hz), 6.17 (1H, d, J=9.4 Hz), 6.69 (1H, dd, J=2.2, 8.2 Hz), 6.78 (1H, s), 6.85 (1H, d, J=7.7 Hz), 7.07-7.25 (7H, m), 7.35 (1H, d, J=2.6 Hz), 7.39-7.47 (3H, m), 13.06 (1H, brs).
MS (ESI, m/z):522 (M+Na)$^+$.

EXAMPLE 154

(2S)-2-[3-({3-[(4S)-4-Benzyl-5,5-dimethyl-2-oxo-1,3-oxazolidin-3-yl]propyl}sulfanyl)phenoxy]propanoic acid.
$^1$H-NMR (DMSO-d$_6$) δ:1.12 (3H, s), 1.25 (3H, s), 1.47 (3H, d, J=6.8 Hz), 1.54-1.72 (2H, m), 2.73-2.86 (3H, m), 2.90-3.00 (2H, m), 3.28-3.35 (1H, m), 3.88 (1H, t, J=7.2 Hz), 4.82 (1H, q, J=6.7 Hz), 6.68 (1H, dd, J=2.3, 8.2 Hz), 6.76 (1H, s), 6.84 (1H, d, J=7.7 Hz), 7.18-7.25 (2H, m), 7.26-7.33 (4H, m), 13.13 (1H, brs).
MS (ESI, m/z):466 (M+Na)$^+$.

EXAMPLE 155

4-[3-({2-[5-(2'-Methylbiphenyl-2-yl)-2-oxopyridin-1(2H)-yl]ethyl}sulfanyl)phenoxy]butanoic acid.
$^1$H-NMR (DMSO-d$_6$) δ: 1.86-1.95 (5H, m), 2.36 (2H, t, J=7.3 Hz), 3.09 (2H, t, J=7.0 Hz), 3.87-4.00 (4H, m), 6.15 (1H, d, J=9.4 Hz), 6.74-6.78 (1H, M),6.87-6.92 (2H, m), 7.03 (1H, dd, J=2.6, 9.4 Hz), 7.08-7.26 (6H, m), 7.33 (1H, d, J=2.5 Hz), 7.39-7.48 (3H, m).
MS (ESI, m/z):522 (M+Na)$^+$.

EXAMPLE 156

(3-{3-[5-(4'-tert-Butylbiphenyl-2-yl)-2-oxopyridin-1(2H)-yl]propyl}phenoxy)acetic acid.
$^1$H-NMR (CDCl$_3$) δ: 1.28 (9H, s), 1.78-1.89 (2H, m), 2.57 (2H, t, J=7.1 Hz), 3.75 (2H, t, J=7.5 Hz), 4.66 (2H, s), 6.66 (1H, d, J=9.2 Hz), 6.73 (1H, d, J=7.6 Hz), 6.77-6.8.2 (2H, m), 6.95 (1H, d, J=2.4 Hz), 7.07-7.43 (10H, m).
MS (ESI, m/z):494 (M−H)$^-$.

EXAMPLE 157

(3-{3-[5-(4'-Methoxybiphenyl-2-yl)-2-oxopyridin-1(2H)-yl]propyl}phenoxy)acetic acid.
$^1$H-NMR (CDCl$_3$) δ: 1.83-1.94 (2H, m), 2.53 (2H, t, J=7.5 Hz), 3.70 (3H, s), 3.83 (2H, t, J=7.3 Hz), 4.67 (2H, s), 6.66-6.86 (6H, m), 7.00 (1H, d, J=2.3 Hz), 7.02-7.11 (2H, m), 7.15-7.43 (6H, m).
MS (ESI, m/z): 468 (M−H)$^-$.

EXAMPLE 158

(3-{3-[5-(4'-Fluorobiphenyl-2-yl)-2-oxopyridin-1(2H)-yl]propyl}phenoxy)acetic acid.
$^1$H-NMR (CDCl$_3$) δ:1.85-1.94 (2H, m), 2.56 (2H, t, J=7.4 Hz), 3.83 (2H, t, J=7.6 Hz), 4.66 (2H, s), 6.66 (1H, d, J=9.2 Hz), 6.74-6.82 (3H, m), 6.96-7.03 (3H, m), 7.10-7.22 (4H, m), 7.29-7.44 (4H, m).
MS (ESI, m/z):456 (M−H)$^-$.

EXAMPLE 159

{3-[3-(2-Oxo-4,5-diphenyl-2,3-dihydro-1H-imidazol-1-yl)propyl]phenoxy}acetic acid.

$^1$H-NMR (DMSO-d$_6$) δ: 1.56-1.64 (2H, m), 2.37 (2H, t, J=7.6 Hz), 3.45 (2H, t, J=7.4 Hz), 4.61 (2H, s), 6.59-6.68 (3H, m), 7.08-7.21 (6H, m), 7.35-7.39 (2H, m), 7.44-7.50 (3H, m), 10.77 (1H, s), 12.95 (1H, brs).

MS (ESI, m/z):429 (M+H)$^+$.

EXAMPLE 160

4-{3-[3-(3-Methyl-2-oxo-4,5-diphenyl-2,3-dihydro-1H-imidazol-1-yl)propyl]phenoxy}butanoic acid.

$^1$H-NMR (DMSO-d$_6$) δ: 1.63-1.68 (2H, m), 1.88-1.95 (2H, m), 2.46-2.54 (4H, m), 3.10 (3H, s), 3.58 (2H, t, J=7.3 Hz), 3.91 (2H, t, J=6.4 Hz), 6.56-6.60 (2H, m), 6.68-6.70 (1H, m), 7.07-7.11 (1H, m), 7.19-7.30 (4H, m), 7.31-7.34 (6H, m), 12.16 (1H, brs).

MS (ESI, m/z):471 (M+H)$^+$.

EXAMPLE 161

To a solution of tert-butyl (2E)-3-(3-{3-[5-(diphenylmethyl)-2-oxo-1(2H)-pyridinyl]propyl}phenoxy) acrylate (31.0 mg) in DCM (0.30 mL) was added TFA (0.30 mL) at ambient temperature and the mixture was stirred at the same temperature for 2 hours. The solvent was removed with stream of N$_2$ gas. Water (1.0 mL) was added to the residue and the mixture was extracted with chloroform (2.0 mL). The organic layer was washed with brine, dried over anhydrous MgSO$_4$, filtered and evaporated in vacuo. The residue was crystallized from solvent (n-hexane and EtOAc) to afford (2E)-3-(3-{3-[5-(diphenylmethyl)-2-oxo-1(2H)-pyridinyl]propyl}phenoxy) acrylic acid (18.2 mg) as colorless crystals.

$^1$H-NMR (CDCl$_3$) δ:2.03 (2H, quint, J=7.5 Hz), 2.65 (2H, t, J=7.5 Hz), 3.81 (2H, t, J=7.5 Hz), 5.26 (1H, s), 5.60 (1H, d, J=12.3 Hz), 6.55 (1H, d, J=9.3 Hz), 6.76 (1H, d, J=2.4 Hz), 6.89-6.97 (3H, m), 7.08-7.12 (4H, m), 7.20 (1H, dd, J=2.6, 9.3 Hz), 7.24-7.36 (7H, m), 7.87 (1H, d, J=12.3 Hz).

MS (ESI, m/z) 466 (M+H)$^+$.

EXAMPLE 162

The mixture of tert-butyl {4-[({2-[5-(diphenylmethyl)-2-oxo-1(2H)-pyridinyl]ethyl}amino)carbonyl]-2,3-dihydro-1H-indol-1-yl}acetate (75 mg) in TFA (2.1 mL) was stood at ambient temperature for 1 hour. The resulting mixture was evaporated in vacuo and was added saturated NaHCO$_3$ aqueous solution (5.0 mL). The aqueous solution was extracted with chloroform (10 mL). The organic layer was washed with brine, dried over anhydrous MgSO$_4$, filtered and evaporated in vacuo to afford {4-[({2-[5-(diphenylmethyl)-2-oxo-1(2H)-pyridinyl]ethyl}amino)carbonyl]-2,3-dihydro-1H-indol-1-yl}acetic acid (45 mg) as an yellow amorphous.

$^1$H-NMR (DMSO-d$_6$) δ: 3.04-3.14 (2H, m), 3.30-3.53 (4H, m), 3.90-3.99 (2H, m), 3.95 (2H, s), 5.28 (1H, s), 6.39 (1H, d, J=9.3 Hz), 6.52 (1H, d, J=7.7 Hz), 6.77 (1H, d, J=7.7 Hz), 6.92-7.27 (13H, m), 8.21-8.28 (1H, m).

MS (ESI, m/z):508 (M+H)$^+$.

The following compound(s) was(were) obtained in a similar manner to that of Example 162.

EXAMPLE 163

{4-[({2-[Benzoyl(3,3-diphenylpropyl)amino]ethyl}amino)carbonyl]-2,3-dihydro-1H-indol-1-yl}acetic acid.

$^1$H-NMR (DMSO-d$_6$) δ:2.20-2.30 (2H, m), 3.03-3.15 (4H, m), 3.18-3.28 (2H, m), 3.40-3.75 (5H, m), 3.94 (2H, s), 6.50 (1H, d, J=8.3 Hz), 6.78 (1H, d, J=8.0 Hz), 6.98-7.42 (16H, m), 8.23-8.31 (1H, brs).

MS (ESI, m/z) 562 (M+H)$^+$.

The following compound(s) was (were) obtained in a similar manner to that of Preparation 4.

EXAMPLE 164

Ethyl(3-{4-[5-(diphenylmethyl)-2-oxo-1(2H)-pyridinyl]butyl}phenoxy)acetate.

$^1$H-NMR (CDCl$_3$) δ: 1.30 (3H, t, J=7.0 Hz), 1.75-1.52 (4H, m), 2.58 (2H, t, J=7.5 Hz), 3.82 (2H, t, J=7.0 Hz), 4.27 (2H, q, J=7.0 Hz), 4.60 (2H, s), 5.23 (1H, s), 6.51 (1H, d, J=9.5 Hz), 6.78-6.71 (4H, m), 7.33-7.09 (12H, m).

MS (ESI, m/z) 496 (M+H)$^+$.

EXAMPLE 165

Ethyl(4-{3-[5-(diphenylmethyl)-2-oxo-1(2H) -pyridinyl]propoxy}-1H-indol-1-yl)acetate.

$^1$H-NMR (CDCl$_3$) δ: 1.22 (3H, t, J=7.0 Hz), 2.31 (2H, quint, J=6.6 Hz), 4.03 (2H, t, J=6.6 Hz), 4.12 (2H, t, J=6.6 Hz), 4.17 (2H, q, J=7.0 Hz), 4.82 (2H, s), 5.01 (1H, s), 6.46 (1H, d, J=7.3 Hz), 6.50-6.56 (2H, m), 6.82 (1H, d, J=2.5 Hz), 6.85-6.96 (5H, m), 7.00 (1H, d, J=3.4 Hz), 7.07-7.20 (8H, m).

MS (ESI, m/z):521 (M+H)$^+$.

EXAMPLE 166

Ethyl(3-{3-[3-(diphenylmethyl)-6-oxo-1(6H) -pyridazinyl]propyl}phenoxy)acetate.

$^1$H-NMR (CDCl$_3$) δ: 1.29 (3H, t, J=7.0 Hz), 2.13-2.05 (2H, m), 2.60 (2H, t, J=7.5 Hz), 4.16 (2H, t, J=7.5 Hz), 4.27 (2H, q, J=7.0 Hz), 4.60 (2H, s), 5.46 (1H, s), 6.78-6.70 (3H, m), 6.84 (1H, d, J=10.0 Hz), 7.08 (1H, d, J=10.0 Hz), 7.17-7.13 (5H, m), 7.35-7.28 (6H, m).

MS (ESI, m/z):483 (M+H)$^+$.

EXAMPLE 167

Ethyl[(3'-{[5-(diphenylmethyl)-2-oxo-1(2H)-pyridinyl]methyl}-3-biphenylyl)oxy]acetate.

$^1$H-NMR (CDCl$_3$) δ: 1.31 (3H, t, J=7.0 Hz), 4.29 (2H, q, J=7.0 Hz), 4.68 (2H, s), 5.09 (2H, s), 5.21 (1H, s), 6.57 (1H, d, J=9.5 Hz), 6.79 (1H, d, J=2.0 Hz), 6.89 (1H, dd, J=8.0, 2.5 Hz), 7.10-7.05 (5H, m), 7.29-7.14 (9H, m), 7.40-7.34 (3H, m), 7.48 (1H, d, J=7.5 Hz).

MS (ESI, m/z):530 (M+H)$^+$.

EXAMPLE 168

Ethyl(2-{3-[5-(diphenylmethyl)-2-oxo-1(2H) -pyridinyl]propyl}phenoxy)acetate.

$^1$H-NMR (CDCl$_3$) δ: 1.26 (3H, t, J=7.0 Hz), 2.10-2.00 (2H, m), 2.69 (2H, t, J=7.0 Hz), 3.88 (2H, t, J=7.0 Hz), 4.22 (2H, q, J=7.0 Hz), 4.58 (2H, s), 5.24 (1H, s), 6.51 (1H, d, J=9.5 Hz), 6.68 (1H, d, J=8.5 Hz), 6.91-6.86 (5H, m), 7.17-7.06 (8H, m).

MS (ESI, m/z):482 (M+H)$^+$.

EXAMPLE 169

Ethyl(3-{(1E)-3-[5-(diphenylmethyl)-2-oxo-1(2H) --pyridinyl]1-propen-1-yl}phenoxy)acetate.
$^1$H-NMR (CDCl$_3$) δ: 1.31 (3H, t, J=7.0 Hz), 4.29 (2H, q, J=7.0 Hz), 4.63 (2H, s), 5.25 (1H, s), 6.28-6.18 (1H, m), 6.43 (1H, d, J=15.0 Hz), 6.57 (1H, d, J=9.5 Hz), 6.89-6.80 (4H, m), 6.97 (1H, d, J=7.5 Hz), 7.33-7.10 (11H, m).
MS (ESI, m/z):480 (M+H)$^+$.

EXAMPLE 170

To a mixture of LiH (6.20 g) in DMF (100 mL) was added a solution of 5-(diphenylmethyl)-2(1H)-pyridinone (82.4 g) in DMF (500 mL) at ambient temperature. A solution of ethyl [3-(3-iodopropyl)phenoxy]acetate (118 g) in DMF (300 mL) was added dropwise to the mixture at ambient temperature over 30 minutes and the mixture was stirred at the same temperature for 24 hours. The resulting mixture was poured into 1M HCl aqueous solution (800 mL) at 0° C. and the mixture was extracted with EtOAc (2 L+1 L). The organic layer was washed successively with 12% NaCl aqueous solution and brine, dried over anhydrous MgSO$_4$, filtered and evaporated in vacuo. The residue was purified by silica gel column chromatography (n-hexane:EtOAc=1:1) to afford ethyl (3-{3-[5-(diphenylmethyl)-2-oxo-1(2H) -pyridinyl]propyl}phenoxy)-acetate(113 g) as a slightly yellow oil.
$^1$H-NMR (CDCl$_3$) δ: 1.30 (3H, t, J=7.1 Hz), 1.95-2.06 (2H, m), 2.58 (2H, t, J=8.0 Hz), 3.84 (2H, t, J=7.4 Hz), 4.26 (2H, q, J=7.1 Hz), 4.59 (2H, s), 5.24 (1H, s), 6.52 (1H, d, J=9.4 Hz), 6.68-6.74 (4H, m), 7.08-7.20 (6H, m), 7.24-7.36 (6H, m).
MS (ESI, m/z) 482 (M+H)$^+$.

The following compound(s) was(were) obtained in a similar manner to that of Example 170.

EXAMPLE 171

Methyl 3-(3-{3-[5-(diphenylmethyl)-2-oxo-1(2H) -pyridinyl]propyl}phenoxy)propanoate.
$^1$H-NMR (CDCl$_3$) δ: 2.01 (2H, quint, J=7.6 Hz), 2.57 (2H, t, J=7.6 Hz), 2.80 (2H, t, J=6.3 Hz), 3.73 (3H, s), 3.85 (2H, t, J=7.6 Hz), 4.22 (2H, t, J=6.3 Hz), 5.24 (1H, s), 6.53 (1H, d, J=9.4 Hz), 6.66-6.75 (4H, m), 7.09-7.18 (6H, m), 7.22-7.35 (6H, m).

The following compound(s) was (were) obtained in a similar manner to that of Example 171.

EXAMPLE 172

Ethyl(3-{3-[5-(diphenylmethyl)-2-oxo-1(2H) -pyridinyl]propyl}-1H-indol-1-yl)acetate.
$^1$H-NMR (CDCl$_3$) δ: 1.26 (3H, t, J=7.1 Hz), 2.08-2.20 (2H, m), 2.74 (2H, t, J=7.3 Hz), 3.90 (2H, t, J=7.0 Hz), 4.20 (2H, q, J=7.1 Hz), 4.74 (2H, s), 5.22 (1H, s), 6.53 (1H, d, J=9.4 Hz), 6.7-6.8 (2H, m), 7.0-7.4 (14H, m), 7.51 (1H, d, J=7.8 Hz).

EXAMPLE 173

To a solution of N-{2-[benzoyl(3,3-diphenylpropyl)amino]ethyl}-4-indolinecarboxamide (77.0 mg) and 2-(tert-butylimino)-2-diethylamino-1,3-dimethylperhydro-1,3,2-diazaphosphorine (106 μL) in DMF (2.3 mL) was added ethyl bromoacetate (39 μL) and the mixture was stirred at ambient temperature for 40 hours. The resulting mixture was diluted with EtOAc (20 mL), washed successively with 1M HCl aqueous solution, saturated NaHCO$_3$ aqueous solution and brine, dried over anhydrous MgSO$_4$, filtered and evaporated in vacuo. The residue was purified by silica gel column chromatography (chloroform: MeOH=99:1) to afford ethyl {4-[({2-[benzoyl(3,3-diphenylpropyl)amino]ethyl}amino)-carbonyl]-2,3-dihydro-1H-indol-1-yl}acetate (87 mg) as an yellow syrup.
$^1$H-NMR (CDCl$_3$) δ: 1.25 (3H, t, J=7.2 Hz), 2.23-2.34 (2H, m), 3.18-3.26 (2H, m), 3.32-3.41 (2H, m), 3.58 (2H, t, J=8.3 Hz), 3.63-3.72 (3H, m), 3.76-3.83 (2H, m), 3.90 (2H, s), 4.13-4.27 (3H, m), 6.44 (1H, d, J=8.1 Hz), 6.90 (1H, d, J=8.4 Hz), 7.00-7.40 (16H, m).
MS (ESI, m/z) 590 (M+H)$^+$.

The following compound(s) was (were) obtained in a similar manner to that of Example 173.

EXAMPLE 174 tert-Butyl {4-[({2-[benzoyl(3,3-diphenylpropyl)amino]ethyl}amino)carbonyl]-2,3-dihydro-1H-indol-1-yl}acetate.
$^1$H-NMR (CDCl$_3$) δ: 1.43 (9H, s), 2.23-2.35 (2H, m), 3.17-3.27 (2H, m), 3.31-3.40 (2H, m), 3.53-3.62 (2H, m), 3.64-3.72 (3H, m), 3.75-3.84 (4H, m),6.43 (1H, d, J=7.8 Hz), 6.89 (1H, d, J=7.5 Hz), 6.99-7.39 (17H, m).
MS (ESI, m/z):618 (M+H)$^+$.

EXAMPLE 175 tert-Butyl {4-[({2-[5-(diphenylmethyl)-2-oxo-1(2H) -pyridinyl]ethyl}amino)carbonyl]-2,3-dihydro-1H-indol-1-yl}acetate.
$^1$H-NMR (CDCl$_3$) δ: 1.43 (9H, s), 3.31 (2H, t, J=8.3 Hz), 3.58 (2H, t, J=8.3 Hz), 3.66-3.75 (2H, m), 3.81 (2H, s), 4.09-4.18 (2H, m), 5.21 (1H, s), 6.44 (1H, d, J=7.8 Hz), 6.55 (1H, d, J=9.4 Hz), 6.79 (1H, s), 6.80 (1H, d, J=7.8 Hz), 7.02-7.35 (13H, m).
MS (ESI, m/z):564 (M+H)$^+$.

EXAMPLE 176

To a stirring solution of ethyl (4-amino-1H-indol-1-yl)acetate (94 mg) in EtOH (7 mL) was added 1-(2-chloroethyl)-5-(diphenylmethyl)-2(1H)-pyridinone (70 mg) at ambient temperature. The reaction mixture was warmed to 50° C. After 24 hours, to the mixture was added water and the resulting mixture was extracted with EtOAc. The organic layer was washed with brine, dried over anhydrous sodium sulfate and evaporated in vacuo. The residue was purified by preparative thin-layer chromatography (chloroform:EtOAc=5:1) to give ethyl [4-({2-[5-(diphenylmethyl)-2-oxo-1(2H)-pyridinyl]ethyl}amino)-1H-indol-1-yl]acetate (45 mg).
$^1$H-NMR (CDCl$_3$) δ: 1.21 (3H, t, J=7.4 Hz), 3.60-3.69 (2H, m), 4.05-4.23 (4H, m), 4.60-4.68 (1H, m), 4.79 (2H, s), 5.11 (1H, s), 6.18 (1H, d, J=7.6 Hz), 6.41 (1H, d, J=4.0 Hz), 6.55 (1H, d, J=9.5 Hz), 6.64-6.72 (2H, m), 6.92-7.28 (13H, m).
MS (ESI, m/z):506 (M+H)$^+$.

EXAMPLE 177

To a solution of 5-(diphenylmethyl)-1-[(2E)-3-(1H-indol-4-yl)-2-propen-1-yl]-2(1H)-pyridinone (80 mg), K$_2$CO$_3$ (80 mg) and benzyltriethylammonium chloride (8.8 mg) in 2-butanone (1 mL) was added ethyl bromoacetate (96 mg) at ambient temperature. The reaction mixture was stirred for 5 hours at 80° C. The resulting mixture was diluted with EtOAc and washed successively with water and brine. The organic layer was dried over anhydrous MgSO$_4$, filtered and evaporated in vacuo. The residue was purified by silica gel column chromatography (chloroform:MeOH=100:0-97:3) to give ethyl (4-{(1E)-3-[5-(diphenylmethyl)-2-oxo-1(2H)-pyridinyl]-1-propen-1-yl}-1H-indol-1-yl)acetate.

$^1$H-NMR (CDCl$_3$) δ: 1.26 (3H, t, J=7.0 Hz), 4.21 (2H, q, J=7.0 Hz), 7.71 (2H, d, J=6.5 Hz), 4.85 (2H, s), 5.24 (1H, s), 6.39 (1H, dt, J=15.5, 6.5 Hz), 6.57 (1H, d, J=9.5 Hz), 6.64 (1H, d, J=3.5 Hz), 6.85 (1H, d, J=15.5 Hz), 6.93-6.92 (1H, m), 7.30-7.09 (15H, m).

MS (ESI, m/z):503 (M+H)$^+$.

The following compound(s) was (were) obtained in a similar manner to that of Example 177.

EXAMPLE 178

Ethyl {4-[({2-[benzoyl(3,3-diphenylpropyl)amino]ethyl}amino)carbonyl]-1H-indol-1-yl}acetate.

$^1$H-NMR (CDCl$_3$) δ: 1.24 (3H, t, J=7.2 Hz), 2.24-2.35 (2H, m), 3.21-3.30 (2H, m), 3.64-3.73 (1H, m), 3.75-3.89 (4H, m), 4.20 (2H, q, J=7.2 Hz), 4.86 (2H, s), 6.98-7.05 (4H, m), 7.09-7.40 (16H, m), 7.52 (1H, d, J=8.0H z).

MS (ESI, m/z):588 (M+H)$^+$.

EXAMPLE 179

Ethyl {4-[({2-[5-(diphenylmethyl)-2-oxo-1(2H)-pyridinyl]ethyl}amino)carbonyl]-1H-indol-1-yl}acetate.

$^1$H-NMR (CDCl$_3$) δ: 1.23 (3H, t, J=6.9 Hz), 3.79-3.87 (2H, m), 4.15-4.25 (4H, m), 4.87 (2H, s), 5.17 (1H, s), 6.55 (1H, d, J=9.4 Hz), 6.84 (1H, d, J=1.6 Hz), 6.98-7.05 (5H, m), 7.15-7.28 (10H, m), 7.38 (1H, d, J=8.1 Hz), 7.46 (1H, d, J=7.3 Hz).

MS (ESI, m/z):534 (M+H)$^+$.

EXAMPLE 180

Ethyl (4-{(1E)-3-[benzoyl(3,3-diphenylpropyl)amino]-1-propen-1-yl}-1H-indol-1-yl)acetate.

$^1$H-NMR (CDCl$_3$) δ: 1.26 (3H, t, J=7.0 Hz), 2.32-2.30 (1H, m), 2.53-2.51 (1H, m), 3.24-3.21 (1H, m), 3.55-3.51 (1H, m), 3.69-3.65 (0.5H, m), 4.04-4.00 (1.5H, m), 4.22 (2H, q, J=7.0 Hz), 4.39-4.37 (1H, m), 4.86 (2H, s), 6.43-6.37, 6.19-6.15 (1H, m), 6.71-6.63 (1H, m), 7.02-7.01 (1H, m), 7.42-7.15 (19H, m).

MS (ESI, m/z):557 (M+H)$^+$.

EXAMPLE 181

Ethyl {3-[({2-[benzoyl(3,3-diphenylpropyl)amino]ethyl}amino)carbonyl]-1H-indol-1-yl}acetate.

$^1$H-NMR (CDCl$_3$) δ: 1.22 (3H, t, J=6.8 Hz), 2.24-2.35 (2H, m), 3.16-3.28 (2H, m), 3.64-3.88 (5H, m), 4.18 (2H, q, J=6.8 Hz), 4.78 (2H, s), 6.96-7.40 (18H, m), 7.61 (1H, s), 8.20-8.28 (1H, m).

MS (ESI, m/z):588 (M+H)$^+$.

EXAMPLE 182

Ethyl [4-(4-{[5-(diphenylmethyl)-2-oxo-1(2H)-pyridinyl]methyl}-1,3-oxazol-2-yl)-1H-indol-1-yl]acetate.

$^1$H-NMR (CDCl$_3$) δ: 1.26 (3H, t, J=7.2 Hz), 4.22 (2H, q, J=7.2 Hz), 4.91 (2H, s), 5.04 (2H, s), 5.26 (1H, s), 6.53 (1H, d, J=9.4 Hz), 7.10-7.40 (16H, m), 7.78 (1H, s), 7.83 (1H, d, J=8.0 Hz).

MS (ESI, m/z):544 (M+H)$^+$.

EXAMPLE 183

Ethyl [4-(4-{[benzoyl(3,3-diphenylpropyl)amino]methyl}-1,3-oxazol-2-yl)-1H-indol-1-yl]acetate.

$^1$H-NMR (CDCl$_3$) δ: 1.26 (3H, t, J=7.2 Hz), 2.38-2.56 (2H, m), 3.32-3.41 (1H, m), 3.49-3.58 (1H, m), 3.95-4.05 (1H, m), 4.23 (2H, q, J=7.2 Hz), 4.34-4.42 (1H, m), 4.70-4.76 (1H, m), 4.90 (2H, s), 7.00-7.44 (18H, m), 7.62-7.79 (2H, m), 7.83-7.91 (1H, m).

MS (ESI, m/z):598 (M+H)$^+$.

EXAMPLE 184

Ethyl (3-{3-[benzoyl(3,3-diphenylpropyl)amino]propyl}-1H-indol-1-yl)acetate.

$^1$H-NMR (CDCl$_3$) δ: 1.25 (3H, t, J=7.1 Hz), 1.75-1.91 (1H, m), 1.95-2.27 (2H, m), 2.35-2.60 (2H, m), 2.75-2.90 (1H, m), 3.06-3.32 (2H, m), 3.35-3.50 (1H, m), 3.50-3.70 (1.5H, m), 3.90-4.06 (0.5H, m), 4.19 (2H, q, J=7.1 Hz), 4.65-4.85 (2H, m), 6.50-6.60 (0.5H, m), 6.90-7.45 (19H, m), 7.50-7.65 (0.5H, m).

MS (ESI, m/z):559 (M+H)$^+$.

EXAMPLE 185

Ethyl (4-{[5-(diphenylmethyl)-2-oxo-1(2H)-pyridinyl]methyl}-1H-indol-1-yl)acetate.

$^1$H-NMR (CDCl$_3$) δ: 1.26 (3H, t, J=7.0 Hz), 4.21 (2H, q, J=7.0 Hz), 4.85 (2H, s), 5.12 (1H, s), 5.33 (2H, s), 6.50 (1H, d, J=3.5 Hz), 6.57 (1H, d, J=9.5 Hz), 6.78 (1H, m), 6.90 (1H, d, J=7.0 Hz), 7.00-6.98 (4H, m), 7.23-7.08 (10H, m).

MS (ESI, m/z):477 (M+H)$^+$.

EXAMPLE 186

Ethyl (4-{3-[5-(diphenylmethyl)-2-oxo-1(2H)-pyridinyl]propyl}-1H-indol-1-yl)acetate.

$^1$H-NMR (CDCl$_3$) δ: 1.26 (3H, t, J=7.3 Hz), 2.08-2.22 (2H, m), 2.89 (2H, t, J=7.2 Hz), 3.90 (2H, t, J=7.3 Hz), 4.21 (2H, q, J=7.3 Hz), 4.8 (2H, s), 5.2 (1H, s), 6.46-6.56 (2H, m), 6.72-6.78 (1H, m), 6.78-6.88 (1H, m), 7.00-7.36 (14H, m).

MS (ESI, m/z):505 (M+H)$^+$.

The following compound(s) was (were) obtained in a similar manner to that of Preparation 20.

EXAMPLE 187

Ethyl (4-{2-[5-(diphenylmethyl)-2-oxo-1(2H)-pyridinyl]ethoxy}-1H-indol-1-yl)acetate.

$^1$H-NMR (CDCl$_3$) δ: 1.25 (3H, t, J=7.4 Hz), 4.20 (2H, q, J=7.4 Hz), 4.30 (2H, t, J=4.7 Hz), 4.42 (2H, t, J=4.7 Hz), 4.81 (2H, s), 5.23 (1H, s), 6.35 (1H, d, J=2.9 Hz), 6.46 (1H, d, J=7.8 Hz), 6.52 (1H, d, J=9.4 Hz), 6.88 (1H, d, J=8.5 Hz), 6.96 (1H, d, J=3.0 Hz), 7.00-7.32 (13H, m).

MS (ESI, m/z):507 (M+H)$^+$.

EXAMPLE 188

To a suspension of N-{2-[5-(diphenylmethyl)-2-oxo-1(2H)-pyridinyl]ethyl}-3-hydroxybenzamide (60.0 mg) and K$_2$CO$_3$ (58.6 mg) in DMF (1.8 mL) was added dropwise ethyl bromoacetate (18.8 μL) at ambient temperature and the mixture was stirred at the same temperature for 14 hours. The resulting mixture was diluted with water (5.0 mL) and the aqueous solution was extracted with EtOAc (10.0 mL). The organic layer was washed successively with 1M HCl aqueous solution, saturated NaHCO$_3$ aqueous solution and brine, dried over anhydrous MgSO$_4$, filtered and evaporated in vacuo. The residue was purified by silica gel column chromatography (chloroform:MeOH=98:2) to give ethyl {3-[({2-[5-(diphenylmethyl)-2-oxo-1(2H)-pyridinyl]ethyl}amino)carbonyl]phenoxy}acetate (70 mg) as a colorless syrup.

$^1$H-NMR (CDCl$_3$) δ: 1.29 (3H, t, J=6.9 Hz), 3.68-3.77 (2H, m), 4.13-4.19 (2H, m), 4.27 (2H, q, J=6.9 Hz), 4.67 (2H, s), 5.22 (1H, s), 6.57 (1H, d, J=9.4 Hz), 6.78 (1H, d, J=2.0 Hz), 7.03-7.10 (5H, m), 7.18-7.43 (10H, m), 7.78-7.83 (1H, m).

MS (ESI, m/z):511 (M+H)$^+$.

The following compound(s) was (were) obtained in a similar manner to that of Example 188.

EXAMPLE 189

Ethyl {3-[({[5-(diphenylmethyl)-2-oxo-1(2H)-pyridinyl]acetyl}amino)methyl]phenoxy}acetate.

$^1$H-NMR (CDCl$_3$) δ: 1.29 (3H, t, J=7.2 Hz), 4.26 (2H, q, J=7.2 Hz), 4.38 (2H, d, J=6.0 Hz), 4.47 (2H, s), 4.59 (2H, s), 5.26 (1H, s), 6.56 (1H, d, J=9.3 Hz), 6.77-6.87 (3H, m), 6.93 (1H, d, J=1.6 Hz), 7.09-7.15 (4H, m), 7.18-7.38 (9H, m).

MS (ESI, m/z):511 (M+H)$^+$.

EXAMPLE 190

Ethyl (2-{3-[benzoyl(3,3-diphenylpropyl)amino]propyl}phenoxy)acetate.

$^1$H-NMR (CDCl$_3$) δ: 1.27 (3H, t, J=7.0 Hz), 1.80-1.77 (1H, m), 1.99-1.95 (1H, m), 2.21-2.18 (1H, m), 2.45-2.43 (2H, m), 2.76-2.73 (1H, m), 3.23-3.18 (2H, m), 3.47-3.42 (1H, m), 3.60-3.57 (1H, m), 4.01, 3.65 (1H, t, J=7.5 Hz), 4.22 (2H, q, J=7.0 Hz), 4.58, 4.50 (2H, s), 6.71-6.63 (1H, m), 6.99-6.85 (3H, m), 7.17-7.15 (5H, m), 7.35-7.25 (10H, m).

MS (ESI, m/z):536 (M+H)$^+$.

EXAMPLE 191

To a solution of N-(3,3-diphenylpropyl)-N-[3-(2-hydroxyphenyl)propyl]benzamide (100 mg) in MeCN (2 mL) was added NMM (2.3 mg) and methyl propionate (22.4 mg) at ambient temperature. The reaction mixture was stirred for 2 hours at the same temperature. The resulting mixture was diluted with EtOAc (15 mL) and washed successively with water and brine. The organic layer was dried over anhydrous MgSO$_4$, filtered and evaporated in vacuo. The residue was purified by silica gel column chromatography (n-hexane:EtOAc=80:20-70:30) to give a methyl (2E)-3-(2-{3-[benzoyl(3,3-diphenylpropyl)amino]propyl}phenoxy)acrylate.

$^1$H-NMR (CDCl$_3$) δ: 1.69-1.66 (1H, m), 1.91-1.88 (1H, m), 2.19-2.17 (1H, m),2.35-2.32 (1H, m), 2.44-2.42 (1H, m), 2.66-2.63 (1H, m), 3.14 (2H, brs),3.44-3.41 (1H, m), 3.53-3.51 (1H, m), 3.73 (3H, s), 7.02-3.98, 3.65-3.61 (1H, m), 5.43, 5.37 (1H, d, J=12.0 Hz), 7.00-6.98 (1H, d, J=12.0 Hz), 7.35-7.15 (15H, m), 7.77, 7.67 (1H, d, J=12.0 Hz).

MS (ESI, m/z):534 (M+H)$^+$.

The following compound(s) was (were) obtained in a similar manner to that of Example 191.

EXAMPLE 192 tert-Butyl (2E)-3-(3-{3-[5-(diphenylmethyl)-2-oxo-1(2H)-pyridinyl]propyl}phenoxy)acrylate.

$^1$H-NMR (CDCl$_3$) δ: 1.49 (9H, s), 2.02 (2H, quint, J=7.5 Hz), 2.61 (2H, t, J=7.5 Hz), 3.85 (2H, t, J=7.5 Hz), 5.24 (1H, s), 5.46 (1H, d, J=12.3 Hz), 6.53 (1H, d, J=9.4 Hz), 6.71 (1H, d, J=2.4 Hz), 6.82-6.84 (1H, m), 6.86-6.93 (2H, m), 6.09-7.13 (4H, m), 7.15 (1H, dd, J=2.6, 9.4 Hz), 7.21-7.36 (7H, m), 7.67 (1H, d, J=12.3 Hz).

EXAMPLE 193

To a solution of (2E)-3-(4-pyridinyl)acrylic acid (23 mg) in DMF (1 mL) was added HOBt (21 mg), ethyl(3-{3-[(3,3-diphenylpropyl)amino]propyl}phenoxy)acetate (55 mg) and WSCD.HCl (29 mg) at ambient temperature. The reaction mixture was stirred for 8 hours at the same temperature. The resulting mixture was diluted with EtOAc and washed successively with water and brine. The organic layer was dried over anhydrous MgSO$_4$, filtered and evaporated in vacuo. The residue was purified by silica gel column chromatography (n-hexane:EtOAc=85:15-70:30) to give a ethyl[3-(3-{(3,3-diphenylpropyl) [(2E)-3-(4-pyridinyl)-2-propenoyl]amino}propyl)phenoxy]acetate.

$^1$H-NMR (CDCl$_3$) δ: 1.29 (3H, t, J=7 Hz), 1.92-1.80 (3H, m), 2.39-2.31 (2H, m),2.64-2.56 (2H, m), 3.40-3.26 (3H, m), 3.48 (1H, t, J=7.5 Hz), 3.88, 3.96 (1H, t, J=7.5 Hz), 4.26 (2H, q, J=7.0 Hz), 4.59, 4.57 (2H, s), 6.52 (1H, d, J=15.0 Hz), 6.83-6.63 (3H, m), 7.09 (1H, d, J=6.0 Hz), 7.33-7.16 (11H, m), 7.55-7.48 (1H, m), 8.59-8.58 (3H, m).

MS (ESI, m/z):563 (M+H)$^+$.

EXAMPLE 194

To a solution of ethyl (3-{3-[(3,3-diphenylpropyl)amino]propyl}phenoxy)acetate (237 mg) and pyridine (87 mg) in DCM (5 mL) was added benzoyl chloride (93 mg) at ambient temperature. The reaction mixture was stirred at the same temperature for 8 hours. The resulting mixture was diluted with EtOAc (15 mL) and washed successively with 1M HCl aqueous solution, NaHCO$_3$ aqueous solution, water and brine. The organic layer was dried over anhydrous MgSO$_4$, filtered and evaporated in vacuo. The residue was purified by silica gel column chromatography(chloroform:MeOH=100:0-97:3) to give ethyl (3-{3-[benzoyl-3,3-diphenylpropyl)amino]propyl}phenoxy)acetate.

$^1$H-NMR (CDCl$_3$) δ: 1.30 (3H, t, J=7.0 Hz), 1.92-1.70 (2H, m), 2.64-2.18 (4H, m), 3.16-3.12 (2H, m), 3.65-3.42 (2H, m), 4.02-3.91, 3.66-3.64 (1H, m), 4.28 (2H, q, J=7.0 Hz), 4.60, 4.58 (2H, s), 7.01-6.58 (5H, m), 7.38-7.17 (11H, m), 7.64-7.45 (2H, m), 8.11 (1H, d, J=8.5 Hz).

MS (ESI, m/z):536 (M+H)$^+$.

The following compound(s) was (were) obtained in a similar manner to that of Example 194.

EXAMPLE 195

Ethyl[(2-{[benzoyl(3,3-diphenylpropyl)amino]methyl}-2,3-dihydro-1H-inden-4-yl)oxy]acetate.

$^1$H-NMR (CDCl$_3$) δ: 1.29 (3H, t, J=7.1 Hz), 2.1-3.75 (11.5H, m), 3.9.5-4.1 (0.5H, m), 4.25 (2H, q, J=7.1 Hz), 4.5-4.65 (2H, m), 6.4-6.6 (1H, m), 6.65-7.45 (17H, m).

MS (ESI, m/z):548 (M+H)$^+$.

EXAMPLE 196

Ethyl(3-{3-[(2E)-2-butenoyl(3,3-diphenylpropyl)amino]propyl}phenoxy)acetate.

$^1$H-NMR (CDCl$_3$) δ: 1.29 (3H, t, J=7.0 Hz), 1.83-1.75 (5H, m), 2.34-2.26 (2H, m), 2.58-2.51 (2H, m), 3.31-3.18 (3H, m), 3.38 (1H, t, J=7.5 Hz), 3.95-3.82 (1H, m), 4.27 (2H, q, J=7.0 Hz), 4.59 (2H, s), 6.00, 5.82 (1H, d, J=14.0 Hz), 6.91-6.70 (4H, m), 7.33-7.15 (11H, m).

MS (ESI, m/z):500 (M+H)$^+$.

EXAMPLE 197

Ethyl(3-{3-[(3,3-diphenylpropyl)(3-pyridinylcarbonyl)amino]propyl}phenoxy)acetate.
$^1$H-NMR (CDCl$_3$) δ: 1.30 (3H, t, J=7.0 Hz), 1.75-1.74 (1H, m), 1.95-1.93 (1H, m), 2.20-2.18 (1H, m), 2.44-2.35 (2H, m), 2.65-2.63 (1H, m), 3.14-3.13 (2H, m), 4.00-3.44 (3H, m), 4.27 (2H, q, J=7.0 Hz), 4.61, 4.58 (2H, s), 6.85-6.58 (3H, m), 7.03-7.02 (2H, m), 7.29-7.20 (10H, m), 7.57-7.50 (1H, m), 8.54-8.53 (1H, m), 8.61-8.60 (1H, m).
MS (ESI, m/z):537 (M+H)$^+$.

EXAMPLE 198

Ethyl(3-{3-[(3,3-Diphenylpropyl)(isonicotinoyl)amino]propyl}phenoxy)acetate.
$^1$H-NMR (CDCl$_3$) δ: 1.30 (3H, t, J=7.0 Hz), 1.74-1.69 (1H, m), 1.98-1.88 (1H, m), 2.22-2.14 (1H, m), 2.43-2.32 (2H, m), 2.64 (1H, dd, J=7.5, 7.5 Hz), 3.09-3.05 (2H, m), 3.45-3.40 (1H, m), 3.55-3.50 (1H, m), 3.99, 3.64 (1H, t, J=7.5 Hz), 4.27 (2H, q, J=7.0 Hz), 4.61, 4.58 (2H, s), 6.59 (1H, s), 6.85-6.67 (2H, m), 7.02-7.00 (2H, m), 7.30-7.16 (11H, m), 8.60-8.55 (2H, m).
MS (ESI, m/z):537 (M+H)$^+$.

EXAMPLE 199

Ethyl(3-{3-[(3,3-diphenylpropyl)(phenoxycarbonyl)amino]propyl}phenoxy)-acetate.
$^1$H-NMR (CDCl$_3$) δ: 1.29 (3H, t, J=7.0 Hz), 1.92-1.83 (2H, m), 2.42-2.37 (2H, m), 2.62-2.54 (2H, m), 3.34-3.29 (4H, m), 3.93 (1H, t, J=7.5 Hz), 4.26 (2H, q, J=7.0 Hz), 4.59, 4.57 (2H, s), 6.80-6.70 (3H, m), 7.08 (2H, d, J=8.0 Hz), 7.38-7.16 (14H, m).
MS (ESI, m/z):552 (M+H)$^+$.

EXAMPLE 200

Ethyl(5-{3-[benzoyl(3,3-diphenylpropyl)amino]propyl}-2-fluorophenoxy)acetate.
$^1$H-NMR (CDCl$_3$) δ: 1.28 (3H, t, J=6.9 Hz), 1.55-1.75 (1H, m), 1.77-1.96 (1H, m), 2.10-2.50 (3H, m), 2.51-2.67 (1H, m), 3.06-3.22 (2H, m), 3.33-3.56 (2H, m), 3.58-3.70 (0.5H, m), 3.90-4.08 (0.5H, m), 4.25 (2H, q, J=6.9 Hz), 4.56-4.70 (2H, m), 6.44-7.44 (18H, m).
MS (ESI, m/z):554 (M+H)$^+$.

EXAMPLE 201

Ethyl(3-{3-[(3,3-diphenylpropyl)(2-pyridinylcarbonyl)amino]propyl}phenoxy)acetate.
$^1$H-NMR (CDCl$_3$) δ: 1.30 (3H, t, J=7.0 Hz), 1.98-1.78 (2H, m), 2.50-2.28 (3H, m), 2.65 (1H, t, J=7.5 Hz), 3.34-3.27 (2H, m), 3.45-3.40 (1H, m), 3.55-3.50 (1H, m), 4.01, 3.69 (1H, t, J=7.5 Hz), 4.27 (2H, q, J=7.0 Hz), 4.60, 4.57 (2H, s), 6.85-6.60 (3H, m), 7.30-7.05 (12H, m), 7.55-7.48 (1H, m), 7.76-7.68 (1H, m), 8.50-8.42 (1H, m).
MS (ESI, m/z):537 (M+H)$^+$.

EXAMPLE 202

Ethyl(3-{3-[(cyclopentylcarbonyl)(3,3-diphenylpropyl)amino]propyl}phenoxy)acetate.
$^1$H-NMR (CDCl$_3$) δ: 1.30 (3H, t, J=7.0 Hz), 1.80-1.41 (11H, m), 2.32-2.24 (2H, m), 2.53 (2H, t, J=7.5 Hz), 3.26-3.16 (3H, m), 3.36-3.31 (1H, m), 3.93-3.81 (1H, m), 4.27 (2H, q, J=7.0 Hz), 4.60, 4.59 (2H, s), 6.80-6.69 (3H, m), 7.32-7.16 (11H, m).
MS (ESI, m/z):528 (M+H)$^+$.

EXAMPLE 203

To a solution of (3-{3-[5-(diphenylmethyl)-2-oxo-1(2H)-pyridinyl]propyl}phenoxy)acetic acid (100 mg) in DMF (2 mL) was added K$_2$CO$_3$ (46 mg) and iodomethane (41 mg) at ambient temperature. The reaction mixture was stirred for 5 hours at the same temperature. The resulting mixture was diluted with EtOAc and washed successively with water and brine. The organic layer was dried over anhydrous MgSO$_4$, filtered and evaporated in vacuo. The residue was purified by silica gel column chromatography (n-hexane:EtOAc=80:20-40:60) to give methyl (3-{3-[5-(diphenylmethyl)-2-oxo-1(2H)-pyridinyl]propyl}phenoxy)acetate-.
$^1$H-NMR (CDCl$_3$) δ: 2.06-1.96 (2H, m) 2.58 (2H, dd, J=7.5, 7.5 Hz), 3.81 (3H, s), 3.84 (2H, dd, J=7.5, 7.5 Hz), 4.62 (2H, s), 5.24 (1H, s), 6.52 (1H, d, J=9.5 Hz), 6.73-6.71 (4H, m), 7.17-7.10 (6H, m), 7.35-7.25 (6H, m MS (ESI, m/z):468 (M+H)$^+$.

EXAMPLE 204

To a solution of 4-[3-({2-[5-(diphenylmethyl)-2-oxopyridin-1(2H)-yl]ethyl}sulfanyl)phenoxy]butanoic acid (82 mg) in formic acid (0.50 mL) was added dropwise 30%—H$_2$O$_2$ (0.56 mL) at 0° C. The reaction mixture was stirred at ambient temperature for 4 hours. The reaction mixture was added saturated sodium sulfate aqueous solution (8 mL) at 0° C. and extracted with EtOAc (10 mL) three times. The combined organic extracts were washed with brine (10 mL). The organic layer was dried over anhydrous MgSO$_4$, filtered and evaporated in vacuo to give crude solid. The crude solid was purified by silica gel column chromatography (n-hexane:EtOAc=1:1-0:1) to give a white solid. The solid was washed with mixed solvent (EtOAc:n-hexane) to give 4-[3-({2-[5-(diphenylmethyl)-2-oxopyridin-1(2H)-yl]ethyl}sulfonyl)phenoxy]butanoic acid (30 mg) as a white solid.
$^1$H-NMR (DMSO-d$_6$) δ: 1.91-1.99 (2H, m), 2.39 (2H, t, J=7.2 Hz), 3.78 (2H, t, J=6.4 Hz), 4.00-4.08 (4H, m), 5.30 (1H, s), 6.28 (1H, d, J=9.3 Hz), 7.15-7.49 (16H, m).
MS (ESI, m/z):530 (M−H)$^-$.
The following compound(s) was (were) obtained in a similar manner to that of Preparation 57.

EXAMPLE 205

(3-{3-[(3,3-Diphenylpropyl)(4-hydroxybenzoyl)amino]propyl}phenoxy)acetic acid.
$^1$H-NMR (DMSO-d$_6$) δ: 1.65-1.86 (2H, m), 2.20-2.35 (3H, m), 2.50-2.60 (1H, m), 3.00-4.10 (5H, m), 4.63 (2H, s), 6.67-6.83 (5H, m), 7.11-7.41 (14H, m).
MS (ESI, m/z):546 (M+Na)$^+$.

EXAMPLE 206

To a solution of (3-{3-[benzoyl(3,3-diphenylpropyl)amino]propyl}phenoxy)acetic acid (110 mg) in MeOH (1 mL) was added 1M NaOH aqueous solution (0.217 mL) at ambient temperature. The mixture was stirred for 0.5 hours at the same temperature. The resulting mixture was evaporated in vacuo. The residue was triturated with diisopropylether to give a sodium (3-{3-[benzoyl(3,3-diphenylpropyl)amino]propyl}phenoxy)acetate.

¹H-NMR (DMSO-d₆) δ: 1.80-1.65 (2H, m), 2.33-2.22 (4H, m), 3.12-3.05 (2H, m), 3.51-3.44 (2H, m), 3.76-3.71 (1H, m), 4.04 (2H, brs), 6.67-6.44 (4H, m), 7.37-7.11 (15H, m).

The following compound(s) was (were) obtained in a similar manner to that of Example 206.

EXAMPLE 207

Sodium (3-{3-[3-(diphenylmethyl)-6-oxopyridazin-1(6H)-yl]propyl}phenoxy)acetate.

¹H-NMR (DMSO-d₆) δ: 1.94-1.89 (2H, m), 2.49-2.43 (2H, m), 4.01 (2H, t, J=7.0 Hz), 4.05 (2H, s), 5.57 (1H, s), 6.62-6.56 (3H, m), 6.90 (1H, d, J=10.0 Hz), 7.07 (1H, t, J=7.5 Hz), 7.36-7.20 (11H, m).

EXAMPLE 208

Sodium {3-[(2-{[3-(diphenylmethyl)-6-oxopyridazin-1(6H)-yl]methyl}cyclohexyl)methyl]phenoxy}acetate.

¹H-NMR (DMSO-d₆) δ: 0.70-1.80 (10H, m), 2.00-3.00 (2H, m), 3.80-4.40 (4H, m), 5.56 (1H, s), 6.50-6.70 (3H, m), 6.80-7.40 (13H, m).

MS (ESI, m/z):567 (M+Na)⁺.

The structures of the compounds of the invention are shown in the following Tables.

TABLE 3

Ex: Example No., Structure: chemical structure.

| Ex | Structure |
|----|-----------|
| 1 | |
| 2 | |
| 3 | |
| 4 | 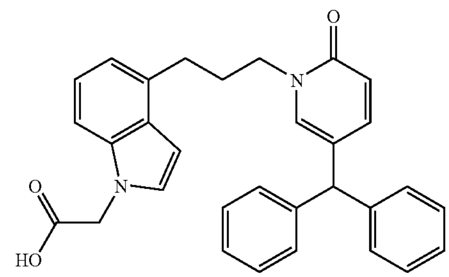 |
| 5 | 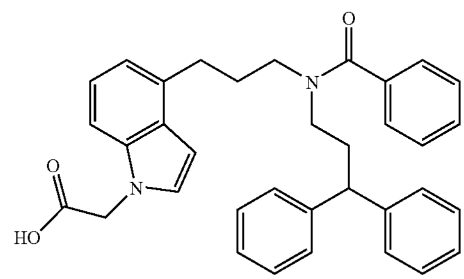 |
| 6 | 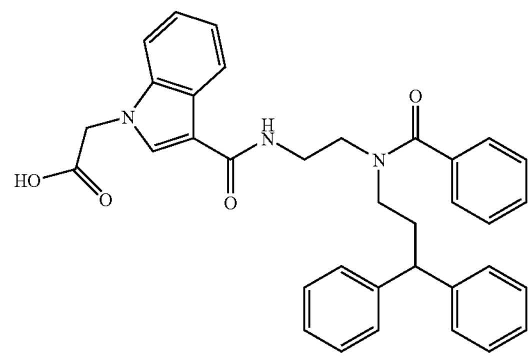 |
| 7 | 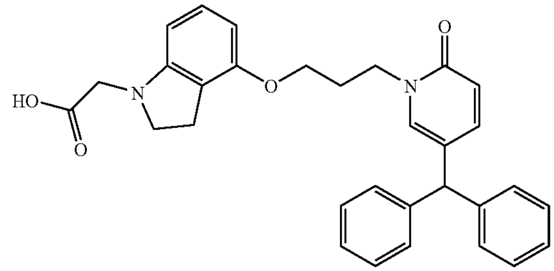 |
| 8 | 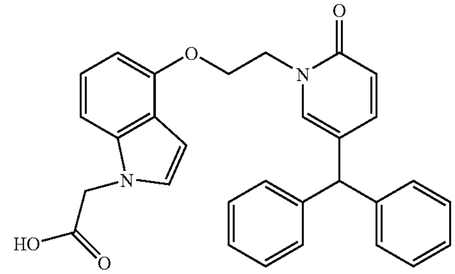 |

TABLE 3-continued
Ex: Example No., Structure: chemical structure.
| Ex | Structure |
|---|---|
| 9 | 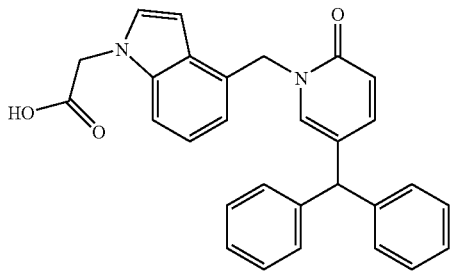 |
| 10 | 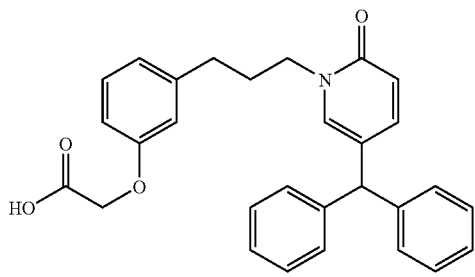 |
| 11 | 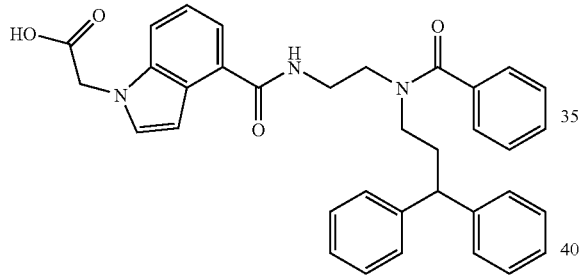 |
| 12 | 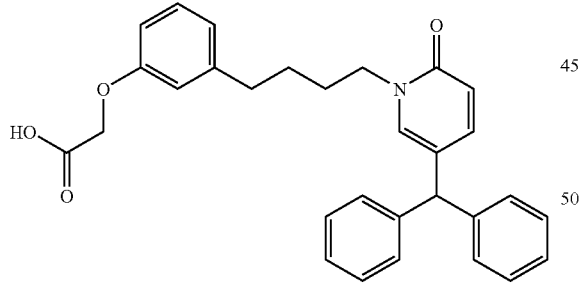 |
| 13 | 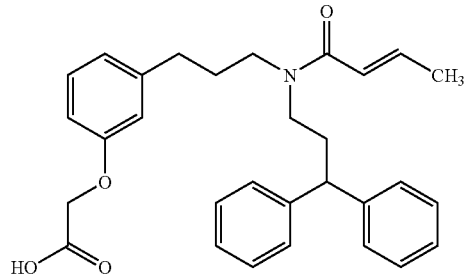 |
TABLE 3-continued
Ex: Example No., Structure: chemical structure.
| Ex | Structure |
|---|---|
| 14 | 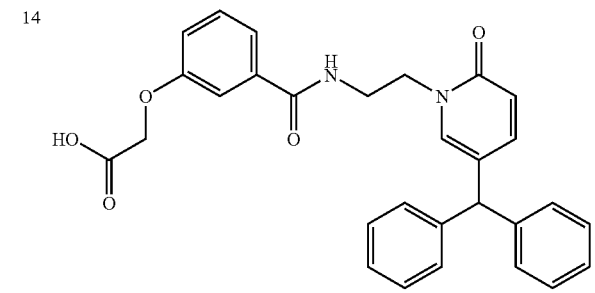 |
| 15 | 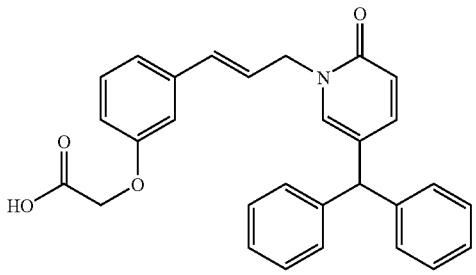 |
| 16 | 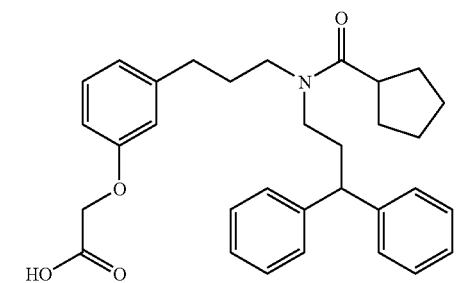 |
| 17 | 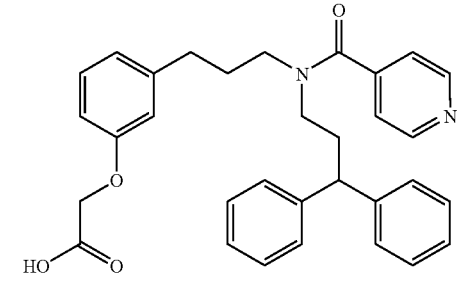 |
| 18 | 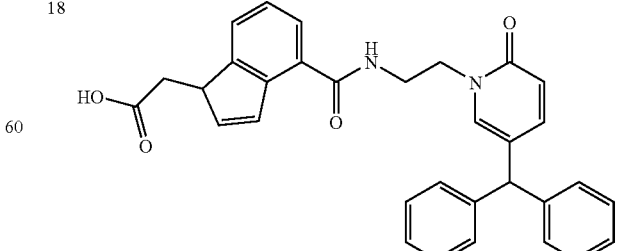 |

TABLE 3-continued

Ex: Example No., Structure: chemical structure.

| Ex | Structure |
|---|---|
| 19 | 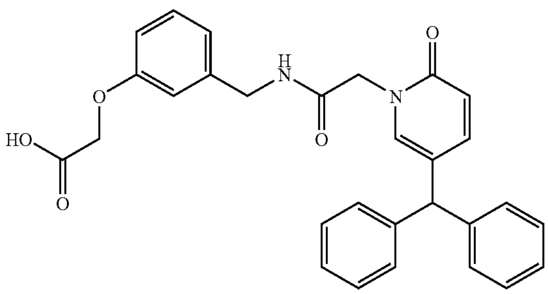 |
| 20 | 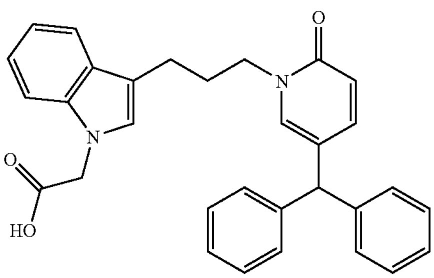 |
| 21 | 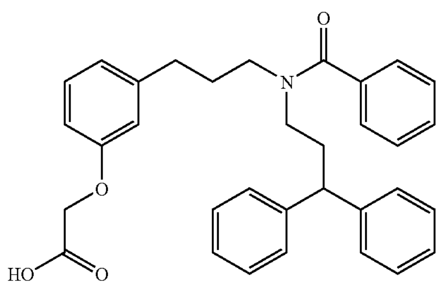 |
| 22 | 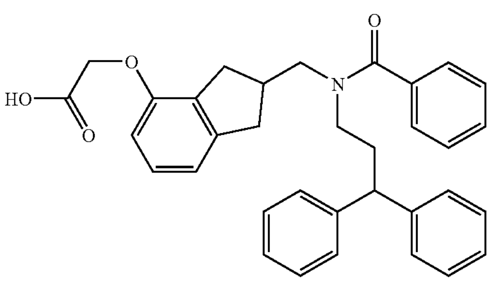 |
| 23 | 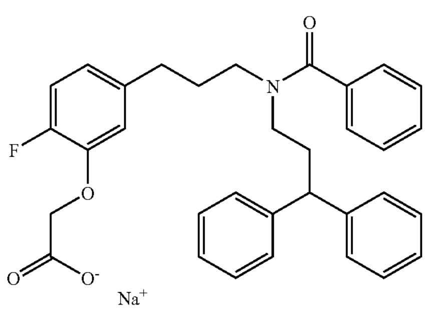 |
| 24 | |
| 25 | |
| 26 | |
| 27 | |
| 28 | |

TABLE 3-continued
Ex: Example No., Structure: chemical structure.
| Ex | Structure |
|---|---|
| 29 | 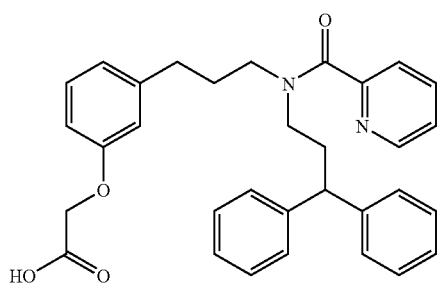 |
| 30 | 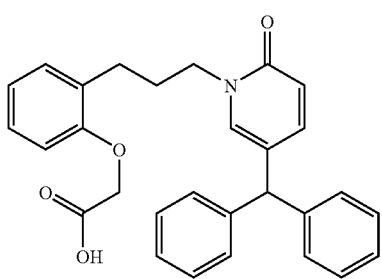 |
| 31 | 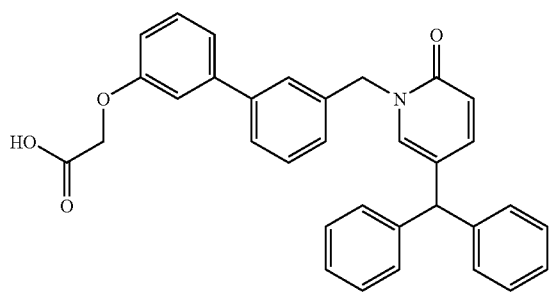 |
| 32 | 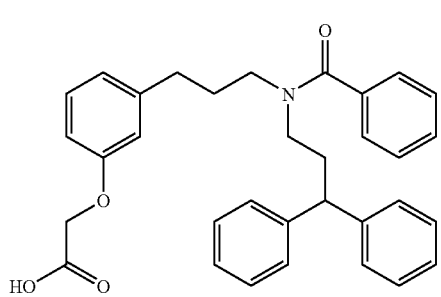 |
| 33 | 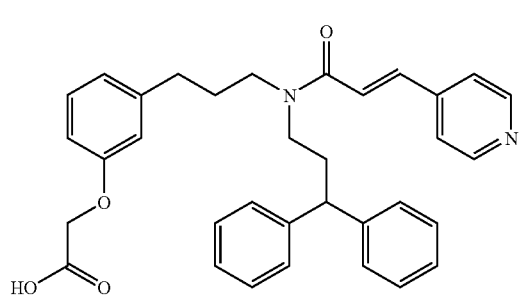 |
| 34 | 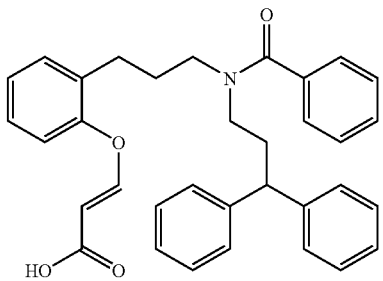 |
| 35 | 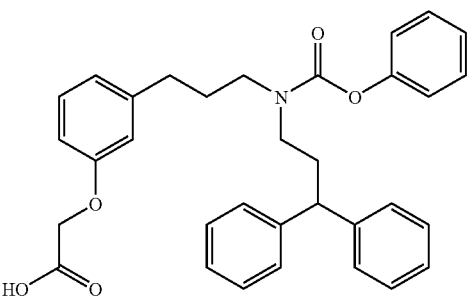 |
| 36 | 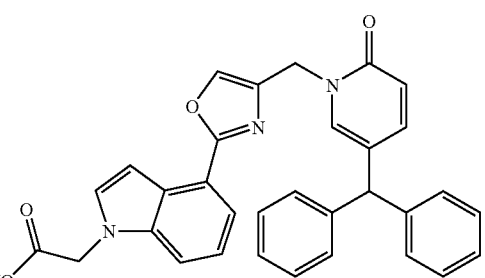 |
| 37 | 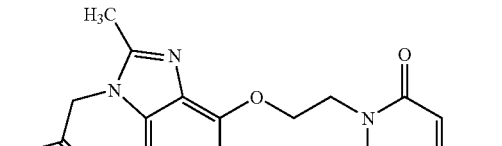 |
| 38 | 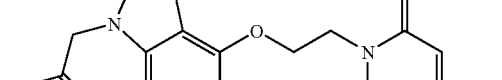 |

TABLE 3-continued
Ex: Example No., Structure: chemical structure.
| Ex | Structure |
|---|---|
| 39 | 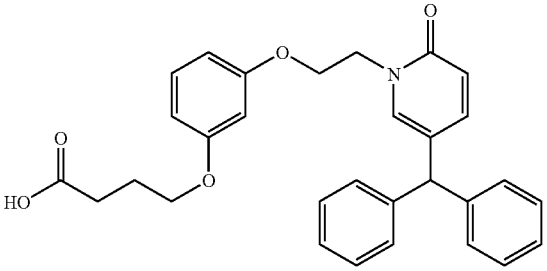 |
| 40 | 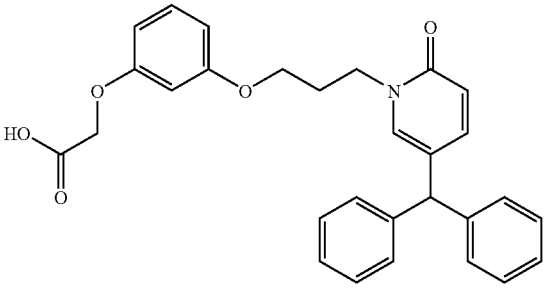 |
| 41 | 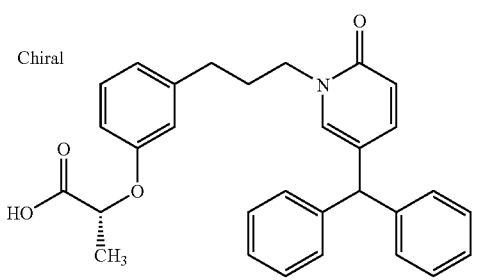 |
| 42 | 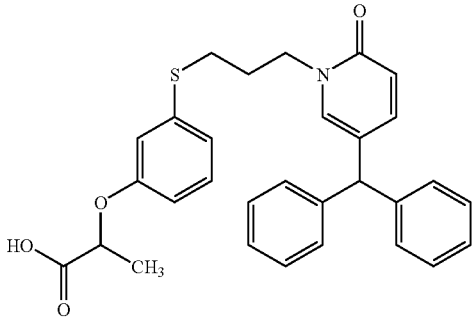 |
| 43 | 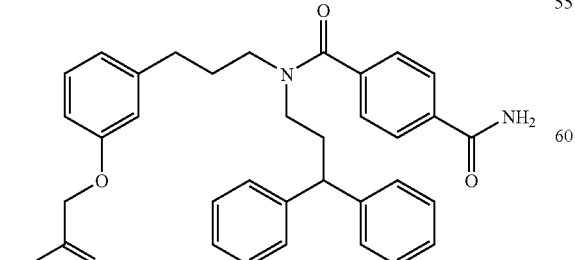 |
| 44 | 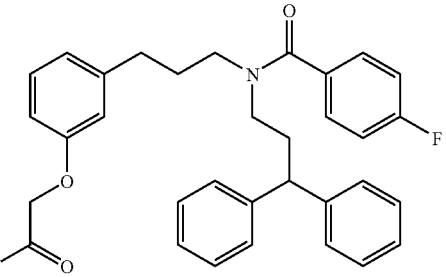 |
| 45 | 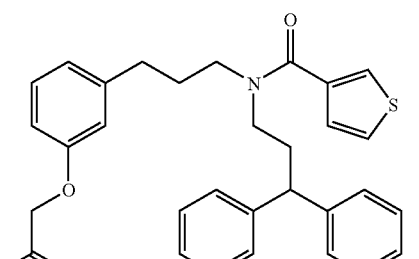 |
| 46 | 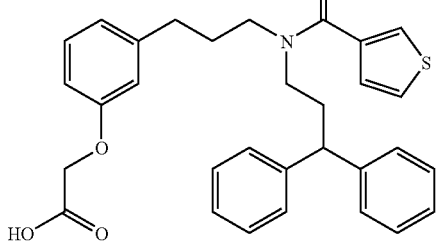 |
| 47 |  |
| 48 |  |

TABLE 3-continued
Ex: Example No., Structure: chemical structure.
| Ex | Structure |
|---|---|
| 49 | 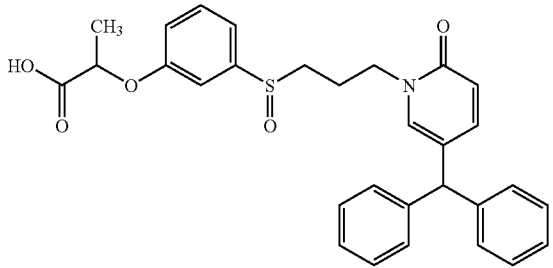 |
| 50 | 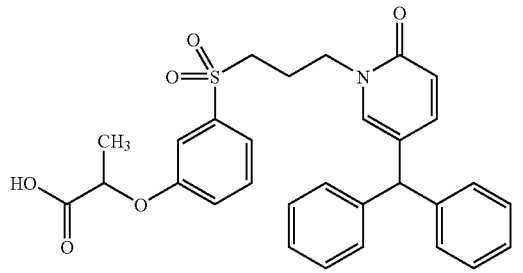 |
| 51 | 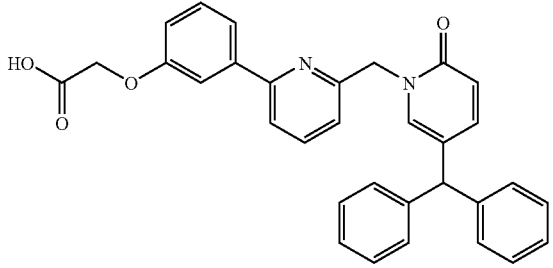 |
| 52 | 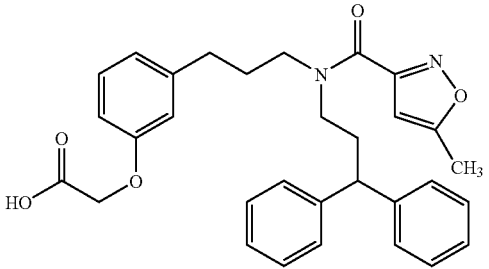 |
| 53 | 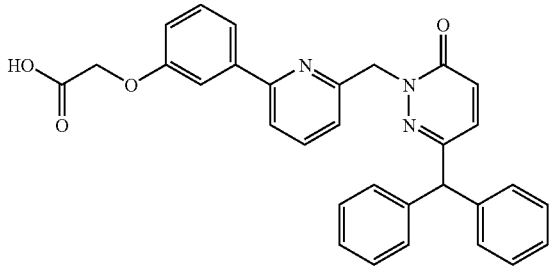 |
| 54 | 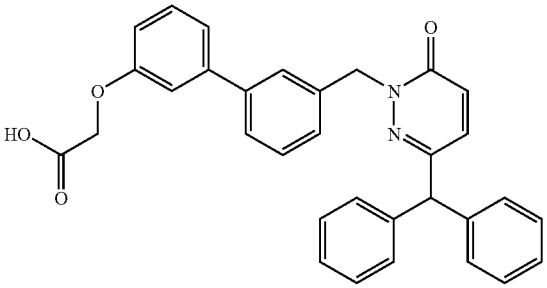 |
| 55 | 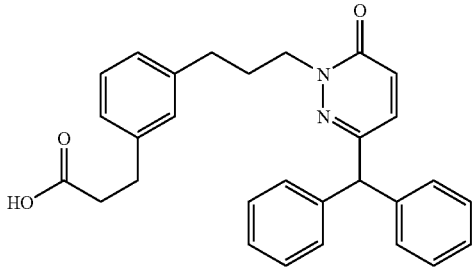 |
| 56 | 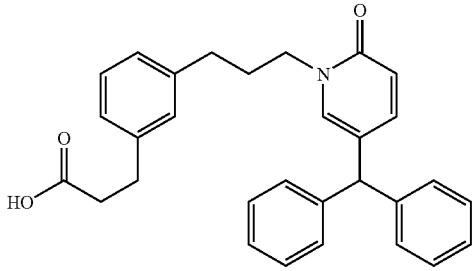 |
| 57 | 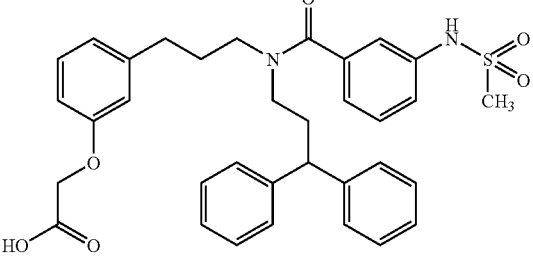 |
| 58 | 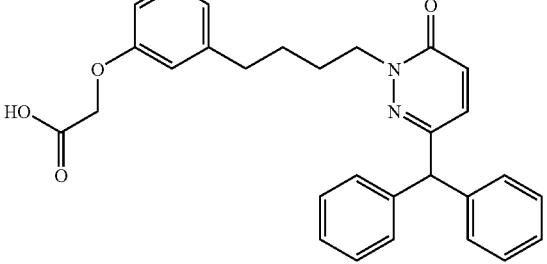 |

TABLE 3-continued

Ex: Example No., Structure: chemical structure.

| Ex | Structure |
|---|---|
| 59 | 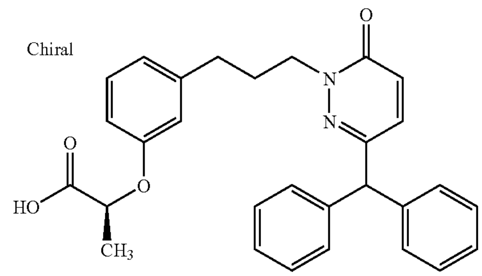 |
| 60 | 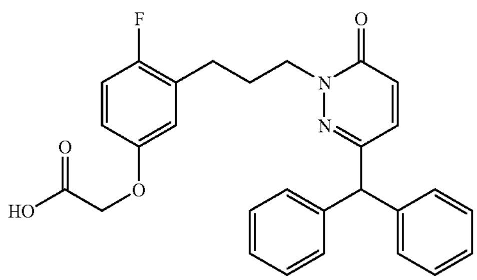 |
| 61 | 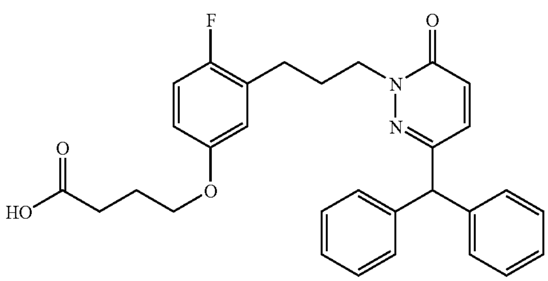 |
| 62 | 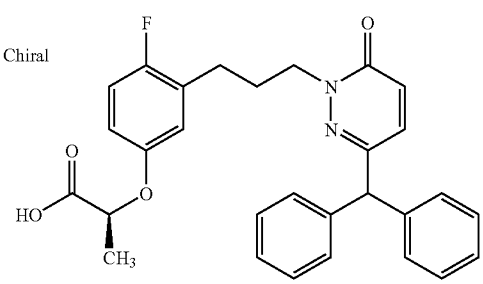 |
| 63 | 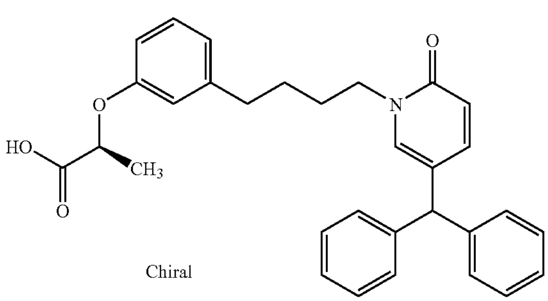 |
| 64 | |
| 65 | |
| 66 | |
| 67 | |
| 68 | |

TABLE 3-continued
Ex: Example No., Structure: chemical structure.
| Ex | Structure |
|----|-----------|
| 69 | 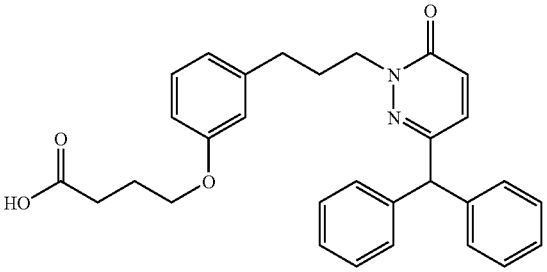 |
| 70 | 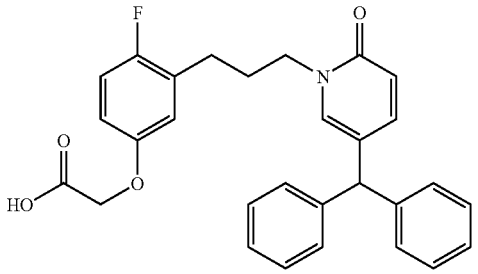 |
| 71 | 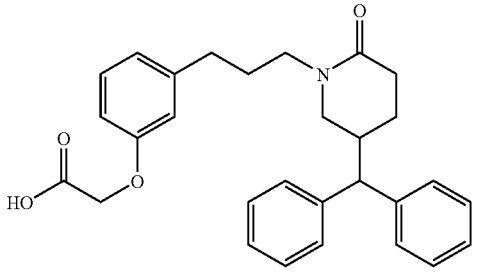 |
| 72 | 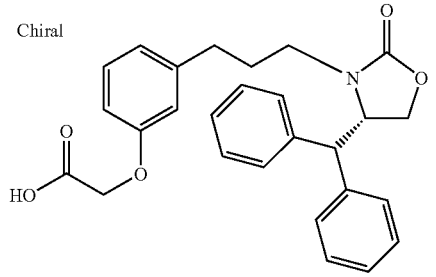 Chiral |
| 73 | 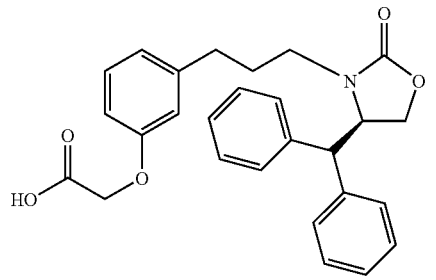 |
| 74 | 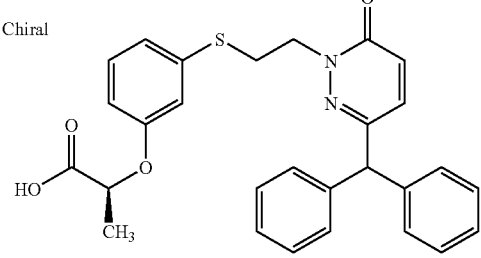 Chiral |
| 75 | 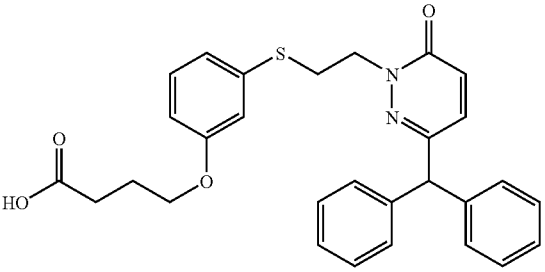 |
| 76 | 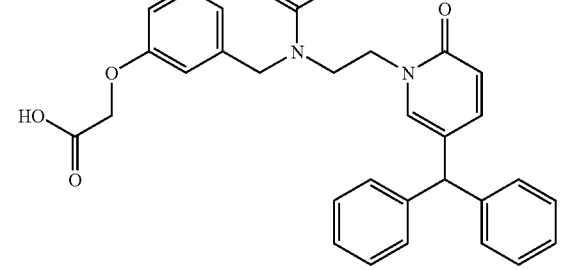 |
| 77 | 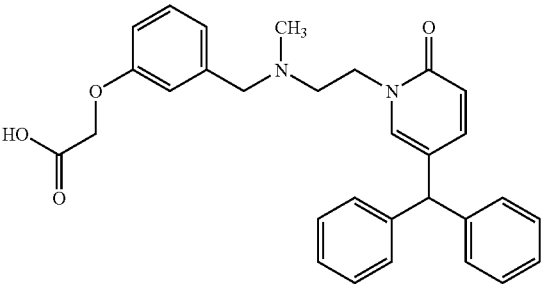 |
| 78 | 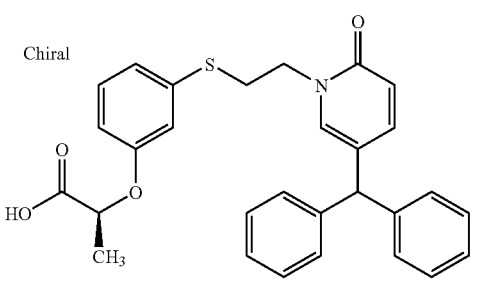 Chiral |

TABLE 3-continued

Ex: Example No., Structure: chemical structure.

| Ex | Structure |
|---|---|
| 79 | 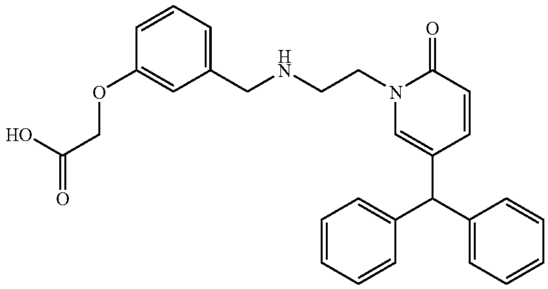 |
| 80 | 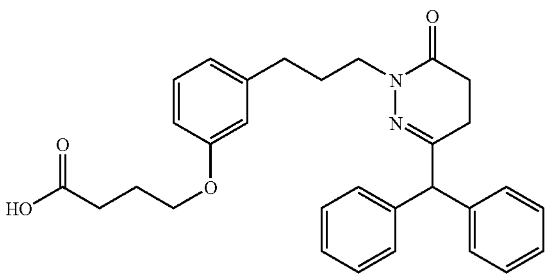 |
| 81 | 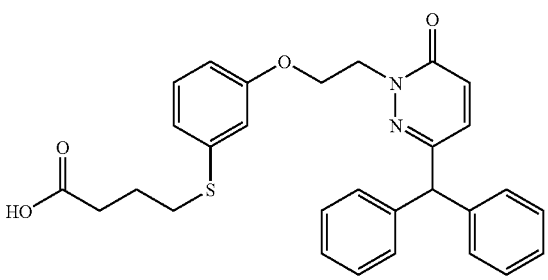 |
| 82 | 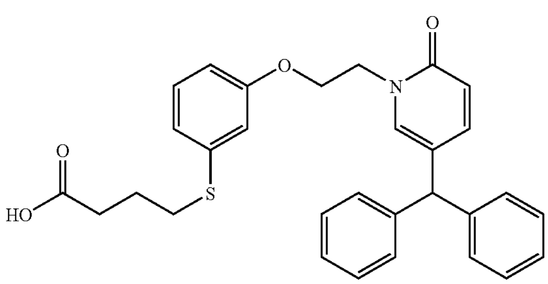 |
| 83 | 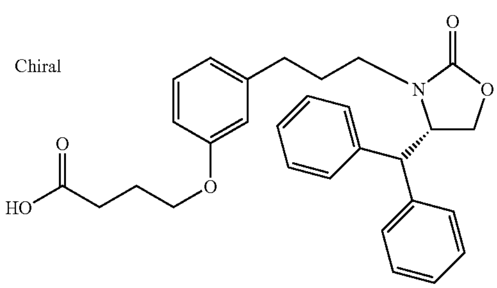 |
| 84 | |
| 85 | |
| 86 | |
| 87 | |
| 88 | |

TABLE 3-continued
Ex: Example No., Structure: chemical structure.
| Ex | Structure |
|---|---|
| 89 | 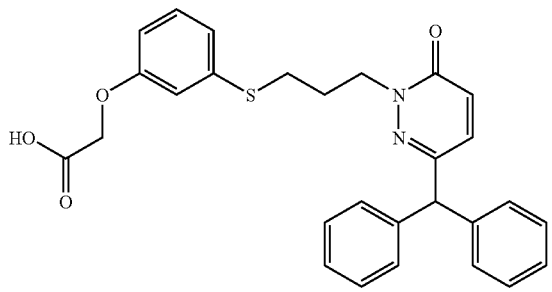 |
| 90 | 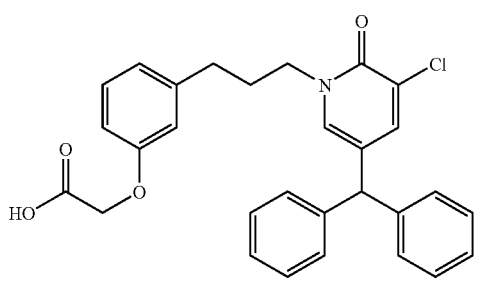 |
| 91 | 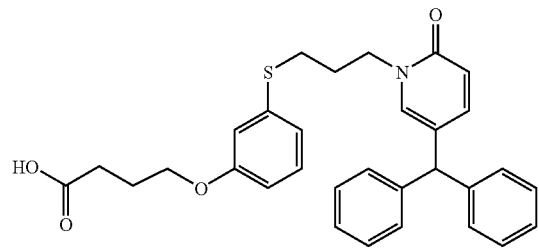 |
| 92 | 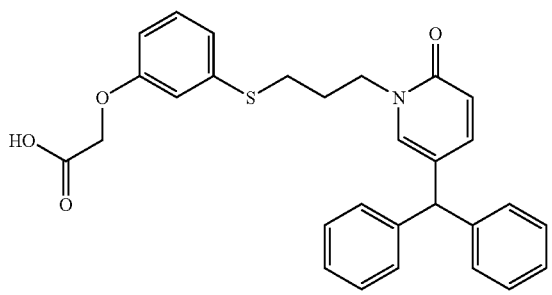 |
| 93 | 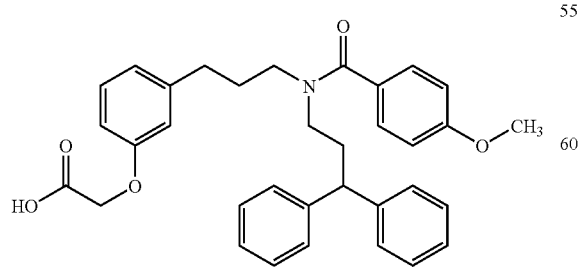 |
TABLE 3-continued
Ex: Example No., Structure: chemical structure.
| Ex | Structure |
|---|---|
| 94 | 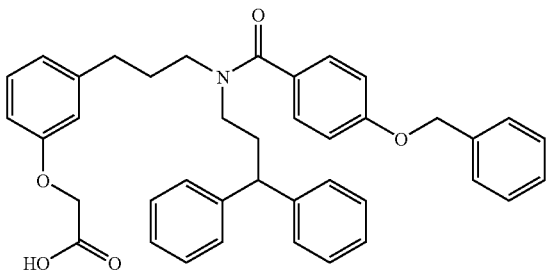 |
| 95 | 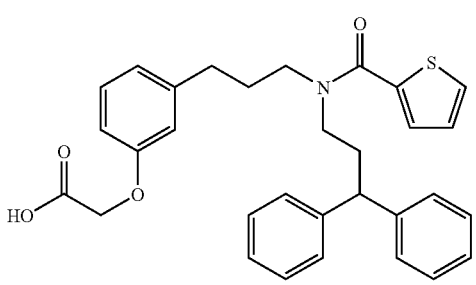 |
| 96 | Chiral 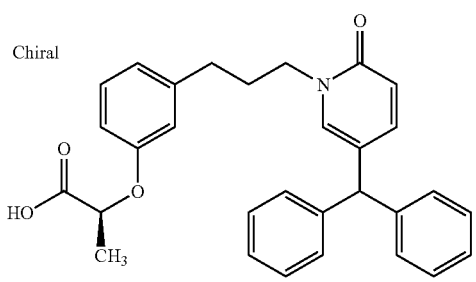 |
| 97 | 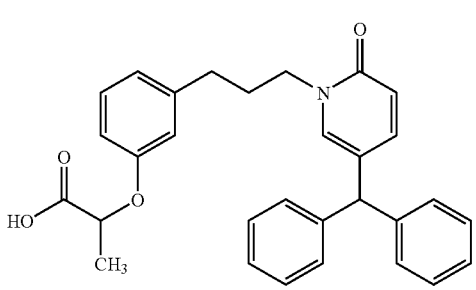 |
| 98 | Chiral 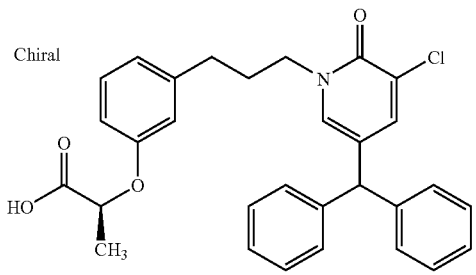 |

TABLE 3-continued

Ex: Example No., Structure: chemical structure.

| Ex | Structure |
|---|---|
| 99 | 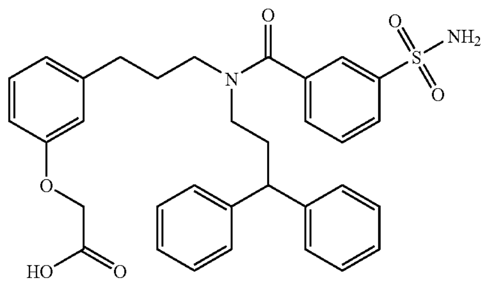 |
| 100 | 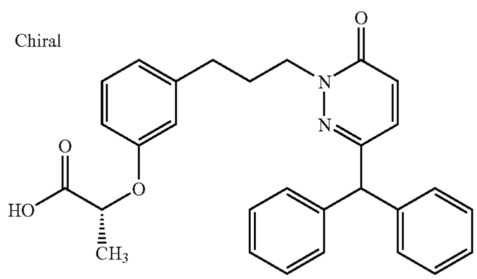 |
| 101 | 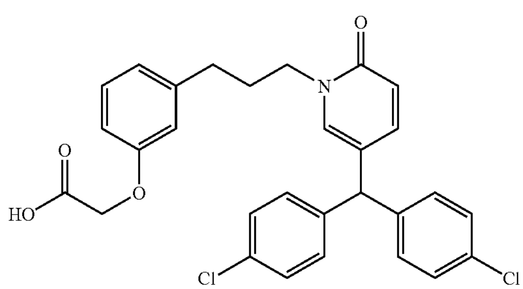 |
| 102 | 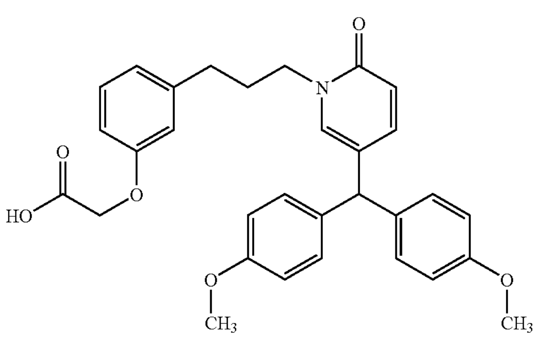 |
| 103 | 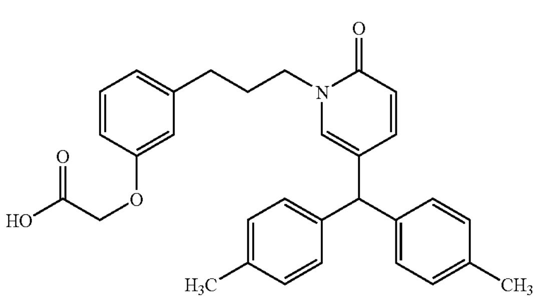 |
| 104 | |
| 105 | |
| 106 | |
| 107 | |
| 108 | |

TABLE 3-continued

Ex: Example No., Structure: chemical structure.

| Ex | Structure |
|---|---|
| 109 | 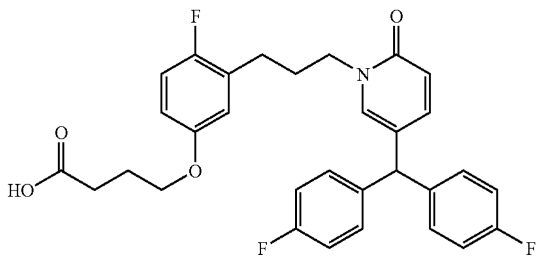 |
| 110 | 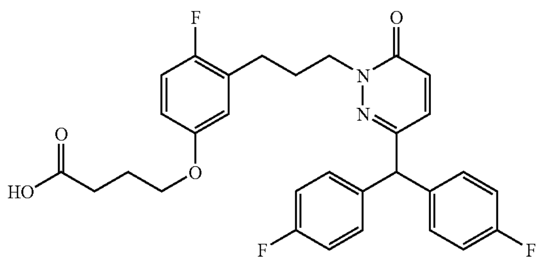 |
| 111 | 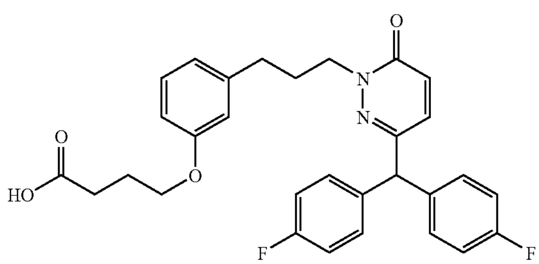 |
| 112 | 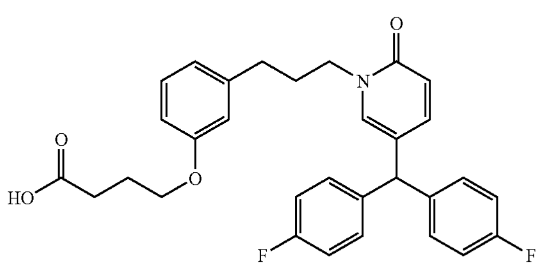 |
| 113 | Chiral |
| 114 | |
| 115 | Chiral |
| 116 | |
| 117 | |
| 118 | |

TABLE 3-continued
Ex: Example No., Structure: chemical structure.
| Ex | Structure |
|---|---|
| 119 | 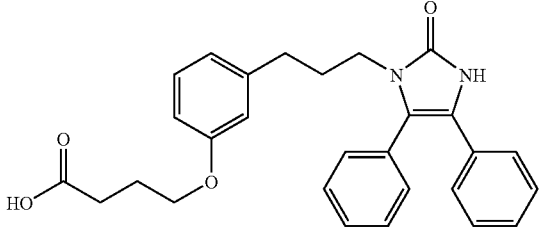 |
| 120 | 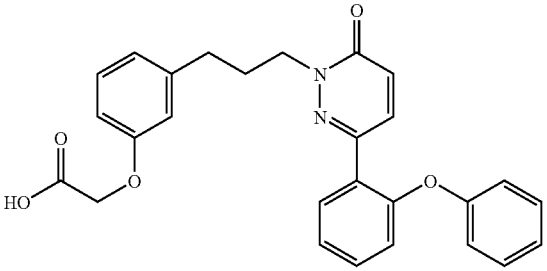 |
| 121 | 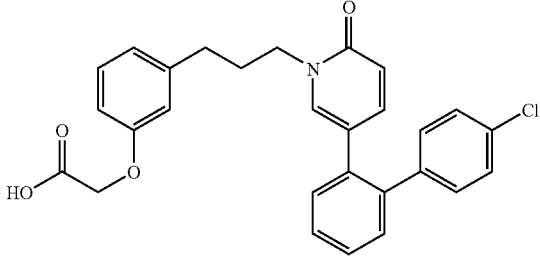 |
| 122 | 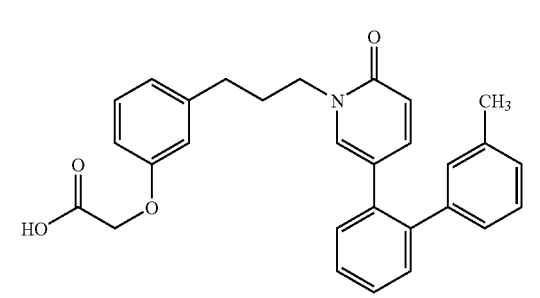 |
| 123 | 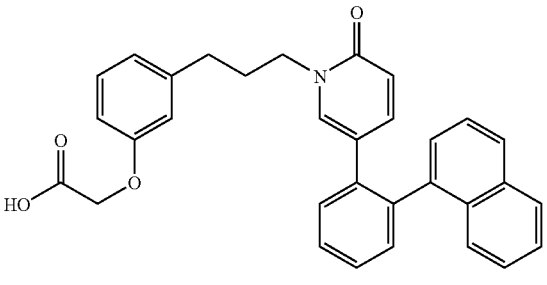 |
TABLE 3-continued
Ex: Example No., Structure: chemical structure.
| Ex | Structure |
|---|---|
| 124 | 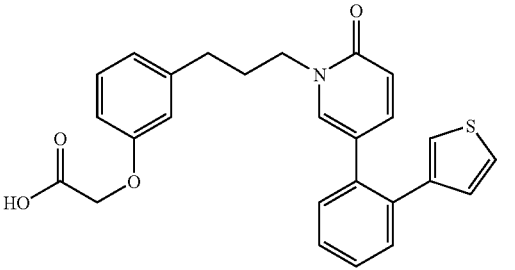 |
| 125 Chiral | 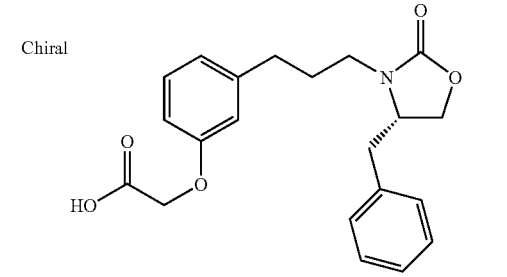 |
| 126 | 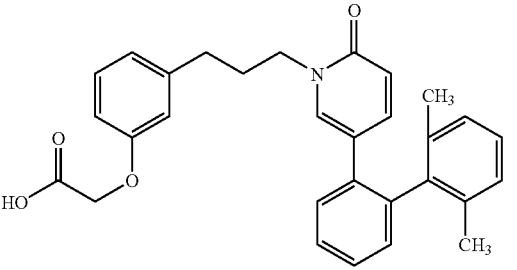 |
| 127 | 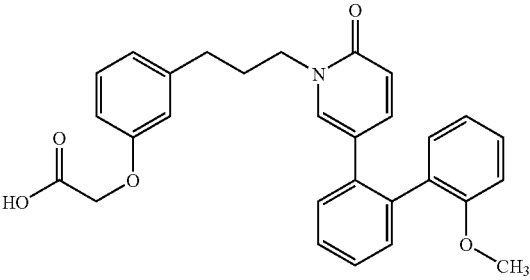 |
| 128 | 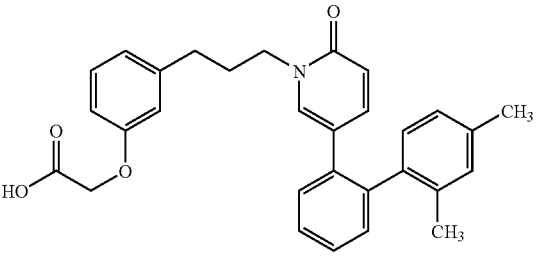 |

TABLE 3-continued

Ex: Example No., Structure: chemical structure.

| Ex | Structure |
|---|---|
| 129 | 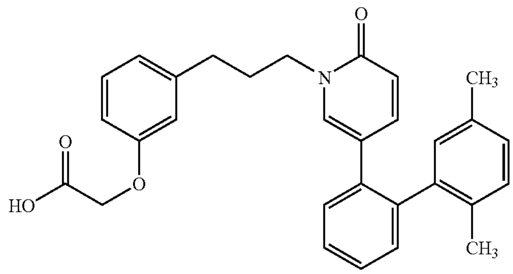 |
| 130 | 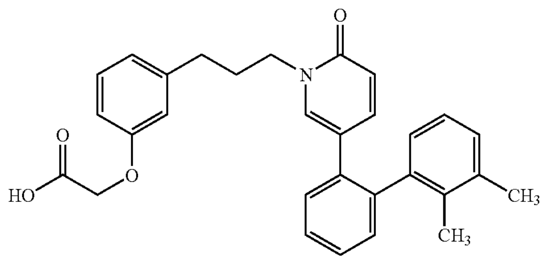 |
| 131 | 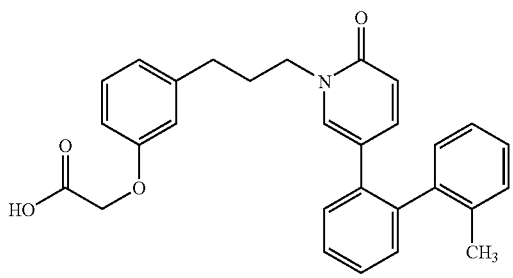 |
| 132 | 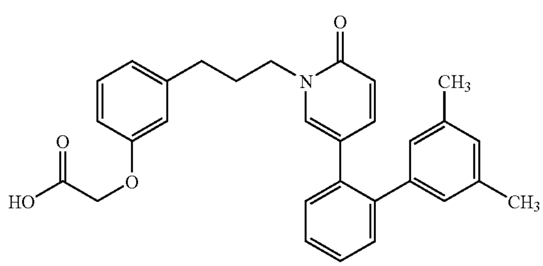 |
| 133 | 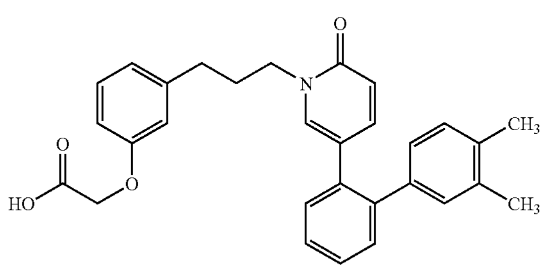 |
| 134 | |
| 135 | |
| 136 | |
| 137 | |
| 138 | |

TABLE 3-continued

Ex: Example No., Structure: chemical structure.

| Ex | Structure |
|---|---|
| 139 | (structure) |
| 140 | (structure) |
| 141 | (structure) |
| 142 | (structure) |
| 143 | Chiral (structure) |
| 144 | (structure) |
| 145 | Chiral (structure) |
| 146 | (structure) |
| 147 | (structure) |
| 148 | (structure) |
| 149 | (structure) |
| 150 | Chiral (structure) |

TABLE 3-continued
Ex: Example No., Structure: chemical structure.
| Ex | Structure |
|---|---|
| 151 | 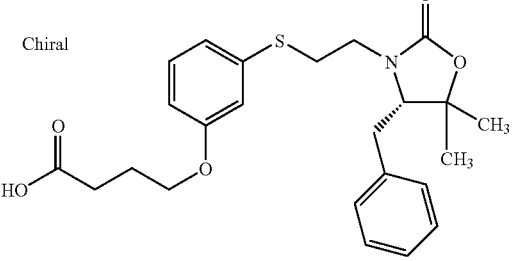 |
| 152 | 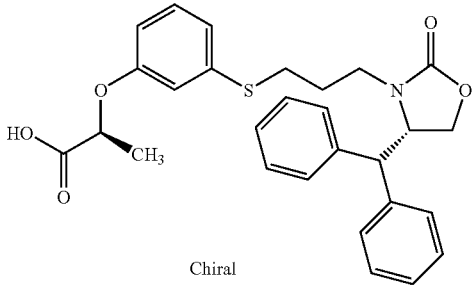 |
| 153 | 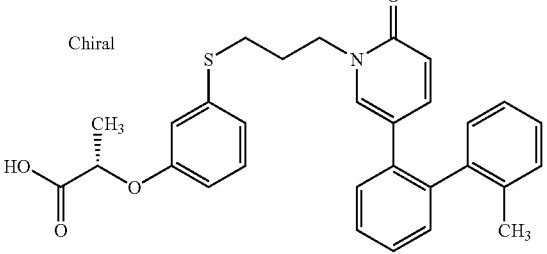 |
| 154 | 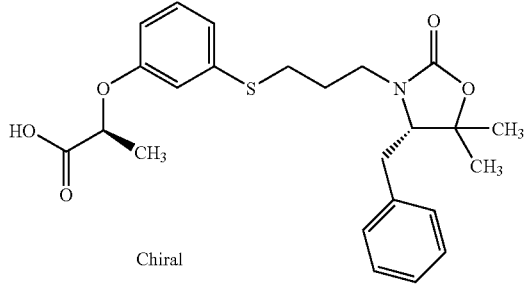 |
| 155 | 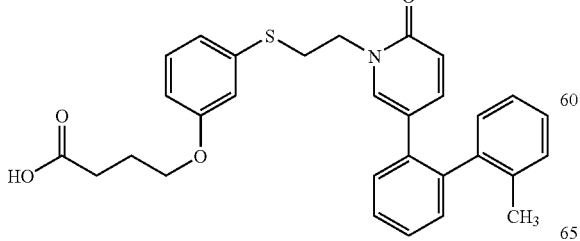 |
| 156 | 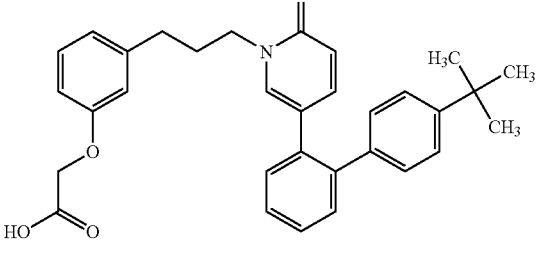 |
| 157 | 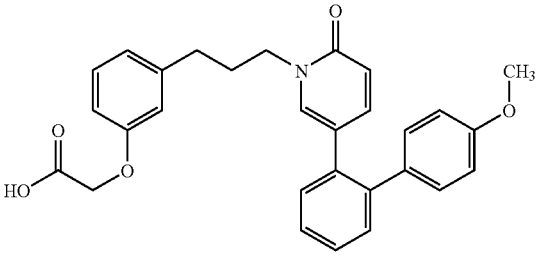 |
| 158 | 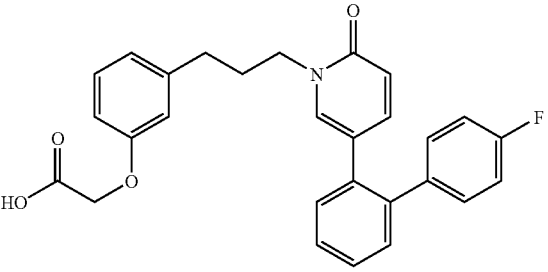 |
| 159 | 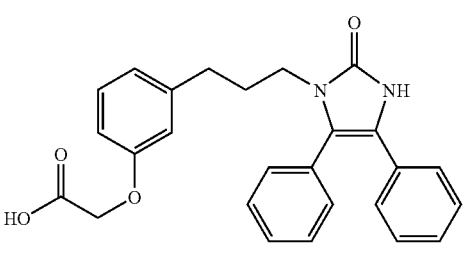 |
| 160 | 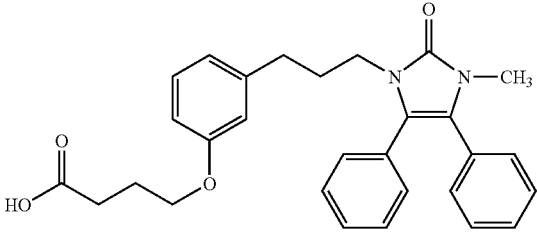 |

TABLE 3-continued

Ex: Example No., Structure: chemical structure.

| Ex | Structure |
|---|---|
| 161 | 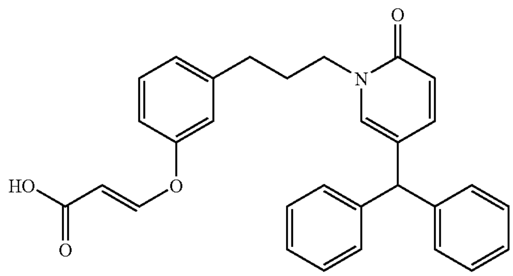 |
| 162 | 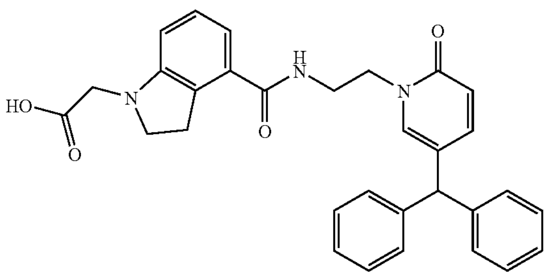 |
| 163 | 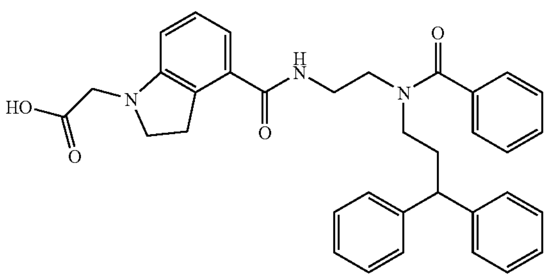 |
| 164 | 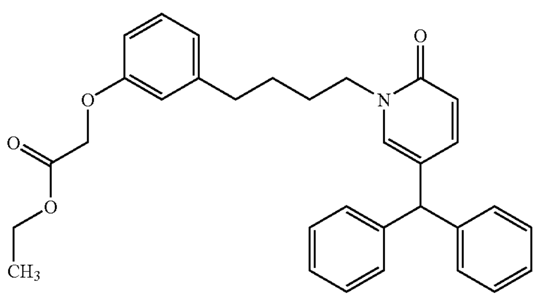 |
| 165 | 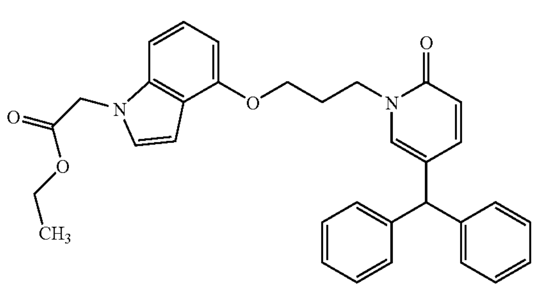 |
| 166 | |
| 167 | |
| 168 | |
| 169 | |
| 170 | |

TABLE 3-continued
Ex: Example No., Structure: chemical structure.
| Ex | Structure |
|---|---|
| 171 | 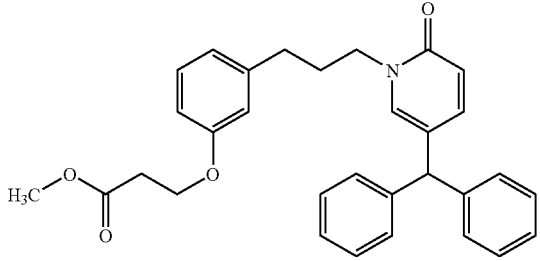 |
| 172 | 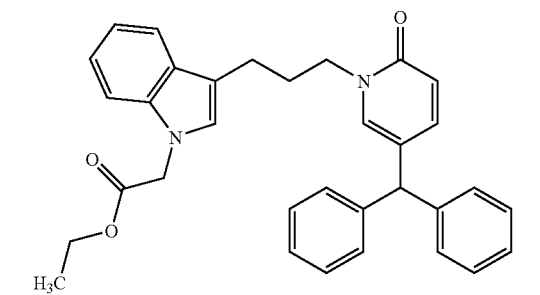 |
| 173 | 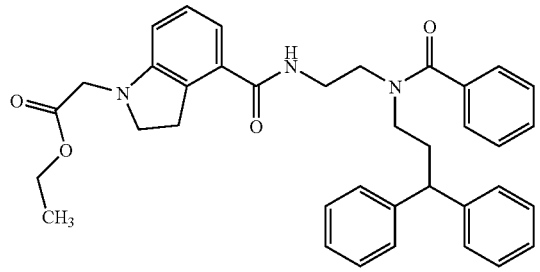 |
| 174 | 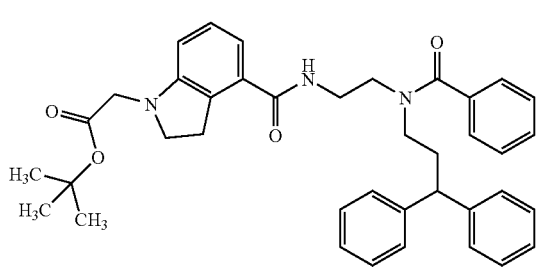 |
| 175 | 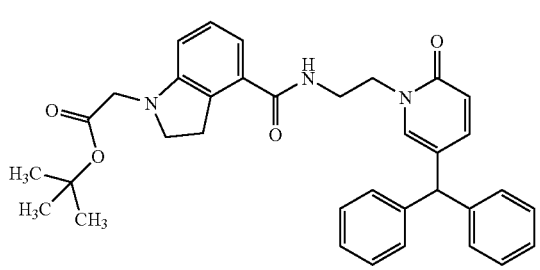 |
| 176 | 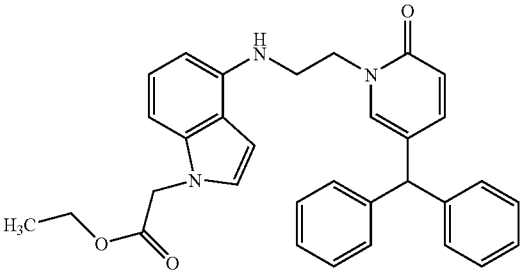 |
| 177 | 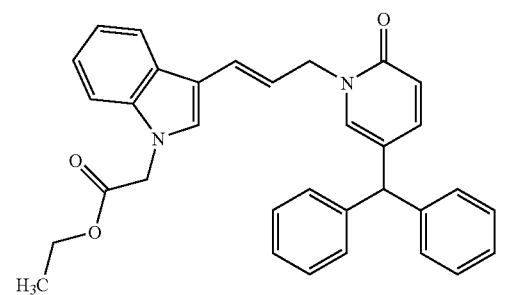 |
| 178 | 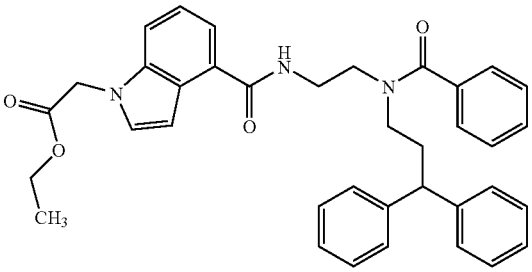 |
| 179 | 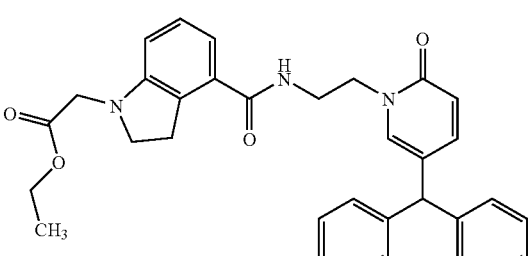 |
| 180 | 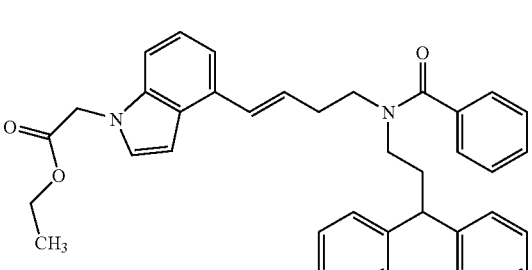 |

TABLE 3-continued

Ex: Example No., Structure: chemical structure.

| Ex | Structure |
|---|---|
| 181 | 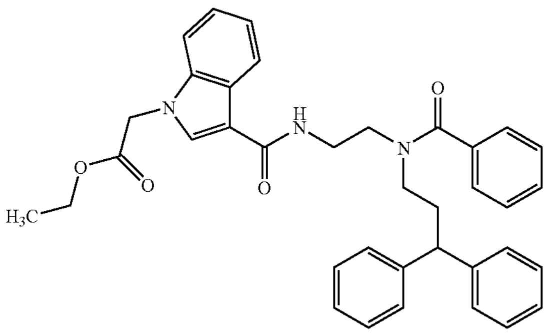 |
| 182 | 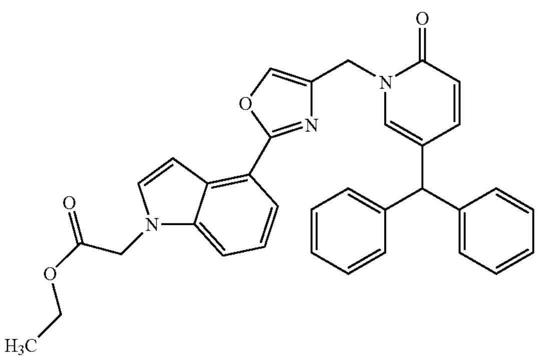 |
| 183 | 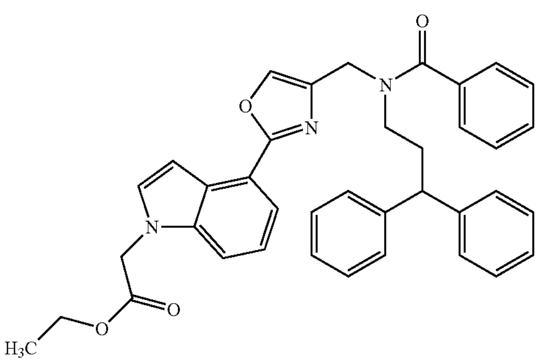 |
| 184 | 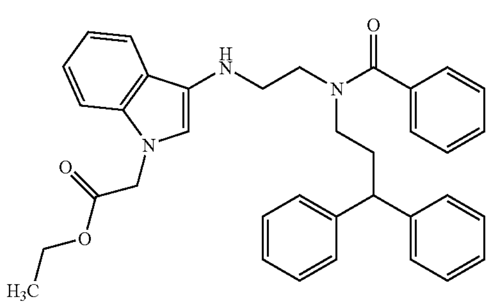 |

TABLE 3-continued

Ex: Example No., Structure: chemical structure.

| Ex | Structure |
|---|---|
| 185 | 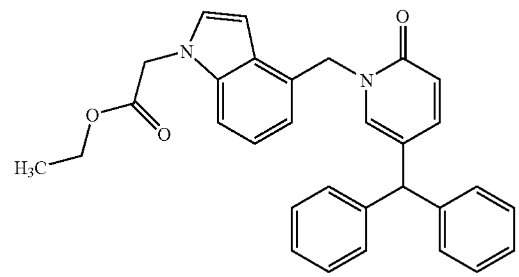 |
| 186 | 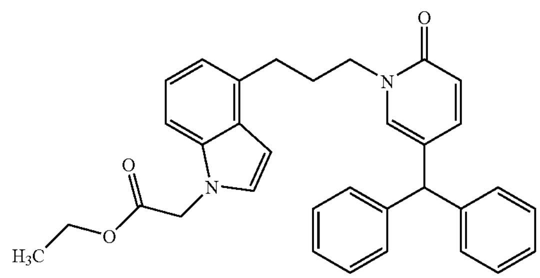 |
| 187 | 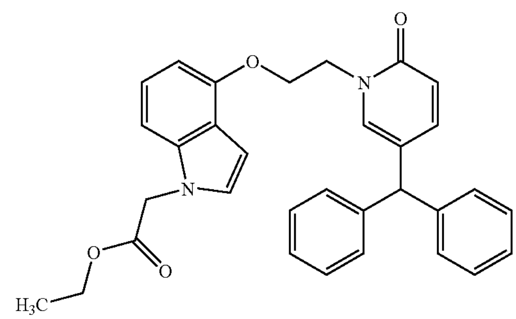 |
| 188 | 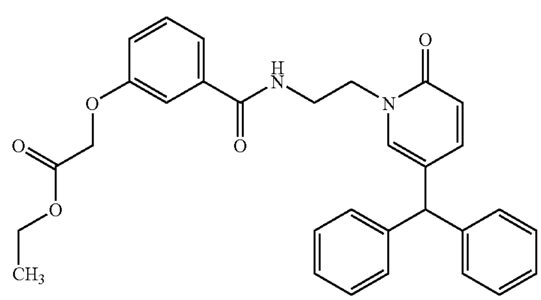 |
| 189 | 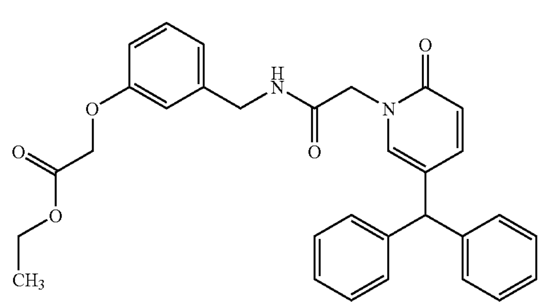 |

TABLE 3-continued

Ex: Example No., Structure: chemical structure.

| Ex | Structure |
|---|---|
| 190 | 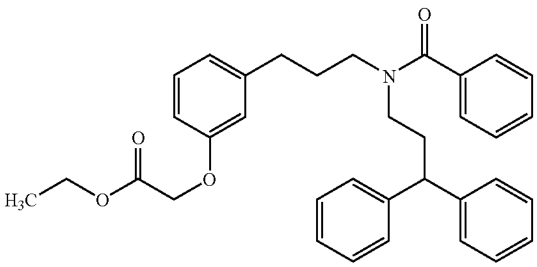 |
| 191 | 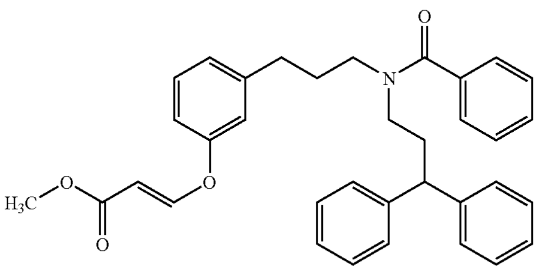 |
| 192 | 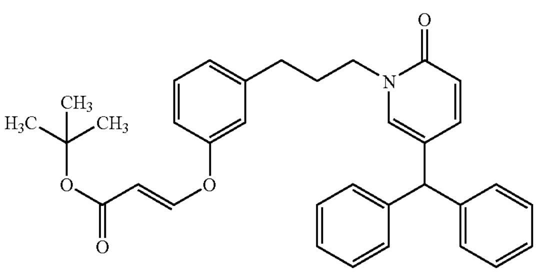 |
| 193 | 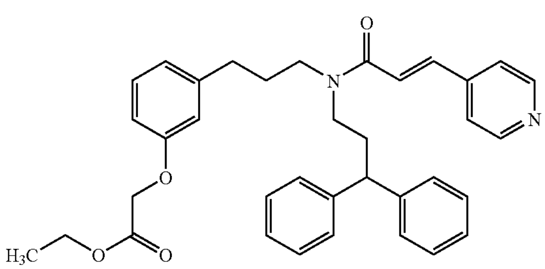 |
| 194 | 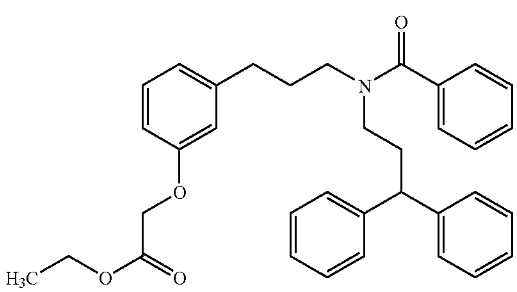 |
| 195 | |
| 196 | |
| 197 | |
| 198 | |
| 199 | |

TABLE 3-continued

Ex: Example No., Structure: chemical structure.

| Ex | Structure |
|---|---|
| 200 | (structure) |
| 201 | (structure) |
| 202 | (structure) |
| 203 | (structure) |
| 204 | (structure) |
| 205 | (structure) |
| 206 | (structure) |
| 207 | (structure) |
| 208 | (structure) |

These compounds shown in the following Tables can be easily prepared by the above preparation methods, methods described in Example(s) or Preparation(s), or methods that are well-known to one skilled in the art, or its variations.

Symbols in the Tables have the following meaning. No: compound number, Structure: chemical structure.

TABLE 4
| No | Structure |
|---|---|
| A1 | 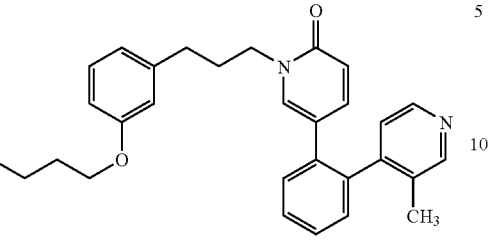 |
| A2 | 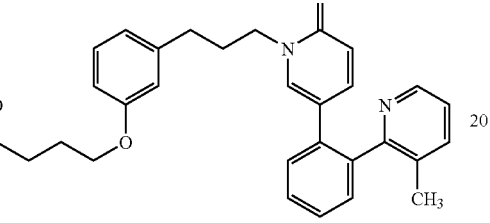 |
| A3 | 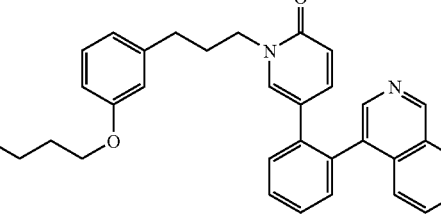 |
| A4 | 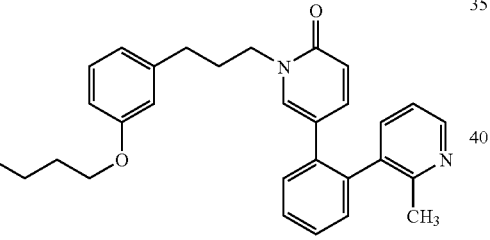 |
| A5 | 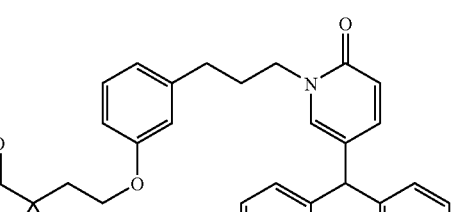 |
| A6 | 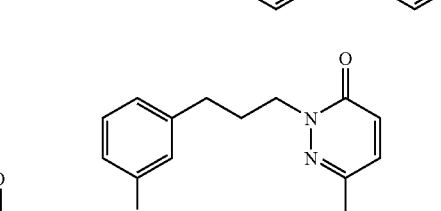 |
TABLE 4-continued
| No | Structure |
|---|---|
| A7 | 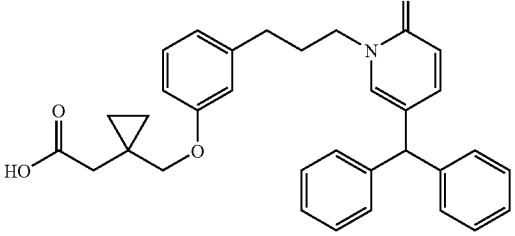 |
| A8 | 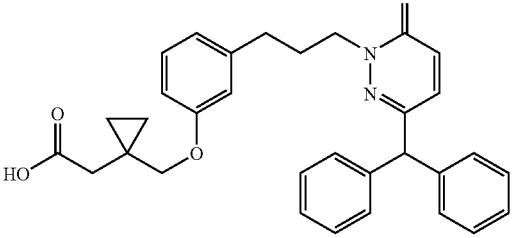 |
| A9 | Chiral 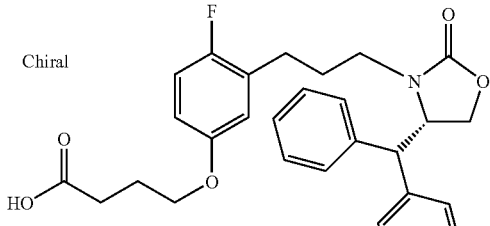 |
| A10 | Chiral 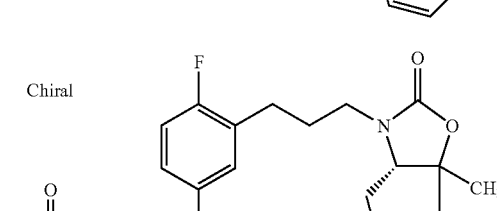 |
| A11 | 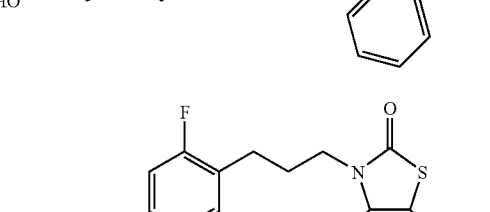 |
| A12 | 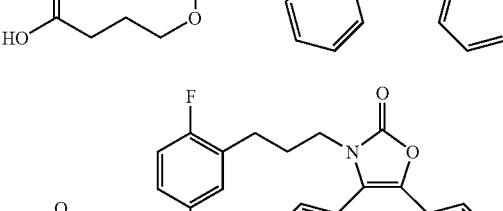 |

TABLE 4-continued

| No | Structure |
|---|---|
| A13 | 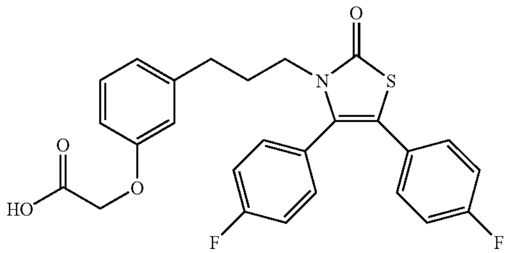 |
| A14 | 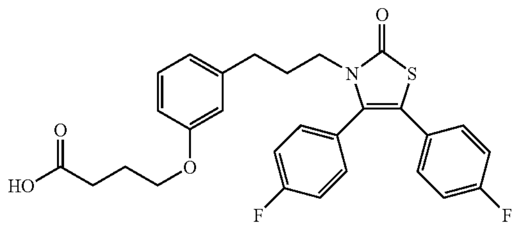 |
| A15 | 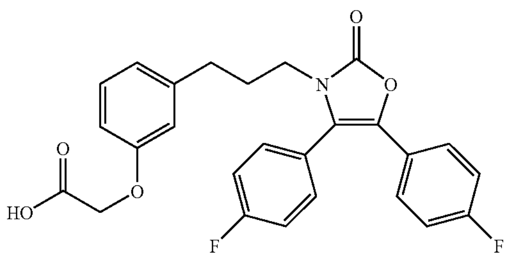 |
| A16 | 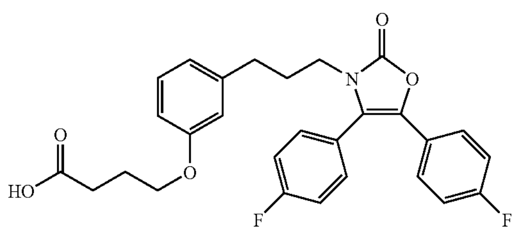 |
| A17 | 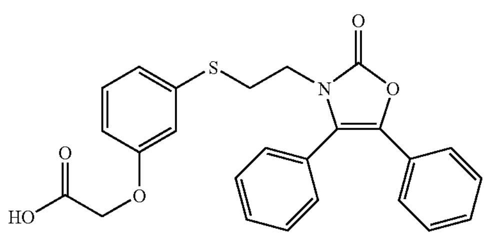 |
| A18 | 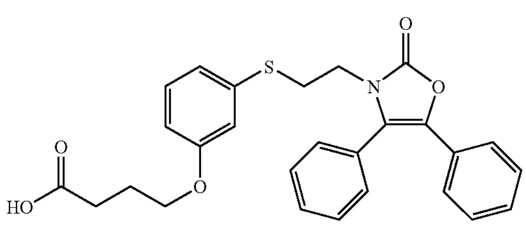 |
| A19 | 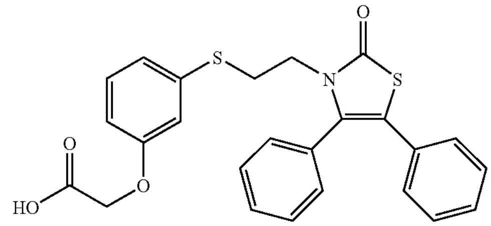 |
| A20 | 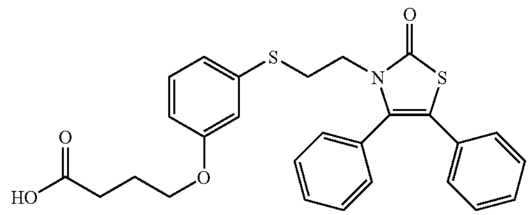 |

The invention claimed is:

1. A compound represented by the formula (I):

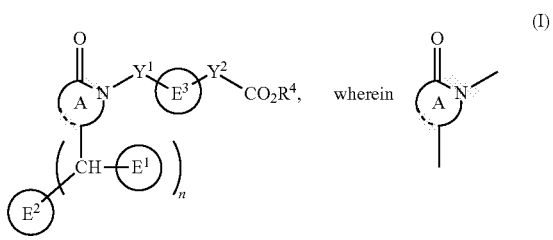

is a ring represented by the formula (i)

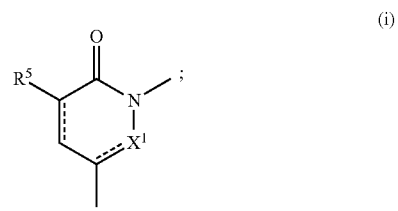

$X^1$ is —N=;

---- is single bond or double bond;

$Y^1$ and $Y^2$ are each $C_1$-$C_6$ alkylene or $C_2$-$C_6$ alknylene, wherein each methylene unit may be replaced with —O—, —NH—, —N(CH$_3$)—, —NHC(=O)—, —N{C(=O)CH$_3$}—, —S—, —S(=O)—, —S(=O)$_2$—, phenylene, pyridinediyl, oxazolediyl, imidazolidiyl or $C_3$-$C_{10}$ cycloalkylene;

$E^1$ is phenyl which may be substituted with one or more substituents $R^1$;

$E^2$ is phenyl or xanthenyl, each of which may be substituted with one or more substituents $R^2$;

$E^3$ is a ring selected from the group consisting of (a),(b),(c),(d) and (e),

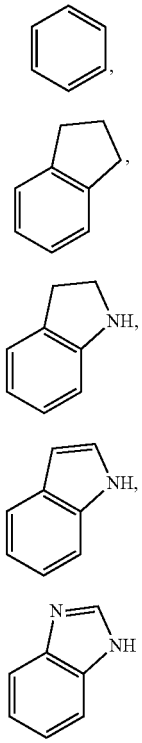

each of which may be substituted with one or more substituents represented by $R^3$;
wherein
$R^1$ is halogen, —$CH_3$ or —$OCH_3$;
$R^2$ is $R^1$, phenyl, naphthyl, —O-phenyl, thienyl or quinolyl,
  each of which may be substituted with one or more substituents $R^1$;
$R^3$ is halogen or —$CH_3$;
$R^4$ is —H, $C_1$-$C_6$ alkyl or alkali metal;
$R^5$ is —H or halogen; and
n is 1;
or a pharmaceutically acceptable salt thereof.

2. A compound of claim 1, wherein
$Y^1$ is $C_1$-$C_6$ alkylene or $C_2$-$C_6$ alkenylene,
  wherein each methylene unit may be replaced with —O— or —S—; and
$Y^2$ is $C_1$-$C_6$ alkylene or $C_2$-$C_6$ alkenylene,
  wherein each methylene unit may be replaced with —O—;
or a pharmaceutically acceptable salt thereof.

3. A compound of claim 2, wherein
$E^1$ is phenyl,
  which may be substituted with one or more substituents represented by $R^1$;
$E^2$ is phenyl,
  which may be substituted with one or more substituents represented by $R^2$; and
$E^3$ is a ring selected from the group consisting of
  (a) and (d),
  each of which may be substituted by one or more substituents represented by $R^3$;
or a pharmaceutically acceptable salt thereof.

4. A compound of claim 3, wherein
$R^2$ is $R^1$, phenyl or naphthyl,
  wherein phenyl or naphthyl may be substituted with one or more substituents represented by $R^1$;
or a pharmaceutically acceptable salt thereof.

5. A compound of claim 4, which is
(1) 4-(3-{2-[3-(Diphenylmethyl)-6-oxopyridazin-1(6H)-yl]ethoxy}phenoxy)butanoic acid,
(2) (2S)-2-(3-{3-[3-(Diphenylmethyl)-6-oxopyridazin-1(6H)-yl]propyl}phenoxy)propanoic acid,
(3) 4-(3-{3-[3-(Diphenylmethyl)-6-oxopyridazin-1(6H)-yl]propyl}phenoxy)butanoic acid,
(4) 4-[3-({2-[3-(Diphenylmethyl)-6-oxopyridazin-1(6H)-yl]ethyl}sulfanyl)phenoxy]butanoic acid,
(5) 4-(3-{3-[3-(Diphenylmethyl)-6-oxo-5,6-dihydropyridazin-1(4H)-yl]propyl}phenoxy)butanoic acid,
(6) (2S)-2-[3-({3-[3-(Diphenylmethyl)-6-oxopyridazin-1(6H)-yl]propyl}sulfanyl)phenoxy]propanoic acid,
(7) 4-[3-(3-{3-[Bis(4-fluorophenyl)methyl]-6-oxopyridazin-1(6H)-yl}propyl)-4-fluorophenoxy]butanoic acid,
(8) 4-[3-(3-{3-[Bis(4-fluorophenyl)methyl]-6-oxopyridazin-1(6H)-yl}propyl)phenoxy]butanoic acid,
(9) {3-[3-(Diphenylmethyl)-6-oxopyridazin-1(6H)-yl]propyl}phenoxy)acetic acid, or a pharmaceutically acceptable salt thereof.

6. A compound of claim 4, which is 4-(3-{3-[3-(Diphenylmethyl)-6-oxopyridazin-1(6H)-yl]propyl}phenoxy)butanoic acid, or a pharmaceutically acceptable salt thereof.

7. A pharmaceutical composition which comprises, as an active ingredient, a compound of claim 1 and a pharmaceutically acceptable carrier.

8. A method of treating asthma or chronic obstructive pulmonary disease comprising administering a therapeutically effective amount, or a prophylactically effective amount, of the compound of claim 1.

* * * * *